US008703783B2

(12) United States Patent
Zheng et al.

(10) Patent No.: US 8,703,783 B2
(45) Date of Patent: Apr. 22, 2014

(54) PURINONE DERIVATIVES AS HM74A AGONISTS

(75) Inventors: Changsheng Zheng, Wilmington, DE (US); Chu-Biao Xue, Hockessin, DE (US); Ganfeng Cao, Wilmington, DE (US); Michael Xia, Wilmington, DE (US); Anlai Wang, Wilmington, DE (US); Hai Fen Ye, Newark, DE (US); Brian Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 13/275,214

(22) Filed: Oct. 17, 2011

(65) Prior Publication Data

US 2012/0035172 A1  Feb. 9, 2012

Related U.S. Application Data

(60) Division of application No. 12/263,990, filed on Nov. 3, 2008, now Pat. No. 8,039,478, which is a continuation of application No. 11/766,981, filed on Jun. 22, 2007, now Pat. No. 7,511,050.

(60) Provisional application No. 60/815,955, filed on Jun. 23, 2006, provisional application No. 60/922,818, filed on Apr. 11, 2007.

(51) Int. Cl.
*A01N 43/54* (2006.01)
*A61K 31/505* (2006.01)

(52) U.S. Cl.
USPC ............................................. 514/267

(58) Field of Classification Search
USPC ............................................. 514/267
See application file for complete search history.

(56) References Cited

U.S. PATENT DOCUMENTS

| | | | |
|---|---|---|---|
| 4,298,734 | A | 11/1981 | Temple, Jr. |
| 4,404,380 | A * | 9/1983 | Temple, Jr. .......... 544/251 |
| 6,902,902 | B2 | 6/2005 | Unett et al. |
| 7,462,624 | B2 | 12/2008 | Xue et al. |
| 7,511,050 | B2 | 3/2009 | Zheng et al. |
| 7,863,285 | B2 | 1/2011 | Xue et al. |
| 7,902,205 | B2 | 3/2011 | Xue et al. |
| 8,039,478 | B2 | 10/2011 | Zheng et al. |
| 2004/0254224 | A1 | 12/2004 | Foord et al. |
| 2005/0004178 | A1 | 1/2005 | Unett et al. |
| 2006/0078916 | A1 | 4/2006 | Aguilar et al. |
| 2006/0160132 | A1 | 7/2006 | Golz et al. |
| 2009/0076269 | A1 | 3/2009 | Xue et al. |
| 2009/0088446 | A1 | 4/2009 | Xue et al. |

FOREIGN PATENT DOCUMENTS

| | | |
|---|---|---|
| EP | 417790 | 3/1991 |
| EP | 1092435 | 4/2001 |
| EP | 1251130 | 10/2002 |
| GB | 1596320 | 8/1981 |
| JP | 3204879 | 9/1991 |
| JP | 83168 | 1/1996 |
| WO | 9001031 | 2/1990 |
| WO | 9803411 | 1/1998 |
| WO | 9803511 | 1/1998 |
| WO | 9856820 | 12/1998 |
| WO | 0001388 | 1/2000 |
| WO | 0147931 | 7/2001 |
| WO | 0200196 | 1/2002 |
| WO | 0244182 | 6/2002 |
| WO | 02084298 | 10/2002 |
| WO | 03022284 | 3/2003 |
| WO | 2004071378 | 8/2004 |
| WO | 2005077950 | 8/2005 |
| WO | 2006004666 | 1/2006 |
| WO | 2006021892 | 3/2006 |
| WO | 2006045564 | 5/2006 |
| WO | 2006045565 | 5/2006 |
| WO | 2007017261 | 2/2007 |
| WO | 2007017262 | 2/2007 |
| WO | 2007017265 | 2/2007 |

OTHER PUBLICATIONS

Defronzo, et al., Dysfunctional Fat Cells, Lipotoxicity and Type 2 Diabetes, Int. J. Clin. Prac., 58: 9-21 (2004).*
Office Action dated Jun. 10, 2010 received in related U.S. Appl. No. 12/237,794.
Notice of Allowance dated Oct. 10, 2010 received in related U.S. Appl. No. 12/237,794.
Wolff, Burger's Medicinal Chemistry and Drug Discovery, Fifth Ed., vol. 1: Principles and Practice, John Wiley & Sons, 1995, 975.
Banker, et al., Modem Pharmaceutics, Marcel Dekker, New York, 1996.
Notice of allowance dated Aug. 19, 2010 received in related U.S. Appl. No. 12/237,807.
Office Action dated Apr. 1, 2010 received in related U.S. Appl. No. 12/237,807.
Altschul et al., "Influence of nicotinic add on serum cholesterol in man," Arch Biochem (1955) 54(2):558-559.
Blom et al., "Preparative LC-MS purification: improved compound-specific method optimization," J Comb Chem (2004) 6(6):874-883.
Aktories et al., "Nicotinic acid inhibits adipocyte adenylate cyclase in a hormone—like manner," FEBS Letters (1980) 115(1):11-14.
Aktories et al., "Islet-activating protein prevents nicotinic acid-induced GTPase stimulation and GTP but not GTP gamma S-induced adenylate cyclase inhibition in rat adipocytes," FEBS Letters (1983) 156(1):88-92.
Defonzo "Dysfunctonal fat cells, lipooxiciy and type 2 dabees," Int J Clin Pract Suppl 2004) (143):9-21.
Higuchi et al., "Pro-drugs s Novel Delivery Systems," vol. 14 of the A.C.S. Symposium Series.

(Continued)

*Primary Examiner* — Erich A Leeser
(74) *Attorney, Agent, or Firm* — Pepper Hamilton LLP

(57) ABSTRACT

The present invention relates to purinone derivatives which are agonists of the HM74a receptor. Further provided are compositions and methods of using the compounds herein, and their pharmaceutically acceptable salts for the treatment of disease.

7 Claims, No Drawings

(56) References Cited

OTHER PUBLICATIONS

Lorenzen et al., "Characterization of a G protein-coupled receptor for nicotinic add," Mol Pharm (2001) 59(2):349-357.

Nicolaou et al., "Lipoxins and related eicosanoids: Biosynthesis, Biological Properties and Chemical Synthesis," Angnew Chem Int Engl (1991) 30:1100-1116.

Sonogashira et al., "A convenient synthesis of acetylenes: catalytic substitutions of acetylenic hydrogen with bromoalkenes iodoarenes and bromopyridines," Tetrahedron Letters (1975) 4467-4470.

Taylor et al., "Arterial Biology for the Investigation of the Treatment Effects of Reducing Cholesterol (ARBITER) 2: a double-blind, placebo-controlled study of extended-release niacin on atherosclerosis progression in secondary prevention patients treated with statins," Circulation (2004) 110(23):3512-3517.

Tunaru et al., "PUMA-G and HM74 aer receptors for nicotinic acid and mediate its anti-lipolytic," Nat Med (2003) 9(3):352-355.

Wise et al., "Molecular identification of high and low affinity receptors for nicotinic acid," J Biol Chem (2003) 278 (11):9869-9874.

Various contributors to Nature Medicine focus atherosclerosis, Nature Med., (2002) 8:1209-1262.

Linton et al., NCEP ATP III, Am J Cardio (2003) 92:19i-26i.

Garcia-Calvo et al., "The target of ezetimibe is Niemann-Pick C1-Like 1 (NPC1L1)," PNAS (2005) 102(23):8132-8137.

Remington's Pharmaceutical Sciences, 17th ed, Mack Publishing Company, Easton, PA, p. 1418.

Journal of Pharmaceutical Science (1977) 66:2.

Bioreversible Carriers in Drug Design, Edward B. Roche, ed., American Pharmaceutical Association an Pergamon Press (1987).

Green et al., Protective Groups in Organic Syntesis, 2nd Ed., Wiley and Sons (1991).

Temple et al., "Substituted 6,7-dihydroimidazo[1,2-a]purin-9(4H)-ones," Journal of Medicinal Chemistry (1980) 23(11):1188-1198.

Mueller et al., "Imidazo[2,1-i]purin-5-ones and related tricyclic water-soluble purine derivatives: potent A(2A)- and A(3)-adenosine receptor antagonists," Journal of Medicinal Chemistry (2002) 45(16):3440-3450.

Haldon et al., "In vitro cytostatic activity of 8-substituted and tricyclic analogues of acyclovir," Polish Journal of Pharmacology (2002) 54(1):45-53.

Nagamatsu et al., "Facile, general and productive syntheses of the fluorescent wye (4,9-dihydro-4,6-dimethyl-9-oxo-1H-imidazol[1,2-a]purine) in phenylalanine tRNA, its 2-substituted derivatives and 7-aza analogs," Journal of the Chemical Society: Chemical Communications (1995) (19):2041-2043.

Itaya et al., "Studies towards the synthesis of the fluorescent bases of phenylalanine transfer ribonucleic acids: synthesis of 7-methylwye isolated from extremely thermophilic archabacterial," Chemical and Pharmaceutical Bulletin (1989) 37(2):284-291.

Nagamatsu et al., "Syntheses of 4-methyl-s-triazolo[4,3-a]purin-9(4H0-ones and tetrazolo[1,5-a]purin-9(4H)-ones as aza analogs of "Y" bases," Chemical & Pharmaceutical Bulletin (1985) 33(8):3113-3121.

Notice of allowance dated Nov. 29, 2010 received in related U.S. Appl. No. 12/237,807.

Office Action dated May 26, 2010 received in related U.S. Appl. No. 12/263,990.

Notice of Allowance dated Aug. 4, 2008 received in related U.S. Appl. No. 11/766,981.

Office Action dated Oct. 19, 2010 received in related U.S. Appl. No. 12/263,990.

Notice of Allowance dated May 27, 2011 received in related U.S. Appl. No. 12/263,990.

Notice of Allowance date Jun. 26, 2008 received in related U.S. Appl. No. 11/766,990.

Notice of Allowance dated Nov. 23, 2010 received in related U.S. Appl. No. 12/237,794.

* cited by examiner

PURINONE DERIVATIVES AS HM74A AGONISTS

CROSS-REFERENCE TO RELATED APPLICATIONS

This application is a divisional filing of U.S. application Ser. No. 12/263,990, filed Nov. 3, 2008, which is a continuation filing of U.S. application Ser. No. 11/766,981, filed Jun. 22, 2007, which claims priority to U.S. Provisional Application No. 60/922,818 filed Apr. 11, 2007, and U.S. Provisional Application No. 60/815,955 filed Jun. 23, 2006, each of which is incorporated herein by reference in its entirety.

FIELD OF THE INVENTION

The present invention relates to agonists of the HM74a receptor, compositions thereof and methods of using the same.

BACKGROUND OF THE INVENTION

Coronary artery disease (or CAD) is the number one cause of death in the United States (Nature Med 2002, 8:1209-1262). The initiation and progression of CAD involves a complex interplay between multiple physiological processes, including inflammation, lipid homeostasis, and insulin resistance/diabetes mellitus. Multiple clinical studies have now shown that the three primary components of plasma lipids, low-density lipoprotein (or LDL), high-density lipoproteins (or HDL), and triglycerides (or TGs), are causally associated with the propensity to develop atherosclerosis and CAD. Along side other risk factors such as positive family history of CAD, elevated body-mass index, hypertension, and insulin resistance/diabetes mellitus, elevated plasma LDL and/or TG-rich lipoproteins and decreased plasma HDL levels have been defined as major cardiovascular risk factors by the National Cholesterol Education Program Adult Treatment Panel 111 (NCEP ATP III; Am J Cardio 2003, 92: 19i-26i). Accordingly, therapeutic intervention strategies designed to impact these plasma lipid components as well as those that underlie insulin resistance are of great interest to the medical community.

In terms of LDL-lowering, drugs of the statin class are structurally similar to the molecule hydroxymethylglutaryl-coenzyme A (HMG-CoA), a biosynthetic precursor of cholesterol. These drugs are competitive inhibitors of the rate-limiting step of cholesterol biosynthesis catalyzed by HMG-CoA reductase. Mechanistically, the statins lower LDL by upregulating the LDL receptor in the liver as well as by reducing the release of LDL into the circulation. As a monotherapy, the statin class of lipid lowering agents can reduce plasma LDL concentrations by 30-60% and triglycerides by 25%, producing a reduction in the incidence of CAD by 25-60% and the risk of death by 30%. Statins do not have an appreciable effect on HDL. A mechanistically distinct agent, Ezetimibe (Zetia, Merck and Co.), also possesses the ability to reduce plasma LDL, however it functions by inhibiting the absorption of cholesterol by the small intestine via antagonism of the NPC1L1 receptor (PNAS 2005, 102: 8132-8137). Monotherapy with Ezetimibe typically lowers LDL by 20%, however when co-formulated with a statin, maximal reductions can exceed 60%. As with the statins, however, Ezetimibe has a negligible effect on plasma HDL.

While statins can have a modest impact on circulating triglycerides, PPAR alpha agonists (or fibrates) are far superior in targeting this lipid endpoint. The fibrates function by increasing lipolysis and elimination of triglyceride-rich particles from plasma by activating lipoprotein lipase and reducing production of apolipoprotein C-III (an inhibitor of lipoprotein lipase activity). One such fibrate, Fenofibrate (Tricor, Abott), has been shown in clinical studies to decrease plasma triglyceride levels upwards of 40-60%. Interestingly, the fibrate class of lipid-lowering drugs also has a modest, but significant effect on both LDL (20% reduction) and HDL (10% increase).

Currently, the statin class of LDL lowering agents remains the cornerstone of dyslipidemia therapy. Despite the substantial reduction in cardiovascular events that have been achieved with this therapeutic approach, however, the cardio-protection that is afforded to patients by these therapies is still incomplete. It is now clear that therapies that are targeted to increase HDL cholesterol are critical in terms of maximizing patient cardio-protection. The only therapy available to date that has the ability to effectively raise circulating levels of cardio-protective HDL and consequently improve the progression of atherosclerosis in CAD patients is nicotinic acid (niacin or vitamin $B_3$). Nicotinic acid was first reported to modify lipoprotein profiles in 1955 (Altschul et al. Arch Biochem Biophys 1955, 54: 558-559). Its effects are the most broad-spectrum of any available therapy, effectively raising HDL levels (20-30%) as well as lowering circulating plasma LDL (16%) and triglycerides (38%). The clinical significance of this broad-spectrum activity has been revealed in multiple large clinical studies. In the most recent ARBITER 2 (Arterial Biology for the Investigation of the Treatment Effects of Reducing Cholesterol 2; Taylor et al. Circulation 2004, 110: 3512-3517) study, patients on statin therapy were randomized to either placebo or 1000 mg extended release (ER) niacin (Niaspan, Kos Pharmaceuticals). Patients receiving niacin exhibited a statistically significant decrease in carotid intima-media thickness, a validated surrogate cardiovascular end point. This study also revealed a significantly reduced rate of intima-media thickness progression in subjects without detectable insulin resistance. This study indicates the incomplete cardio-protection that is offered by statin therapy and substantiates the utility of nicotinic acid in reducing overall cardiac risk in low-HDL patients.

While nicotinic acid has been used clinically to modify lipid profiles for over four decades, the mechanism of action of the compound has remained largely obscure. It has long been known that acute nicotinic acid dosing results in a profound decrease in circulating free fatty acids (FFAs). This anti-lipolytic activity was first hypothesized in 1980 to be mediated by a membrane receptor linked to a decrease in intracellular cAMP (cyclic AMP, or cyclic adenosine monophosphate, or 3'-5'-cyclic adenosine monophosphate) levels (Aktories et al. FEBS Letters 1980, 115: 11-14). This hypothesis was later confirmed and the implied $G_{i/o}$ GPCR-coupling was verified using pertussis toxin sensitivity studies (Aktories et al. FEBS Letters 1983, 156: 88-92). The identification of specific nicotinic acid binding sites on the surface of adipose and spleen cells confirmed the membrane hypothesis and refined, using modern-day techniques, the G-protein coupling of the receptor itself (Lorenzen et al. Mol Pharm 2001, 59: 349-357). This G-protein mediated, anti-lipolytic activity of nicotinic acid was used for two decades to identify and characterize nicotinic acid analogues in terms of their therapeutic potential. Finally, in 2003, two independent groups simultaneously published the cloning of an orphan $G_{i/o}$-coupled GPCR, HM74a (Wise et al. J Biol Chem 2003, 278: 9869-9874; Tunaru et al. Nat Med 2003, 9: 352-355), which binds to nicotinic acid with high affinity. As predicted, this receptor was shown to be expressed in adipose tissue and spleen, and binds to not only nicotinic acid, but also to the structurally related derivatives that had been previously shown to exhibit adipocyte anti-lipolytic activity. Mice that have been made deficient in the rodent ortholog of HM74a (Puma-g) by homologous recombination resist nicotinic acid-dependent FFA reduction and TG lowering. It is currently hypothesized that the nicotinic acid anti-lipolytic activity is based on the activation of this high affinity GPCR (HM74a), resulting in a decrease in intracellular cAMP and a subsequent attenuation of hormone sensitive lipase (HSL) activity. Decreased adipocyte lipolytic output results in a reduction in circulating FFA and a corresponding reduction in hepatic TGs, very-low density LDL (VLDL), and LDL. The increased levels of HDL arise from an effective reduction of cholesterol ester transfer protein activity due to decreased availability of VLDL acceptor molecules.

Beyond impacting lipid levels and lipoprotein profiles, FFAs play fundamental roles in the regulation of glycemic control. It is now recognized that chronically elevated plasma FFA concentrations cause insulin resistance in muscle and liver, and impair insulin secretion (reviewed in Defronzo et al. Int. J. Clin. Prac. 2004, 58: 9-21). In muscle, acute elevations in plasma FFA concentrations can increase intramyocellular lipid content; this can have direct negative effects on insulin receptor signaling and glucose transport. In liver, increased plasma FFAs lead to accelerated lipid oxidation and acetyl-CoA accumulation, the later of which stimulates the rate-limiting steps for hepatic glucose production. In the pancreas, long-term exposure to elevated FFAs has been shown to impair the beta-cell's ability to secrete insulin in response to glucose. This data has driven the hypothesis that adipose tissue FFA release is a primary driver of the underlying pathologies in type 2 diabetes, and strategies designed to reduce FFAs, for example by agonizing HM74A, may prove effective in improving insulin sensitivity and lowering blood glucose levels in patients with type 2 diabetics/metabolic syndrome The utility of nicotinic acid as a hypolipidemic/FFA lowering agent is currently limited by four main factors. First, significant doses of nicotinic acid are required to impact FFA release and improve lipid parameters Immediate release (1R) nicotinic acid is often dosed at 3-9 g/day in order to achieve efficacy, and ER nicotinic acid (Niaspan) is typically dosed between 1-2 g/day. These high doses drive the second issue with nicotinic acid therapy, hepatotoxicity. One of the main metabolic routes for nicotinic acid is the formation of nicotinamide (NAM). Increased levels of NAM have been associated with elevated liver transaminase which can lead to hepatic dysfunction. This toxicity is particularly problematic for sustained release formulations and results in the need to monitor liver enzymes during the initiation of therapy. Third, high doses of nicotinic acid are associated with severe prostaglandin-mediated cutaneous flushing. Virtually all patients experience flushing when on IR-nicotinic acid at or near the $T_{max}$ of the drug and discontinuation of therapy occurs in 20-50% of individuals. Niaspan, while exhibiting an increased dissolution time, still possesses a flushing frequency of approximately 70%, and this is in spite of the recommended dosing regimen that includes taking Niaspan along with an aspirin after a low-fat snack. Fourth, nicotinic acid therapy often results in FFA rebound, a condition whereby free fatty acid levels are not adequately suppressed throughout the dosing regimen, resulting in a compensatory increase in adipose tissue lipolysis. With immediate release nicotinic acid therapy, this rebound phenomenon is so great that daily FFA AUCs are actually increased after therapy. Such FFA excursions can lead to impaired glycemic control and elevated blood glucose levels, both of which have been shown to occur in some individuals after nicotinic acid therapy.

Giving the importance of nicotinic acid in modulating (especially agonizing) HM74a receptor and its limitations, novel small molecules designed to mimic the mechanism of nicotinic acid's action on HM74a offer the possibility of achieving greater HDL, LDL, TG, and FFA efficacy while avoiding adverse effects such as hepatotoxicity and cutaneous flushing. Such therapies are envisioned to have significant impact beyond dyslipidemia to include insulin resistance, hyperglycemia, and associated syndromes by virtue of their ability to more adequately reduce plasma FFA levels during the dosing interval. The present invention is directed to these, as well as other, important ends.

SUMMARY OF THE INVENTION

The present invention provides, inter alia, compounds of Formula I:

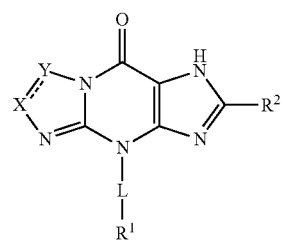

or pharmaceutically acceptable salts or prodrugs thereof, wherein constituent members are defined herein.

The present invention further provides compositions comprising a compound of the invention and at least one pharmaceutically acceptable carrier.

The present invention further provides methods of modulating HM74a receptor with a compound of the invention.

The present invention further provides methods of agonizing HM74a receptor by contacting the HM74a receptor with a compound of the invention.

The present invention further provides methods of treating diseases associated with HM74a receptor.

The present invention further provides a compound of the invention for use in therapy.

The present invention further provides a compound of the invention for use in the preparation of a medicament for use in therapy.

DETAILED DESCRIPTION

The present invention provides, inter alia, compounds which are agonists or partial agonists of HM74a and are useful in the treatment of a variety of diseases, such as cardiovascular diseases.

The compounds can have Formula I:

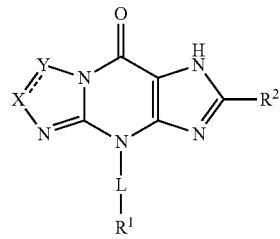

or pharmaceutically acceptable salt or prodrug thereof, wherein:
a dashed line indicates an optional bond;
X is N, $CR^{3a}$, $CR^{4a}R^{5a}$, or $NR^{6a}$;
Y is N, $CR^{3b}$, $CR^{4b}R^{5b}$, or $NR^{6b}$;
L is —($C_{1-6}$ alkylene)-$(Q^1)_m$-($C_{1-6}$ alkylene)$_p$-$(Q^2)_q$-($C_{1-6}$ alkylene)$_r$-, optionally substituted with 1, 2, 3, 4, or 5 $R^{L1}$, wherein if m and q are both 1, then p is 1;
$R^1$ is H, $C_{1-10}$ alkyl, $C_{2-10}$ alkenyl, $C_{2-10}$ alkynyl, or Cy, wherein said $C_{1-10}$ alkyl, $C_{2-10}$ alkenyl, or $C_{2-10}$ alkynyl is optionally substituted with 1, 2, 3, 4, or 5 $R^{L2}$;
$R^2$ is halo, cyano, $C_{1-3}$ haloalkyl, Z, $SR^A$, or a moiety having the formula:

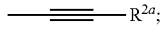

$R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, or $C_{2-6}$ alkynyl is optionally substituted with 1, 2, or 3 substitutents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$;

$R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substitutents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{6a}$ and $R^{6b}$ are independently selected from H, $C_{1-6}$ alkyl, $C_{2-6}$ alkenyl, $C_{2-6}$ alkynyl, $C_{1-6}$ haloalkyl, $Cy^2$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substitutents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{2a}$ is H, $C_{1-6}$ alkyl, $C_{2-6}$ alkenyl, $C_{2-10}$ alkynyl, $C_{1-6}$ haloalkyl, $C_{1-6}$ hydroxyalkyl, $C_{1-6}$ cyanoalkyl, $Cy^4$, CN, $NO_2$, $C(O)R^{bb}$, $C(O)NR^{c6}R^{d6}$, or $C(O)OR^{a6}$;

Cy is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$Cy^1$ and $Cy^2$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, or $C_{2-4}$ alkynyl is optionally substituted with 1, 2, or 3 substituents independently selected from CN, $NO_2$, halo, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$;

$Cy^3$ and $Cy^4$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

Z is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

$R^A$ is H or $C_{1-4}$ alkyl;

$Q^1$ and $Q^2$ are independently selected from O, S, NH, $CH_2$, CO, CS, SO, $SO_2$, $OCH_2$, $SCH_2$, $NHCH_2$, $CH_2CH_2$, $COCH_2$, CONH, COO, $SOCH_2$, SONH, $SO_2CH_2$, and $SO_2NH$;

$R^a$ and $R^{a1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{a2}$, $R^{a3}$, $R^{a4}$, $R^{a5}$, and $R^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^b$ and $R^{b1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{b2}$, $R^{b3}$, $R^{b4}$, $R^{b5}$, and $R^{b6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^c$ and $R^d$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^c$ and $R^d$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c1}$ and $R^{d1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^{c1}$ and $R^{d1}$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c2}$ and $R^{d2}$ together with the N atom to which they are attached form a 4-, 5-, 6- or 7-membered heterocycloalkyl group;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c3}$ and $R^{d3}$ together with the N atom to which they are attached form a 4-, 5-, 6- or 7-membered heterocycloalkyl group;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c5}$ and $R^{d5}$ together with the N atom to which they are attached form a 4-, 5-, 6- or 7-membered heterocycloalkyl group; and $R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c6}$ and $R^{d6}$ together with the N atom to which they are attached form a 4-, 5-, 6- or 7-membered heterocycloalkyl group; and m, p, q, and r are independently selected from 0 and 1.

In some embodiments, when $X\!=\!\!=\!\!=Y$ is $CR^{4a}R^{5a}$—$CR^{4b}R^{5b}$, then $R^2$ is other than halo, $C_{1-3}$ haloalkyl, Z or $SR^A$.

In some embodiments, when $X\!=\!\!=\!\!=Y$ is $CR^{3a}\!=\!\!N$, then $R^2$ is other than Z;

In some embodiments, when $X\!=\!\!=\!\!=Y$ is $N\!=\!\!CR^{3b}$ and $R^{3b}$ is H or unsubstituted aryl, then $R^2$ is other than unsubstituted aryl;

In some embodiments, when $X\!=\!\!=\!\!=Y$ is $N\!=\!\!N$, then $R^2$ is other than aryl; and In some embodiments, when X═Y is $CR^{3a}$═$CR^{3b}$, then -L-$R^1$ is other than methyl.

In some embodiments, when X is $CR^{4a}R^{5a}$ and Y is $CR^{4b}R^{5b}$, then $R^2$ is other than halo or $C_1$ trihaloalkyl.

In some embodiments, when X is $CR^{4a}R^{5a}$ and Y is $CR^{4b}R^{5b}$, then $R^2$ is other than Br or $C_3$ trihaloalkyl.

In some embodiments, X═Y is other than $CR^{4a}R^{5a}$—$CR^{4b}R^{5b}$.

In some embodiments, $R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, or $C_{2-6}$ alkynyl is optionally substituted with 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, $Cy^1$ and $Cy^2$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, or $C_{2-4}$ alkynyl is optionally substituted with 1, 2, or 3 substituents independently selected from CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$.

In some embodiments, X is N.
In some embodiments, X is $CR^{3a}$.
In some embodiments, X is $CR^{4a}R^{5a}$.
In some embodiments, X is CH.
In some embodiments, Y is N.
In some embodiments, Y is $CR^{3b}$.
In some embodiments, Y is CH.
In some embodiments, Y is C-Me.
In some embodiments, Y is $CR^{4b}R^{5b}$.
In some embodiments, X is N and Y is $CR^{3b}$.
In some embodiments, X is $CR^{3a}$ and Y is N.
In some embodiments, X is CH and Y is N.
In some embodiments, X and Y are both N.
In some embodiments, at least one of X and Y is N.

In some embodiments, $R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, $S(O)R^b$, $S(O)_2R^b$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, $R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, $R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, $C(O)NR^cR^d$, $C(O)OR^a$, and $NR^cC(O)R^b$.

In some embodiments, $R^{3a}$ and $R^{3b}$ are independently selected from H, $C_{1-6}$ alkyl, $C_{1-6}$ haloalkyl, $Cy^1$, $OR^a$, $SR^a$, $S(O)R^b$, $S(O)_2R^b$, and $NR^cR^d$, wherein said $C_{1-6}$ alkyl is optionally substituted with 1, 2, or 3 substituents independently selected from $Cy^1$, $C(O)NR^cR^d$, $C(O)OR^a$, halo, $OR^a$, $NR^cR^d$, $NR^cC(O)NR^cR^d$, and $NR^cC(O)R^b$.

In some embodiments:
at least one of $R^{3a}$ and $R^{3b}$ is selected from $Cy^1$;
$Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, $C(O)OR^{a4}$, and Cy, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$; and
$Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, at least one of $R^{3a}$ and $R^{3b}$ is selected from $C_{1-6}$ alkyl and $C_{1-6}$ haloalkyl, wherein said $C_{1-6}$ alkyl is optionally substituted with 1, 2, or 3 substituents independently selected from $C(O)NR^cR^d$, $C(O)OR^a$, $NR^cR^d$, $NR^cC(O)NR^cR^d$, and $NR^cC(O)R^b$.

In some embodiments:
at least one of $R^{3a}$ and $R^{3b}$ is selected from $C_{1-3}$ alkyl, wherein said $C_{1-3}$ alkyl is substituted with $Cy^1$ and optionally substituted with 1 or 2 substituents independently selected from halo, $OR^a$, and $SR^a$;
$Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$; and
$Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$.

In some embodiments:
at least one of $R^{3a}$ and $R^{3b}$ is selected from $C_{1-3}$ alkyl, wherein said $C_{1-3}$ alkyl is substituted with $Cy^1$ and optionally substituted with 1 or 2 substituents independently selected from halo, $OR^a$, and $SR^a$;
$Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$; and $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments:

at least one of $R^{3a}$ and $R^{3b}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;

$Cy^1$ is selected from aryl, heteroaryl, cycloalkyl, and heterocycloalkyl, each substituted with 1 or 2 $R^7$ and optionally substituted by 1, 2, or 3 $R^8$;

$R^7$ is, at each occurrence, independently selected from $Cy^3$ and $C_{1-4}$ alkyl, wherein said $C_{1-4}$ alkyl is substituted with 1 or 2 $Cy^3$ and optionally substituted with 1 or 2 substituents independently selected from halo and $OR^{a4}$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, at least one of $R^{3a}$ and $R^{3b}$ is $-L^A-Cy^1$, wherein $L^A$ is $C_{1-3}$ alkylene optionally substituted with 1 or 2 substitutents independently selected from halo, $OR^a$, and $SR^a$. In some further embodiments, $Cy^1$ is aryl or heteroaryl, each optionally substituted by 1, 2, or 3 substituents independently selected from $Cy^3$, halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$. In yet further embodiments, $Cy^1$ is 1,2,4-oxadiazolyl optionally substituted by 1, 2, or 3 substituents independently selected from $Cy^3$, halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$.

In some embodiments, one of $R^{3a}$ and $R^{3b}$ is $-L^A-Cy^1$, and the other is selected from H, $C_{1-4}$ alkyl, and $C_{1-4}$ haloalkyl.

In some embodiments, at least one of $R^{3a}$ and $R^{3b}$ is $-L^A-Cy^1-(L^B)_{t1}-Cy^3$, wherein $L^A$ is $C_{1-3}$ alkylene optionally substituted with 1 or 2 substitutents independently selected from halo, $OR^a$, and $SR^a$; $L^B$ is $C_{1-4}$ alkylene optionally substituted with 1 or 2 substitutents independently selected from halo and $OR^{a4}$; and t1 is 0 or 1. In some further embodiments, $L^A$ is $C_{1-3}$ alkylene optionally substituted with OH. In yet embodiments, $L^A$ is $C_{2-3}$ alkylene optionally substituted with OH. In further embodiments, $L^A$ is $C_{2-3}$ alkylene. In some embodiments, t1 is 0. In some embodiments, t1 is 1. In some embodiments, $L^B$ is $C_{1-4}$ alkylene optionally substituted with OH. In some further embodiments, $L^B$ is $C_{1-3}$ alkylene optionally substituted with OH.

In some embodiments, at least one of $R^{3a}$ and $R^{3b}$ is $-L^A-Cy^1-(L^B)_{t1}-Cy^3$, wherein $L^A$ is $C_{1-3}$ alkylene optionally substituted with 1 or 2 substitutents independently selected from halo and $OR^a$. In some further embodiments, $L^A$ is $C_{1-3}$ alkylene optionally substituted with halo or OH.

In some embodiments, at least one of $R^{3a}$ and $R^{3b}$ is $-L^A-Cy^1-(L^B)_{t1}-Cy^3$, wherein $L^B$ is $C_{1-4}$ alkylene optionally substituted with 1 or 2 substituents independently selected from halo and $OR^{a4}$. In some further embodiments, $L^B$ is $C_{1-4}$ alkylene optionally substituted with halo or OH.

In some embodiments, at least one of $R^{3a}$ and $R^{3b}$ is $-L^A-Cy^1-(L^B)_{t1}-Cy^3$; and $Cy^1$ is aryl or heteroaryl, each optionally substituted by 1, 2, or 3 substituents independently selected from $Cy^3$, halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$. In some further embodiments, $Cy^1$ is 1,2,4-oxadiazolyl. In some embodiments, $Cy^3$ is selected from aryl and heteroaryl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, $NR^{c6}R^{d6}$, and $OR^{a6}$. In some further embodiments, $Cy^3$ is selected from aryl and heteroaryl, each substituted by OH and optionally substituted with 1, 2, or 3 substituents selected from halo, $C_{1-4}$ alkyl, $C_{2-4}$ alkenyl, $C_{2-4}$ alkynyl, $C_{1-4}$ haloalkyl, aryl, heteroaryl, $NR^{c6}R^{d6}$ and $OR^{a6}$.

In some embodiments, one of $R^{3a}$ and $R^{3b}$ is $-L^A-Cy^1-(L^B)_{t1}-Cy^3$, and the other is selected from H, $C_{1-4}$ alkyl, and $C_{1-4}$ haloalkyl.

In some embodiments, $R^{3a}$ and $R^{3b}$ are independently selected from H, halo, $C_{1-6}$ alkyl, $C_{2-6}$ alkenyl, $C_{2-6}$ alkynyl, and $C_{1-6}$ haloalkyl.

In some embodiments, $R^{3a}$ and $R^{3b}$ are independently selected from H, halo, and $C_{1-6}$ alkyl.

In some embodiments, $R^{3a}$ and $R^{3b}$ are independently selected from H and $C_{1-4}$ alkyl. In some further embodiments, $R^{3a}$ and $R^{3b}$ are independently selected from H and methyl. In yet further embodiments, $R^{3a}$ or $R^{3b}$ is methyl.

In some embodiments, one of $R^{3a}$ and $R^{3b}$ is selected from aryl, heteroaryl, cycloalkyl, and heterocycloalkyl.

In some embodiments, $R^{3a}$ and $R^{3b}$ are independently selected from aryl, heteroaryl, cycloalkyl, and heterocycloalkyl.

In some embodiments, $R^{3b}$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, $C(O)OR^{a4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$; and $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, $R^{3b}$ is heteroaryl that is optionally substituted with 1, 2, 3, 4, or 5 substituents independently selected from aryl, cycloalkyl, and heterocycloalkyl, each optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, and $SR^{a6}$.

In some embodiments, $R^{3b}$ is thiazolyl that is optionally substituted with phenyl, wherein said phenyl is optionally substituted with 1, 2, 3, 4, or 5 substituents independently selected from OH and halo.

In some embodiments, m and q are both 0.
In some embodiments, m is 0.
In some embodiments, q is 0.
In some embodiments, m is 1.
In some embodiments, q is 1.
In some embodiments, p is 1.
In some embodiments, r is 1.
In some embodiments, p is 0.
In some embodiments, r is 0.
In some embodiments, L is $-(C_{1-18}$ alkylene)- optionally substituted by 1, 2, 3, 4, or 5 $R^{L1}$. In some further embodiments, each $R^{L1}$ is independent selected from halo, OH, and CN. In yet further embodiments, each $R^{L1}$ is independent halo.

In some embodiments, L is $C_{1-6}$ alkylene optionally substituted by 1, 2, 3, 4, or 5 $R^{L1}$. In some further embodiments, each $R^{L1}$ is independent selected from halo, OH, and CN. In yet further embodiments, each $R^{L1}$ is independent halo.

In some embodiments, L is —($C_{1-18}$ alkylene)-. In some further embodiments, L is $C_{1-6}$ alkylene.

In some embodiments, $R^1$ is H, $C_{1-10}$ alkyl, or Cy, wherein said $C_{1-10}$ alkyl is optionally substituted with 1, 2, 3, 4, or 5 $R^{L2}$.

In some embodiments, $R^1$ is H, $C_{1-10}$ alkyl optionally substituted with 1, 2, 3, 4, or 5 $R^{L2}$.

In some embodiments, $R^1$ is H or $C_{1-3}$ alkyl, wherein said $C_{1-3}$ alkyl is optionally substituted with 1, 2, 3, 4, or 5 $R^{L2}$. In some further embodiments, $R^{L2}$ is, at each occurrence, independently selected from halo, CN, $NO_2$, and $OR^{a2}$. In yet further embodiments, each $R^{L2}$ is independent halo.

In some embodiments, $R^1$ is H or $C_{1-10}$ alkyl.

In some embodiments, $R^1$ is Cy.

In some embodiments, -L-$R^1$ is $C_{1-10}$ alkyl.

In some embodiments, -L-$R^1$ is $C_{1-7}$ alkyl optionally substituted with 1, 2, 3, 4 or 5 halo. In some embodiments, -L-$R^1$ is $C_{3-7}$ alkyl optionally substituted with 1, 2, 3, 4 or 5 halo. In some embodiments, -L-$R^1$ is $C_{2-6}$ alkyl optionally substituted with 1, 2, 3, 4 or 5 halo. In some embodiments, -L-$R^1$ is $C_{2-6}$ alkyl. In some embodiments, -L-$R^1$ is $C_{3-7}$ alkyl.

In some embodiments, -L-$R^1$ is $C_{4-7}$ alkyl optionally substituted with 1, 2, 3, 4 or 5 halo.

In some embodiments, -L-$R^1$ is butyl or pentyl.

In some embodiments, $R^2$ is halo, cyano, $C_1$ haloalkyl, Z, $SR^A$, or a moiety having the formula:

In some embodiments, $R^2$ is halo, cyano, $C_1$ haloalkyl, Z, or, $SR^A$.

In some embodiments, $R^2$ is halo, cyano, $C_1$ haloalkyl, or a moiety having the formula:

In some embodiments, $R^2$ is halo, cyano, or $C_{1-3}$ haloalkyl.

In some embodiments, $R^2$ is halo or $C_{1-3}$ haloalkyl.

In some embodiments, $R^2$ is Cl, Br, or $CF_3$.

In some embodiments, $R^2$ is $C_{1-3}$ haloalkyl. In some further embodiments, $R^2$ is $CF_3$ or $CF_2CF_3$. In yet further embodiments, $R^2$ is $CF_3$. In some other embodiments, $R^2$ is $CF_2CF_3$.

In some embodiments, $R^2$ is $C_1$ haloalkyl.

In some embodiments, $R^2$ is halo. In some further embodiments, $R^2$ is Cl or Br.

In some embodiments, $R^2$ is Br.

In some embodiments, $R^2$ is Cl.

In some embodiments, $R^2$ is $CF_3$.

In some embodiments, $R^2$ is a moiety having the formula:
In some embodiments, $R^2$ is S-Me.

In some embodiments, $R^2$ is selected from aryl, heteroaryl, cycloalkyl, and heterocycloalkyl, each optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, and $OR^{a4}$.

In some embodiments, $R^{2a}$ is H (i.e., $R^2$ is acetylenyl).

In some embodiments, $R^{4a}$, $R^{4b}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, and $C_{1-6}$ cyanoalkyl.

In some embodiments, $R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, and $OR^{a2}$.

In some embodiments, Cy is aryl optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is aryl.

In some embodiments, Cy is heteroaryl optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is heteroaryl.

In some embodiments, Cy is cycloalkyl optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is cycloalkyl.

In some embodiments, Cy is heterocycloalkyl optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, Cy is heterocycloalkyl.

In some embodiments, $Cy^1$ and $Cy^2$ are independently selected from aryl, heteroaryl, cycloalkyl, and heterocycloalkyl, each optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, and $S(O)_2NR^{c4}R^{d4}$.

In some embodiments, $Cy^1$ is selected from aryl, heteroaryl, cycloalkyl, and heterocycloalkyl, each optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, and $C_{2-4}$ alkynyl are optionally substituted by 1, 2, or 3 substituents independently selected from halo, $OR^{a4}$ and $Cy^3$.

In some embodiments, $Cy^1$ is selected from aryl, heteroaryl, cycloalkyl, and heterocycloalkyl, each optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, and $C_{2-4}$ alkynyl are optionally substituted by 1, 2, or 3 substituents independently selected from $OR^{a4}$ and $Cy^3$.

In some embodiments, $Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$.

In some embodiments, $Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from $OR^{a4}$ and $Cy^3$.

In some embodiments, $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, $Cy^3$ is selected from aryl or heteroaryl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, OH, —O—($C_{1-4}$ alkyl) and —O—($C_{1-4}$ haloalkyl).

In some embodiments, $Cy^3$ is selected from aryl or heteroaryl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $NH_2$, —NH($C_{1-4}$ alkyl), —N($C_{1-4}$ alkyl)$_2$, OH, —O—($C_{1-4}$ alkyl) and —O—($C_{1-4}$ haloalkyl).

In some embodiments, the compounds of the invention have Formula II:

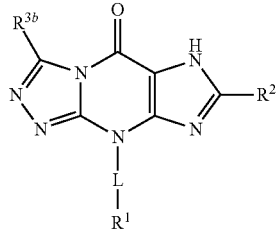

II wherein constituent members are provided herein.

In some embodiments, the compounds of the invention have Formula II, wherein -L-$R^1$ is $C_{1-7}$ alkyl optionally substituted with 1, 2, 3, 4 or 5 halo. In some further embodiments, -L-$R^1$ is $C_{2-7}$ alkyl optionally substituted with 1, 2, 3, 4 or 5 halo. In some further embodiments, -L-$R^1$ is $C_{3-6}$ alkyl optionally substituted with 1, 2, 3, 4 or 5 halo. In some further embodiments, -L-$R^1$ is $C_{3-6}$ alkyl. In some further embodiments, -L-$R^1$ is butyl or pentyl.

In some embodiments, the compounds of the invention have Formula II, wherein $R^2$ is halo. In some further embodiments, $R^2$ is Cl or Br. In yet further embodiments, $R^2$ is Br. In other further embodiments, $R^2$ is Cl.

In some embodiments, the compounds of the invention have Formula II, wherein $R^{3b}$ is selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, $S(O)R^b$, $S(O)_2R^b$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, the compounds of the invention have Formula II, wherein $R^{3b}$ is selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, $S(O)R^b$, $S(O)_2R^b$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, the compounds of the invention have Formula II, wherein $R^{3b}$ is selected from H, $C_{1-6}$ alkyl, $C_{1-6}$ haloalkyl, $Cy^1$, $OR^a$, $SR^a$, $S(O)R^b$, $S(O)_2R^b$, and $NR^cR^d$, wherein said $C_{1-6}$ alkyl is optionally substituted with 1, 2, or 3 substitutents independently selected from $Cy^1$, $C(O)NR^cR^d$, $C(O)OR^a$, halo, $OR^a$, $NR^cR^d$, $NR^cC(O)NR^cR^d$, and $NR^cC(O)R^b$. In some further embodiments, $R^{3b}$ is $C_{1-3}$ alkyl. In yet further embodiments, $R^{3b}$ is methyl.

In some embodiments, the compounds of the invention have Formula II, wherein:

$R^{3b}$ is $Cy^1$;

$Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^{c4}R^{d4}$, $C(O)OR^{a4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$; and $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, the compounds of the invention have Formula II, wherein $R^{3b}$ is $C_{1-6}$ alkyl or $C_{1-6}$ haloalkyl, wherein said $C_{1-6}$ alkyl is optionally substituted with 1, 2, or 3 substituents independently selected from $C(O)NR^cR^d$, $C(O)OR^a$, $NR^cR^d$, $NR^cC(O)NR^cR^d$, and $NR^cC(O)R^b$.

In some embodiments, the compounds of the invention have Formula II, wherein:

$R^{3b}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;

$Cy^1$ is selected from aryl, heteroaryl, cycloalkyl, and heterocycloalkyl, each substituted with 1 or 2 $R^7$ and optionally substituted by 1, 2, or 3 $R^8$;

$R^7$ is, at each occurrence, independently selected from $Cy^3$ and $C_{1-4}$ alkyl, wherein said $C_{1-4}$ alkyl is substituted with 1 or 2 $Cy^3$ and optionally substituted with 1 or 2 substituents independently selected from halo and $OR^{a4}$;

$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, the compounds of the invention have Formula II, wherein:

L is $C_{1-6}$ alkylene;

$R^1$ is H or $C_{1-3}$ alkyl, wherein said $C_{1-3}$ alkyl is optionally substituted with 1, 2, 3, 4, or 5 $R^{L2}$; and $R^{L2}$ is, at each occurrence, independently selected from halo, CN, $NO_2$, and $OR^{a2}$.

In some embodiments, the compounds of the invention have Formula II, wherein $R^2$ is halo or $C_{1-3}$ haloalkyl.

In some embodiments, the compounds of the invention have Formula II, wherein $R^2$ is Br.

In some embodiments, the compounds of the invention have Formula II, wherein:

L is $C_{1-18}$ alkylene;

$R^{3b}$ is H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, or $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, halo, ORE, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$; and $R^2$ is halo, cyano, $C_1$ haloalkyl, Z, $SR^A$, or a moiety having the formula:

—$R^{2a}$.

In some embodiments, the compounds of the invention have Formula II, wherein:

L is $C_{1-18}$ alkylene;

$R^{3b}$ is H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, or $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$; and $R^2$ is halo, cyano, $C_1$ haloalkyl, Z, $SR^A$, or a moiety having the formula:

—$R^{2a}$.

In some embodiments, the compounds of the invention have Formula II, wherein:

L is $C_{1-18}$ alkylene;

$R^{3b}$ is H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^E$, or $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, halo, ORE, $C(O)NR^cR^d$, $C(O)OR^a$, and $NR^cC(O)R^b$; and $R^2$ is halo, cyano, $C_1$ haloalkyl, Z, $SR^A$, or a moiety having the formula:

—$R^{2a}$.

In some embodiments, the compounds of the invention have Formula II, wherein:

L is $C_{1-18}$ alkylene;

$R^{3b}$ is heteroaryl that is optionally substituted with 1, 2, 3, 4, or 5 substituents independently selected from aryl, cycloalkyl, and heterocycloalkyl, wherein said aryl, cycloalkyl, or heterocycloalkyl is optionally substituted by 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, and $R^2$ is halo, cyano, $C_1$ haloalkyl, Z, $SR^A$, or a moiety having the formula:

—$R^{2a}$.

In some embodiments, the compounds of the invention have Formula II, wherein:

L is $C_{1-18}$ alkylene;

$R^{3b}$ is thiazolyl that is optionally substituted with phenyl, wherein said phenyl is optionally substituted with 1, 2, 3, 4, or 5 substituents independently selected from OH and halo and $R^2$ is halo, cyano, $C_1$ haloalkyl, Z, $SR^A$, or a moiety having the formula:

—$R^{2a}$.

In some embodiments, the compounds of the invention have Formula II, wherein:

L is $C_{1-18}$ alkylene;

$R^{3b}$ is H, halo, $C_{1-6}$ alkyl, $C_{2-6}$ alkenyl, $C_{2-6}$ alkynyl, or $C_{1-6}$ haloalkyl; and $R^2$ is halo, cyano, or $C_1$ haloalkyl.

In some embodiments, the compounds of the invention have Formula II, wherein:

$R^{3b}$ is $C_{1-6}$ alkyl, $C_{1-6}$ haloalkyl, or $Cy^1$, wherein said $C_{1-6}$ alkyl is optionally substituted with 1, 2, or 3 substituents independently selected from $Cy^1$, $C(O)NR^cR^d$, $C(O)OR^a$, halo, $OR^a$, $SR^a$, $NR^cR^d$, $NR^cC(O)NR^cR^d$, and $NR^cC(O)R^b$;

L is $C_{1-6}$ alkylene optionally substituted with 1, 2, 3, 4, or 5 $R^{L1}$;

$R^1$ is H or $C_{1-3}$ alkyl, wherein said $C_{1-3}$ alkyl is optionally substituted with 1, 2, 3, 4, or 5 $R^{L2}$;

$R^{L1}$ and $R^{L2}$ are, at each occurrence, independently selected from halo, CN, $NO_2$, and $OR^{E2}$; and $R^2$ is halo or $C_{1-3}$ haloalkyl.

In some embodiments, the compounds of the invention have Formula II, wherein -L-$R^1$ is $C_{1-7}$ alkyl optionally substituted with 1, 2, 3, 4 or 5 halo; and $R^2$ is halo. In some further embodiments, -L-$R^1$ is $C_{2-7}$ alkyl optionally substituted with 1, 2, 3, 4 or 5 halo. In some further embodiments, $R^2$ is Br or Cl. In further embodiments, $R^2$ is Br.

In some embodiments, the compounds of the invention have Formula II, wherein -L-$R^1$ is $C_{3-7}$ alkyl optionally substituted with 1, 2, 3, 4 or 5 halo; and $R^2$ is halo. In some further embodiments, -L-$R^1$ is $C_{4-7}$ alkyl optionally substituted with 1, 2, 3, 4 or 5 halo. In yet further embodiments, -L-$R^1$ is butyl or pentyl.

In some embodiments, the novel compounds of Formula II have Formula IIa:

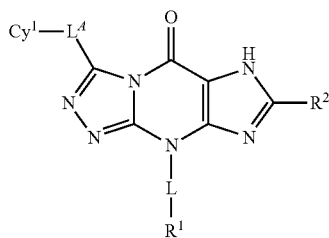

wherein $L^A$ is $C_{1-3}$ alkylene optionally substituted with 1 or 2 substitutents independently selected from halo, $OR^a$, and $SR^a$; and wherein $Cy^1$, $L$, $R^1$, and $R^2$ are defined as the same as hereinabove.

In some embodiments, the compounds of the invention have Formula IIa, wherein -L-$R^1$ is $C_{1-7}$ alkyl optionally substituted with 1, 2, 3, 4 or 5 halo. In some further embodiments, -L-$R^1$ is $C_{2-7}$ alkyl optionally substituted with 1, 2, 3, 4 or 5 halo. In some embodiments, -L-$R^1$ is $C_{3-6}$ alkyl optionally substituted with 1, 2, 3, 4 or 5 halo. In some further embodiments, -L-$R^1$ is $C_{3-6}$ alkyl.

In some embodiments, the compounds of the invention have Formula IIa, wherein -L-$R^1$ is $C_{3-7}$ alkyl optionally substituted with 1, 2, 3, 4 or 5 halo. In some further embodiments, -L-$R^1$ is $C_{4-7}$ alkyl optionally substituted with 1, 2, 3, 4 or 5 halo. In yet embodiments, -L-$R^1$ is butyl or pentyl.

In some embodiments, the compounds of the invention have Formula IIa, wherein $R^2$ is halo or $C_{1-3}$ haloalkyl. In some further embodiments, $R^2$ is halo. In yet further embodiments, $R^2$ is Br.

In some embodiments, the compounds of the invention have Formula IIa, wherein $Cy^1$ is optionally substituted 1,2,4-oxadiazolyl. In some embodiments, the 1,2,4-oxadiazolyl of $Cy^1$ is optionally substituted by 1, 2, or 3 substituents independently selected from $Cy^3$, halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$.

In some embodiments, the novel compounds of Formula II have Formula IIb:

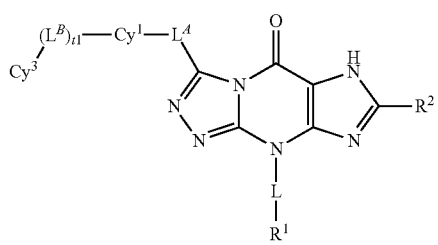

wherein:
$L^A$ is $C_{1-3}$ alkylene optionally substituted with 1 or 2 substitutents independently selected from halo, $ORE$, and $SR^a$;
$L^B$ is $C_{1-4}$ alkylene optionally substituted with 1 or 2 substitutents independently selected from halo and $OR^{a4}$;
t1 is 0 or 1; and
$Cy^1$, $Cy^3$, $L$, $R^1$, and $R^2$ are defined as the same as hereinabove.

In some embodiments, the compounds of the invention have Formula IIb, wherein -L-$R^1$ is $C_{1-7}$ alkyl optionally substituted with 1, 2, 3, 4 or 5 halo. In some further embodiments, -L-$R^1$ is $C_{2-7}$ alkyl optionally substituted with 1, 2, 3, 4 or 5 halo. In some further embodiments, -L-$R^1$ is $C_{3-6}$ alkyl optionally substituted with 1, 2, 3, 4 or 5 halo. In some further embodiments, -L-$R^1$ is $C_{3-6}$ alkyl.

In some embodiments, the compounds of the invention have Formula IIb, wherein -L-$R^1$ is $C_{3-7}$ alkyl optionally substituted with 1, 2, 3, 4 or 5 halo. In some further embodiments, -L-$R^1$ is $C_{4-7}$ alkyl optionally substituted with 1, 2, 3, 4 or 5 halo. In yet embodiments, -L-$R^1$ is butyl or pentyl.

In some embodiments, the compounds of the invention have Formula IIb, wherein $R^2$ is halo or $C_{1-3}$ haloalkyl. In some further embodiments, $R^2$ is halo. In some further embodiments, $R^2$ is Cl or Br. In yet further embodiments, $R^2$ is Br.

In some embodiments, the compounds of the invention have Formula IIb, wherein $Cy^1$ is 1,2,4-oxadiazolyl.

In some embodiments, the compounds of the invention have Formula IIb, wherein $L^A$ is $C_{1-3}$ alkylene optionally substituted with 1 or 2 substituents independently selected from halo and OH. In some further embodiments, $L^A$ is $C_{2-3}$ alkylene optionally substituted with OH. In yet further embodiments, $L^A$ is $C_{2-3}$ alkylene.

In some embodiments, the compounds of the invention have Formula IIb, wherein $L^A$ is $C_{1-3}$ alkylene optionally substituted with 1 or 2 substituents independently selected from halo and OH. In some further embodiments, $L^A$ is $C_{2-3}$ alkylene optionally substituted with 1 or 2 halo. In yet further embodiments, $L^A$ is $C_{2-3}$ alkylene optionally substituted with halo.

In some embodiments, the compounds of the invention have Formula IIb, wherein t1 is 0. In some embodiments, the compounds of the invention have Formula IIb, wherein t1 is 1.

In some embodiments, the compounds of the invention have Formula IIb, wherein t1 is 0.

In some embodiments, the compounds of the invention have Formula IIb, wherein $L^B$ is $C_{1-4}$ alkylene optionally substituted with 1 or 2 substituents independently selected from halo and OH. In some further embodiments, $L^B$ is $C_{1-3}$ alkylene optionally substituted with OH.

In some embodiments, the compounds of the invention have Formula IIb, wherein $L^B$ is $C_{1-4}$ alkylene optionally substituted with 1 or 2 halo. In some further embodiments, $L^B$ is $C_{1-3}$ alkylene optionally substituted with halo. In some further embodiments, $L^B$ is $C_{1-3}$ alkylene.

In some embodiments, the compounds of the invention have Formula IIb, wherein $Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, $NR^{c6}R^{d6}$, and $OR^{a6}$.

In some embodiments, the compounds of the invention have Formula IIb, wherein $Cy^3$ is selected from aryl and heteroaryl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, $NR^{c6}R^{d6}$, and $OR^{a6}$. In some further embodiments, $Cy^3$ is selected from aryl and heteroaryl, each substituted by OH and optionally substituted with 1, 2, or 3 substituents selected from halo, $C_{1-4}$ alkyl, $C_{2-4}$ alkenyl, $C_{2-4}$ alkynyl, $C_{1-4}$ haloalkyl, aryl, heteroaryl, $NR^{c6}R^{d6}$, and $OR^{a6}$.

In some embodiments, the compounds of the invention have Formula III:

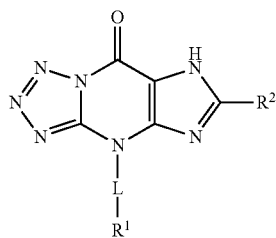

wherein constituent members are provided herein. In some further embodiments, $R^2$ is halo or $C_{1-3}$ haloalkyl. In yet further embodiments, $R^2$ is halo. In still further embodiments, $R^2$ is Br.

In some embodiments, the compounds of the invention have Formula III, wherein $R^2$ is halo. In some further embodiments, $R^2$ is Cl or Br. In yet further embodiments, $R^2$ is Br. In other further embodiments, $R^2$ is Cl.

In some embodiments, the compounds of the invention have Formula III, wherein -L-$R^1$ is $C_{1-7}$ alkyl optionally substituted with 1, 2, 3, 4 or 5 halo. In some further embodiments, -L-$R^1$ is $C_{2-7}$ alkyl optionally substituted with 1, 2, 3, 4 or 5 halo. In some further embodiments, -L-$R^1$ is $C_{3-6}$ alkyl optionally substituted with 1, 2, 3, 4 or 5 halo. In some further embodiments, -L-R" is $C_{3-6}$ alkyl.

In some embodiments, the compounds of the invention have Formula III, wherein -L-$R^1$ is $C_{3-7}$ alkyl optionally substituted with 1, 2, 3, 4 or 5 halo. In some further embodiments, -L-$R^1$ is $C_{4-7}$ alkyl optionally substituted with 1, 2, 3, 4 or 5 halo. In yet embodiments, -L-$R^1$ is butyl or pentyl.

In some embodiments, the compounds of the invention have Formula IV:

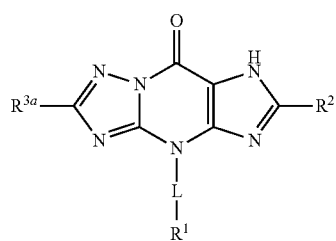

wherein constituent members are provided herein. In some further embodiments, $R^2$ is halo or $C_{1-3}$ haloalkyl. In yet further embodiments, $R^2$ is halo. In still further embodiments, $R^2$ is Br or Cl. In further embodiments, $R^2$ is Br. In other further embodiments, $R^2$ is Cl.

In some embodiments, the compounds of the invention have Formula IV, wherein -L-$R^1$ is $C_{1-7}$ alkyl optionally substituted with 1, 2, 3, 4 or 5 halo. In some further embodiments, -L-$R^1$ is $C_{2-7}$ alkyl optionally substituted with 1, 2, 3, 4 or 5 halo. In some further embodiments, -L-$R^1$ is $C_{3-6}$ alkyl optionally substituted with 1, 2, 3, 4 or 5 halo. In some further embodiments, -L-$R^1$ is $C_{3-6}$ alkyl.

In some embodiments, the compounds of the invention have Formula IV, wherein -L-$R^1$ is $C_{3-7}$ alkyl optionally substituted with 1, 2, 3, 4 or 5 halo. In some further embodiments, -L-$R^1$ is $C_{4-7}$ alkyl optionally substituted with 1, 2, 3, 4 or 5 halo. In yet embodiments, -L-$R^1$ is butyl or pentyl.

In some embodiments, the compounds of the invention have Formula IV, wherein $R^{3a}$ is selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $Cy^1$, $OR^a$, $SR^a$, $S(O)R^b$, $S(O)_2R^b$, and $NR^cR^d$, wherein said $C_{1-6}$ alkyl, $C_{2-6}$ alkenyl, and $C_{2-6}$ alkynyl are optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$.

In some embodiments, the compounds of the invention have Formula IV, wherein $R^{3a}$ is selected from H, $C_{1-6}$ alkyl, $C_{1-6}$ haloalkyl, $Cy^1$, $OR^a$, $SR^a$, $S(O)R^b$, $S(O)_2R^b$, and $NR^cR^d$, wherein said $C_{1-6}$ alkyl is optionally substituted with 1, 2, or 3 substituents independently selected from $Cy^1$, $C(O)NR^cR^d$, $C(O)OR^a$, halo, ORE, $NR^cR^d$, $NR^cC(O)NR^cR^d$, and $NR^cC(O)R^b$. In some further embodiments, $R^{3a}$ is selected from H and $C_{1-6}$ alkyl. In yet further embodiments, $R^{3a}$ is selected from H and methyl.

In some embodiments, the compounds of the invention have Formula IV, wherein:
$R^{3a}$ is $Cy^1$;
$Cy^1$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, $OR^{a4}$, $SR^{a4}$, $C(O)R^{b4}$, $C(O)NR^cR^{d4}$, $C(O)OR^{a4}$, and $Cy^3$, wherein said $C_{1-4}$ alkyl, $C_{2-4}$ alkenyl, and $C_{2-4}$ alkynyl are optionally substituted with 1, 2, or 3 substituents independently selected from halo, $OR^{a4}$ and $Cy^3$; and
$Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

In some embodiments, the compounds of the invention have Formula IV, wherein $R^{3a}$ is $C_{1-6}$ alkyl or $C_{1-6}$ haloalkyl, wherein said $C_{1-6}$ alkyl is optionally substituted with 1, 2, or 3 substitutents independently selected from $C(O)NR^cR^d$, $C(O)OR^a$, $NR^cR^d$, $NR^cC(O)NR^cR^d$, and $NR^cC(O)R^b$.

In some embodiments, the compounds of the invention have Formula IV, wherein $R^{3a}$:
$R^{3a}$ is selected from $C_{1-3}$ alkyl, wherein said $C_{1-3}$ alkyl is substituted with $Cy^1$ and optionally substituted with 1 or 2 substitutents independently selected from halo, $OR^a$, and $SR^a$;
$Cy^1$ is selected from aryl, heteroaryl, cycloalkyl, and heterocycloalkyl, each substituted with 1 or 2 $R^7$ and optionally substituted by 1, 2, or 3 $R^8$;
$R^7$ is, at each occurrence, independently selected from $Cy^3$ and $C_{1-4}$ alkyl, wherein said $C_{1-4}$ alkyl is substituted with 1 or 2 $Cy^3$ and optionally substituted with 1 or 2 substituents independently selected from halo and $OR^{a4}$;
$R^8$ is, at each occurrence, independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, and $C(O)OR^{a4}$; and
$Cy^3$ is selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, CN, $NO_2$, $NR^{c6}R^{d6}$, $OR^{a6}$, and $SR^{a6}$.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl (e.g., n-propyl or isopropyl), $C_4$ alkyl (e.g., n-butyl, isobutyl, t-butyl), or, $C_5$ alkyl (e.g., n-pentyl, isopentyl, or neopentyl), and $C_6$ alkyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R. In another example, when an optionally multiple substituent is designated in the form:

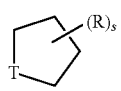

then it is understood that substituent R can occur s number of times on the ring, and R can be a different moiety at each occurrence. Further, in the above example, should the variable T be defined to include hydrogens, such as when T is said to be $CH_2$, NH, etc., any floating substituent such as R in the above example, can replace a hydrogen of the T variable as well as a hydrogen in any other non-variable component of the ring.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group. One example of alkylene is —$CH_2CH_2$—.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CH_2F$, $CHF_2$, $CF_3$, $C_2F_5$, $CCl_3$, $CHCl_2$, $CH_2CF_3$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzothiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "arylalkyl" refers to alkyl substituted by aryl and "cycloalkylalkyl" refers to alkyl substituted by cycloalkyl. One example of arylalkyl is benzyl. One example of cycloalkylalkyl is —CH$_2$CH$_2$— cyclopropyl.

As used herein, "heteroarylalkyl" refers to an alkyl group substituted by a heteroaryl group, and "heterocycloalkylalkyl" refers to alkyl substituted by heterocycloalkyl. One example of heteroarylalkyl is —CH$_2$-(pyridin-4-yl). One example of heterocycloalkylalkyl is —CH$_2$-(piperidin-3-yl).

As used herein, "halo" or "halogen" includes fluoro, chloro, bromo, and iodo.

As used herein, "hydroxyalkyl" refers to an alkyl group substituted with a hydroxyl group.

As used herein, "cyanoalkyl" refers to an alkyl group substituted with a cyano group.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, are also meant to include solvated or hydrated forms.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of Compounds can Involve the Protection and Deprotection of Various Chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques as described below.

Compounds of formula 1i and 1j can be prepared using the generally protocol described in Scheme 1. Intermediates 1c can be synthesized by reaction of thiourea 1a with a cyanoacetic acid ester such as ethyl cyanoacetate 1b in the present of a base such as sodium ethoxide to generate cyclic intermediates 1c. Nitrosation of intermediate 1c using sodium nitrite gives rise to the nitroso intermediate 1d, which can be reduced to the diamino intermediate 1e using $Na_2S_2O_4$ or a similar reducing agent. Cyclization of the diamino intermediate 1e with trifluoroacetic anhydride yields the thioxopurinone intermediate 1f. Following selective methylation on the sulfur of compound 1f, the resulting thioether intermediate 1g is subjected to a displacement with hydrazine to produce the hydrazone intermediate 1h. Treatment of the hydrazone intermediate 1h with an orthoester [such as $R^{3b}C$(O-alkyl)$_3$, e.g., $R^{3b}C(OEt)_3$] yields the cyclized triazole compounds of formula 1i. Alternatively, intermediate 1h can be treated with $NaNO_2$ to provide a cyclized tetrazole compound of formula 1j.

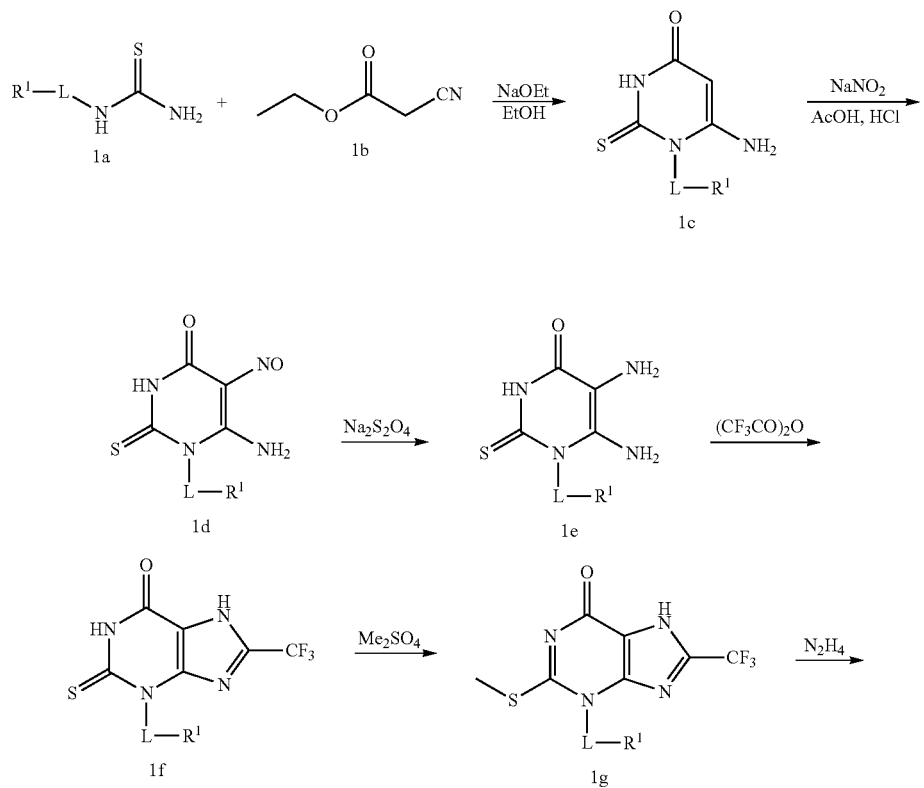

Scheme 1

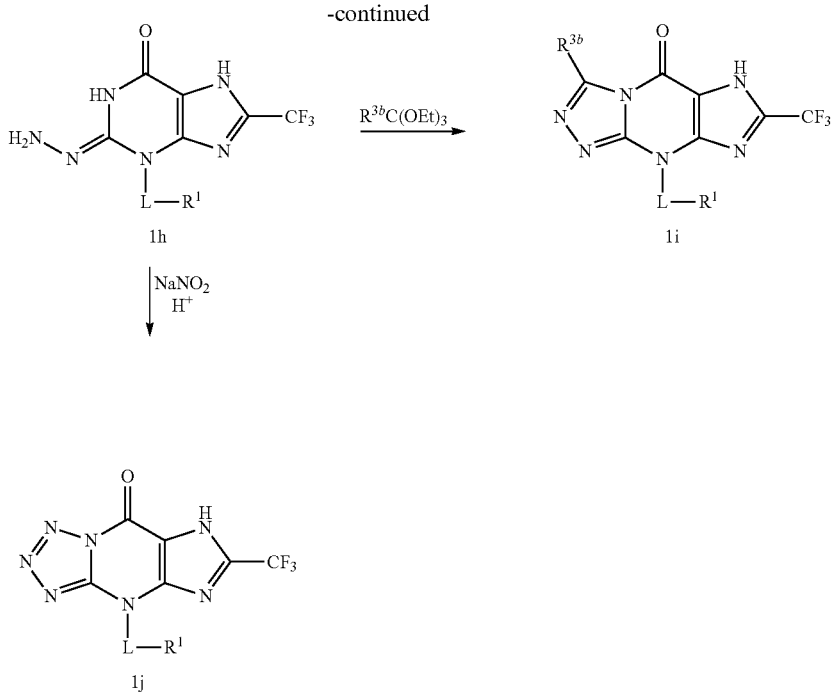

Compounds of formula 2g and 2i can be prepared using the procedures outlined in Scheme 2. Selective alkylation at the amino group of commercially available 3-amino-1H-pyrrole-2-carboxamide (2a) by reductive amination with an aldehyde $R^1L^1$-CHO [wherein $L^1$-$CH_2$ has the same definition as that of L defined hereinwith] provides the alkylated product 2b. Reaction of intermediate 2b with benzoyl isothiocyanate yields the thiourea intermediate 2c, which can be treated with a base such as aqueous NaOH to provide the cyclized thioxopurinone intermediate 2d. Treatment of intermediate 2d with aqueous hydrazine produces the hydrazone derivative 2e. Cyclization of the hydrazone intermediate 2e can be achieved by treatment with an orthoester [such as $R^{3b}C(O\text{-}alkyl)_3$, e.g., $R^{3b}C(OEt)_3$] to yield the triazole derivative 2f. Selective halogenation at the 7-position of 2f can be carried out using a halogenating reagent, for example, N-bromosuccinimide (NBS) or N-chlorosuccinimide (NCS) to provide the halo-substituted triazolopurinone derivative of formula 2g. Alternatively, the tetrazolopurinone derivatives of formula 2i can be obtained by cyclization of the intermediate 2e using $NaNO_2$ under acidic condition [such as in the presence of aqueous HCl] followed by halogenation using a halogenating reagent, for example, NBS or NCS.

Scheme 2

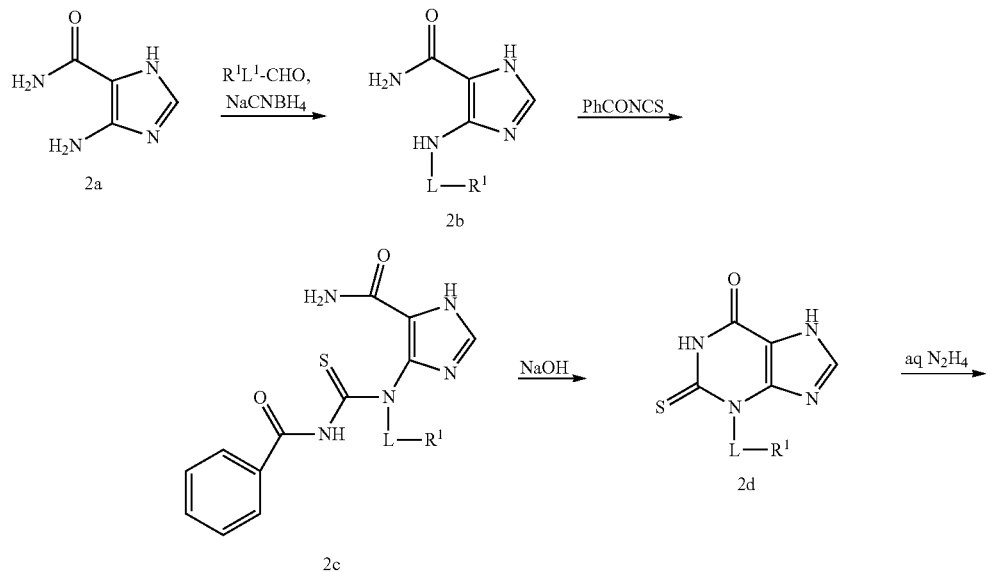

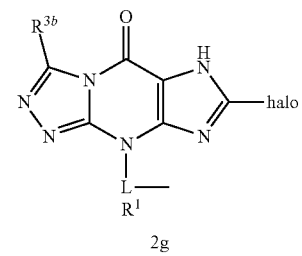

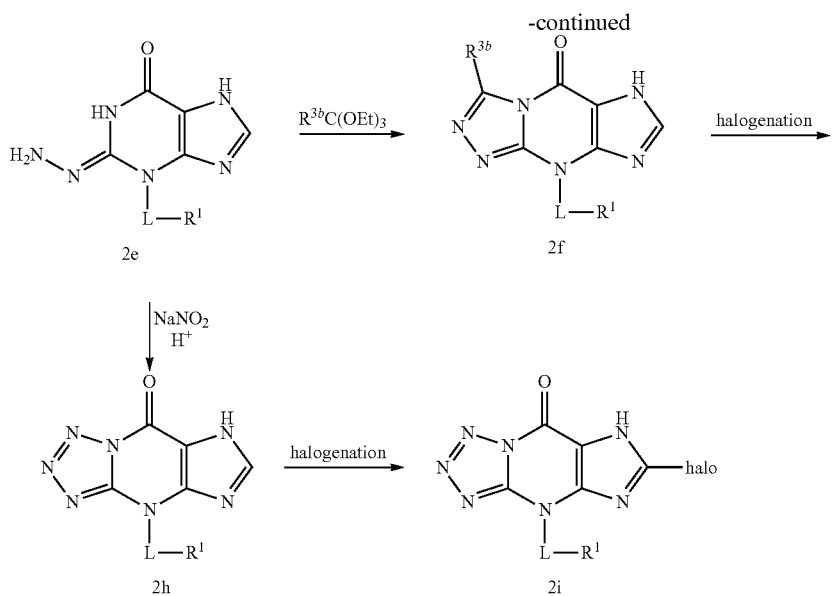

Compounds of formula 3d can be prepared using the protocol outlined in Scheme 3. Reaction of hydrazone derivative 2e with an appropriate aldehyde $R^{3b}$CHO in a suitable solvent such as an alcohol (e.g. ethanol) yields intermediate 3b. Oxidative cyclization of 3b in acetic acid (in air) provides the corresponding triazolopurine 3c. Alternatively, triazolopurine 3c can be prepared by cyclization (and condensation) of the intermediate 3f, which is derived from the amide bond formation by coupling of hydrazone 2e with acid 3e, in a suitable solvent such as acetic acid or in toluene. Selective halogenation at the 7-position of the triazolopurinone core of 3c using a halogenation reagent, for example NBS or NCS, provides the halo-substituted triazolopurinone derivative of formula 3d.

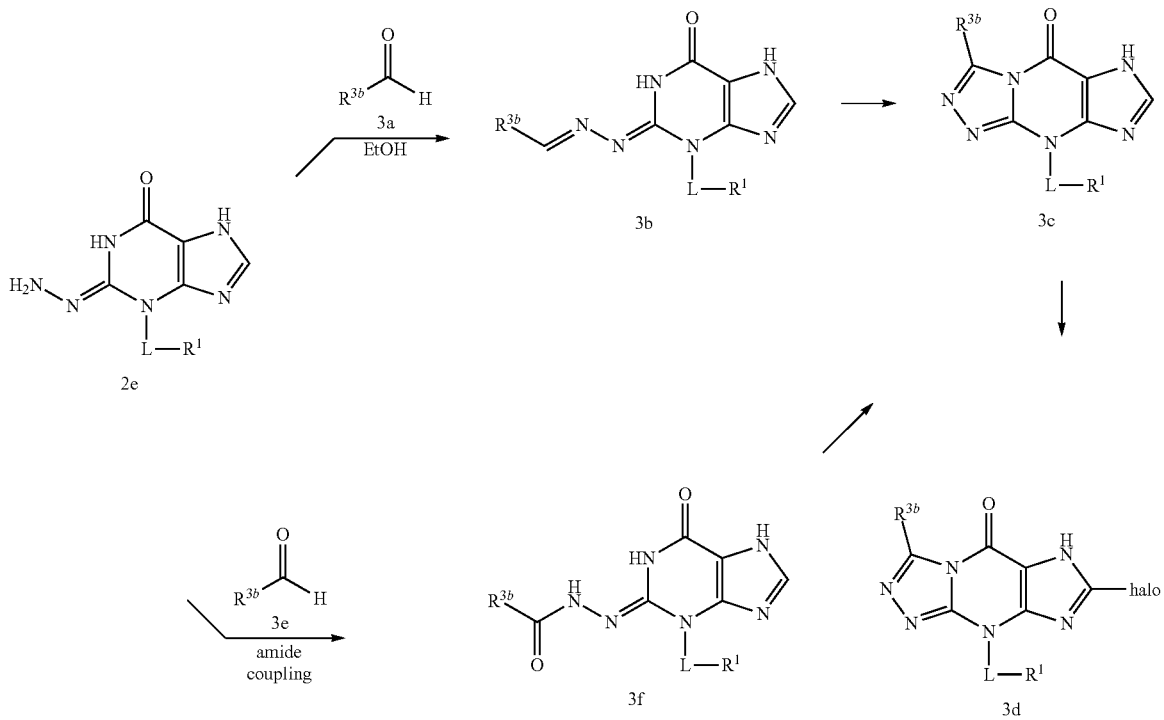

Compounds of formula 4f and 4j [wherein $R^7$ can be aryl, heteroaryl, arylakyl, heteroarylalkyl, and the like] can be prepared using the procedures described in Scheme 4. Oxidative cyclization of hydrazone 4b, which is generated from treatment of hydrazone 2e with an aldehyde 4a in a suitable solvent such as ethanol, provides the intermediate acid 4c. Reaction of acid 4c with amine 4d under amide formation condition [such as in the presence of an amide coupling reagent, for example, benzotriazolyloy-tris-(dimethylamino) phosphonium hexafluorophosphate (or BOP)] produces amide 4e, which can be treated with a halogenating reagent such as NBS or NCS to provide a halo-substituted triazolopurinone amide derivative of formula 4f. Oxadiazol intermediate 4I can be prepared by coupling of acid 4c with N-hydroxy imidamide 4g using a coupling reagent such as 1,1'-carbonyldiimidazole (CDI), followed by cyclization (and condensation). Alternatively, coupling of oxadiazol acid 4h with hydrazone 2e under suitable conditions (such as in the presence of an amid coupling reagent, for example BOP), followed by cyclization (and condensation), can also yield oxadiazole 4i. Selective halogenation at the 7-position of the triazolopurinone core of compound 4I, using a halogenating reagent such as NBS or NCS, provides the halo-substituted triazolopurinone oxadiazol derivative of formula 4j.

Scheme 4

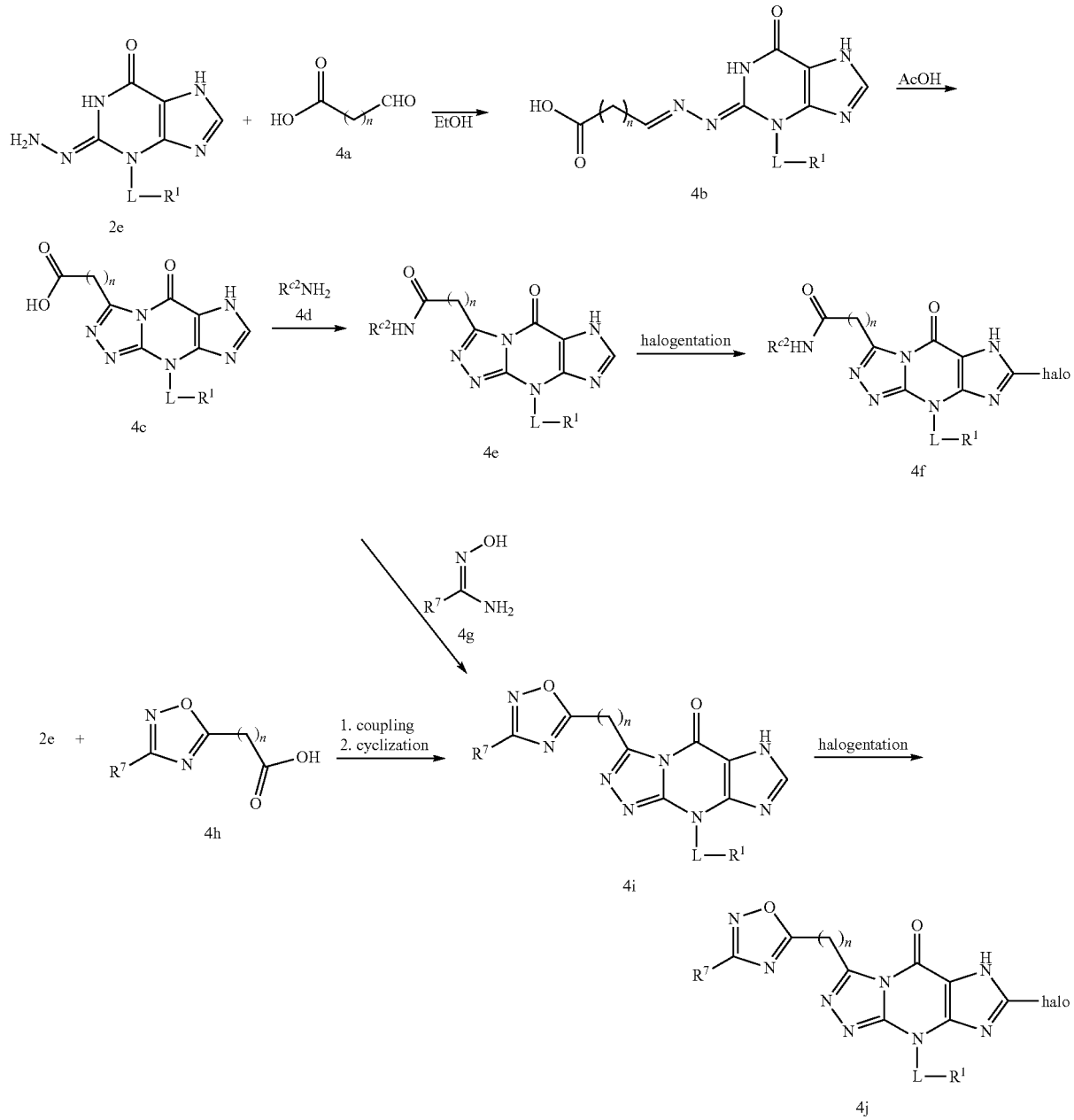

Compounds of formula 5b can be synthesized using the general procedures outlined in Scheme 5. Reaction of halide 3d with a boric acid 5a (such as those commercially available or disclosed in the literatures, wherein Z is optionally substituted aryl or optionally substituted hetaryl) under Suzuki coupling conditions can yield triazolopurinone derivatives of formula 5b.

An alternative general synthetic pathway for 5b starts with intermediate 1e. Reaction of intermediate 1e with acid 5c (wherein Z can be optionally substituted aryl, heteroaryl, cycloalkyl, or heterocycloalkyl) under amide coupling conditions (such as in the presence of an amid coupling reagent, for example BOP) provides amide 5d, which can be treated with a base such as aqueous NaOH to give thioxopurinone intermediate 5e. Treatment of intermediate 5e with aqueous hydrazine produces the hydrazone derivative 5f. Reaction of dyazone 5f with an orthoester [such as $R^{3b}C(O\text{-alkyl})_3$, e.g., $R^{3b}C(OEt)_3$] yields triazolopurinone derivative 5b.

Alternatively, halide 3d can be reacted with an alkyne 5g under Sonogashira coupling condition to afford an allyne derivative 5h. (See, e.g., Sonogashira, K. et al. *Tetrahetron Letter*, 1975, 4467; see also, Nicolaou, K. C. Et al. *Angew. Chem. Int. Engl.* 1991, 30, 1100)

Scheme 6 exemplifies the preparation of 3-substituted triazolopurinone derivatives such as those having formula 6d, 6g or 6j. Treatment of hydrazone 2e with N-(dichloromethylene)-N-methylmethananaminium chloride provide 6c, which can be treated with a halogenated reagent such as NBS or NCS to yield halo-substituted amino triazolopurinone derivative 6d. Reaction of 2e with carbon disulfide in a suitable solvent such as pyridine produces cyclic thiourea 6e. Alkylation of thiourea 6e on the sulfur atom using an appropriate alkylating agent such as dimethyl sulfate or ethyl iodide under basic condition (such as in the presence of aqueous NaOH), followed by oxidation of the resultant thioether in the presence of an oxidizing reagent such as m-chloroperbenzoic acid, affords sulfinyl intermediate 6f, which can be treated with a halogenating reagent such as NBS or NCS to provide halo-substituted sulfinyl-triazolopurinone derivative 6g. Sulfinyl intermediate 6f (or its precursor thioether) can be further oxidized to its corresponding sulfonyl counterpart, which in turn can further undergo selective halogenation.

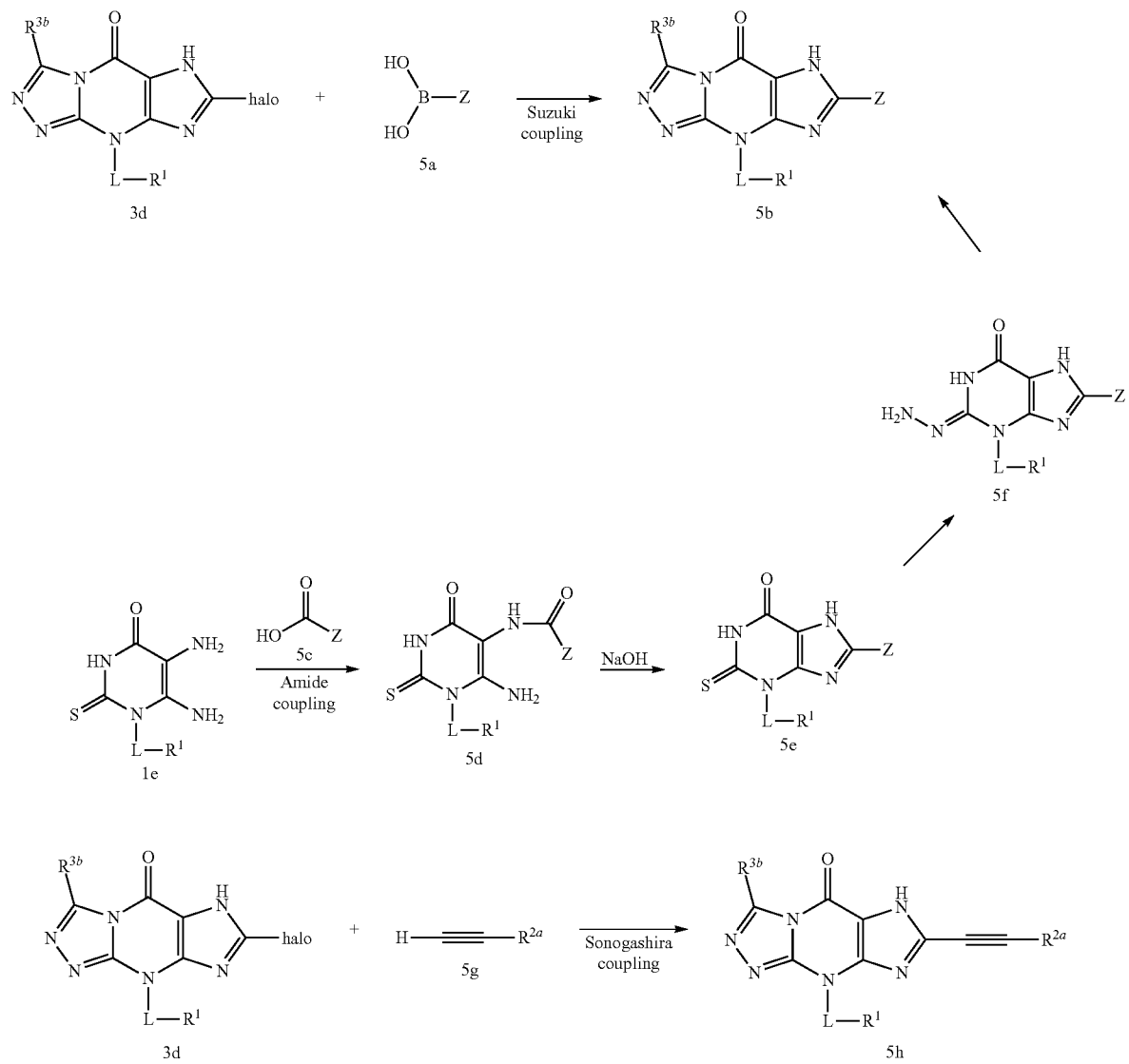

Scheme 5

Treatment of hydrazone 2e with CDI give intermediates 6h. Alkylation of intermediate 6h on the hydroxyl group (such as using alkyl halide $R^aX^1$ wherein $X^1$ is bromo), followed by halogenation with a halogenating reagent such as NBS or NCS, provides triazolopurinone derivatives of formula 6j.

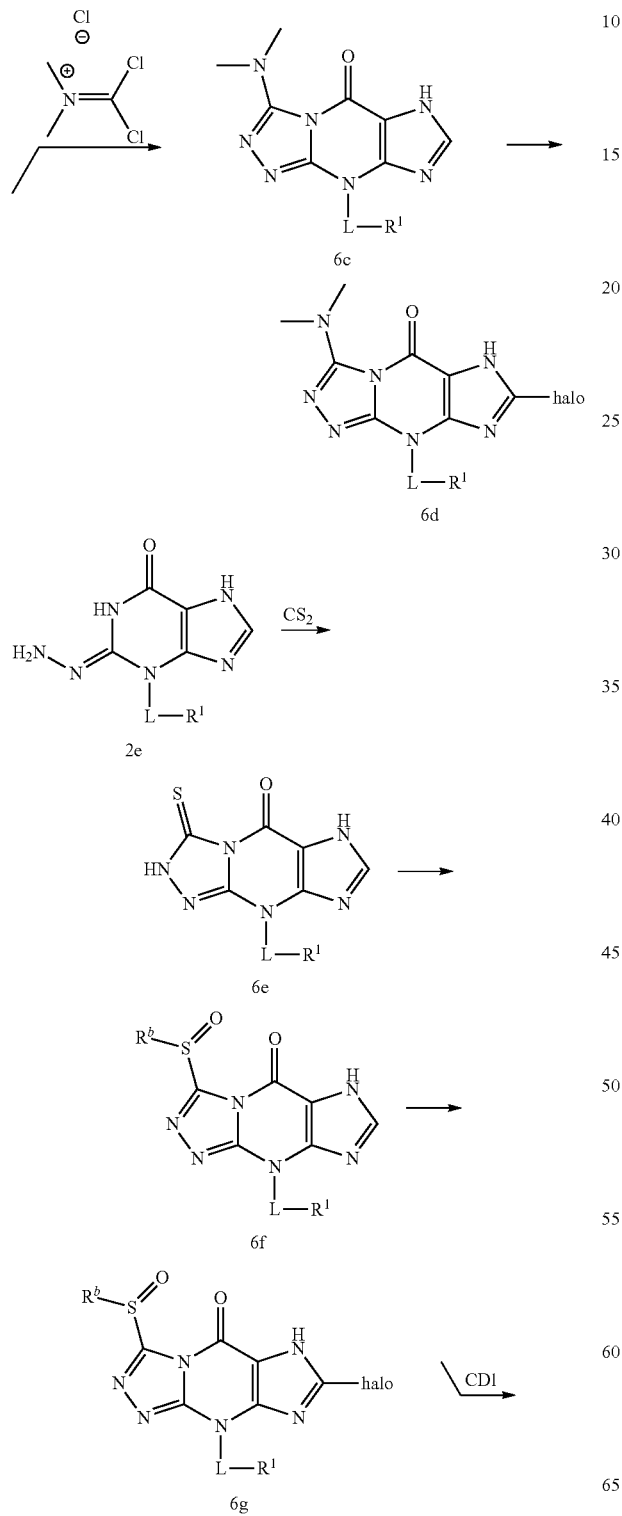

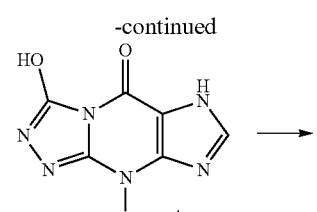

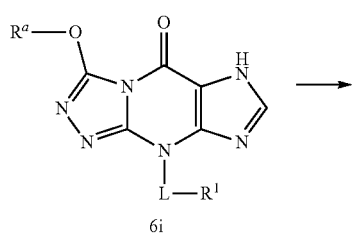

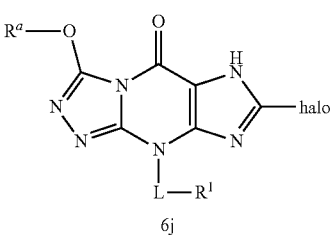

Compounds of formula 4j can be also prepared using the procedures described in Scheme 7. Reaction of hydrazone 2e with cyclic anhydride 7a (wherein n can be 1, 2 or 3) under suitable conditions (such as refluxing in dioxane) furnishes triazolopurinone acid derivative 7b. Selective halogenation at the 7-position of the triazolopurinone core of compound 7b using a halogenating reagent such as NBS or NCS provides the halo-substituted triazolopurinone derivative 7c. Coupling of acid 7c with N-hydroxy imidamide 4g [wherein $R^7$ can be aryl, heteroaryl, arylakyl, heteroarylalkyl, and the like] using a coupling reagent such as CDI, followed by cyclization (and condensation), yields halo-substituted triazolopurinone oxadiazol derivative 4j.

Scheme 7

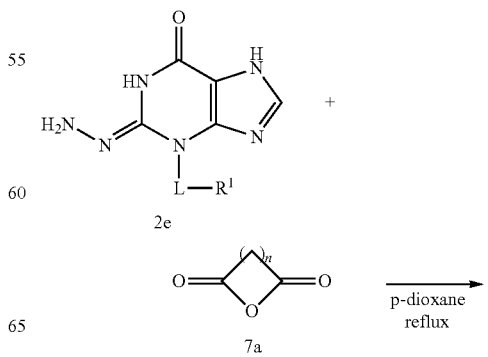

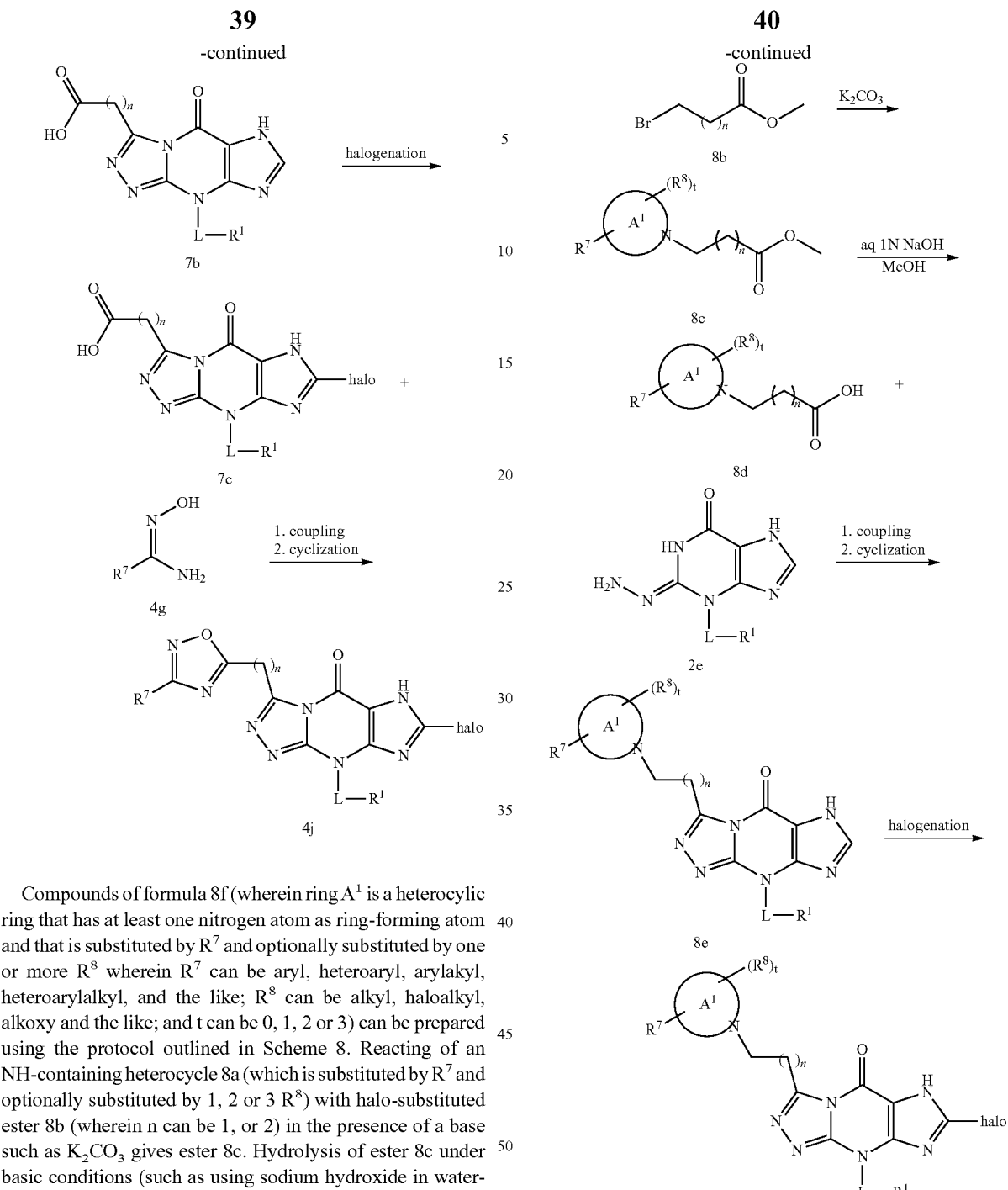

Compounds of formula 8f (wherein ring $A^1$ is a heterocylic ring that has at least one nitrogen atom as ring-forming atom and that is substituted by $R^7$ and optionally substituted by one or more $R^8$ wherein $R^7$ can be aryl, heteroaryl, arylakyl, heteroarylalkyl, and the like; $R^8$ can be alkyl, haloalkyl, alkoxy and the like; and t can be 0, 1, 2 or 3) can be prepared using the protocol outlined in Scheme 8. Reacting of an NH-containing heterocycle 8a (which is substituted by $R^7$ and optionally substituted by 1, 2 or 3 $R^8$) with halo-substituted ester 8b (wherein n can be 1, or 2) in the presence of a base such as $K_2CO_3$ gives ester 8c. Hydrolysis of ester 8c under basic conditions (such as using sodium hydroxide in water-methanol) provides acid 8d. Coupling of acid 8d with hydrazone 2e, followed by cyclization (and condensation), affords trazolopurinone derivative 8e, which is subjected to selective halogenation to yield the halo-substituted trazolopurinone derivative formula 8f.

Scheme 8

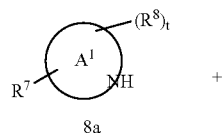

8a

Compounds of formula 9h can be prepared using the general procedures described in Scheme 9. Addition of hydroxylamine to commercially available 4,4-diethoxybutanenitrile 9a (wherein n can be 1, or 2) in methanol provide imidamide 9b. Coupling of imidamide 9b with acid 9c (wherein $R^7$ can be aryl, heteroaryl, arylakyl, heteroarylalkyl, and the like) in the presence of a coupling reagent such as CDI, followed by cyclization (and condensation), affords oxadiazole derivative 9d, which can undergo acid catalyzed ketal deprotection to furnish oxadiazole aldehyde 9e. Reaction of aldehyde 9e with hydrazone derivative 2e in a suitable solvent such as ethanol provides intermediate 9f. Oxidative cyclization of 9f (such as in acetic acid and in the presence of air) provides the corresponding triazolopurine 9g, which can be treated with a halogenating reagent NBS or NCS to yield halo-substituted triazolopurinone oxadiazol derivative 9h.

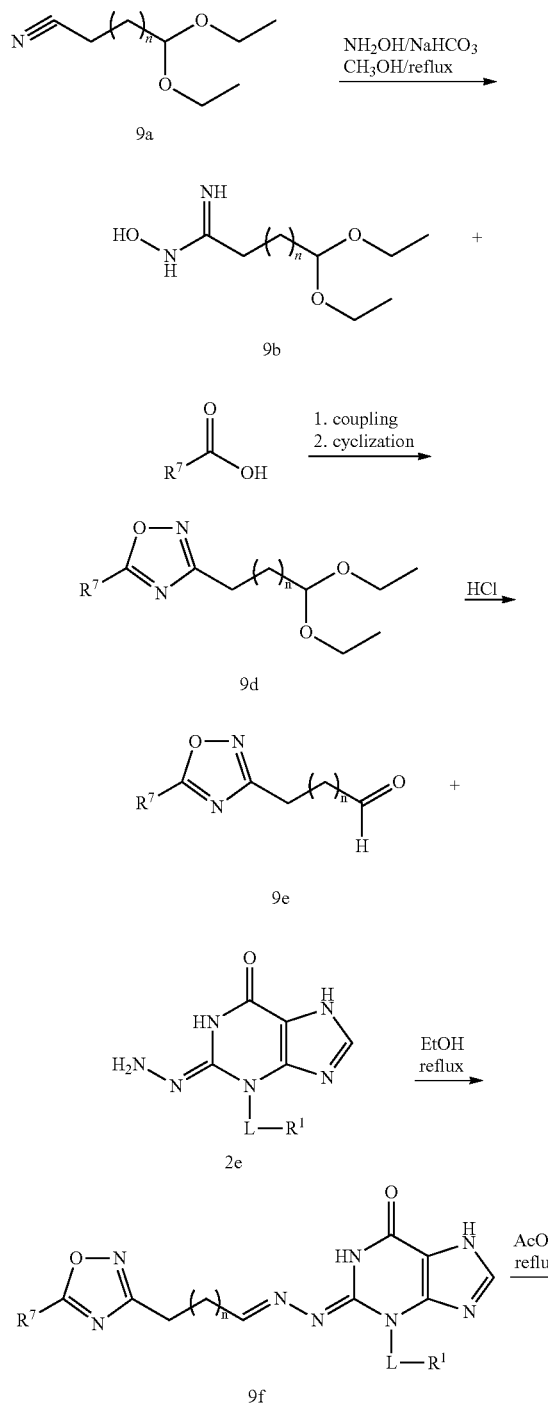

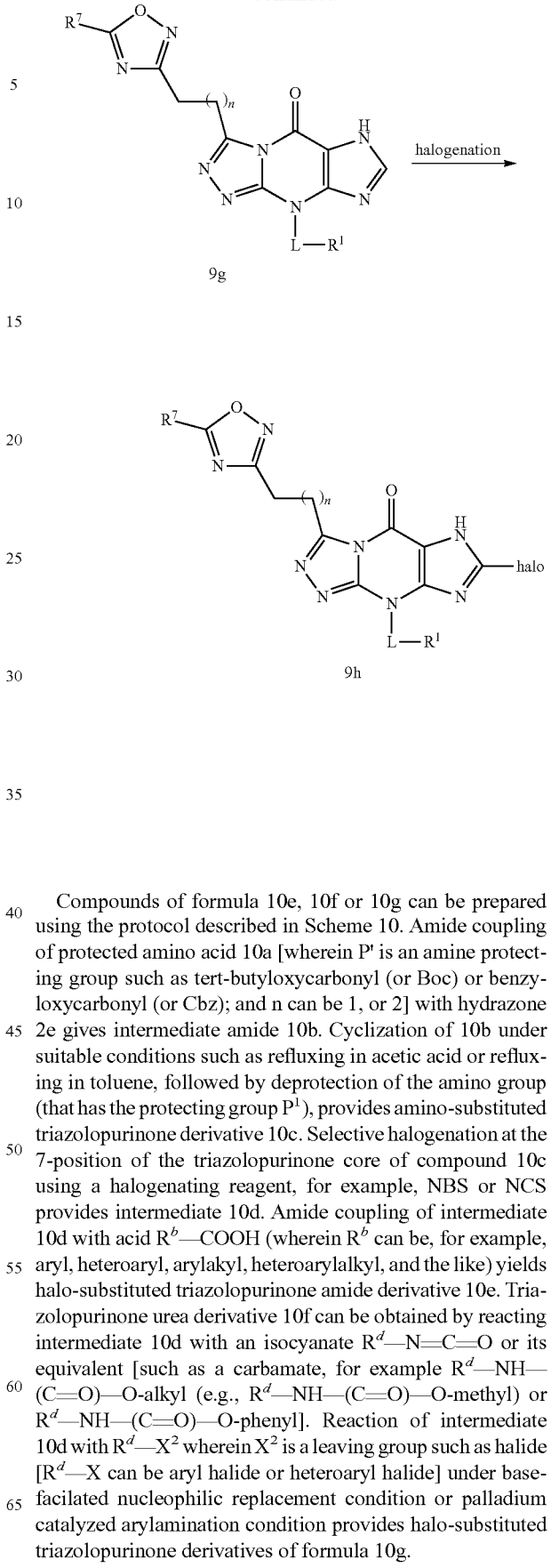

Compounds of formula 10e, 10f or 10g can be prepared using the protocol described in Scheme 10. Amide coupling of protected amino acid 10a [wherein P' is an amine protecting group such as tert-butyloxycarbonyl (or Boc) or benzyloxycarbonyl (or Cbz); and n can be 1, or 2] with hydrazone 2e gives intermediate amide 10b. Cyclization of 10b under suitable conditions such as refluxing in acetic acid or refluxing in toluene, followed by deprotection of the amino group (that has the protecting group $P^1$), provides amino-substituted triazolopurinone derivative 10c. Selective halogenation at the 7-position of the triazolopurinone core of compound 10c using a halogenating reagent, for example, NBS or NCS provides intermediate 10d. Amide coupling of intermediate 10d with acid $R^b$—COOH (wherein $R^b$ can be, for example, aryl, heteroaryl, arylakyl, heteroarylalkyl, and the like) yields halo-substituted triazolopurinone amide derivative 10e. Triazolopurinone urea derivative 10f can be obtained by reacting intermediate 10d with an isocyanate $R^d$—N=C=O or its equivalent [such as a carbamate, for example $R^d$—NH—(C=O)—O-alkyl (e.g., $R^d$—NH—(C=O)—O-methyl) or $R^d$—NH—(C=O)—O-phenyl]. Reaction of intermediate 10d with $R^d$—$X^2$ wherein $X^2$ is a leaving group such as halide [$R^d$—X can be aryl halide or heteroaryl halide] under base-facilated nucleophilic replacement condition or palladium catalyzed arylamination condition provides halo-substituted triazolopurinone derivatives of formula 10g.

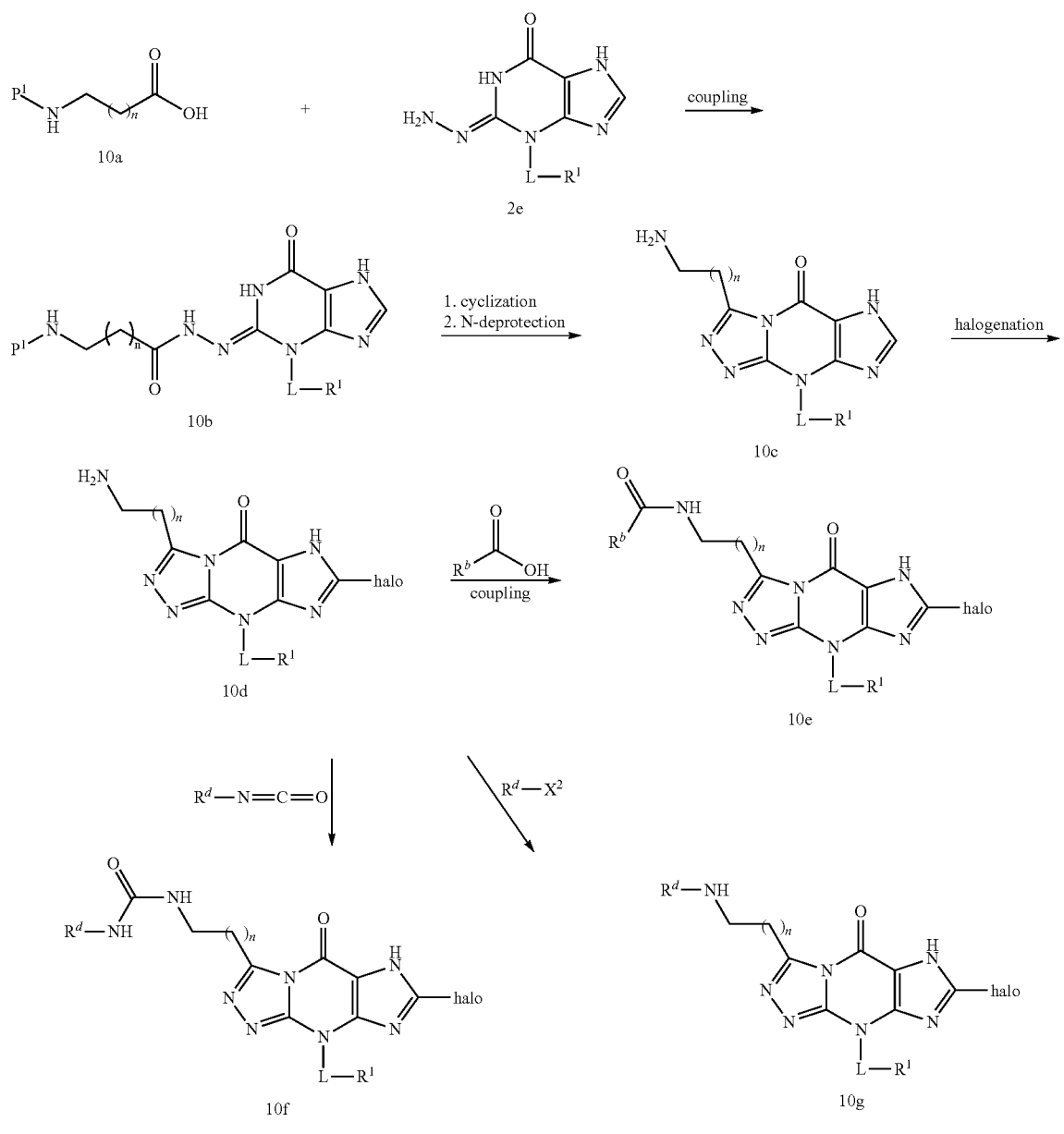

Scheme 10

Pharmaceutical Methods

Compounds of the invention can modulate activity of the HM74a receptor. The term "modulate" is meant to refer to an ability to increase or decrease activity of a receptor. Accordingly, compounds of the invention can be used in methods of modulating HM74a receptor by contacting the receptor with any one or more of the compounds or compositions described herein. In some embodiments, compounds of the present invention can act as full or partial agonists of HM74a receptors. In further embodiments, the compounds of the invention can be used to modulate activity of HM74a receptors in an individual by administering a modulating amount of a compound of the invention.

The present invention further provides methods of treating diseases associated with the HM74a receptor, such as dyslipidemia, insulin resistance, hyperglycemia, and others, in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to the HM74a receptor, such as diseases, disorders or conditions associated with low expression or low activity of HM74a receptor.

Examples of HM74a receptor-associated diseases include, but are not limited to, dyslipidemia, highly-active anti-retroviral therapy (HAART)-associated lipodystrophy, insulin resistance, diabetes such as type 2 diabetes mellitus, metabolic syndrome, atherosclerosis, coronary heart disease, stroke, obesity, elevated body mass index (BMI), elevated waist circumference, non-alcoholic fatty liver disease, hepatic steatosis, hypertension, and other pathologies, such as those (like many of the aforementioned) associated with elevated plasma FFAs.

Other diseases treatable by administration of compounds of the invention (and salts or prodrugs there) include chronic inflammatory diseases such as, for example, pancreatitis and gout.

As used herein, the term "dyslipidemia" refers to any one or more of the following diseases or conditions: low-HDL cholesterol, elevated cholesterol, elevated LDL cholesterol (including any combination of small, dense LDL, intermediate density lipoproteins, very-low density lipoproteins, and chylomicrons), elevated total cholesterol/HDL ratio, elevated plasma triglycerides, elevated circulating free fatty acid levels, and elevated lipoprotein (a).

In some embodiments, the present invention provides methods of lowering cholesterol level, lowering LDL, lowering total cholesterol/HDL ratio, lowering plasma triglycerides, lowering circulating free fatty acid levels, lowering lipoprotein (a), or raising HDL cholesterol, in a mammal by administering an effective amount of a compound or composition herein to the mammal.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the HM74a receptor with a compound of the invention includes the administration of a compound of the present invention to an individual or patient, such as a human, having the HM74a receptor, as well as, for example, introducing a compound of the invention into a sample containing a cellular or purified preparation containing the HM74a receptor.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing or retarding the pathology and/or symptomatology) such as decreasing the severity of disease.

Combination Therapies

The compounds of the present invention can be used in combination with other enzyme or receptor modulators. Examples of other enzyme or receptor modulators include, but are not limited to, any one or more of the following: steroidal and non-steroidal anti-inflammatory agents (e.g., inhibitors or prostaglandin synthesis), inhibitors of PCSK9, inhibitors of ACC1, inhibitors of ACC2, inhibitors of SCD1, inhibitors of DGAT, activators of AMPK, thyroid receptor modulators, renin inhibitors, agents that degrade or inhibit formation of advanced glycation end products, HMG-CoA reductase inhibitors (so-called statins), PPAR alpha agonists or selective modulators, PPAR gamma agonists or selective modulators (both TZD and non-TZD), PPAR delta agonists or selective modulators, PPAR alpha/gamma dual agonists, pan-PPAR agonists or selective modulators, glucocorticoid receptor antagonists or selective modulators, bile acid-binding resins, NPC1L1 receptor antagonists, cholesterol ester transfer protein inhibitors, apoA-I or synthetic apoA-VHDL molecules, LXR agonists or selective modulators, FXR agonists or selective modulators, endothelial lipase inhibitors, hepatic lipase inhibitors, SR-BI modulators, estrogen receptor agonists or selective modulators, anabolic steroid or steroid derivatives, insulin or insulin mimetics, sulfonylureas, metformin or other biguanides, DPP-IV inhibitors, PTP-1B modulators, glucose-6-phosphatase inhibitors, T1-translocase inhibitors, fructose-1,6-bisphosphatase inhibitors, glycogen phosphorylase inhibitors, glucagon receptor antagonists, 11-beta-hydroxysteroid dehydrogenase type 1 inhibitors, intestinal lipase inhibitors, neurotransmitter reuptake inhibitor, endocannabinoid receptor antagonist, NPY antagonist, MCH antagonists, MC4R agonists, GLP-1 or GLP-1 analogues (incretins), GLP-1 receptor agonists, thiazide diuretics, beta-adrenergic receptor antagonists, angiotensin II converting enzyme inhibitors, angiotensin II receptor antagonists, calcium channel antagonists, and mineralocorticoid receptor antagonists, or combinations thereof.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to fluorescent dye, spin table, heavy metal or radio-labeled compounds of the invention that would be useful not only in imaging but also in assays, both in vitro and in vivo, for localizing and quantitating HM74a in tissue samples, including human, and for identifying HM74a ligands by binding of a labeled compound. Accordingly, the present invention includes HM74a assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to HM74a. Accordingly, the ability of a test compound to compete with the radio-labeled compound for binding to HM74a directly correlates to its binding affinity.

Kits

The present invention also includes pharmaceutical kits useful, for example, in the treatment or prevention of HM74a-associated diseases or disorders. The kits can include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

The compounds of the example section were found to be agonists or partial agonists of HM74a receptor according to one or more of the assays provided herein.

EXAMPLES

General Information

All reagents and solvents were obtained from commercial sources and were used directly without further purification. LCMS analysis was performed on a Water SunFire C18 column ((2.1×50 mm, 5 μM particle size), eluting with 0.025% TFA/water and 0.025% TFA/acetonitrile using a mass spectrum scan range of 105-900 Da. Preparative LCMS purifications were performed on a Water FractionLynx system using mass directed fraction and compound-specific method optimization (J. Comb. Chem. 2004, 6, 874-883). The LC method utilized a Water SunFire column (19×100 mm, 5 μM particle size), eluting with either 0.1% TFA/water and 0.1% TFA/acetonitrile gradient at a flow rate of 30 mL/min over a total run time of 5 min NMR spectra were obtained using a Varian Mercury-300 or Mercury-400 spectrometer. Chemical shifts are reported in parts per million (ppm) relative to tetramethylsilane as an internal standard.

Example 1

Preparation of 3-methyl-9-pentyl-7-(trifluoromethyl)-6,9-dihydro-5H-[1,2,4]triazolo[4,3-a]purin-5-one

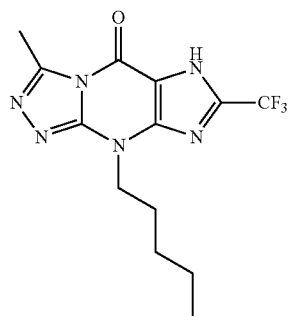 [SMILES: CCCCCn1c2nc(C(F)(F)F)[nH]c2c(=O)n2c(C)nnc12]

Step A: N-Pentylthiourea

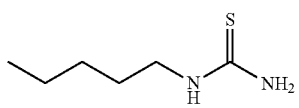

Pentylisothiocyanate (10 g, 0.08 mol) was added slowly (about 10 mins) to a mixture of ammonia (50 mL, 0.2 mol) in methanol (7 N) at 0° C. After being stirred at room temperature for 1 h, the solvent was stripped off and the product was obtained as a white solid (10 g, 88.4%), which was used for next step without further purification. LCMS calculated for $C_6H_{15}N_2S$: (M+H) 147.1. Found 147.1.

Step B: 6-Amino-1-pentyl-2-thioxo-2,3-dihydropyrimidin-4(1H)-one

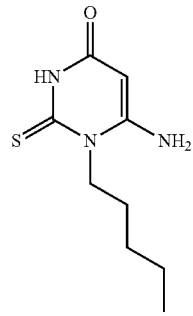

N-Pentylthiourea (10.0 g, 0.068 mol) was mixed with ethyl cyanoacetate (9.3 g, 0.082 mol) and sodium ethoxide (6.4 g, 0.094 mol) in ethanol (60 mL). The mixture was stirred at 75° C. overnight. After cooling, a solution of 10% acetic acid in water (150 mL) was added. The solid formed was collected by filtration and washed with water to afford the desired product (9.5 g, 65% yield). LCMS calculated for $C_9H_{16}N_3OS$: (M+H) 214.1. Found 214.1.

Step C: 6-Amino-5-nitroso-1-pentyl-2-thioxo-2,3-dihydropyrimidin-4(1H)-one

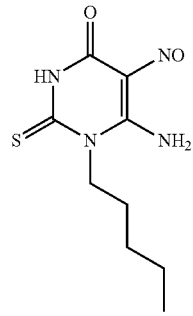

6-Amino-1-pentyl-2-thioxo-2,3-dihydropyrimidin-4 (1H)-one (8.0 g, 0.038 mol) was mixed with sodium nitrite (3.1 g, 0.045 mol) in acetic acid (120 mL). The mixture was stirred at 75° C. for 1 h. The color of the reaction mixture became pink and then purple. The solution was allowed to cool down to room temperature, and water (40 mL) was added. The solid was collected by suction filtration and washed with water (50 mL) to produce the desired product, which was used directly for next step without further purification. LCMS calculated for $C_9H_{15}N_4O_2S$: (M+H) 243.1. Found 243.1.

Step D: 5,6-Diamino-1-pentyl-2-thioxo-2,3-dihydropyrimidin-4(1H)-one

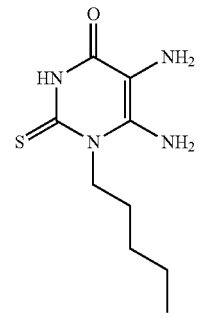

To a mixture of 6-amino-1-pentyl-5-nitroso-2-thioxo-2,3-dihydropyrimidin-4(1H)-one (6.4 g, 0.0264 mol), aqueous ammonia (60 mL, 0.60 mol) and water (60 mL) at 75° C. was added sodium dithionite (9.0 g, 0.050 mol) in small portions. After the addition was complete, the color of the solution changed from red to pale yellow. After stirring at 75° C. for another 5 mins, a precipitate was formed. Stirring was continued at room temperature for 1.5 h. The solution was then neutralized with 10% acetic acid (150 mL). The solid was filtered and washed with water to yield the product (4.5 g, 86.1%). LCMS calculated for $C_9H_{17}N_4OS$: (M+H) 229.1. Found 229.1.

Step E: 3-Pentyl-2-thioxo-8-(trifluoromethyl)-1,2,3,7-tetrahydro-6H-purin-6-one

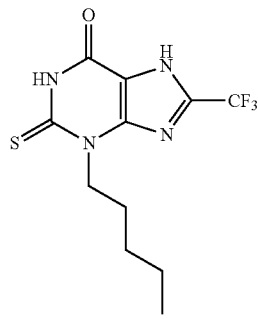 [SMILES: CCCCCn1c(=S)[nH]c(=O)c2[nH]c(C(F)(F)F)nc21]

5,6-Diamino-1-pentyl-2-thioxo-2,3-dihydropyrimidin-4 (1H)-one (2.0 g, 0.0088 mol) was mixed with trifluoroacetic anhydride (10 mL, 0.07 mol). After stirring at 45° C. for 2 h, the excess trifluoroacetic anhydride was removed at reduced pressure. The residue was dissolved in N,N-dimethylformamide (5 mL) and heated at 95° C. for 1 h. After cooling to room temperature, the reaction mixture was diluted with water and extracted with ethyl acetate. The combined organic layers were dried over anhydrous $Na_2SO_4$, filtered and concentrated. The solid residue was washed with ether to provide the desired product (1.50 g, 55.9%). LCMS calculated for C₁₁H₁₄F₃N₄OS: (M+H) 307.1. Found 307.1.

Step F: 2-(Methylthio)-3-pentyl-8-(trifluoromethyl)-3,7-dihydro-6H-purin-6-one

To the solution of 3-pentyl-2-thioxo-8-(trifluoromethyl)-1,2,3,7-tetrahydro-6H-purin-6-one (600 mg, 2 mmol) in a 2 M solution of sodium hydroxide in water (12.0 mL) was added dimethyl sulfate (0.30 mL, 3.2 mmol). The reaction mixture was stirred at room temperature for 1.5 h and quenched with acetic acid. The resulting solution was extracted with methylene chloride three times. The combined organic layer was dried, filtered and concentrated to give the desired product (0.60 g, 95.6%). LCMS calculated for C₁₂H₁₆F₃N₄OS: (M+H) 321.1. Found 321.1.

Step G: (2E)-3-Pentyl-8-(trifluoromethyl)-3,7-dihydro-1H-purine-2,6-dione-2-hydrazone

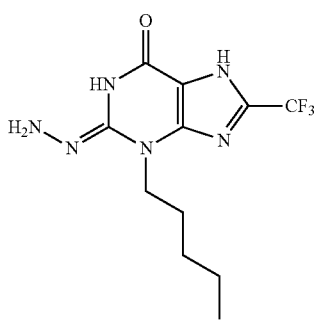 [SMILES: CCCCCn1/c(=N/N)[nH]c(=O)c2[nH]c(C(F)(F)F)nc21]

A mixture of 2-(methylthio)-3-pentyl-8-(trifluoromethyl)-1,2,3,7-tetrahydro-6H-purin-6-one (0.61 g, 0.95 mmol), hydrazine (3 mL, 100 mmol) and water (3 mL) was stirred at 100° C. for 1 h. The reaction solution was concentrated under reduced pressure. The residue was dissolved in DMSO and purified by preparative LCMS. The product fractions were collected and lyophilized to give the desired product (0.25 g, 65%). LCMS calculated for C₁₁H₁₅F₃N₆O: (M+H) 305.1. Found 305.1.

Step H: 3-Methyl-9-pentyl-7-(trifluoromethyl)-6,9-dihydro-5H-[1,2,4]triazolo[4,3-a]purin-5-one

A mixture of (2E)-3-pentyl-8-(trifluoromethyl)-3,7-dihydro-1H-purine-2,6-dione-2-hydrazone (0.020 g, 0.14 mmol) and triethyl orthoacetate (2 mL, 10 mmol) was stirred at room temperature for 1 h. The reaction mixture was concentrated under vacuum and the residue was purified by preparative LCMS. The product fractions were collected and lyophilized to yield pure product as white powder. LCMS calculated for C₁₃H₁₅F₃N₆O: (M+H) 329.1. Found: 329.1.

Example 2

Preparation of 9-butyl-3-methyl-7-(trifluoromethyl)-6,9-dihydro-5H-[1,2,4]triazolo[4,3-a]purin-5-one

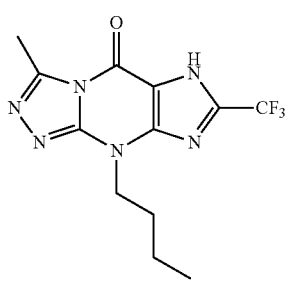 [SMILES: CCCCn1c2nc(C(F)(F)F)[nH]c2c(=O)n2c(C)nnc12]

The title compound was prepared using procedures analogous to those described for Example 1. LCMS calculated for C₁₂H₁₃F₃N₆O: (M+H) 315.1. Found 315.1.

Example 3

Preparation of 9-pentyl-7-(trifluoromethyl)-6,9-dihydro-5H-[1,2,4]triazolo[4,3-a]purin-5-one

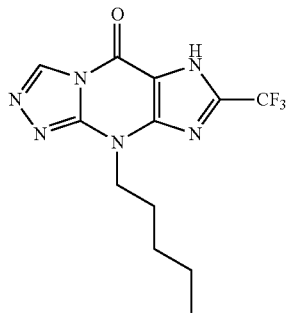 [SMILES: CCCCCn1c2nc(C(F)(F)F)[nH]c2c(=O)n2cnnc12]

A mixture of (2E)-3-pentyl-8-(trifluoromethyl)-3,7-dihydro-1H-purine-2,6-dione-2-hydrazone (0.020 g, 0.14 mmol) and triethyl orthoformate (2 mL, 0.01 mol) was stirred at room temperature for 1 h. The reaction mixture was concentrated under vacuum and the residue was purified by preparative LCMS. The product fractions were collected and lyophilized to yield pure product as white powder (0.1 g, 48%). LCMS calculated for $C_{12}H_{13}F_3N_6O$: (M+H) 315.1. Found: 315.1.

Example 4

Preparation of 9-butyl-7-(trifluoromethyl)-6,9-dihydro-5H-[1,2,4]triazolo[4,3-a]purin-5-one

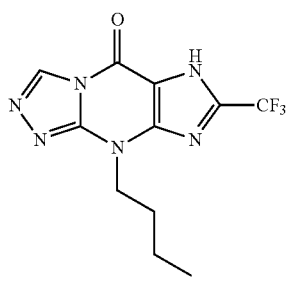 [SMILES: CCCCn1c2nc(C(F)(F)F)[nH]c2c(=O)n2cnnc12]

The title compound was prepared using procedures analogous to those described for Example 3. LCMS calculated for $C_{11}H_{11}F_3N_6O$: (M+H) 301.1. Found 301.1.

Example 5

Preparation of 7-bromo-3-methyl-9-pentyl-6,9-dihydro-5H-[1,2,4]triazolo[4,3-a]purin-5-one

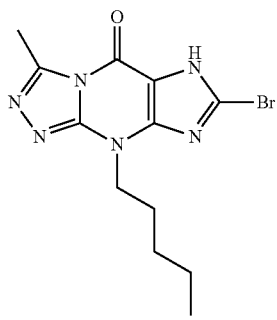 [SMILES: CCCCCn1c2nc(Br)[nH]c2c(=O)n2c(C)nnc12]

Step A:
4-(Pentylamino)-1H-imidazole-5-carboxamide

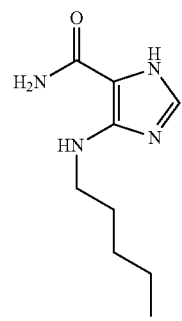

4-Amino-1H-imidazole-5-carboxamide (13.0 g, 0.104 mol) and valeraldehyde (11 mL, 0.10 mol) were mixed in methanol (200 mL). After being stirred for 30 min, sodium cyanoborohydride (6.5 g, 0.10 mol) was added to the solution and stirring was continued overnight. The reaction mixture was concentrated under reduced pressure. The remaining residue was taken up in EtOAc and the resulting solution was washed with saturated $NaHCO_3$. The aqueous layer was extracted with EtOAc three times. The combined organic layers were dried ($MgSO_4$) and concentrated. The residue was purified by flash chromatography (DCM to 5% MeOH/DCM) to give the desired product (12.9 g, 63.1%). LCMS calculated for $C_9H_{16}N_4O$ (M+H): 197.1. Found: 180.1 (M+H−$NH_3$).

Step B: 4-[[(Benzoylamino)carbonothioyl](pentyl)amino]-1H-imidazole-5-carboxamide

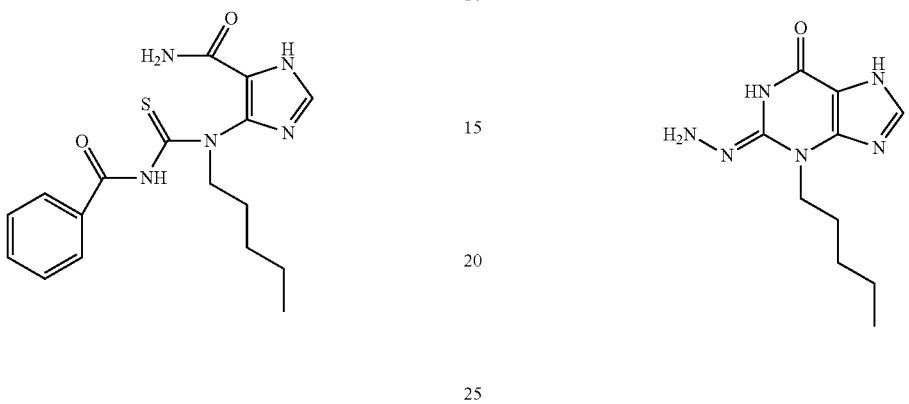

To a solution of 4-(pentylamino)-1H-imidazole-5-carboxamide (4.0 g, 0.020 mol) in DCM (50 mL) was added benzoyl isothiocyanate (3.3 mL, 0.024 mol). After being stirred overnight, the solid formed was filtered to give the crude product (10 g, ca 60% purity, 80% yield). This product was used for next step without further purification. LCMS calculated for $C_{17}H_{22}N_5O_2S$ (M+H): 360.1. Found: 360.1.

Step C: 3-Pentyl-2-thioxo-1,2,3,7-tetrahydro-6H-purin-6-one

A mixture of 4-[[(benzoylamino)carbonothioyl](pentyl)amino]-1H-imidazole-5-carboxamide (11.8 g, 0.0263 mol) and 1 M of sodium hydroxide in water (75 mL) was heated to reflux for 3 h. Solid was formed in the reaction mixture. The reaction mixture was adjusted to pH 3-4 with concentrated HCl with cooling in an ice bath. The solid was filtered, washed with water and air-dried to give the product (9.0 g, 65% purity, 94% yield). The product was used for the next step without further purification. LCMS calculated for $C_{10}H_{15}N_4OS$ (M+H): 239.1. Found: 239.1.

Step D: (2E)-3-Pentyl-3,7-dihydro-1H-purine-2,6-dione 2-hydrazone

3-Pentyl-2-thioxo-1,2,3,7-tetrahydro-6H-purin-6-one (6.0 g, 16 mmol) was mixed with hydrazine (10 mL, 300 mmol) and water (10 mL). The mixture was heated at 100° C. for 8 h. The solid formed was filtered and washed with water to give the desired product (3.0 g, 78%). LCMS calculated for $C_{10}H_{17}N_6O$ (M+H): 237.1. Found: 237.1.

Step E: 3-Methyl-9-pentyl-6,9-dihydro-5H-[1,2,4]triazolo[4,3-a]purin-5-one

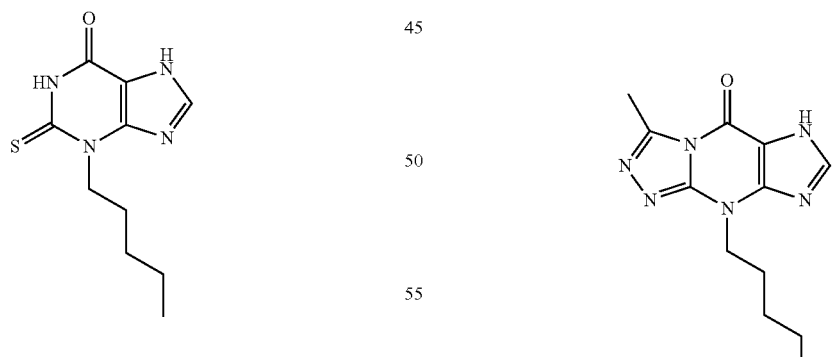

A mixture of (2Z)-3-pentyl-3,7-dihydro-1H-purine-2,6-dione 2-hydrazone (3.1 g, 0.013 mol) and triethyl orthoacetate (20 mL, 0.1 mol) was heated at 100° C. for 3 h. The suspension was cooled to room temperature and the solid formed was filtered and washed with DCM/Hex (1:1) mixture to provide the desired product (3.1 g, 91% yield). LCMS calculated for $C_{12}H_{17}N_6O$ (M+H): 261.1. Found: 261.1.

Step F: 7-Bromo-3-methyl-9-pentyl-6,9-dihydro-5H-[1,2,4]triazolo[4,3-a]purin-5-one

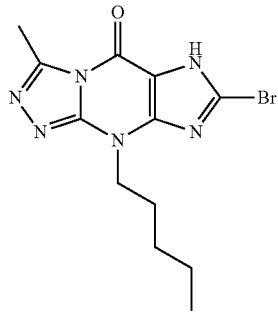 [SMILES: CCCCCn1c2nc(Br)[nH]c2c(=O)n2c(C)nnc12]

To a solution of 3-methyl-9-pentyl-6,9-dihydro-5H-[1,2,4]triazolo[4,3-a]purin-5-one (1.0 g, 3.8 mmol) in THF (50 mL) was added N-bromosuccinimide (0.75 g, 4.2 mol). The mixture was heated at 70° C. for 1 h and concentrated in vacuum. The residue was taken up in water and EtOAc. The organic layer was separated and the aqueous layer was extracted with ethyl acetate three times. The combined organic layers were dried (MgSO$_4$), filtered, and concentrated in vacuum. The residue was purified by preparative LCMS to provide the desired product as a white powder (0.4 g, 30% yield). $^1$HNMR (400 MHz, d$_6$-DMSO): δ 4.18 (t, J=7.5 Hz, 2H), 2.71 (s, 3H), 1.79 (m, 2H), 1.29 (m, 4H), 0.84 (m, 3H). LCMS calculated for C$_{12}$H$_{16}$BrN$_6$O (M+H): 339.1, 341.1. Found: 339.1, 341.1.

Example 6

Preparation of 7-bromo-3-methyl-9-butyl-6,9-dihydro-5H-[1,2,4]triazolo[4,3-a]purin-5-one

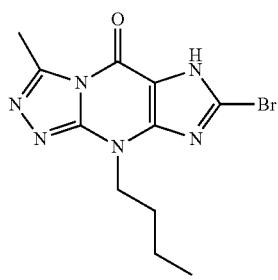 [SMILES: CCCCn1c2nc(Br)[nH]c2c(=O)n2c(C)nnc12]

The title compound was prepared using procedures analogous to those described for Example 5. LCMS calculated for: C$_{11}$H$_{14}$BrN$_6$O (M+H) 325.1, 327.1. Found: 325.1, 327.1.

Example 7

Preparation of 7-chloro-3-methyl-9-pentyl-6,9-dihydro-5H-[1,2,4]triazolo[4,3-a]purin-5-one

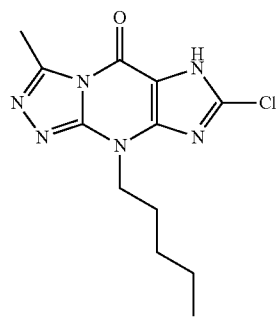 [SMILES: CCCCCn1c2nc(Cl)[nH]c2c(=O)n2c(C)nnc12]

To a solution of 3-methyl-9-pentyl-6,9-dihydro-5H-[1,2,4]triazolo[4,3-a]purin-5-one (0.10 g, 0.38 mmol) in THF (5 mL) in a microwave reaction tube was added N-chlorosuccinimide (0.046 g, 0.42 mmol). The mixture was heated at 70° C. in a microwave oven for 20 min After cooling to room temperature, it was purified using preparative LCMS to provide the product (0.021 g). $^1$HNMR (300 MHz, CD$_3$OD): δ 4.39 (t, J=7.5 Hz, 2H), 2.46 (s, 3H), 1.91 (m, 2H), 1.39 (m, 4H), 0.92 (m, 3H). LCMS calculated for C$_{12}$H$_{16}$ClN$_6$O (M+H): 295.1. Found: 295.1.

Example 8

Preparation of 7-chloro-3-methyl-9-butyl-6,9-dihydro-5H-[1,2,4]triazolo[4,3-a]purin-5-one

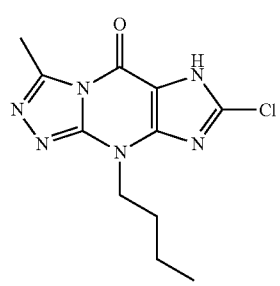 [SMILES: CCCCn1c2nc(Cl)[nH]c2c(=O)n2c(C)nnc12]

The title compound was prepared using procedures analogous to those described for Example 7. LCMS calculated for: C$_{11}$H$_{14}$ClN$_6$O (M+H) 281.1. Found: 281.1.

Example 9

7-bromo-3-(methylthio)-9-pentyl-6,9-dihydro-5H-[1,2,4]triazolo[4,3-a]purin-5-one

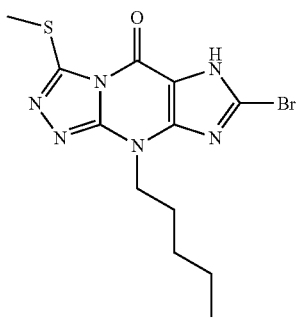 [SMILES: CCCCCn1c2nc(Br)[nH]c2c(=O)n2c(SC)nnc12]

Step A: 9-pentyl-3-thioxo-2,3,6,9-tetrahydro-5H-[1,2,4]triazolo[4,3-a]purin-5-one

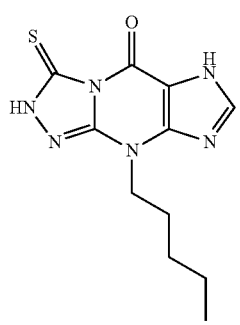 [SMILES: CCCCCn1c2nc[nH]c2c(=O)n2c(=S)[nH]nc12]

A solution of (2e)-3-pentyl-3,7-dihydro-1h-purine-2,6-dione 2-hydrazone (1.90 g, 8.04 mmol) and carbon disulfide (0.58 ml, 9.64 mmol) in pyridine (30 ml) was stirred at 60° C. for 3 hours. After cooling to room temperature, the solid formed was filtered and dried to yield the desired product (1.90 g, 84.9%). LCMS calculated for: $C_{11}H_{14}N_6OS$ (M+H) 280.1. Found: 280.1.

Step B: 3-(methylthio)-9-pentyl-6,9-dihydro-5H-[1,2,4]triazolo[4,3-a]purin-5-one

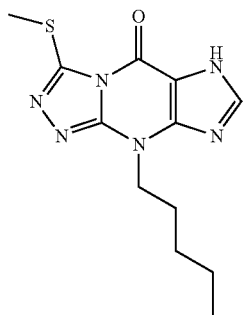 [SMILES: CCCCCn1c2nc[nH]c2c(=O)n2c(SC)nnc12]

A solution of 9-pentyl-3-thioxo-2,3,6,9-tetrahydro-5h-[1,2,4]triazolo[4,3-a]purin-5-one (1.90 g, 6.83 mmol), dimethyl sulfate (1.03 g, 8.19 mmol) and 1 m of sodium hydroxide in water (25 ml) was stirred at room temperature for 1 hour. The mixture was neutralized to pH=7. The solid formed was filtered and dried to provide the desired product (1.70 g, 85.2%). $^1$HNMR (300 MHz, CD$_3$OD): δ 4.29 (t, J=7.2 Hz, 2H), 2.65 (s, 3H), 1.89 (m, 2H), 1.40 (m, 4H), 0.92 (m, 3H). LCMS calculated for: $C_{12}H_{17}N_6OS$ (M+H) 294.1. Found: 294.1.

Step C: 7-bromo-3-(methylthio)-9-pentyl-6,9-dihydro-5H-[1,2,4]triazolo[4,3-a]purin-5-one

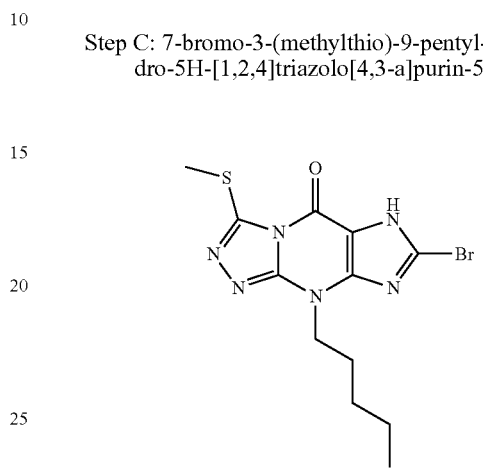

A solution of 3-(methylthio)-9-pentyl-6,9-dihydro-5h-[1,2,4]triazolo[4,3-a]purin-5-one (111 mg, 0.380 mmol), N-bromosuccinimide (81.1 mg, 0.456 mmol) in THF (3 ml) was stirred at 70° C. for 3 hours. The reaction was diluted with water and extracted with ethyl acetate three times, dried with sodium sulfate, filtered, and concentrated in vacuo. The crude residue was purified by Prep LCMS to yield the desired product. LCMS calculated for: $C_{12}H_{16}BrN_6OS$ (M+H) 371.0. Found: 371.0, 373.0.

Example 10

7-bromo-3-(methylsulfinyl)-9-pentyl-6,9-dihydro-5H-[1,2,4]triazolo[4,3-a]purin-5-one

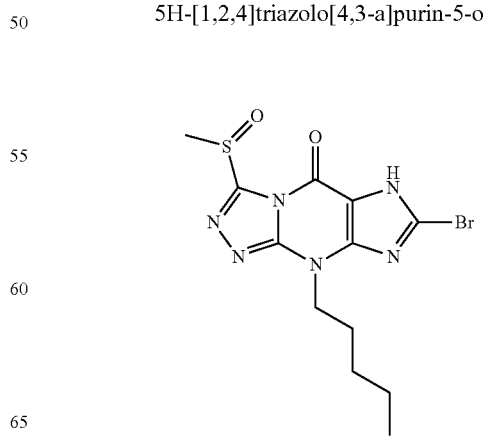

Step A: 3-(methylsulfinyl)-9-pentyl-6,9-dihydro-5H-[1,2,4]triazolo[4,3-a]purin-5-one (A1) and 3-(methylsulfonyl)-9-pentyl-6,9-dihydro-5H-[1,2,4]triazolo[4,3-a]purin-5-one (A2)

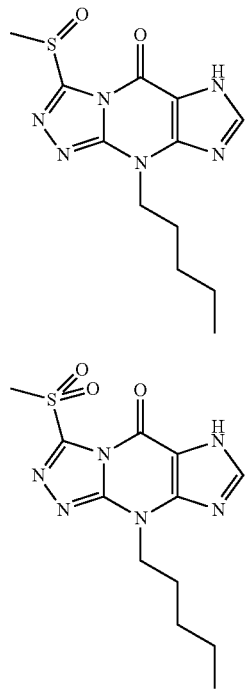

To a solution of 3-(methylthio)-9-pentyl-6,9-dihydro-5H-[1,2,4]triazolo[4,3-a]purin-5-one (200 mg, 0.7 mmol) in THF (5 mL) was added m-chloroperbenzoic acid (283.3 mg, 1.64 mmol) at room temperature. After stirring at room temperature for 30 minutes, the reaction mixture was diluted with water and extracted with ethyl acetate three times. The combined organic layers were dried with sodium sulfate, filtered, and concentrated in vacuo. The crude residue was purified by flash column chromatography to yield the desired products A1 and A2 as a mixture (A1:A2=3:2) (41 mg, 8.5% for A1, 10% for A2). LCMS calculated for: $C_{12}H_{16}N_6O_2S$ (A1) (M+H) 309.1. Found: 310.1. LCMS calculated for: $C_{12}H_{16}N_6O_3S$ (A2) (M+H) 325.1. Found: 325.1.

Step B: 7-bromo-3-(methylsulfinyl)-9-pentyl-6,9-dihydro-5H-[1,2,4]triazolo[4,3-a]purin-5-one

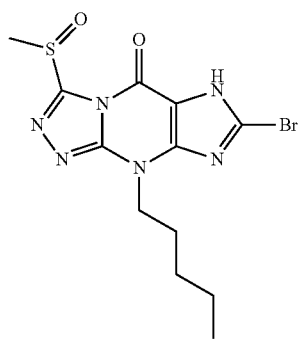 [SMILES: CCCCCn1c2nc(Br)[nH]c2c(=O)n2c(S(C)=O)nnc12]

To a mixture of 3-(methylsulfinyl)-9-pentyl-6,9-dihydro-5h-[1,2,4]triazolo[4,3-a]purin-5-one and 3-(methylsulfo-nyl)-9-pentyl-6,9-dihydro-5h-[1,2,4]triazolo[4,3-a]purin-5-one (3:2, 125 mg, 0.40 mmol) in THF (3 mL) was added N-bromosuccinimide (82.3 mg, 0.462 mmol) The mixture was stirred at 70° C. for 3 hours. The reaction was diluted with water and extracted with ethyl acetate three times, dried with sodium sulfate, filtered, and concentrated in vacuo. The crude residue was purified by Prep LCMS to yield the desired product. LCMS calculated for: $C_{12}H_{15}BrN_6O_2S$ (M+H) 387.0. Found: 387.0, 389.0.

Example 11

7-bromo-3-(methylsulfonyl)-9-pentyl-6,9-dihydro-5H-[1,2,4]triazolo[4,3-a]purin-5-one

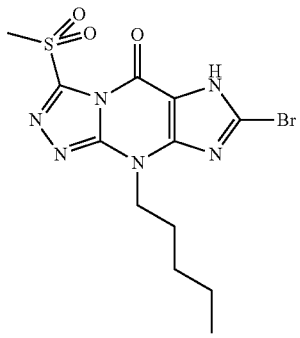 [SMILES: CCCCCn1c2nc(Br)[nH]c2c(=O)n2c(S(C)(=O)=O)nnc12]

The title compound was prepared using procedures analogous to those described for Example 10. LCMS calculated for: $C_{12}H_{15}BrN_6O_3S$ (M+H) 403.0. Found: 403.0, 405.0.

Example 12

7-bromo-3-hydroxy-9-pentyl-6,9-dihydro-5H-[1,2,4]triazolo[4,3-a]purin-5-one

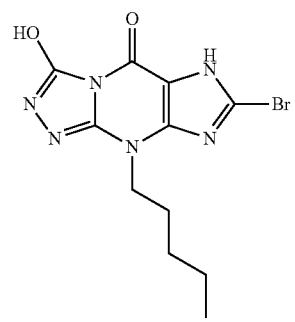 [SMILES: CCCCCn1c2nc(Br)[nH]c2c(=O)n2c(O)nnc12]

Step A: 3-hydroxy-9-pentyl-6,9-dihydro-5H-[1,2,4]triazolo[4,3-a]purin-5-one

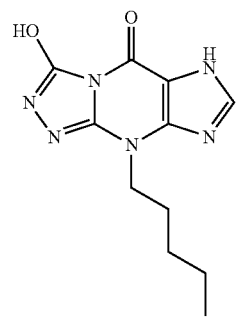 [SMILES: CCCCCn1c2nc[nH]c2c(=O)n2c(O)nnc12]

A solution of (2z)-3-pentyl-3,7-dihydro-1h-purine-2,6-dione 2-hydrazone (200 mg, 0.846 mmol), N,N-carbonyldiimidazole (1.65 g, 10.2 mmol) in THF (10 ml) was stirred at 70° C. overnight. The reaction mixture was then heated in microwave reactor at 100° C. for 10 min. The reaction was completed checked by LCMS analysis. The reaction mixture was concentrated, diluted with EtOAc and washed with sat. NaHCO$_3$. The aqueous was extracted with EtOAc (3×). The combined organic layers were dried (MgSO$_4$) and concentrated to yield the desired product (230 mg, 98.4%). LCMS calculated for $C_{11}H_{15}N_6O_2$ (M+H) 263.1. Found: 263.1.

Step B: 7-bromo-3-hydroxy-9-pentyl-6,9-dihydro-5H-[1,2,4]triazolo[4,3-a]purin-5-one

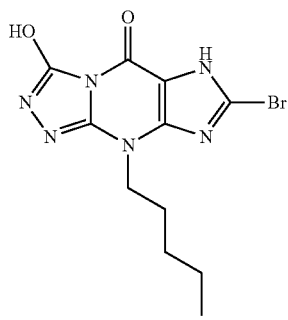

The mixture of solution of 3-hydroxy-9-pentyl-6,9-dihydro-5h-[1,2,4]triazolo[4,3-a]purin-5-one (100 mg, 0.381 mmol) and N-bromosuccinimide (204 mg, 1.14 mmol) in THF (2 ml) was stirred in a microwave reactor at 70° C. for 10 min. The reaction mixture was filtrated and the filtrate was purified by prep LCMS to yield the desired product. LCMS calculated for $C_{11}H_{14}BrN_6O_2$ (M+H) 341.0. Found: 341.0, 343.0.

Example 13

7-bromo-9-butyl-6,9-dihydro-5H-[1,2,4]triazolo[4,3-a]purin-5-one

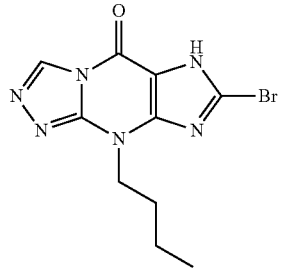 [SMILES: CCCCn1c2nc(Br)[nH]c2c(=O)n2cnnc12]

Step A: 9-butyl-6,9-dihydro-5H-[1,2,4]triazolo[4,3-a]purin-5-one

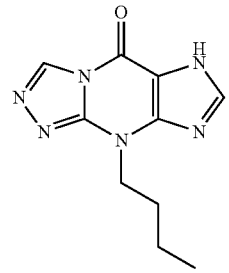 [SMILES: CCCCn1c2nc[nH]c2c(=O)n2cnnc12]

The mixture of (2E)-3-butyl-3,7-dihydro-1H-purine-2,6-dione 2-hydrazone (200 mg, 0.0009 mol) in Ethyl orthoformate (5 mL, 0.03 mol) was heated at 100° C. overnight. After cooling to room temperature, the reaction mixture was filtrated and dried to give the desired product (150 mg, 71.8%). LCMS calculated for $C_{10}H_{13}N_6O$ (M+H): 233.1. Found: 233.1.

Step B: 7-bromo-9-butyl-6,9-dihydro-5H-[1,2,4]triazolo[4,3-a]purin-5-one

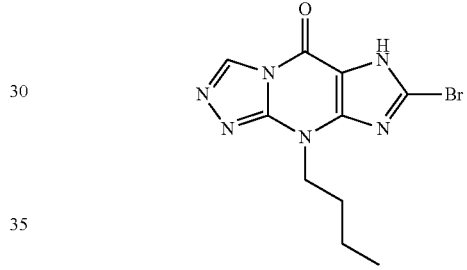

To a mixture of 9-butyl-6,9-dihydro-5H-[1,2,4]triazolo[4,3-a]purin-5-one (65 mg, 0.28 mmol) in THF (2 mL) was added N-bromosuccinimide (49.8 mg, 0.280 mmol). The mixture was heated in a microwave reactor at 70° C. for 10 minutes. The mixture was purified with prep LCMS to give the desired product (4.8 mg, 6%). LCMS calculated for $C_{10}H_{12}BrN_6O$ (M+H): 311.0. Found: 311.0, 313.0.

Example 14

7-bromo-9-pentyl-6,9-dihydro-5H-[1,2,4]triazolo[4,3-a]purin-5-one

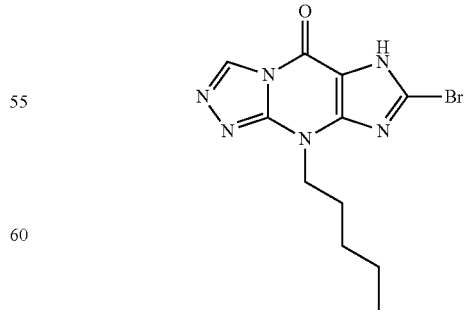

The title compound was prepared using procedures analogous to those described for Example 13. LCMS calculated for: $C_{11}H_{13}BrN_6O$ (M+H) 325.0. Found: 325.0, 327.0.

Example 15

7-bromo-9-pentyl-3-(methoxymethyl)-6,9-dihydro-5H-[1,2,4]triazolo[4,3-a]purin-5-one

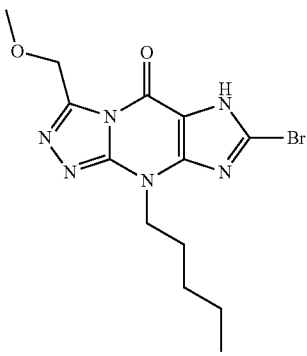 [SMILES: CCCCCn1c2nc(Br)[nH]c2c(=O)n2c(COC)nnc12]

Step A: 9-butyl-3-(methoxymethyl)-6,9-dihydro-5H-[1,2,4]triazolo[4,3-a]purin-5-one

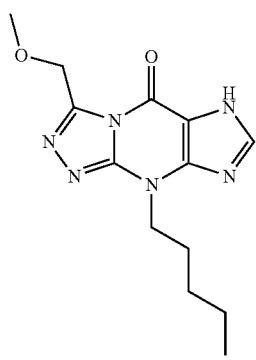 [SMILES: CCCCCn1c2nc[nH]c2c(=O)n2c(COC)nnc12]

The mixture of 9-butyl-3-(chloromethyl)-6,9-dihydro-5h-[1,2,4]triazolo[4,3-a]purin-5-one (35 mg, 125 mmol) in 4 M of sodium methoxide in methanol (0.5 mL, 2 mmol) was stirred at room temperature overnight. The reaction mixture was diluted with water and extracted with ethyl acetate three times. The combined organic layers was dried with sodium sulfate, filtered, and concentrated in vacuo to yield the desired product (6 mg, 17.42%). LCMS calculated for $C_{13}H_{19}N_6O_2$ (M+H): 290.2. Found 290.2.

Step B: 7-bromo-9-butyl-3-(methoxymethyl)-6,9-dihydro-5H-[1,2,4]triazolo[4,3-a]purin-5-one

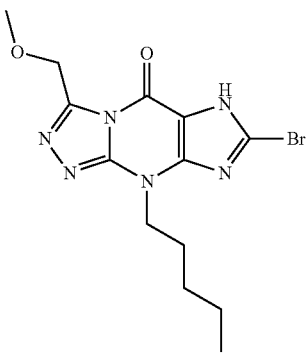 [SMILES: CCCCCn1c2nc(Br)[nH]c2c(=O)n2c(COC)nnc12]

The mixture of 9-butyl-3-(methoxymethyl)-6,9-dihydro-5h-[1,2,4]triazolo[4,3-a]purin-5-one (6 mg, 21.7 mmol), N-bromosuccinimide (4.64 mg, 26.0 mmol) in tetrahydrofuran (10 ml) was stirred at 70° C. for 2 hours. The reaction mixture was concentrated in vacuo and the residue was purified by prep LCMS to yield the desired product. LCMS calculated for $C_{13}H_{18}BrN_6O_2$ (M+H): 369.1. Found 371.1.

Example 16

7-bromo-9-pentyl-3-phenyl-6,9-dihydro-5H-[1,2,4]triazolo[4,3-a]purin-5-one

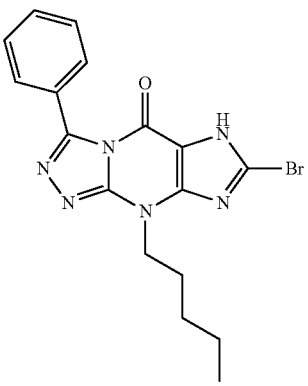 [SMILES: CCCCCn1c2nc(Br)[nH]c2c(=O)n2c(-c3ccccc3)nnc12]

Step A: benzaldehyde[(2E)-6-oxo-3-pentyl-1,3,6,7-tetrahydro-2H-purin-2-ylidene]hydrazone

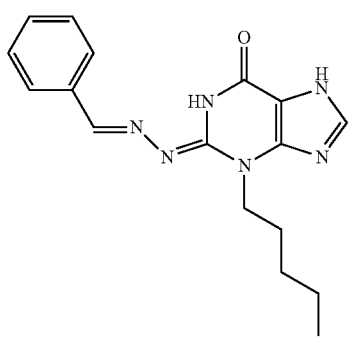 [SMILES: CCCCCn1/c(=N/N=C/c2ccccc2)[nH]c(=O)c2[nH]cnc21]

A solution of (2E)-3-pentyl-3,7-dihydro-1h-purine-2,6-dione 2-hydrazone (104 mg, 44 µmol), benzaldehyde (44.7 µl, 44 µmol) in ethanol (10 ml) was stirred at 70° C. for 3 hours. The reaction solution was concentrated in vacuo to give the desired product. LCMS calculated for $C_{17}H_{21}N_6O$ (M+H): 325.2. Found: 325.2.

Step B: 9-pentyl-3-phenyl-6,9-dihydro-5H-[1,2,4]triazolo[4,3-a]purin-5-one

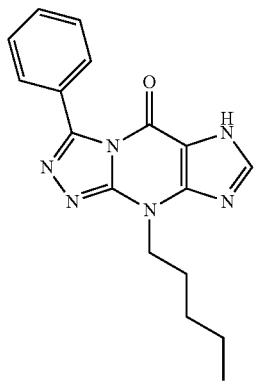 [SMILES: CCCCCn1c2nc[nH]c2c(=O)n2c(-c3ccccc3)nnc12]

A solution of benzaldehyde[(2E)-6-oxo-3-pentyl-1,3,6,7-tetrahydro-2h-purin-2-ylidene]hydrazone (140 mg, 0.432 mmol) in acetic acid (5 ml) was stirred at 130° C. for 5 hours. The reaction mixture was concentrated in vacuo and purified by prep LCMS to yield the desired product (30 mg, 22% yield). LCMS calculated for $C_{17}H_{19}N_6O$ (M+H): 323.2. Found: 323.2.

Step C: 7-bromo-9-pentyl-3-phenyl-6,9-dihydro-5H-[1,2,4]triazolo[4,3-a]purin-5-one

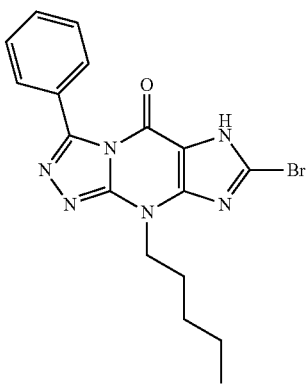 [SMILES: CCCCCn1c2nc(Br)[nH]c2c(=O)n2c(-c3ccccc3)nnc12]

To a mixture of 9-pentyl-3-phenyl-6,9-dihydro-5h-[1,2,4]triazolo[4,3-a]purin-5-one (30 mg, 0.093 mmol) in THF (30 mL) was added N-bromosuccinimide (19.9 mg, 0.112 mmol). The mixture was stirred at 70° C. for 3 hours. The reaction mixture was concentrated in vacuo and the crude residue was purified using preparative LCMS to yield the desired product (8.7 mg, 23.3% yield). LCMS calculated for $C_{17}H_{18}BrN_6O$ (M+H) 401.1. Found 401.1, 403.1

Example 17

7-bromo-9-pentyl-3-pyridin-3-yl-6,9-dihydro-5H-[1,2,4]triazolo[4,3-a]purin-5-one trifluoroacetate

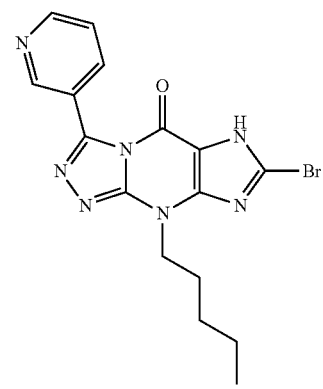

The title compound was prepared using procedures analogous to those described for Example 16. LCMS calculated for $C_{16}H_{17}BrN_7O$ (M+H): 402.1. Found: 402.1, 404.1.

Example 18

7-bromo-9-pentyl-3-pyridin-4-yl-6,9-dihydro-5H-[1,2,4]triazolo[4,3-a]purin-5-one trifluoroacetate

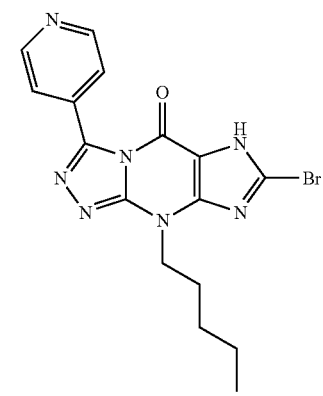

The title compound was prepared using procedures analogous to those described for Example 16. LCMS calculated for $C_{16}H_{17}BrN_7O$ (M+H): 402.1. Found: 402.1, 404.1.

Example 19

7-bromo-9-pentyl-3-pyridin-2-yl-6,9-dihydro-5H-[1,2,4]triazolo[4,3-a]purin-5-one trifluoroacetate

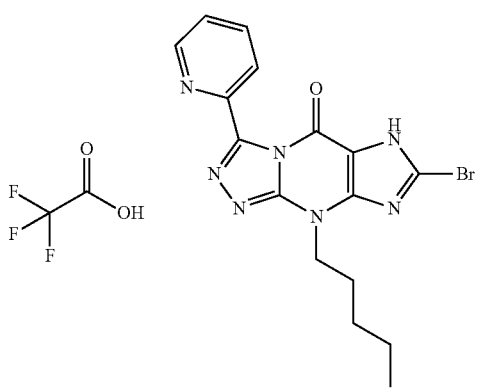 [SMILES: O=C(O)C(F)(F)F ; CCCCCn1c2nc(Br)[nH]c2c(=O)n2c(-c3ccccn3)nnc12]

The title compound was prepared using procedures analogous to those described for Example 16. LCMS calculated for $C_{16}H_{17}BrN_7O$ (M+H): 402.1. Found: 402.1, 404.1.

Example 20

7-bromo-9-pentyl-3-(1,3-thiazol-2-yl)-6,9-dihydro-5H-[1,2,4]triazolo[4,3-a]purin-5-one

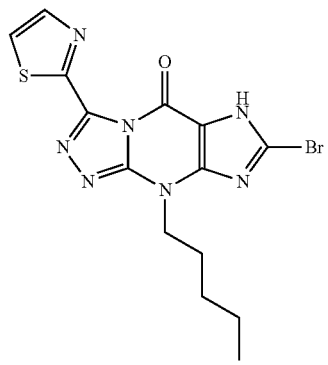 [SMILES: CCCCCn1c2nc(Br)[nH]c2c(=O)n2c(-c3nccs3)nnc12]

The title compound was prepared using procedures analogous to those described for Example 16. LCMS calculated for $C_{14}H_{15}BrN_7OS$ (M+H): 408.0. Found: 408.1.

Example 21

7-bromo-9-pentyl-3-propyl-6,9-dihydro-5H-[1,2,4]triazolo[4,3-a]purin-5-one

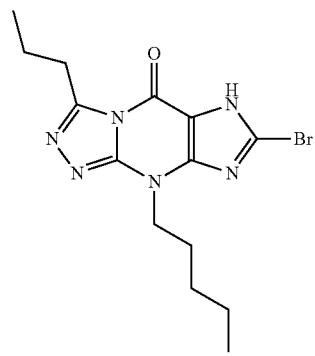 [SMILES: CCCCCn1c2nc(Br)[nH]c2c(=O)n2c(CCC)nnc12]

The title compound was prepared using procedures analogous to those described for Example 5. LCMS calculated for $C_{14}H_{20}BrN_6O$: 367.1. Found; 367.1, 369.1.

Example 22

7-bromo-3-[(dimethylamino)methyl]-9-pentyl-6,9-dihydro-5H-[1,2,4]triazolo[4,3-a]purin-5-one trifluoroacetate

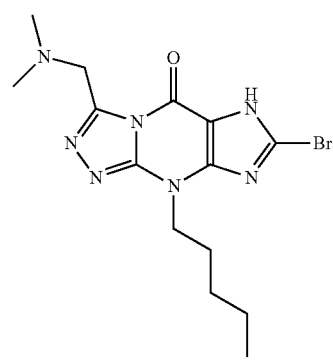

The mixture of 7-bromo-9-pentyl-6,9-dihydro-5H-[1,2,4]triazolo[4,3-a]purin-5-one (130 mg, 0.40 mmol) and Eschenmoser's salt (1.1 eq.) in DMF (5 mL) was heated at 100° C. for 30 minutes. The reaction mixture was directly purified using preparative LCMS to yield the desired product. LCMS calculated for $C_{14}H_{21}BrN_7O$: 382.1. Found 382.1, 384.1.

Example 23

3-methyl-9-pentyl-7-(1,3-thiazol-2-yl)-6,9-dihydro-5H-[1,2,4]triazolo[4,3-a]purin-5-one

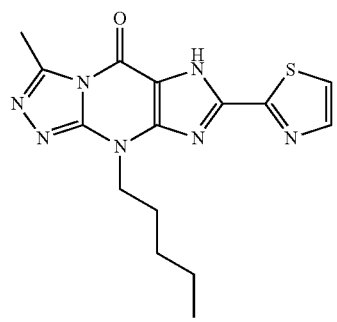 [SMILES: CCCCCn1c2nc(-c3nccs3)[nH]c2c(=O)n2c(C)nnc12]

Step A: 7-bromo-6-(4-methoxybenzyl)-3-methyl-9-pentyl-6,9-dihydro-5H-[1,2,4]triazolo[4,3-a]purin-5-one

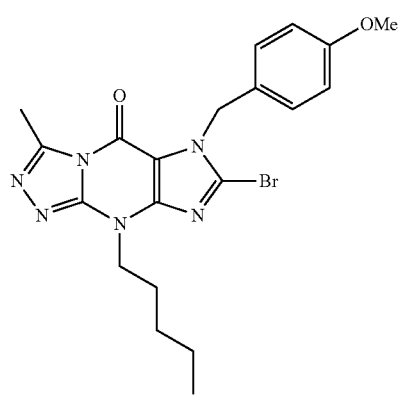 [SMILES: CCCCCn1c2nc(Br)n(Cc3ccc(OC)cc3)c2c(=O)n2c(C)nnc12]

The mixture of 7-bromo-3-methyl-9-pentyl-6,9-dihydro-5h-[1,2,4]triazolo[4,3-a]purin-5-one (200 mg, 0.59 mmol), 4-methoxyphenyl methylbromide (0.094 mL, 0.65 mmol), potassium carbonate (244 mg, 1.77 mmol) in DMF (10 ml) was stirred at room temperature for 2 hours. The reaction was quenched with water and the solid formed was filtered and dried over to yield the desired product (270 mg, 99.7%). LCMS calculated for $C_{20}H_{24}BrN_6O_2$: 459.1. Found 460.1.

Step B: 6-(4-methoxybenzyl)-3-methyl-9-pentyl-7-(1,3-thiazol-2-yl)-6,9-dihydro-5H-[1,2,4]triazolo[4,3-a]purin-5-one

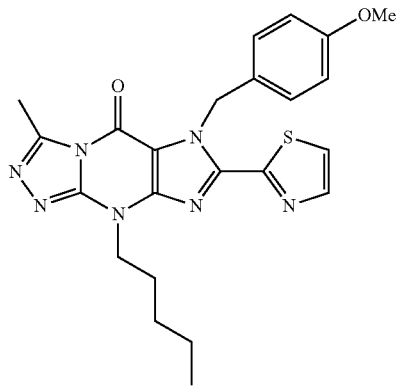 [SMILES: CCCCCn1c2nc(-c3nccs3)n(Cc3ccc(OC)cc3)c2c(=O)n2c(C)nnc12]

To the mixture of 7-bromo-6-(4-methoxybenzyl)-3-methyl-9-pentyl-6,9-dihydro-5h-[1,2,4]triazolo[4,3-a]purin-5-one (100 mg, 0.22 mmol), 2-(tributylstannyl)-1,3-thiazole (122 mg, 0.33 mmol) in toluene (14 mL) was added tetrakis(triphenylphosphine)palladium(0) (12.6 mg, 0.011 mmol) under $N_2$. The mixture was refluxed overnight. The reaction mixture was concentrated in vacuo. The crude residue was purified using preparative LCMS to yield the desired product (80 mg, 79%). LCMS calculated for $C_{23}H_{26}N_7O_2S$ (M+H): 464.2. Found 464.2.

Step C: 3-methyl-9-pentyl-7-(1,3-thiazol-2-yl)-6,9-dihydro-5H-[1,2,4]triazolo[4,3-a]purin-5-one

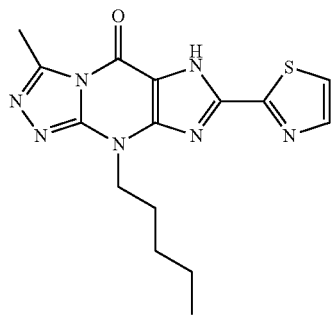

The mixture of 6-(4-methoxybenzyl)-3-methyl-9-pentyl-7-(1,3-thiazol-2-yl)-6,9-dihydro-5H-[1,2,4]triazolo[4,3-a] purin-5-one (100 mg, 0.22 mmol) in trifluoroacetic acid (5 mL, 65 mmol) was stirred at 55° C. overnight. The reaction solution was concentrated and purified using preparative LCMS to yield the desired product. LCMS calculated for $C_{15}H_{18}N_7OS$: 344.1. Found: 344.1.

Example 24

3-methyl-7-(methylthio)-9-pentyl-6,9-dihydro-5H-[1,2,4]triazolo[4,3-a]purin-5-one

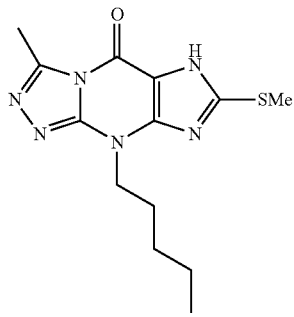 [SMILES: CCCCCn1c2nc(SC)[nH]c2c(=O)n2c(C)nnc12]

Step A: 6-(4-methoxybenzyl)-3-methyl-7-(methylthio)-9-pentyl-6,9-dihydro-5H-[1,2,4]triazolo[4,3-a]purin-5-one

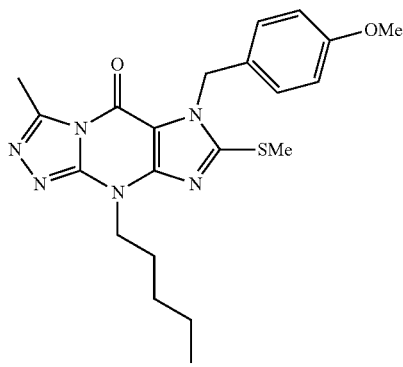 [SMILES: CCCCCn1c2nc(SC)n(Cc3ccc(OC)cc3)c2c(=O)n2c(C)nnc12]

A mixture of 7-bromo-6-(4-methoxybenzyl)-3-methyl-9-pentyl-6,9-dihydro-5h-[1,2,4]triazolo[4,3-a]purin-5-one (271 mg, 0.6 mmol) and sodium methyl sulfide (45.5 mg, 0.65 mmol) in dimethoxyethane (13.4 ml, 129 mmol) was refluxed for 2 h. The reaction was quenched with water. The solid formed was filtered and dried to yield the desired product (200 mg, 79.5%). LCMS calculated for $C_{21}H_{27}N_6O_2S$ (M+H): 427.2. Found 427.2.

Step B: 3-methyl-7-(methylthio)-9-pentyl-6,9-dihydro-5H-[1,2,4]triazolo[4,3-a]purin-5-one

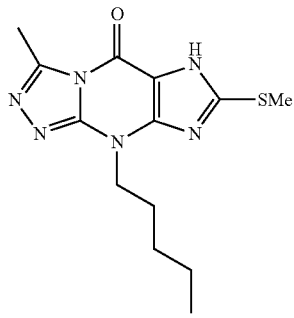 [SMILES: CCCCCn1c2nc(SC)[nH]c2c(=O)n2c(C)nnc12]

A solution of 6-(4-methoxybenzyl)-3-methyl-7-(methylthio)-9-pentyl-6,9-dihydro-5H-[1,2,4]triazolo[4,3-a]purin-5-one (200 mg, 469 mmol) in trifluoroacetic acid (5 ml, 64.9 mmol) was stirred at 55° C. overnight. The solution was concentrated and purified by prep LCMS to yield the desired product (60 mg, 42%). $^1$HNMR (300 MHz, CD$_3$OD): δ 4.42 (t, J=7.5 Hz, 2H), 2.74 (s, 3H), 2.45 (s, 3H), 1.92 (m, 2H), 1.39 (m, 4H), 0.92 (m, 3H). LCMS calculated for $C_{13}H_{19}N_6OS$ (M+H): 307.1. Found 307.1.

Example 25

3-methyl-9-pentyl-7-phenyl-6,9-dihydro-5H-[1,2,4]triazolo[4,3-a]purin-5-one

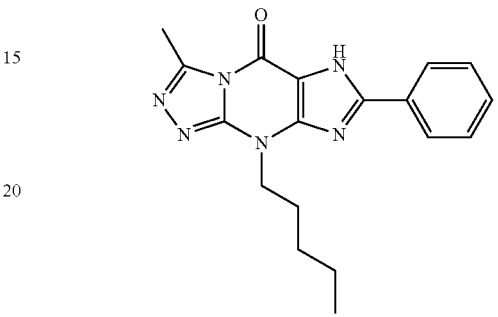

To a mixture of 7-bromo-3-methyl-9-pentyl-6,9-dihydro-5h-[1,2,4]triazolo[4,3-a]purin-5-one (100 mg, 0.30 mmol), phenylboronic acid (39.5 mg, 0.32 mmol), sodium carbonate (100 mg, 0.94 mmol) in water (2 ml) and 1,2-dimethoxyethane (20 ml) was added tetrakis(triphenylphosphine)-palladium(0) (200 mg, 0.10 mmol) The mixture was heated to reflux overnight. The reaction mixture was diluted with water and extracted with ethyl acetate three times. The combined organic layers were dried with sodium sulfate, filtered, and concentrated in vacuo. The residue was purified by preparative LCMS to yield the desired product (16 mg, 16%). $^1$HNMR (400 MHz, CD$_3$OD): δ 8.06 (m, 2H), 7.49 (m, 3H), 4.38 (t, J=8.0 Hz, 2H), 2.83 (s, 3H), 1.95 (m, 2H), 1.42 (m, 4H), 0.92 (m, 3H). LCMS calculated for $C_{18}H_{21}N_6O$ (M+H): 337.2. Found 337.2.

Example 26

3-methyl-9-pentyl-7-pyridin-4-yl-6,9-dihydro-5H-[1,2,4]triazolo[4,3-a]purin-5-one trifluoroacetate

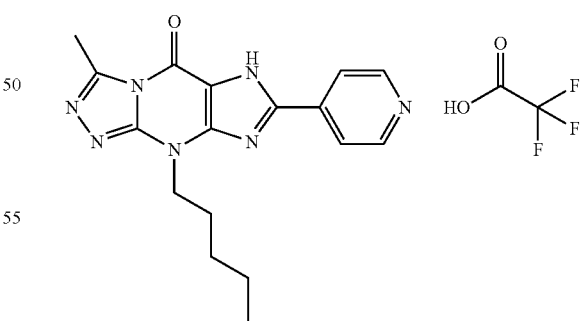

To a mixture of 7-bromo-3-methyl-9-pentyl-6,9-dihydro-5h-[1,2,4]triazolo[4,3-a]purin-5-one (100 mg, 0.30 mmol), 4-pyridinylboronic acid (40 mg, 0.32 mmol), sodium carbonate (100 mg, 0.94 mmol) in water (2 ml) and toluene (20 ml) was added tetrakis(triphenylphosphine)palladium(0) (200 mg, 0.10 mmol) The mixture was heated to reflux overnight. The reaction mixture was diluted with water and extracted with ethyl acetate three times. The combined organic layers were dried with sodium sulfate, filtered, and concentrated in vacuo. The residue was purified by preparative LCMS to yield the desired product (16 mg, 16%). $^1$HNMR (400 MHz, CD$_3$OD): δ 8.83 (dd, J=1.6, 4.9 Hz, 2H), 8.33 (dd, J=1.6, 4.9 Hz, 2H), 4.44 (t, J=7.7 Hz, 2H), 2.88 (s, 3H), 1.97 (m, 2H), 1.44 (m, 4H), 0.93 (m, 3H). LCMS calculated for C$_{17}$H$_{20}$N$_7$O (M+H): 338.2. Found 338.2.

Example 27

7-(3,5-dimethylisoxazol-4-yl)-3-methyl-9-pentyl-6,9-dihydro-5H-[1,2,4]triazolo[4,3-a]purin-5-one

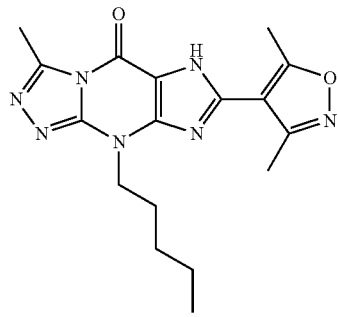 [SMILES: CCCCCn1c2nc(-c3c(C)noc3C)[nH]c2c(=O)n2c(C)nnc12]

The title compound was prepared using procedures analogous to those described for Example 25. LCMS calculated for C$_{17}$H$_{22}$N$_7$O$_2$ (M+H): 356.2. Found 356.2.

Example 28

7-cyclopropyl-3-methyl-9-pentyl-6,9-dihydro-5H-[1,2,4]triazolo[4,3-a]purin-5-one

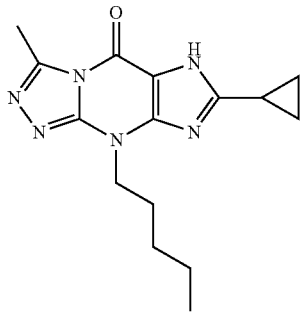 [SMILES: CCCCCn1c2nc(C3CC3)[nH]c2c(=O)n2c(C)nnc12]

The title compound was prepared using procedures analogous to those described for Example 25. $^1$HNMR (300 MHz, d$_6$-DMSO): δ 4.18 (d, J=7.5 Hz, 2H), 2.70 (s, 3H), 2.05 (m, 1H), 1.78 (m, 2H), 1.28 (m, 4H), 1.06 (m, 4H), 0.92 (m, 3H). LCMS calculated for C$_{15}$H$_{21}$N$_6$O (M+H): 301.2. Found 301.2.

Example 29

3-methyl-7-(1-methyl-1H-pyrazol-4-yl)-9-pentyl-6,9-dihydro-5H-[1,2,4]triazolo[4,3-a]purin-5-one

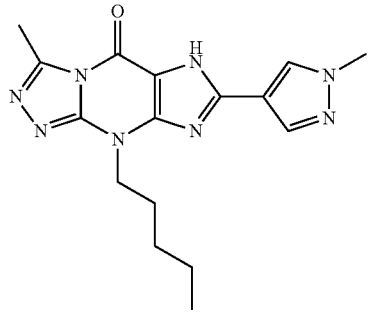

Step A: 6-(4-methoxybenzyl)-3-methyl-7-(1-methyl-1H-pyrazol-4-yl)-9-pentyl-6,9-dihydro-5H-[1,2,4]triazolo[4,3-a]purin-5-one

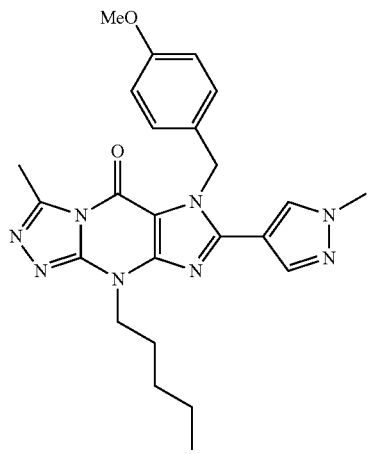 [SMILES: CCCCCn1c2nc(-c3cnn(C)c3)n(Cc3ccc(OC)cc3)c2c(=O)n2c(C)nnc12]

To a solution of 7-bromo-6-(4-methoxybenzyl)-3-methyl-9-pentyl-6,9-dihydro-5H-[1,2,4]triazolo[4,3-a]purin-5-one (100 mg, 0.3 mmol), 1-methyl-4-(4,4,5,5-tetramethyl-1,3,2-dioxaborolan-2-yl)-1H-pyrazole (92 mg, 0.44 mmol) and sat. sodium carbonate (100 mg, 0.9 mmol) in toluene (20 mL, 0.2 mol) was added tetrakis(triphenylphosphine)palladium(0) (20 mg, 0.01 mmol) under N$_2$ at room temperature. The mixture was heated to reflux overnight. The mixture was stripped down and purified by preparative LC-MS to yield the desired product (50 mg, 37%). LCMS calculated for C$_{24}$H$_{29}$N$_8$O$_2$ (M+H): 461.2. Found 461.2.

Step B: 3-methyl-7-(1-methyl-M-pyrazol-4-yl)-9-pentyl-6,9-dihydro-5H-[1,2,4]triazolo[4,3-a]purin-5-one

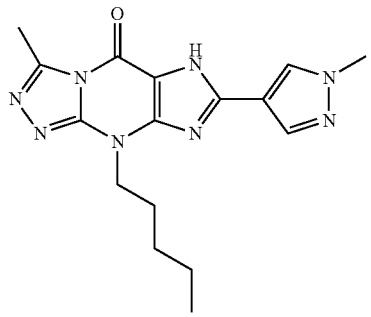 [SMILES: CCCCCn1c2nc(-c3cnn(C)c3)[nH]c2c(=O)n2c(C)nnc12]

6-(4-Methoxybenzyl)-3-methyl-7-(1-methyl-1H-pyrazol-4-yl)-9-pentyl-6,9-dihydro-5H-[1,2,4]triazolo[4,3-a]purin-5-one (50 mg, 0.10 mmol) in trifluoroacetic acid (5 mL) was stirred at 60° C. overnight. The mixture was concentrated, and the residue was purified by preparative LC-MS to give final product. $^1$HNMR (300 MHz, CD$_3$OD): δ 8.23 (d, J=4.9 Hz, 1H), 8.05 (d, J=4.9 Hz, 1H), 4.45 (t, J=7.0 Hz, 2H), 3.98 (s, 3H), 2.46 (s, 3H), 1.93 (m, 2H), 1.41 (m, 4H), 0.92 (m, 3H). LCMS calculated for $C_{16}H_{21}N_8O$ (M+H): 341.2. Found 341.2.

Example 30

3-methyl-9-pentyl-7-(4H-1,2,4-triazol-4-yl)-6,9-dihydro-5H-[1,2,4]triazolo[4,3-a]purin-5-one

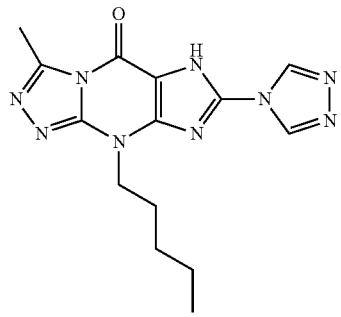 [SMILES: CCCCCn1c2nc(-n3cnnc3)[nH]c2c(=O)n2c(C)nnc12]

Step A: 6-(4-methoxybenzyl)-3-methyl-9-pentyl-7-(4H-1,2,4-triazol-1-yl)-6,9-dihydro-5H-[1,2,4]triazolo[4,3-c]purin-5-one

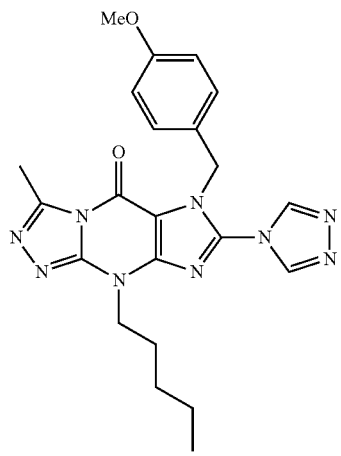 [SMILES: CCCCCn1c2nc(-n3cnnc3)n(Cc3ccc(OC)cc3)c2c(=O)n2c(C)nnc12]

Sodium hydride 60% in mineral oil (18 mg, 0.74 mmol) was added to a solution of 1H-1,2,4-Triazole (45 mg, 0.65 mmol) in DMF (10 mL) at room temperature. After stirring for 1 hour at room temperature, 7-bromo-6-(4-methoxybenzyl)-3-methyl-9-pentyl-6,9-dihydro-5H-[1,2,4]triazolo[4,3-a]purin-5-one (200 mg, 0.40 mmol) in DMF was added to above solution and the mixture was stirred overnight. The reaction was quenched with a drop of water and the reaction mixture was purified by pre LC-MS to give the desired product (53 mg, 27.2%) and its region-isomer 6-(4-methoxybenzyl)-3-methyl-9-pentyl-7-(1H-1,2,4-triazol-1-yl)-6,9-dihydro-5H-[1,2,4]triazolo[4,3-a]purin-5-one (53 mg, 27%). LCMS calculated for $C_{22}H_{26}N_9O_2$ (M+H): 448.2. Found 448.2.

Step B: 3-methyl-9-pentyl-7-(4H-1,2,4-triazol-4-yl)-6,9-dihydro-5H-[1,2,4]triazolo[4,3-a]purin-5-one

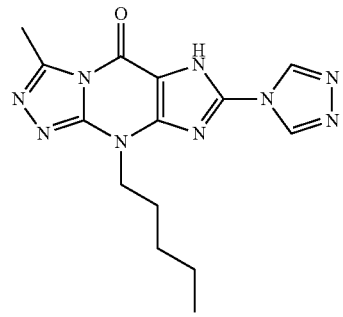 [SMILES: CCCCCn1c2nc(-n3cnnc3)[nH]c2c(=O)n2c(C)nnc12]

A mixture of 6-(4-methoxybenzyl)-3-methyl-9-pentyl-7-(1H-1,2,4-triazol-1-yl)-6,9-dihydro-5H-[1,2,4]triazolo[4,3-a]purin-5-one (53 mg, 0.12 mmol) in trifluoroacetic acid (10 mL) was stirred at 60° C. overnight. The mixture was concentrated and purified by preparative LC-MS to give the desired product (20 mg, 52%). LCMS calculated for $C_{14}H_{18}N_9O$ (M+H): 328.2. Found: 328.2.

Example 31

3-methyl-9-pentyl-7-(1H-1,2,4-triazol-1-yl)-6,9-dihydro-5H-[1,2,4]triazolo[4,3-a]purin-5-one

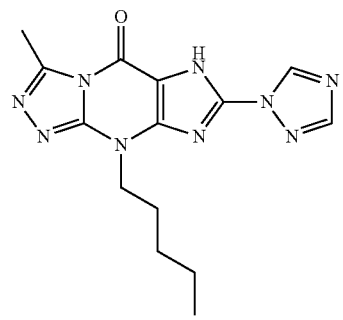 [SMILES: CCCCCn1c2nc(-n3cncn3)[nH]c2c(=O)n2c(C)nnc12]

The title compound was prepared using procedures analogous to those described for Example 30. LCMS calculated for $C_{14}H_{18}N_9O$ (M+H): 328.2. Found: 328.2.

Example 32

7-cyclobutyl-3-methyl-9-pentyl-6,9-dihydro-5H-[1,2,4]triazolo[4,3-a]purin-5-one

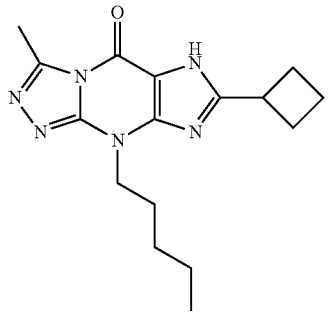 [SMILES: CCCCCn1c2nc(C3CCC3)[nH]c2c(=O)n2c(C)nnc12]

Step A: N-(5-amino-6-oxo-3-pentyl-2-thioxo-1,2,3,6-tetrahydropyrimidin-4-yl)cyclobutanecarboxamide

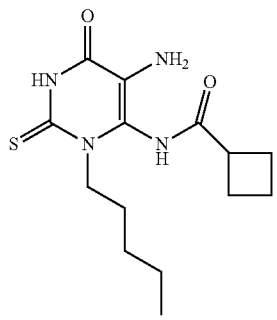 [SMILES: CCCCCn1c(NC(=O)C2CCC2)c(N)c(=O)[nH]c1=S]

The mixture of 5,6-diamino-1-pentyl-2-thioxo-2,3-dihydropyrimidin-4(1H)-one (1060 mg, 0.00464 mol), cyclobutane carboxylic acid (0.55 g, 5.5 mmol), benzotriazol-1-yloxytris-(dimethylamino)phosphonium hexafluorophosphate (2.2 g, 5.1 mmol) and triethylamine (1.3 mL, 9.3 mmol) in DMF (20 mL) was stirred at room temperature for 4 hours. The mixture was diluted with water. The precipatate formed was filtered and dried to yield the desired product (1.20 g, 83.27%). LCMS calculated for $C_{14}H_{23}N_4O_2S$ (M+H): 311.2. Found 311.2.

Step B: 8-cyclobutyl-3-pentyl-2-thioxo-1,2,3,7-tetrahydro-6H-purin-6-one

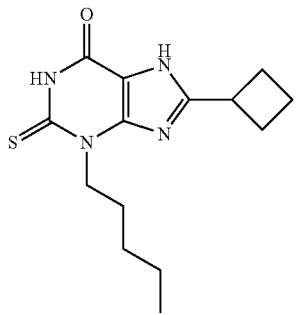 [SMILES: CCCCCn1c(=S)[nH]c(=O)c2[nH]c(C3CCC3)nc21]

The mixture of N-(5-amino-6-oxo-3-pentyl-2-thioxo-1,2,3,6-tetrahydropyrimidin-4-yl)cyclobutanecarboxamide (720 mg, 2.3 mmol) and 2.5 M of sodium hydroxide in water (25 mL) and methanol (25 mL) was stirred at 70° C. for 1 hour. After cooling to room temperature, The reaction mixture was concentrated to remove methanol and then acidified to pH=5. The precipitate formed was filtered and dried to yield the desired product (500 mg, 73.7%). LCMS calculated for $C_{14}H_{21}N_4OS$ (M+H): 293.1. Found: 293.1.

Step C: (2E)-8-cyclobutyl-3-pentyl-3,7-dihydro-1H-purine-2,6-dione 2-hydrazone

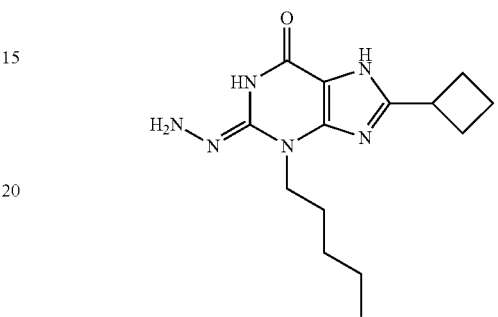

The mixture of 8-cyclobutyl-3-pentyl-2-thioxo-1,2,3,7-tetrahydro-6H-purin-6-one (0.6 g, 2.0 mmol) in 20 M of hydrazine in water (20 mL) was stirred at 100° C. overnight. After cooling to room temperature, the solid formed was filtered and dried Cooled down, the solid was isolated to give yield the desired product (230 mg, 38.6%). LCMS calculated for $C_{14}H_{23}N_6O$ (M+H): 291.2. Found: 291.2.

Step D: 7-cyclobutyl-3-methyl-9-pentyl-6,9-dihydro-5H-[1,2,4]triazolo[4,3-a]purin-5-one

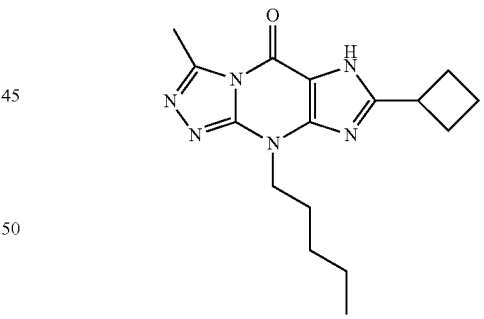

(2E)-8-cyclobutyl-3-pentyl-3,7-dihydro-1H-purine-2,6-dione 2-hydrazone (100 mg, 0.0003 mol) was mixed with triethyl orthoacetate (10 mL, 0.05 mol) and then stirred at 100° C. overnight. After cooling to room temperature, the mixture was concentrated and purified by preparative LCMS to yield the desired product (10 mg, 9.2%). $^1$HNMR (300 MHz, CD$_3$OD): δ 4.35 (m, 2H), 3.72 (m, 1H), 2.84 (s, 3H), 2.44 (m, 4H), 2.05 (m, 2H), 1.90 (m, 2H), 1.40 (m, 4H), 0.92 (m, 3H). LCMS calculated for $C_{16}H_{23}N_6O$ (M+H): 315.2. Found: 315.2.

Example 33

7-bromo-3-(4-methoxyphenyl)-9-pentyl-6,9-dihydro-5H-[1,2,4]triazolo[4,3-a]purin-5-one

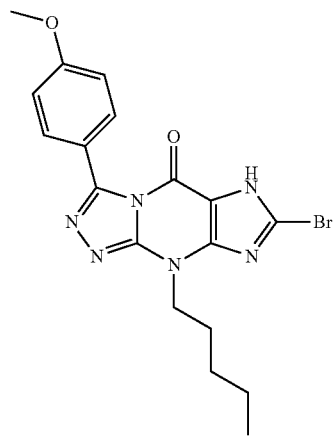 [SMILES: CCCCCn1c2nc(Br)[nH]c2c(=O)n2c(-c3ccc(OC)cc3)nnc12]

The title compound was prepared using procedures analogous to those described for Example 16. $^1$HNMR (300 MHz, CD$_3$OD): δ 7.67 (d, J=9.2 Hz, 2H), 7.03 (d, J=9.2 Hz, 2H), 4.41 (t, J=7.8 Hz, 2H), 3.88 (s, 3H), 1.96 (m, 2H), 1.44 (m, 4H), 0.94 (m, 3H). LCMS calculated for C$_{18}$H$_{20}$BrN$_6$O$_2$ (M+H): 431.1. Found 431.1.

Example 34

7-bromo-9-pentyl-3-(4-(trifluoromethyl)phenyl)-6,9-dihydro-5H-[1,2,4]triazolo[4,3-a]purin-5-one

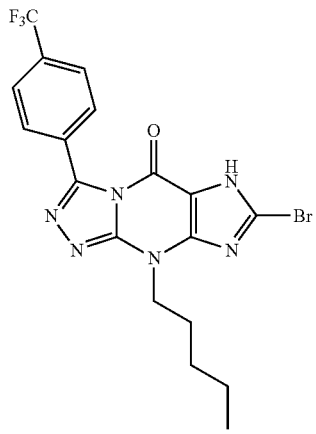 [SMILES: CCCCCn1c2nc(Br)[nH]c2c(=O)n2c(-c3ccc(C(F)(F)F)cc3)nnc12]

The title compound was prepared using procedures analogous to those described for Example 16. $^1$HNMR (300 MHz, CD$_3$OD): δ 7.94 (d, J=8.6 Hz, 2H), 7.78 (d, J=9.2 Hz, 2H), 4.44 (t, J=7.3 Hz, 2H), 1.97 (m, 2H), 1.44 (m, 4H), 0.94 (m, 3H). LCMS calculated for C$_{18}$H$_{16}$BrF$_3$N$_6$O (M+H): 469.1. Found 469.1.

Example 35

7-bromo-3-(4-methoxybenzyl)-9-pentyl-6,9-dihydro-5H-[1,2,4]triazolo[4,3-a]purin-5-one

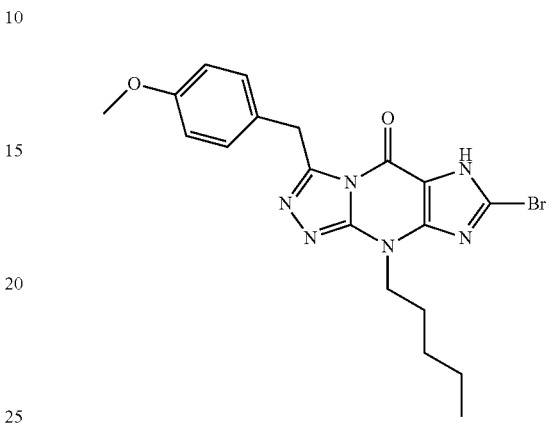

Step A: 2-(4-methoxyphenyl)-N'-[(2E)-6-oxo-3-pentyl-1,3,6,7-tetrahydro-2H-purin-2-ylidene]acetohydrazide The mixture of (2E)-3-pentyl-3,7-dihydro-1H-purine-2,6-dione 2-hydrazone (0.30 g, 1.3 mmol), benzeneacetic acid, 4-methoxy- (0.23 g, 1.4 mmol), benzotriazol-1-yloxytris-(dimethylamino)phosphonium hexafluorophosphate (0.62 g, 1.40 mol) and triethylamine (0.53 mL, 3.8 mmol) in DMF (10 mL) were stirred at room temperature overnight. The reaction mixture was diluted with ethyl acetate and washed sat. NaHCO$_3$. The aqueous was extracted with ethyl acetate (3×). The combined organic layers were dried (MgSO$_4$), filtered and concentrated to yield the desired product (560 mg, 98%). LCMS calculated for C$_{19}$H$_{25}$N$_6$O$_3$ (M+H): 385.2. Found: 385.2.

Step B: 3-(4-methoxybenzyl)-9-pentyl-6,9-dihydro-5H-[1,2,4]triazolo[4,3-a]purin-5-one

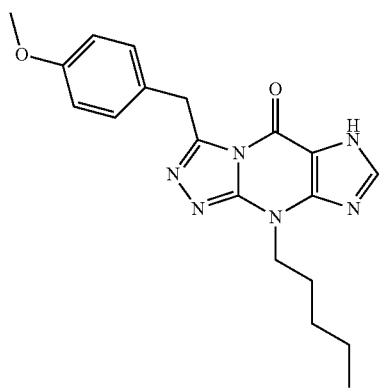 [SMILES: CCCCCn1c2nc[nH]c2c(=O)n2c(Cc3ccc(OC)cc3)nnc12]

The mixture of 2-(4-methoxyphenyl)-N'-[(2E)-6-oxo-3-pentyl-1,3,6,7-tetrahydro-2H-purin-2-ylidene]acetohydrazide (0.66 g, 1.4 mmol) in toluene (30 mL) was refluxed overnight. The reaction mixture was concentrated to give the crude product as a solid. The solid was washed with ethyl acetate and dried to yield the desired product (490 mg, 92%). LCMS calculated for $C_{19}H_{23}N_6O_2$ (M+H): 367.2. Found: 367.2.

Step C: 7-bromo-3-(4-methoxybenzyl)-9-pentyl-6,9-dihydro-5H-[1,2,4]triazolo[4,3-a]purin-5-one

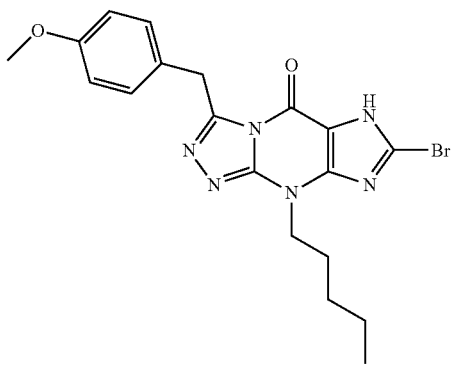 [SMILES: CCCCCn1c2nc(Br)[nH]c2c(=O)n2c(Cc3ccc(OC)cc3)nnc12]

To the solution of 3-(4-methoxybenzyl)-9-pentyl-6,9-dihydro-5H-[1,2,4]triazolo[4,3-a]purin-5-one (0.40 g, 1.1 mmol) in THF was added N-Bromosuccinimide (0.29 g, 1.6 mol). The mixture was stirred at 70° C. for 1 hour. The mixture was concentrated and purified by preparative LCMS to yield the desired product (290 mg, 60%). $^1$HNMR (300 MHz, $d_6$-DMSO): δ 7.16 (d, J=8.3 Hz, 2H), 6.81 (d, J=8.3 Hz, 2H), 4.46 (s, 3H), 4.20 (t, J=7.2 Hz, 2H), 3.67 (s, 2H), 1.79 (m, 2H), 1.28 (m, 4H), 0.83 (m, 3H). LCMS calculated for $C_{19}H_{21}BrN_6O_2$ (M+H): 445.1. Found: 445.0, 447.0.

Example 36

7-bromo-9-pentyl-3-(3-bromobenzyl)-6,9-dihydro-5H-[1,2,4]triazolo[4,3-a]purin-5-one

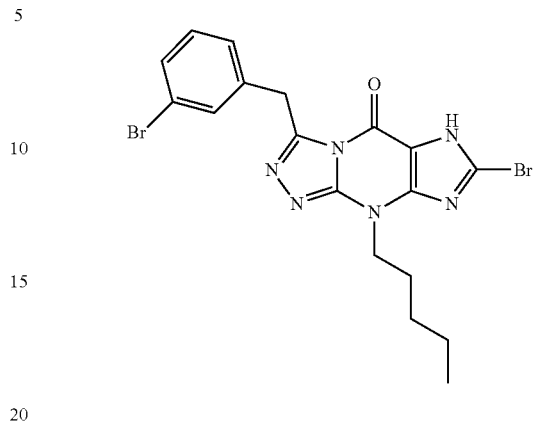

Step A: 2-(3-bromophenyl)-N'-[(2E)-6-oxo-3-pentyl-1,3,6,7-tetrahydro-2H-purin-2-ylidene]acetohydrazide The mixture of (2E)-3-pentyl-3,7-dihydro-1H-purine-2,6-dione 2-hydrazone (0.30 g, 1.3 mmol), (3-bromophenyl)acetic acid (0.30 g, 1.4 mol), benzotriazol-1-yloxytris-(dimethylamino)phosphonium hexafluorophosphate (0.62 g, 1.4 mol) and triethylamine (0.53 mL, 3.8 mmol) in DMF (10 mL) were stirred at rt overnight. The reaction mixture was diluted with EtOAc. The solid was filtered, washed with EA and dried to yield the desired product (430 mg, 78.2%). LCMS calculated for $C_{18}H_{22}BrN_6O_2$ (M+H): 433.1. Found: 433.1.

Step B: 3-(3-bromobenzyl)-9-pentyl-6,9-dihydro-5H-[1,2,4]triazolo[4,3-a]purin-5-one

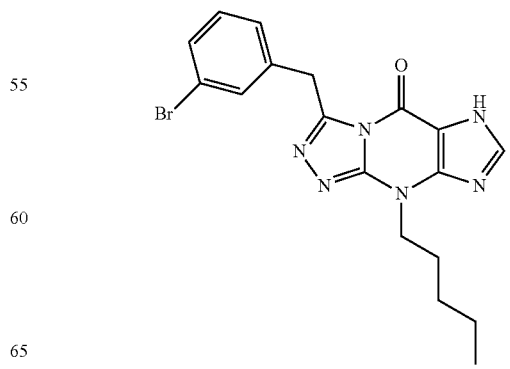

The mixture of 2-(3-bromophenyl)-N'-[(2E)-6-oxo-3-pentyl-1,3,6,7-tetrahydro-2H-purin-2-ylidene]acetohydrazide (1.8 g, 4.2 mmol) in benzene (100 mL) was refluxed overnight. The reaction mixture was concentrated to give the desired product 1.5 g. LCMS calculated for $C_{18}H_{20}BrN_6O$ (M+H): 415.1. Found: 415.1.

Step C: 7-bromo-9-pentyl-3-(3-bromobenzyl)-6,9-dihydro-5H-[1,2,4]triazolo[4,3-a]purin-5-one

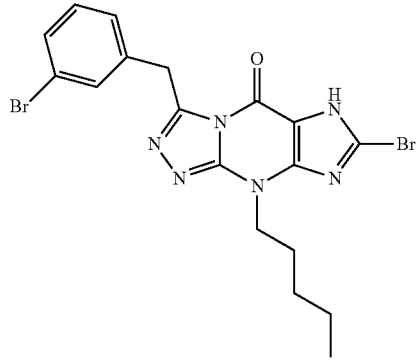 [SMILES: CCCCCn1c2nc(Br)[nH]c2c(=O)n2c(Cc3cccc(Br)c3)nnc12]

To the solution of 3-(3-bromobenzyl)-9-pentyl-6,9-dihydro-5H-[1,2,4]triazolo[4,3-a]purin-5-one (210 mg, 0.50 mmol) in tetrahydrofuran (20 mL) was added N-bromosuccinimide (140 mg, 0.00076 mol). The mixture was stirred at 70° C. for 1 hour. The reaction mixture was concentrated and the residue was purified by preparative LCMS to yield the desired product (0.15 g, 60%). $^1$HNMR (300 MHz, $d_6$-DMSO): δ 7.16 (d, J=8.3 Hz, 2H), 6.81 (d, J=8.3 Hz, 2H), 4.46 (s, 3H), 4.20 (t, J=7.2 Hz, 2H), 3.67 (s, 2H), 1.79 (m, 2H), 1.28 (m, 4H), 0.83 (m, 3H). LCMS calculated for $C_{18}H_{19}Br_2N_6O$ (M+H): 493. Found: 493, 495 and 497.

Example 37

7-bromo-9-pentyl-3-(3-pyrimidin-5-ylbenzyl)-6,9-dihydro-5H-[1,2,4]triazolo[4,3-a]purin-5-one trifluoroacetate

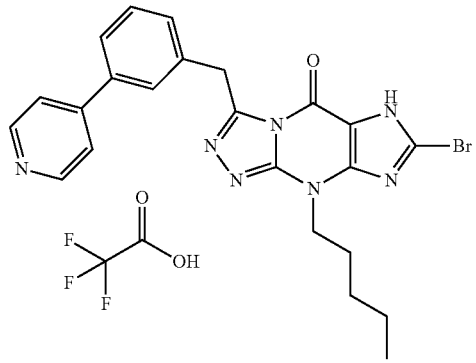 [SMILES: CCCCCn1c2nc(Br)[nH]c2c(=O)n2c(Cc3cccc(-c4ccncc4)c3)nnc12 ; O=C(O)C(F)(F)F]

The title compound was prepared using procedures analogous to those described for Example 35. LCMS calculated for $C_{23}H_{21}BrN_8O$ (M+H): 493.1. Found: 493.1, 495.1.

Example 38

7-bromo-9-pentyl-3-pyrimidin-4-yl-6,9-dihydro-5H-[1,2,4]triazolo[4,3-a]purin-5-one

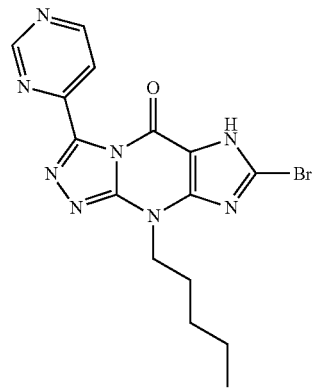 [SMILES: CCCCCn1c2nc(Br)[nH]c2c(=O)n2c(-c3ccncn3)nnc12]

The title compound was prepared using procedures analogous to those described for Example 35. $^1$HNMR (400 MHz, CD$_3$OD): δ 9.30 (d, J=1.3 Hz, 1H), 8.96 (d, J=5.2 Hz, 1H), 7.96 (d, J=5.3, 1.3 Hz, 1H), 4.47 (t, J=7.4 Hz, 2H), 1.99 (m, 2H), 1.46 (m, 4H), 0.96 (m, 3H). LCMS calculated for $C_{15}H_{15}BrN_8O$ (M+H): 403.1. Found: 403.1, 405.1.

Example 39

7-bromo-9-pentyl-3-pyrazin-2-yl-6,9-dihydro-5H-[1,2,4]triazolo[4,3-a]purin-5-one trifluoroacetate

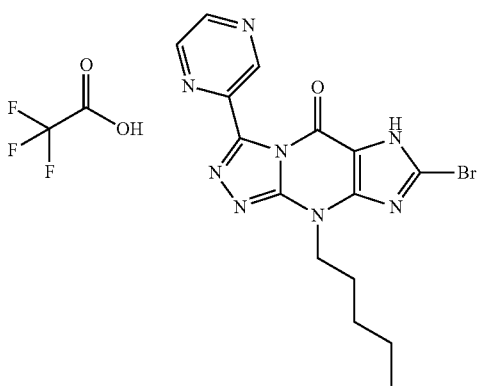 [SMILES: O=C(O)C(F)(F)F ; CCCCCn1c2nc(Br)[nH]c2c(=O)n2c(-c3cnccn3)nnc12]

The title compound was prepared using procedures analogous to those described for Example 35. $^1$HNMR (400 MHz, CD$_3$OD): δ 9.30-9.25 (d, J=1.0 Hz, 1H), 8.95-8.90 (dd, J=1.0, 3.0 Hz, 1H), 7.95-7.91 (dd, J=1.0, 3.0 Hz, 1H), 4.50-4.40 (m, 2H), 2.00-1.90 (m, 2H), 1.48-1.40 (m, 4H), 0.95-0.90 (m, 3H). LCMS calculated for $C_{15}H_{15}BrN_8O$ (M+H): 403.1. Found: 403.1, 405.1.

Example 40

7-bromo-3-cyclopropyl-9-pentyl-6,9-dihydro-5H-[1,2,4]triazolo[4,3-a]purin-5-one

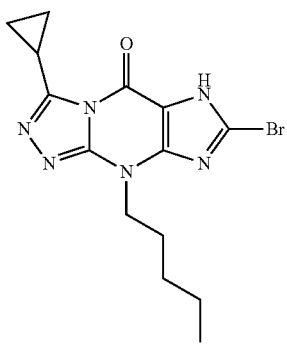 [SMILES: CCCCCn1c2nc(Br)[nH]c2c(=O)n2c(C3CC3)nnc12]

The title compound was prepared using procedures analogous to those described for Example 16. $^1$HNMR (300 MHz, $d_6$-DMSO): δ 4.18 (t, J=7.6 Hz, 3H), 2.82 (m, 1H), 1.77 (m, 2H), 1.28 (m, 4H), 0.99 (m, 4H), 0.83 (m, 3H). LCMS calculated for $C_{14}H_{17}BrN_6O$ (M+H): 365.1. Found: 365.1, 365.1.

Example 41

7-bromo-3-(dimethylamino)-9-pentyl-6,9-dihydro-5H-[1,2,4]triazolo[4,3-a]purin-5-one trifluoracetate

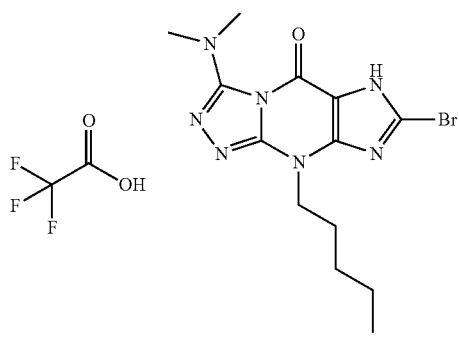 [SMILES: O=C(O)C(F)(F)F ; CCCCCn1c2nc(Br)[nH]c2c(=O)n2c(N(C)C)nnc12]

Step A: 3-(dimethylamino)-9-pentyl-6,9-dihydro-5H-[1,2,4]triazolo[4,3-a]purin-5-one

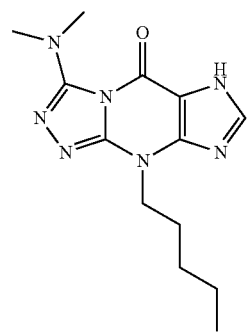 [SMILES: CCCCCn1c2nc[nH]c2c(=O)n2c(N(C)C)nnc12]

To methylene chloride (10 mL) was added [B] N-(dichloromethylene)-N-methylmethanaminium chloride (0.21 g, 1.3 mmol) After stirring for 5 mins, (2Z)-3-pentyl-3,7-dihydro-1H-purine-2,6-dione 2-hydrazone (0.10 g, 0.42 mmol) was added, and the mixture was stirred at rt for 5 hrs. LCMS analysis showed product as a major peak was formed. 1N NaoH was carefully added to neutralize the acid, and the mixture was extracted with methylene chloride three times. The combined organic layers were dried by MgSO$_4$, filtered and concentrated in vacuo to yield the desired product (84 mg, 69%). LCMS calculated for $C_{13}H_{20}N_7O$ (M+H): 290.2. Found 290.1.

Step B: 7-bromo-3-(dimethylamino)-9-pentyl-6,9-dihydro-5H-[1,2,4]triazolo[4,3-a]purin-5-one trifluoroacetate

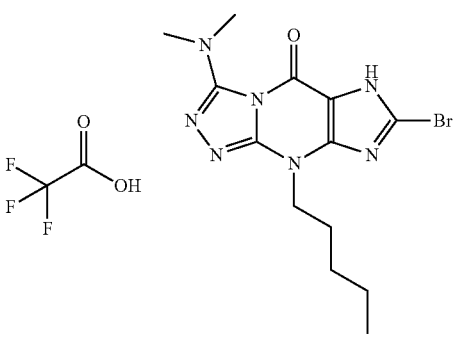 [SMILES: O=C(O)C(F)(F)F ; CCCCCn1c2nc(Br)[nH]c2c(=O)n2c(N(C)C)nnc12]

To a mixture of 3-(dimethylamino)-9-pentyl-6,9-dihydro-5H-[1,2,4]triazolo[4,3-a]purin-5-one (80 mg, 0.28 mmol) in Tetrahydrofuran (20 mL) was added N-Bromosuccinimide (59 mg, 0.33 mol). The mixture was stirred at 70° C. for 1 hour. The reaction mixture was concentrated and purified by preparative LCMS to provide the desired product. LCMS calculated for $C_{13}H_{19}BrN_7O$ (M+H): 368.1. Found: 368.0, 370.0.

Example 42

7-bromo-9-pentyl-3-(3,3,3-trifluoropropyl)-6,9-dihydro-5H-[1,2,4]triazolo[4,3-a]purin-5-one

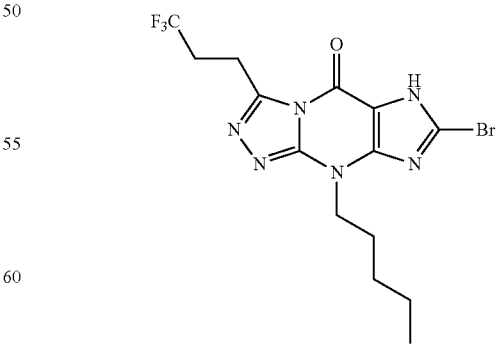

The title compound was prepared using procedures analogous to those described for Example 16. LCMS calculated for $C_{14}H_{16}BrF_3N_6O$ (M+H): 421.1. Found: 421.1, 423.1.

Example 43

7-bromo-9-pentyl-3-(2-phenylethyl)-6,9-dihydro-5H-[1,2,4]triazolo[4,3-a]purin-5-one

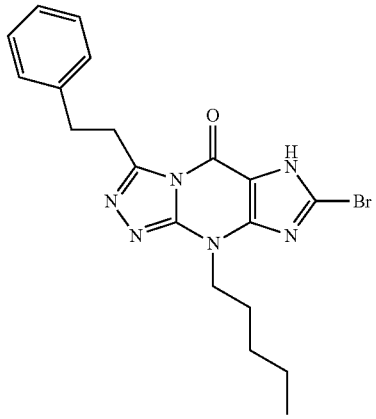 [SMILES: CCCCCn1c2nc(Br)[nH]c2c(=O)n2c(CCc3ccccc3)nnc12]

The title compound was prepared using procedures analogous to those described for Example 16. ¹HNMR (300 MHz, CD$_3$OD): δ 7.23 (m, 5H), 4.32 (t, J=8.0 Hz, 2H), 3.53 (t, J=8.0 Hz, 2H), 3.11 (t, J=8.0 Hz, 2H), 1.90 (m, 2H), 1.40 (m, 4H), 0.92 (m, 3H). LCMS calculated for C$_{19}$H$_{21}$BrN$_6$O (M+H): 429.1. Found: 429.1, 431.1.

Example 44

7-bromo-9-pentyl-3-(trifluoromethyl)-6,9-dihydro-5H-[1,2,4]triazolo[4,3-a]purin-5-one

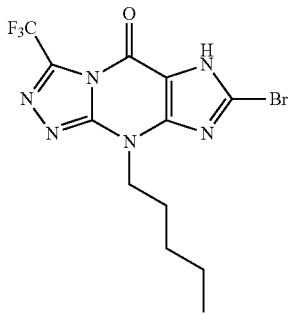 [SMILES: CCCCCn1c2nc(Br)[nH]c2c(=O)n2c(C(F)(F)F)nnc12]

Step A: 9-pentyl-3-(trifluoromethyl)-6,9-dihydro-5H-[1,2,4]triazolo[4,3-a]purin-5-one

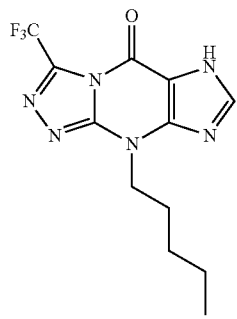

The mixture of (2E)-3-pentyl-3,7-dihydro-1H-purine-2,6-dione 2-hydrazone (200 mg, 0.85 mol) in trifluoroacetic acid (10 mL) was refluxed overnight. The reaction mixture was concentrated and purified by preparative LCMS to yield the desired product (160 mg, 60.2%). LCMS calculated for C$_{12}$H$_{14}$F$_3$N$_6$O (M+H): 315.1. Found 315.0.

Step B: 7-bromo-9-pentyl-3-(trifluoromethyl)-6,9-dihydro-5H-[1,2,4]triazolo[4,3-a]purin-5-one

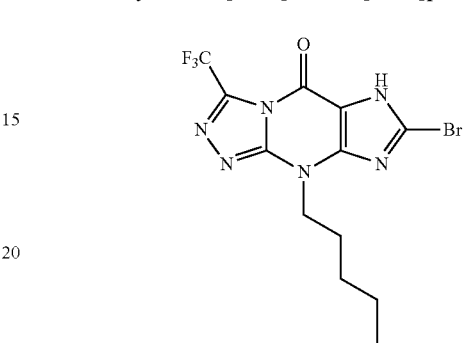

To the mixture of 9-pentyl-3-(trifluoromethyl)-6,9-dihydro-5H-[1,2,4]triazolo[4,3-a]purin-5-one (50 mg, 0.16 mmol) in tetrahydrofuran (10 mL) was added N-bromosuccinimide (42 mg, 0.24 mmol). The mixture was stirred at 70° C. for 3 hour. The reaction mixture was concentrated and purified by preparative LCMS to yield the desired product. ¹HNMR (300 MHz, CD$_3$OD): δ 4.44 (t, J=7.6 Hz, 2H), 1.94 (m, 2H), 1.42 (m, 4H), 0.93 (m, 3H). LCMS calculated for C$_{12}$H$_{13}$BrF$_3$N$_6$O (M+H): 393.0. Found: 393.0, 395.0.

Example 45

7-bromo-9-pentyl-3-(pyridine-4-ylmethyl)-6,9-dihydro-5H-[1,2,4]triazolo[4,3-a]purin-5-one trifluoroacetate

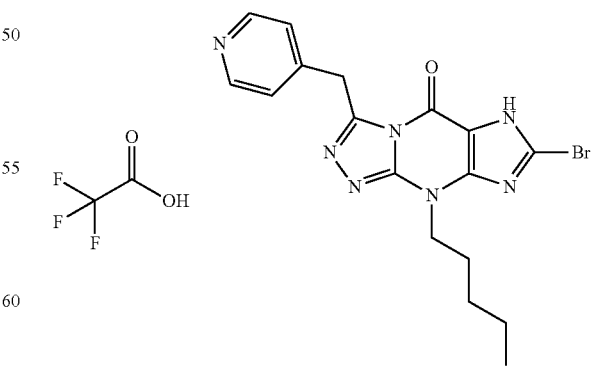

The title compound was prepared using procedures analogous to those described for Example 35. LCMS calculated for C$_{17}$H$_{18}$BrN$_7$O (M+H): 416.1. Found: 416, 418.

Example 46

7-bromo-9-pentyl-3-(2-pyridine-3-ylethyl)-6,9-dihydro-5H-[1,2,4]triazolo[4,3-a]purin-5-one trifluoroacetate

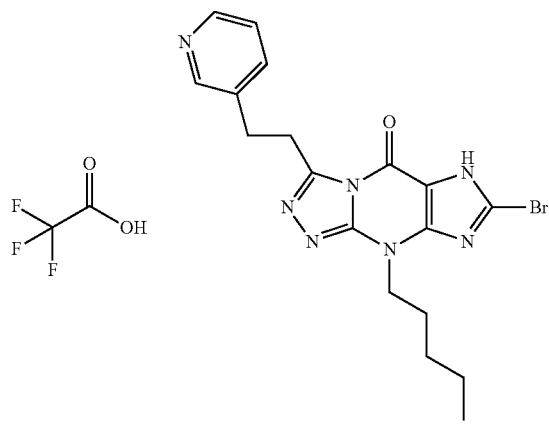 [SMILES: O=C(O)C(F)(F)F ; CCCCCn1c2nc(Br)[nH]c2c(=O)n2c(CCc3cccnc3)nnc12]

The title compound was prepared using procedures analogous to those described for Example 35. LCMS calculated for $C_{18}H_{20}BrN_7O$ (M+H): 429.1. Found: 430.0, 432.0.

Example 47

7-bromo-9-pentyl-3-(1-phenylcyclopropyl)-6,9-dihydro-5H-[1,2,4]triazolo[4,3-a]purin-5-one

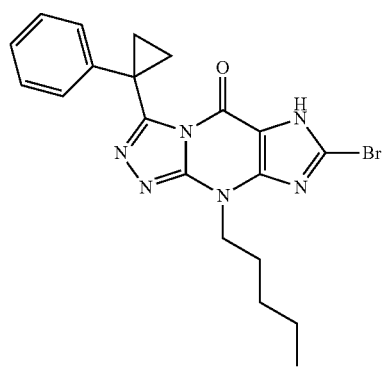 [SMILES: CCCCCn1c2nc(Br)[nH]c2c(=O)n2c(C3(c4ccccc4)CC3)nnc12]

The title compound was prepared using procedures analogous to those described for Example 35. LCMS calculated for $C_{20}H_{21}BrN_6O$ (M+H): 441.1. Found: 441.0, 443.0.

Example 48

7-bromo-3-(2-methylpyridin-4-yl)-9-pentyl-6,9-dihydro-5H-[1,2,4]triazolo[4,3-a]purin-5-one trifluoroacetate

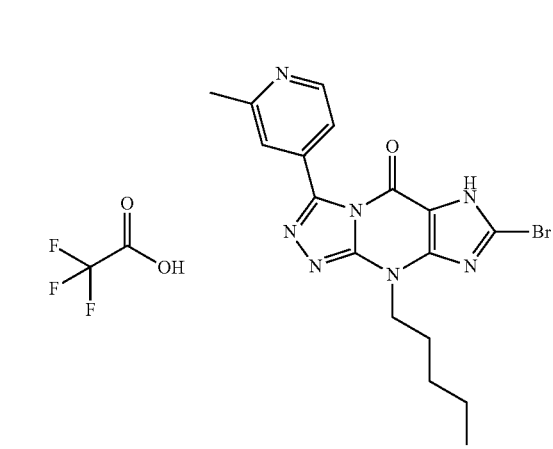 [SMILES: O=C(O)C(F)(F)F ; CCCCCn1c2nc(Br)[nH]c2c(=O)n2c(-c3ccnc(C)c3)nnc12]

The title compound was prepared using procedures analogous to those described for Example 16. LCMS calculated for $C_{17}H_{18}BrN_7O$ (M+H): 416.1. Found: 416.0, 418.0.

Example 49

7-bromo-3-(3-fluoropyridin-4-yl)-9-pentyl-6,9-dihydro-5H-[1,2,4]triazolo[4,3-a]purin-5-one trifluoroacetate

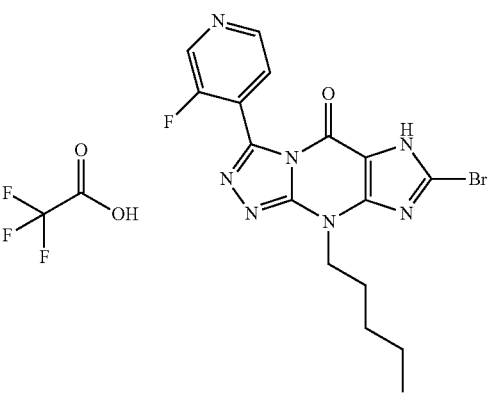 [SMILES: O=C(O)C(F)(F)F ; CCCCCn1c2nc(Br)[nH]c2c(=O)n2c(-c3ccncc3F)nnc12]

The title compound was prepared using procedures analogous to those described for Example 16. LCMS calculated for $C_{16}H_{15}BrFN_7O$ (M+H): 421.1. Found: 421.0, 423.0.

Example 50

7-bromo-3-(3-fluorobenzyl)-9-pentyl-6,9-dihydro-5H-[1,2,4]triazolo[4,3-a]purin-5-one

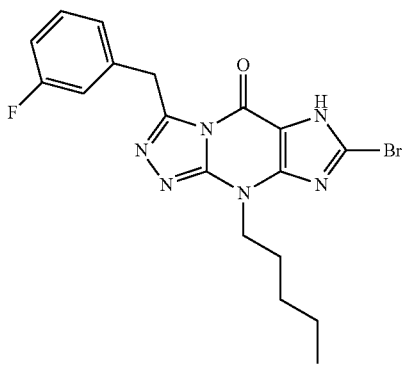 [SMILES: CCCCCn1c2nc(Br)[nH]c2c(=O)n2c(Cc3cccc(F)c3)nnc12]

The title compound was prepared using procedures analogous to those described for Example 35. LCMS calculated for $C_{18}H_{18}BrFN_6O$ (M+H): 433.1. Found: 433.0, 435.0.

Example 51

7-bromo-3-(3-methoxybenzyl)-9-pentyl-6,9-dihydro-5H-[1,2,4]triazolo[4,3-a]purin-5-one

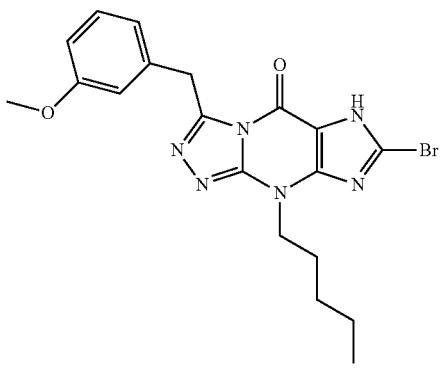 [SMILES: CCCCCn1c2nc(Br)[nH]c2c(=O)n2c(Cc3cccc(OC)c3)nnc12]

The title compound was prepared using procedures analogous to those described for Example 35. LCMS calculated for $C_{19}H_{21}BrN_6O_2$ (M+H): 445.1. Found: 445.1, 447.0.

Example 52

7-bromo-3-(1,3-oxazol-4-yl)-9-pentyl-6,9-dihydro-5H-[1,2,4]triazolo[4,3-a]purin-5-one

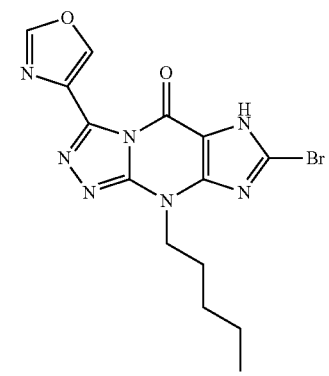 [SMILES: CCCCCn1c2nc(Br)[nH]c2c(=O)n2c(-c3cocn3)nnc12]

The title compound was prepared using procedures analogous to those described for Example 35. $^1$HNMR (300 MHz, CD$_3$OD): δ 8.68 (d, J=0.9 Hz, 1H), 8.33 (d, J=0.9 Hz, 1H), 4.40 (t, J=7.3 Hz, 2H), 1.95 (m, 2H), 1.42 (m, 4H), 0.93 (m, 3H). LCMS calculated for $C_{14}H_{14}BrN_7O_2$ (M+H): 392.1. Found: 392.0, 394.0.

Example 53

7-bromo-3-isoxazol-3-yl-9-pentyl-6,9-dihydro-5H-[1,2,4]triazolo[4,3-a]purin-5-one

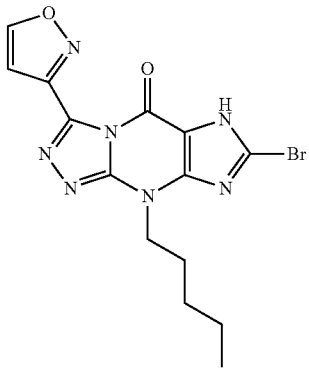 [SMILES: CCCCCn1c2nc(Br)[nH]c2c(=O)n2c(-c3ccon3)nnc12]

The title compound was prepared using procedures analogous to those described for Example 35. $^1$HNMR (300 MHz, CD$_3$OD): δ 8.85 (d, J=1.8 Hz, 1H), 6.97 (d, J=1.8 Hz, 1H), 4.45 (t, J=7.5 Hz, 2H), 1.96 (m, 2H), 1.43 (m, 4H), 0.94 (m, 3H). LCMS calculated for $C_{14}H_{14}BrN_7O_2$ (M+H): 392.1. Found: 392.0, 394.0.

Example 54

7-bromo-3-(1-methyl-1H-imidazol-2-yl)-9-pentyl-6,9-dihydro-5H-[1,2,4]triazolo[4,3-a]purin-5-one trifluoroacetate

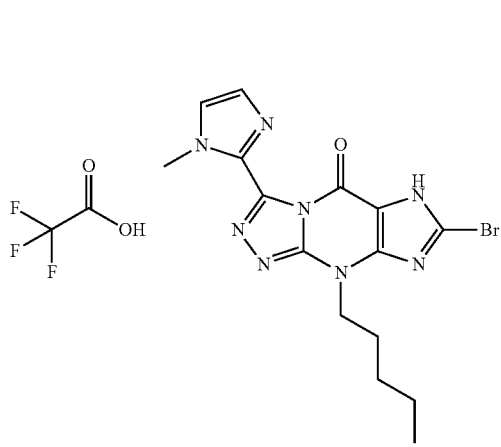 [SMILES: O=C(O)C(F)(F)F ; CCCCCn1c2nc(Br)[nH]c2c(=O)n2c(-c3nccn3C)nnc12]

The title compound was prepared using procedures analogous to those described for Example 35. LCMS calculated for $C_{15}H_{17}BrN_8O$ (M+H): 405.1. Found: 405.0, 407.0.

Example 55

7-bromo-9-pentyl-3-(3-pyridin-4-ylbenzyl)-6,9-dihydro-5H-[1,2,4]triazolo[4,3-a]purin-5-one trifluoroacetate

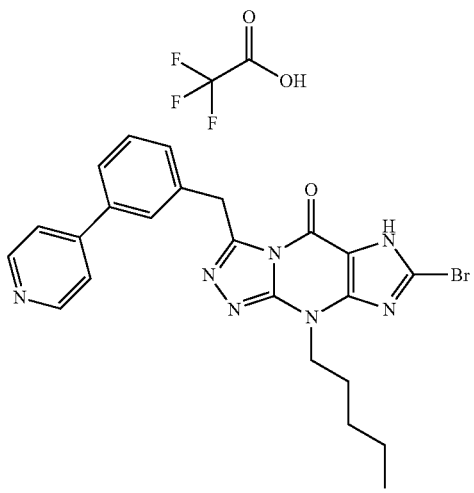

The title compound was prepared using procedures analogous to those described for Example 35. LCMS calculated for $C_{23}H_{22}BrN_7O$ (M+H): 492.1. Found: 492.1, 494.1.

Example 56

7-bromo-3-(2-methoxybenzyl)-9-pentyl-6,9-dihydro-5H-[1,2,4]triazolo[4,3-a]purin-5-one

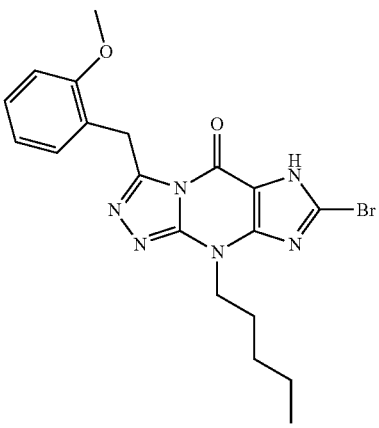 [SMILES: CCCCCn1c2nc(Br)[nH]c2c(=O)n2c(Cc3ccccc3OC)nnc12]

The title compound was prepared using procedures analogous to those described for Example 35. LCMS calculated for $C_{19}H_{21}BrN_6O_2$ (M+H): 445.1. Found: 445.0, 447.0.

Example 57

1-(7-bromo-5-oxo-9-pentyl-6,9-dihydro-5H-[1,2,4]triazolo[4,3-a]purin-3-yl)cyclopropanecarboxamide

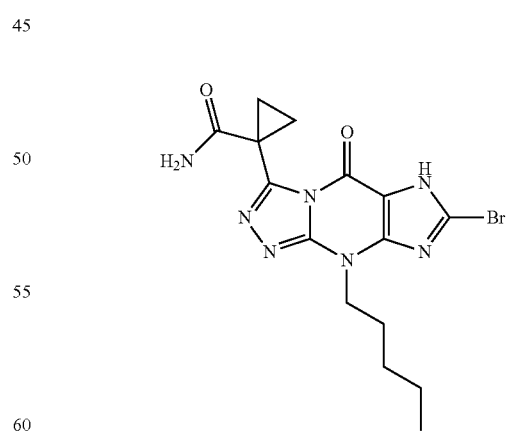

The title compound was prepared using procedures analogous to those described for Example 35. $^1$HNMR (300 MHz, CD$_3$OD): δ 4.35 (t, J=7.0 Hz, 2H), 1.92 (m, 2H), 1.68 (m, 2H), 1.51 (m, 2H), 1.43 (m, 4H), 0.94 (m, 3H). LCMS calculated for $C_{15}H_{18}BrN_7O_2$ (M+H): 408.1. Found: 408.0, 410.0.

Example 58

1-(7-bromo-5-oxo-9-pentyl-6,9-dihydro-5H-[1,2,4]triazolo[4,3-a]purin-3-yl)cyclopropanecarboxylic acid

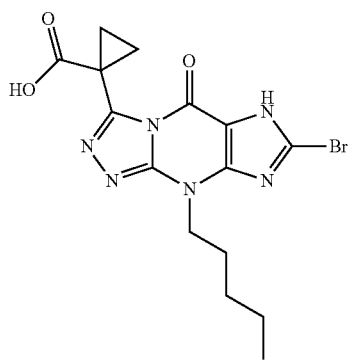 [SMILES: CCCCCn1c2nc(Br)[nH]c2c(=O)n2c(C3(C(=O)O)CC3)nnc12]

The title compound was prepared using procedures analogous to those described for Example 35. $^1$HNMR (300 MHz, CD$_3$OD): δ 4.35 (t, J=7.3 Hz, 2H), 1.91 (m, 2H), 1.72 (m, 2H), 1.62 (m, 2H), 1.41 (m, 4H), 0.92 (m, 3H). LCMS calculated for C$_{15}$H$_{17}$BrN$_6$O$_3$ (M+H): 409.1. Found: 409.0, 411.0.

Example 59

7-bromo-9-pentyl-3-[1-(trifluoromethyl)cyclopropyl]-6,9-dihydro-5H-[1,2,4]triazolo[4,3-a]purin-5-one

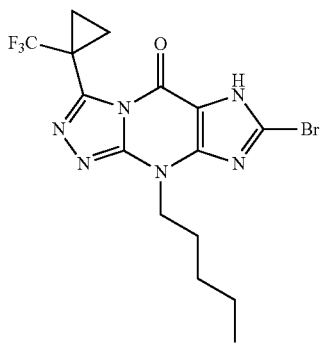 [SMILES: CCCCCn1c2nc(Br)[nH]c2c(=O)n2c(C3(C(F)(F)F)CC3)nnc12]

The title compound was prepared using procedures analogous to those described for Example 35. $^1$HNMR (300 MHz, CD$_3$OD): δ 4.37 (t, J=7.7 Hz, 2H), 1.91 (m, 2H), 1.62 (m, 2H), 1.54 (m, 2H), 1.41 (m, 4H), 0.92 (m, 3H). LCMS calculated for C$_{15}$H$_{16}$BrF3N$_6$O (M+H): 433.1. Found: 433.0, 435.0.

Example 60

7-bromo-3-(2,3-dihydro-1,4-benzodioxin-6-ylmethyl)-9-pentyl-6,9-dihydro-5H-[1,2,4]triazolo[4,3-a]purin-5-one

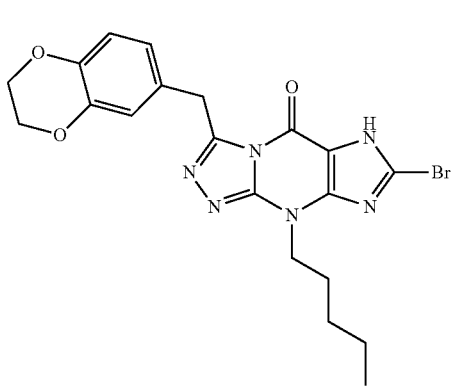 [SMILES: CCCCCn1c2nc(Br)[nH]c2c(=O)n2c(Cc3ccc4c(c3)OCCO4)nnc12]

The title compound was prepared using procedures analogous to those described for Example 35. $^1$HNMR (300 MHz, d$_6$-DMSO): δ 6.71 (m, 3H), 4.41 (s, 2H), 4.20 (t, J=7.7 Hz, 2H), 4.15 (s, 4H), 1.79 (m, 2H), 1.29 (m, 4H), 0.84 (m, 3H). LCMS calculated for C$_{20}$H$_{21}$BrN$_6$O$_3$ (M+H): 473.1. Found: 473.0, 475.0.

Example 61

7-bromo-3-[(3-oxo-3,4-dihydro-2H-1,4-benzoxazin-6-yl)methyl])-9-pentyl-6,9-dihydro-5H-[1,2,4]triazolo[4,3-a]purin-5-one

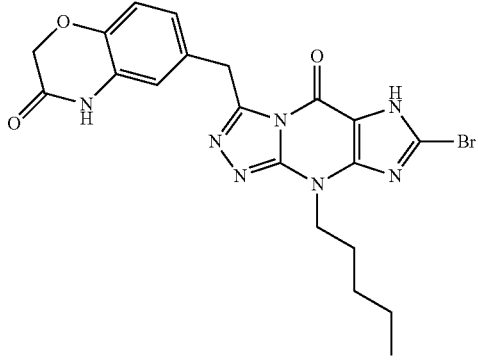 [SMILES: CCCCCn1c2nc(Br)[nH]c2c(=O)n2c(Cc3ccc4c(c3)NC(=O)CO4)nnc12]

The title compound was prepared using procedures analogous to those described for Example 35. LCMS calculated for C$_{20}$H$_{20}$BrN$_7$O$_3$ (M+H): 486.1. Found: 486.0, 488.0.

Example 62

3-Benzyl-7-bromo-9-pentyl-6,9-dihydro-5H-[1,2,4]triazolo[4,3-a]purin-5-one

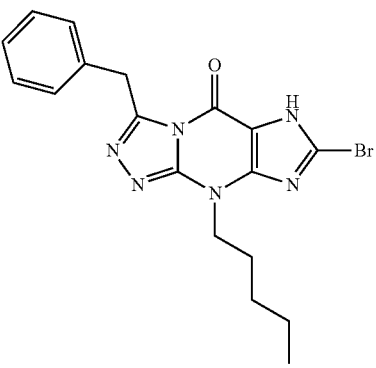 [SMILES: CCCCCn1c2nc(Br)[nH]c2c(=O)n2c(Cc3ccccc3)nnc12]

The title compound was prepared using procedures analogous to those described for Example 16. LCMS calculated for $C_{18}H_{19}BrN_6O$ (M+H): 415.1. Found: 415.0, 417.0.

Example 63

7-bromo-3-ethyl-9-pentyl-6,9-dihydro-5H-[1,2,4]triazolo[4,3-a]purin-5-one

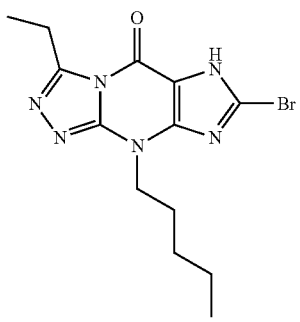 [SMILES: CCCCCn1c2nc(Br)[nH]c2c(=O)n2c(CC)nnc12]

The title compound was prepared using procedures analogous to those described for Example 5. $^1$HNMR (400 MHz, $d_6$-DMSO): δ 4.18 (t, J=7.0 Hz, 2H), 3.33 ((br, 1H), 3.14 (dd, J=7.5 Hz, 2H), 1.78 (m, 2H), 1.27 (m, 7H), 0.83 (m, 3H). LCMS calculated for $C_{18}H_{19}BrN_6O$ (M+H): 353.1. Found: 353.0, 353.0.

Example 64

6-bromo-4-pentyl-4,7-dihydro-8H-tetrazolo[1,5-a]purin-8-one

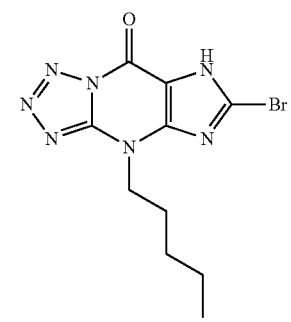 [SMILES: CCCCCn1c2nc(Br)[nH]c2c(=O)n2nnnc12]

Step A: 4-pentyl-4,7-dihydro-8H-tetrazolo[1,5-c]purin-8-one

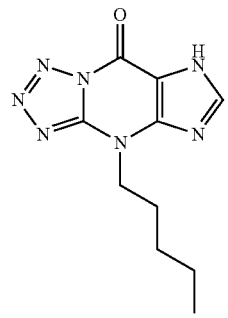 [SMILES: CCCCCn1c2nc[nH]c2c(=O)n2nnnc12]

A saturated aqueous $NaNO_2$ (130 mg, 1.89 mmol) solution was added dropwise to a solution of (2E)-3-pentyl-3,7-dihydro-1H-purine-2,6-dione 2-hydrazone (150 mg, 0.63 mmol) in 5% aqueous HCl solution (3 ml) under stirring at room temperature. The mixture was stirred at room temperature for 1 hour. The mixture was neutralized by saturated $NaHCO_3$ solution and extracted by ethyl acetate (3×). The combined organic phases were washed by brine and dried over $MgSO_4$. The filtration and evaporation of solvent gave the desired product (94.6 mg, 60.7%) as white solid. LCMS calculated for $C_{10}H_{14}N_7O$ (M+H): 248.1. Found: 248.0.

Step B: 6-bromo-4-pentyl-4,7-dihydro-8H-tetrazolo[1,5-c]purin-8-one

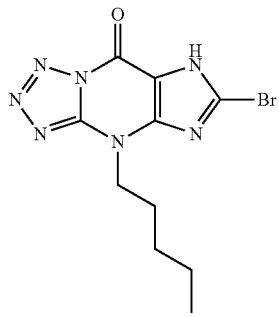 [SMILES: CCCCCn1c2nc(Br)[nH]c2c(=O)n2nnnc12]

The mixture of 4-pentyl-4,7-dihydro-8H-tetrazolo[1,5-a]purin-8-one (94.6 mg, 0.38 mmol) and NBS (75 mg, 0.42 mmol) in THF (20 ml) was stirred at 70° C. for 1 hour. After evaporation of solvent, the residue was purified by preparative LC-MS to yield the desired product (17.1 mg, 13.7%). LCMS calculated for $C_{10}H_{13}BrN_7O$ (M+H): 326.0. Found: 326.0.

Example 65

3-(7-bromo-5-oxo-9-pentyl-6,9-dihydro-5H-[1,2,4]triazolo[4,3-a]purin-3-yl)propanoic acid

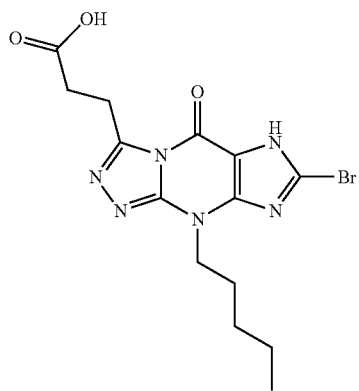 [SMILES: CCCCCn1c2nc(Br)[nH]c2c(=O)n2c(CCC(=O)O)nnc12]

Step A: (4E)-4-[(2E)-(6-oxo-3-pentyl-1,3,6,7-tetrahydro-2H-purin-2-ylidene)hydrazono]butanoic acid

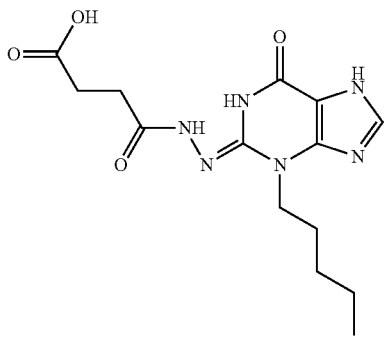 [SMILES: CCCCCn1/c(=N/NC(=O)CCC(=O)O)[nH]c(=O)c2[nH]cnc21]

The mixture of (2E)-3-pentyl-3,7-dihydro-1H-purine-2,6-dione 2-hydrazone (1.0 g, 4.2 mmol) and 4-oxobutanoic acid (3.4 g, 15% in water, 5.1 mmol) in EtOH (70 ml) was refluxed for 1.5 hours. Evaporation of solvent gave the desired product (1.3 g, 96%) as a yellowish solid. LCMS calculated for $C_{14}H_{21}N_6O_3$ (M+H): 321.1. Found: 321.1.

Step B: 3-(5-oxo-9-pentyl-6,9-dihydro-5H-[1,2,4]triazolo[4,3-a]purin-3-yl)propanoic acid

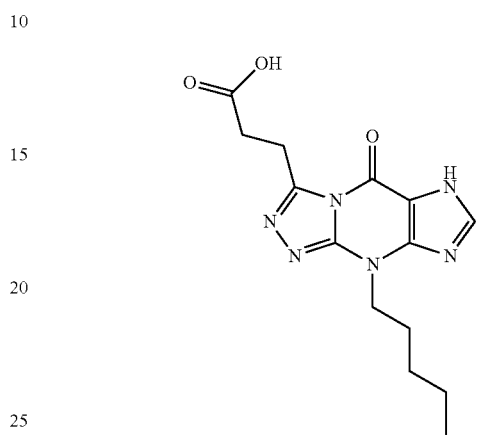

The mixture of (4E)-4-[(2E)-(6-oxo-3-pentyl-1,3,6,7-tetrahydro-2H-purin-2-ylidene)hydrazono]butanoic acid (1.367 g, 5.1 mmol) in acetic acid (70 ml) was refluxed for 1 hour. Evaporation of solvent afforded the desired product (1.29 g, 99%) as yellowish solid. LCMS calculated for $C_{14}H_{19}N_6O_3$ (M+H): 319.2. Found: 319.2.

Step C: 3-(7-bromo-5-oxo-9-pentyl-6,9-dihydro-5H-[1,2,4]triazolo[4,3-a]purin-3-yl)propanoic acid

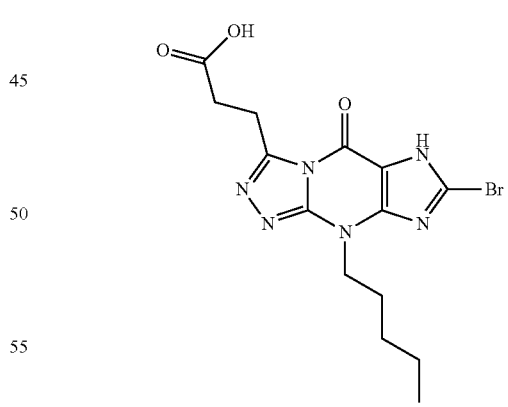

The mixture of 3-(5-oxo-9-pentyl-6,9-dihro-5H[1,2,4]triazolo[4,3-a]purin-3-yl)propanoic acid (203 mg, 0.64 mmole) and NBS (125.8 mg, 7.0 mmol) in THF (25 ml) was stirred at 70° C. for 2 hours. After evaporation of solvent, the residue was purified by preparative LC-MS to afford 60.2 mg (23.7%) of the desired product (60.2 mg, 23.7%) as white solid. LCMS calculated for $C_{14}H_{18}BrN_6O_3$ (M+H): 397.1. Found: 371.1.

Example 66

7-bromo-3-(3-morpholin-4-yl-3-oxopropyl)-9-pentyl-6,9-dihydro-5H-[1,2,4]triazolo[4,3-a]purin-5-one

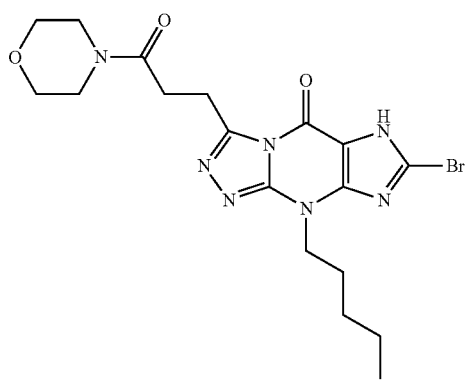 [SMILES: CCCCCn1c2nc(Br)[nH]c2c(=O)n2c(CCC(=O)N3CCOCC3)nnc12]

The mixture of 3-(7-bromo-5-oxo-9-pentyl-6,9-dihydro-5H[1,2,4]triazolo[4,3-a]purin-3-yl]propanoic acid (50 mg, 0.126 mmol), morpholine (21.0 mg, 0.252 mmol), triethylamine (25.5 mg, 0.252 mmol) and BOP (61.5 mg, 0.139 mmol) in $CH_2Cl_2$ (10 ml) was stirred at room temperature for 2 hours. After evaporation of solvent, the residue was purified by preparative LC-MS to afford the desired product (37.2 mg, 60%) as white solid. LCMS calculated for $C_{18}H_{25}BrN_7O_3$ (M+H): 466.1. Found: 466.1.

Example 67

N-benzyl-3-(7-bromo-5-oxo-9-pentyl-6,9-dihydro-5H-[1,2,4]triazolo[4,3-a]purin-3-yl)propanamide

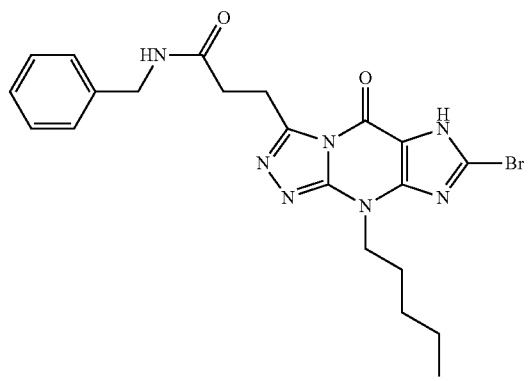 [SMILES: CCCCCn1c2nc(Br)[nH]c2c(=O)n2c(CCC(=O)NCc3ccccc3)nnc12]

The title compound was prepared using procedures analogous to those described for Example 66. $^1$HNMR (400 MHz, $d_6$-DMSO): δ 8.43 (m, 1H), 7.25 (m, 5H), 4.22 (m, 4H), 3.42 (m, 2H), 2.68 (m, 2H), 1.79 (m, 2H), 1.30 (m, 4H), 0.84 (m, 3H). LCMS calculated for $C_{21}H_{25}BrN_7O_2$ (M+H): 486.1. Found: 486.1, 488.0.

Example 68

7-bromo-3-(3-oxo-3-pyrrolidin-1-ylpropyl)-9-pentyl-6,9-dihydro-5H-pyrrolo[3,2-d][1,2,4]triazolo[4,3-a]pyrimidin-5-one

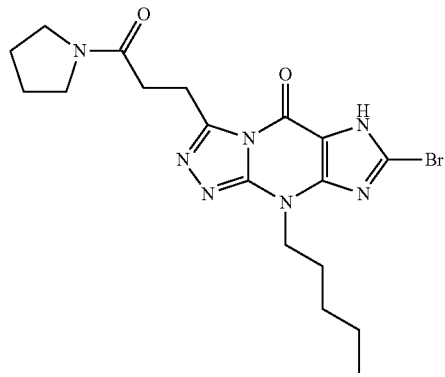 [SMILES: CCCCCn1c2nc(Br)[nH]c2c(=O)n2c(CCC(=O)N3CCCC3)nnc12]

The title compound was prepared using procedures analogous to those described for Example 66. $^1$HNMR (400 MHz, $d_6$-DMSO): δ 4.19 (t, J=7.2 Hz, 2H), 3.40 ((m, 4H), 3.26 (t, J=6.8 Hz, 2H), 2.73 (t, J=7.2 Hz, 2H), 1.80 (m, 6H), 1.29 (m, 4H), 0.83 (m, 3H). LCMS calculated for $C_{19}H_{26}BrN_6O_2$ (M+H): 449.130. Found 449.1, 451.1.

Example 69

3-(7-bromo-5-oxo-9-pentyl-6,9-dihydro-5H-pyrrolo[3,2-d][1,2,4]triazolo[4,3-a]pyrimidin-3-yl)-N-methylpropanamide

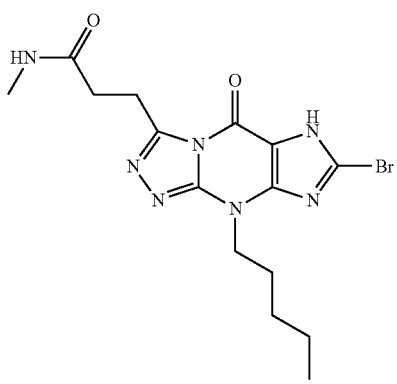 [SMILES: CCCCCn1c2nc(Br)[nH]c2c(=O)n2c(CCC(=O)NC)nnc12]

The title compound was prepared using procedures analogous to those described for Example 66. LCMS calculated for $C_{16}H_{22}BrN_6O_2$ (M+H): 409.1. Found: 409.1, 411.1.

Example 70

3-(7-bromo-5-oxo-9-pentyl-6,9-dihydro-5H-[1,2,4]triazolo[4,3-a]purin-3-yl)-N-(2-phenylethyl)propanamide

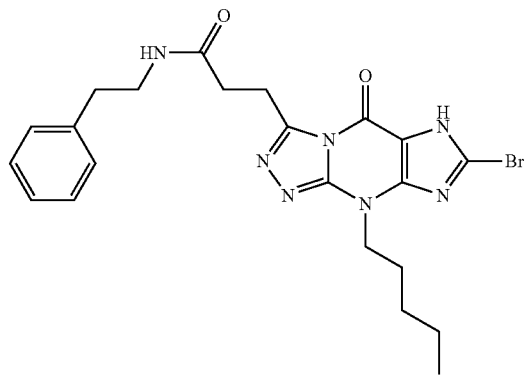 [SMILES: CCCCCn1c2nc(Br)[nH]c2c(=O)n2c(CCC(=O)NCCc3ccccc3)nnc12]

The title compound was prepared using procedures analogous to those described for Example 66. ¹HNMR (400 MHz, d₆-DMSO): δ 8.01 (t, J=5.3 Hz, 1H), 7.26 (dd, J=5.3, 6.9 Hz, 2H), 7.17 (d, J=6.9, 2H), 4.20 (t, J=7.2 Hz, 2H), 3.23 (m, 2H), 2.66 (t, J=8.3 Hz, 2H), 2.57 (t, J=8.3 Hz, 2H), 1.78 (m, 2H), 1.29 (m, 4H), 0.83 (m, 3H). LCMS calculated for $C_{22}H_{27}BrN_7O_2$ (M+H): 500. Found: 500.1, 502.1.

Example 71

3-(7-bromo-5-oxo-9-pentyl-6,9-dihydro-5H-[1,2,4]triazolo[4,3-a]purin-3-yl)-N-(pyridin-4-ylmethyl)propanamide trifluoroacetate

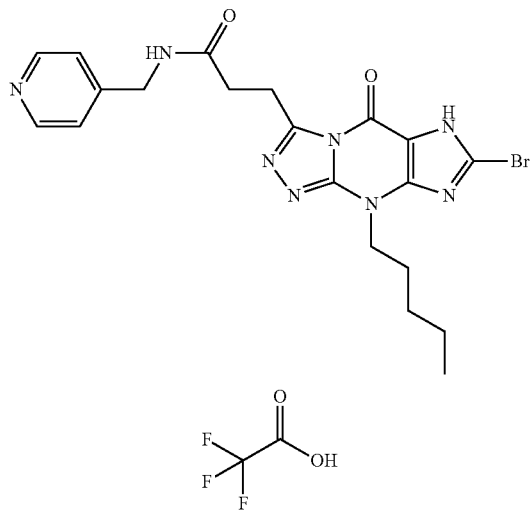

The title compound was prepared using procedures analogous to those described for Example 66. LCMS calculated for $C_{20}H_{24}BrN_8O_2$ (M+H): 487.1. Found 487.1, 489.0.

Example 72

3-[2-(3-benzyl-1,2,4-oxadiazol-5-yl)ethyl]-7-bromo-9-pentyl-6,9-dihydro-5H-[1,2,4]triazolo[4,3-a]purin-5-one

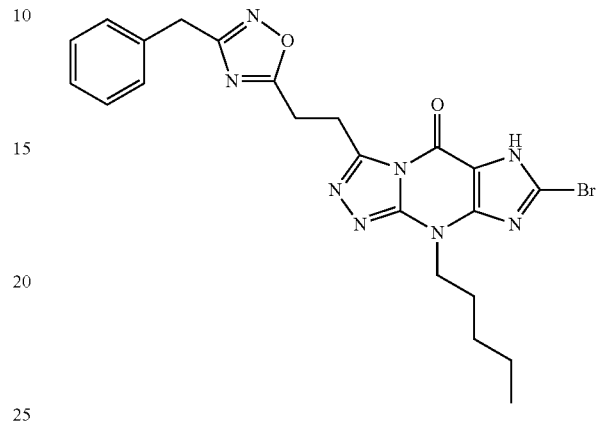

3-(7-bromo-5-oxo-9-pentyl-6,9-dihydro-5H-[1,2,4]triazolo[4,3-a]purin-3-yl)propanoic acid (50 mg, 0.126 mmole) and CDI (21.8 mg, 0.139 mmole) were mixed in anhydrous DMF (4 ml). After stirring the solution for 3 hours at room temperature, benzylamidoxime (22.5 mg, 0.139 mmole) was added and the solution heated at 90° C. for 20 hours, then at 110° C. for 4 hours. After evaporation of solvent, the residue was purified by preparative LCMS to yield the desired product (8.2 mg, 12.7%). LCMS calculated for $C_{22}H_{24}BrN_8O_2$ (M+H): 511.1. Found: 511.1, 513.1.

Example 73

7-bromo-9-pentyl-3-{2-[3-(2-thienylmethyl)-1,2,4-oxadiazol-5-yl]ethyl}-6,9-dihydro-5H-[1,2,4]triazolo[4,3-a]purin-5-one

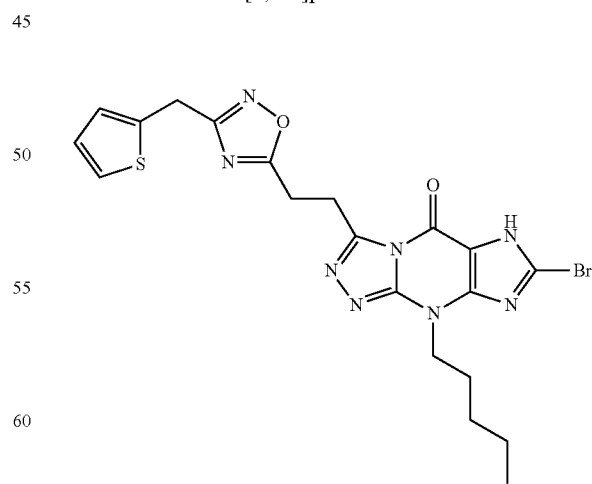

The title compound was prepared using procedures analogous to those described for Example 72. LCMS calculated for $C_{20}H_{22}BrN_8O_2S$ (M+H): 517.1. Found 517.1, 519.1.

Example 74

7-bromo-9-pentyl-3-(2-{3-[4-(trifluoromethyl)benzyl]-1,2,4-oxadiazol-5-yl}ethyl)-6,9-dihydro-5H-pyrrolo[3,2-d][1,2,4]triazolo[4,3-a]pyrimidin-5-one

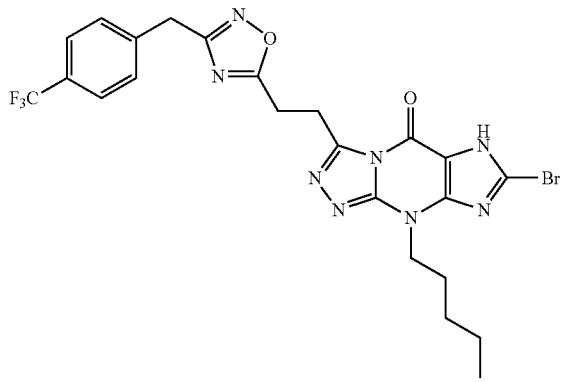 [SMILES: CCCCCn1c2nc(Br)[nH]c2c(=O)n2c(CCc3nc(Cc4ccc(C(F)(F)F)cc4)no3)nnc12]

Step A: (1Z)—N'-hydroxy-2-[4-(trifluoromethyl)phenyl]ethanimidamide

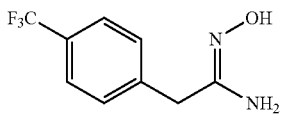

A suspension of [4-(trifluoromethyl)phenyl]acetonitrile (1.0 g, 5.4 mmoles), hydroxylamine hydrochloride (0.41 g, 5.9 mmoles) and NaHCO$_3$ (0.50 g, 5.9 mmoles) in MeOH (15 ml) was refluxed for 4 hours. The reaction mixture was then concentrated to remove the solvent methanol. The residue was extracted with ethyl acetate. The combined organic layers were washed with brine and dried over Na$_2$SO$_4$ and concentrated to afford the desired product (1.0 g, 84.9%) as white solid. LCMS calculated for C$_9$H$_{10}$F$_3$N$_2$O (M+H): 219.1. Found: 219.1.

Step B: 7-bromo-9-pentyl-3-(2-3-[4-(trifluoromethyl)benzyl]-1,2,4-oxadiazol-5-ylethyl)-6,9-dihydro-5H-pyrrolo[3,2-d][1,2,4]triazolo[4,3-a]pyrimidin-5-one

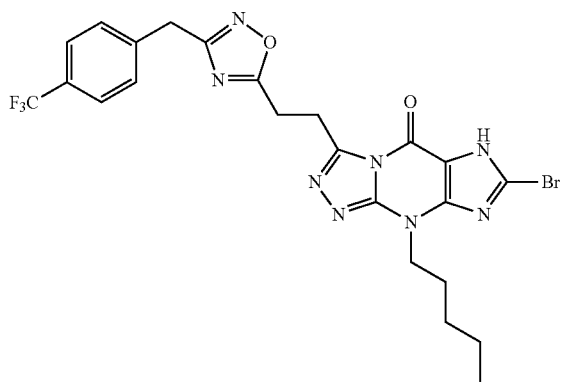 [SMILES: CCCCCn1c2nc(Br)[nH]c2c(=O)n2c(CCc3nc(Cc4ccc(C(F)(F)F)cc4)no3)nnc12]

3-(7-Bromo-5-oxo-9-pentyl-6,9-dihydro-5H-[1,2,4]triazolo[4,3-a]purin-3-yl)propanoic acid (100 mg, 0.252 mmole) and CDI (44.9 mg, 0.277 mmole) were dissolved in anhydrous DMF (4 ml). After stirring the solution for 3 hours at room temperature, (1Z)—N'-hydroxy-2-[4-(trifluoromethyl)phenyl]ethanimidamide (60.4 mg, 0.277 mmole) was added and the solution heated at 90° C. for 20 hours, then at 110° C. for 4 hours. After evaporation of solvent, the residue was purified by preparative LC-MS to afford the desired product (6.4 mg, 4.4%) as white solid. LCMS calculated for C$_{24}$H$_{24}$BrF$_3$N$_7$O$_2$ (M+H): 578.1. Found 578.1, 580.1.

Example 75

7-bromo-3-{2-[3-(4-fluorobenzyl)-1,2,4-oxadiazol-5-yl]ethyl}-9-pentyl-6,9-dihydro-5H-[1,2,4]triazolo[4,3-a]purin-5-one

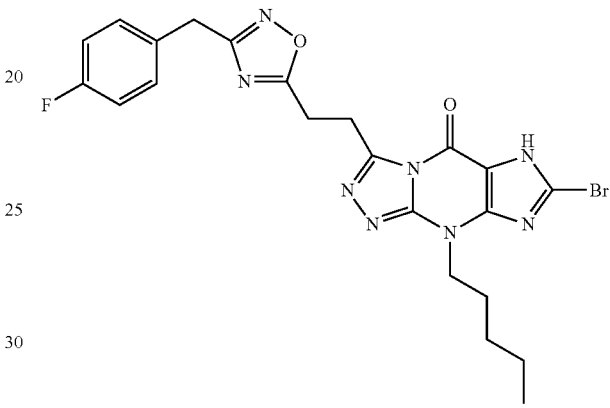 [SMILES: CCCCCn1c2nc(Br)[nH]c2c(=O)n2c(CCc3nc(Cc4ccc(OC)cc4)no3)nnc12]

The title compound was prepared using procedures analogous to those described for Example 74. LCMS calculated for C$_{22}$H$_{22}$BrFN$_8$O$_2$ (M+H): 529.1. Found: 529.1, 531.1.

Example 76

7-bromo-9-pentyl-3-{2-[3-(4-methoxybenzyl)-1,2,4-oxadiazol-5-yl]ethyl}-6,9-dihydro-5H-pyrrolo[3,2-d][1,2,4]triazolo[4,3-a]pyrimidin-5-one

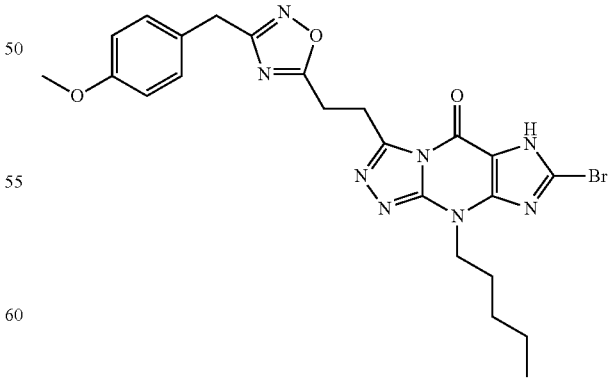

The title compound was prepared using procedures analogous to those described for Example 74. LCMS calculated for C$_{23}$H$_{25}$BrN$_8$O$_3$ (M+H): 541.1. Found 541.1, 543.1.

Example 77

7-bromo-9-pentyl-3-{2-[3-(pyridine-4-ylmethyl)-1,2,4-oxadiazol-5-yl]ethyl}-6,9-dihydro-5H-[1,2,4]triazolo[4,3-a]purin-5-one

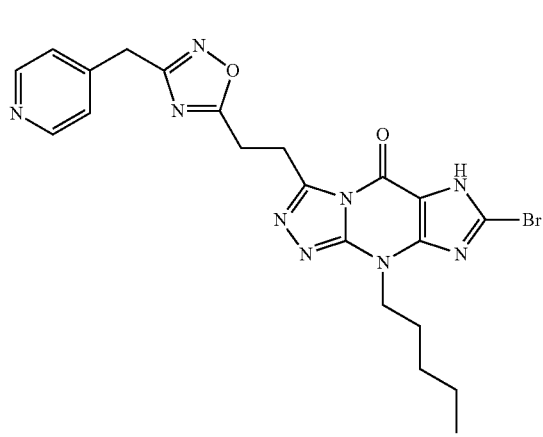 [SMILES: CCCCCn1c2nc(Br)[nH]c2c(=O)n2c(CCc3nc(Cc4ccncc4)no3)nnc12]

The title compound was prepared using procedures analogous to those described for Example 74. LCMS calculated for $C_{21}H_{22}BrN_9O_2$ (M+H): 512.1. Found: 512.1, 514.1.

Example 78

7-bromo-9-pentyl-3-(2-{3-[3-(trifluoromethyl)benzyl]-1,2,4-oxadiazol-5-yl}ethyl)-6,9-dihydro-5H-pyrrolo[3,2-d][1,2,4]triazolo[4,3-a]pyrimidin-5-one

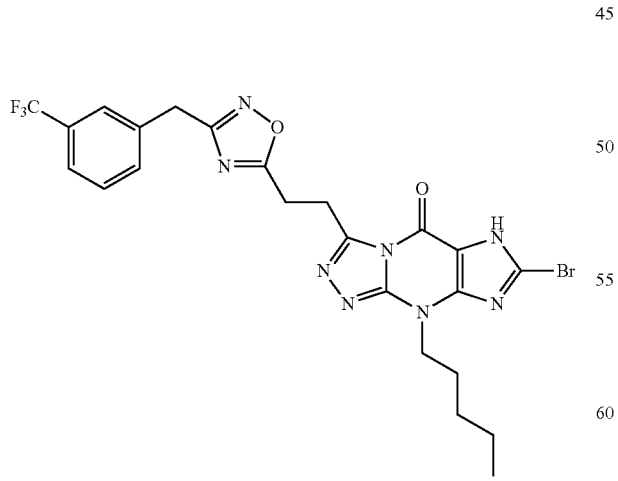

The title compound was prepared using procedures analogous to those described for Example 74. LCMS calculated for $C_{24}H_{24}BrF_3N_7O_2$ (M+H): 578.1. Found 578.1, 580.1.

Example 79

7-bromo-9-pentyl-3-(2-{3-[2-(trifluoromethyl)benzyl]-1,2,4-oxadiazol-5-yl}ethyl)-6,9-dihydro-5H-pyrrolo[3,2-d][1,2,4]triazolo[4,3-a]pyrimidin-5-one

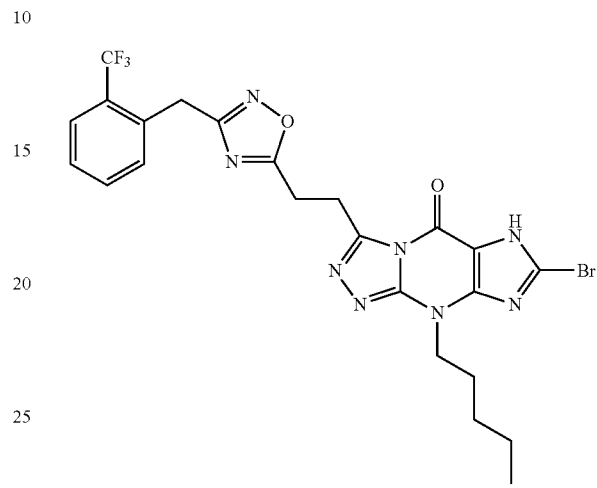

The title compound was prepared using procedures analogous to those described for Example 74. LCMS calculated for $C_{24}H_{24}BrF_3N_7O_2$ (M+H): 578.1. Found 578.1, 580.1.

Example 80

7-bromo-9-pentyl-3-{2-[3-(pyridine-3-ylmethyl)-1,2,4-oxadiazol-5-yl]ethyl}-6,9-dihydro-5H-[1,2,4]triazolo[4,3-a]purin-5-one trifluoroacetate

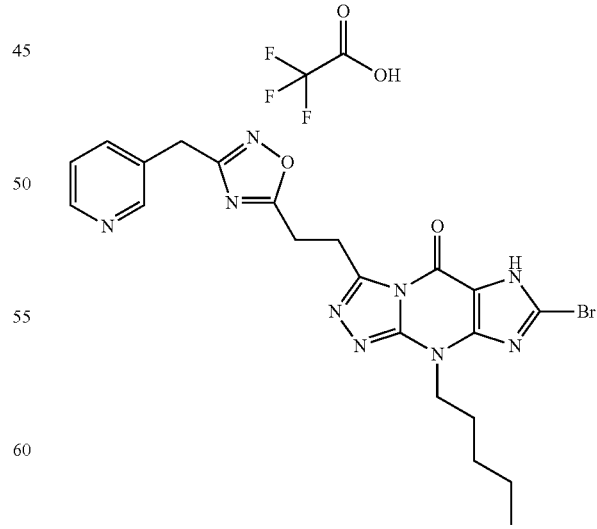

The title compound was prepared using procedures analogous to those described for Example 74. LCMS calculated for $C_{21}H_{22}BrN_9O_2$ (M+H): 512.1. Found: 512.1, 514.1.

Example 81

7-bromo-9-pentyl-3-{2-[3-(2-phenylethyl)-1,2,4-oxadiazol-5-yl]ethyl}-6,9-dihydro-5H-[1,2,4]triazolo[4,3-a]purin-5-one

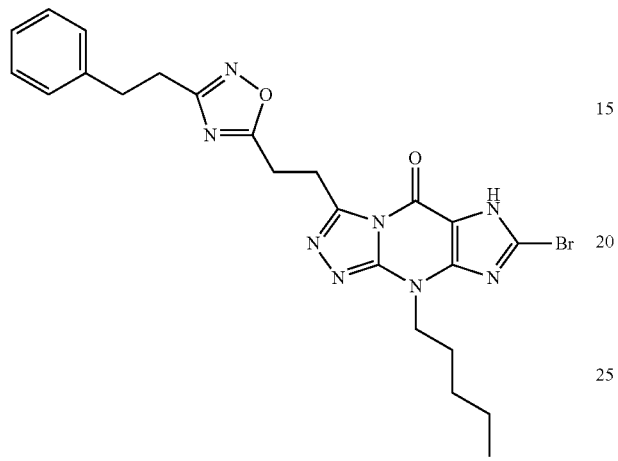

The title compound was prepared using procedures analogous to those described for Example 74. $^1$HNMR (400 MHz, $d_6$-DMSO): δ 7.20 (m, 5H), 4.20 (t, J=7.4 Hz, 2H), 3.67 (t, J=7.4 Hz, 2H), 3.41 (t, J=7.4 Hz, 4H), 3.35 (br, 1H), 2.91 (s, 4H), 1.78 (m, 2H), 1.27 (m, 4H), 0.81 (m, 3H). LCMS calculated for $C_{23}H_{25}BrN_8O_2$ (M+H): 525.1. Found: 525.1, 527.0.

Example 82

7-bromo-9-pentyl-3-{2-(3-phenyl-1,2,4-oxadiazol-5-yl) ethyl}-6,9-dihydro-5H-[1,2,4]triazolo[4,3-a]purin-5-one

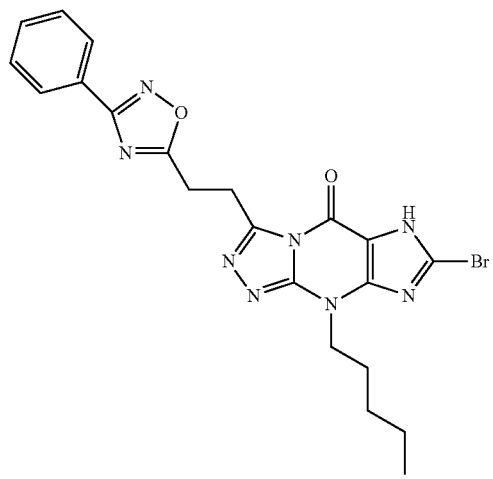 [SMILES: CCCCCn1c2nc(Br)[nH]c2c(=O)n2c(CCc3nc(-c4ccccc4)no3)nnc12]

The title compound was prepared using procedures analogous to those described for Example 74. LCMS calculated for $C_{21}H_{21}BrN_8O_2$ (M+H): 497.1. Found: 497.1, 499.1.

Example 83

7-bromo-3-{2-[3-(3-fluorobenzyl)-1,2,4-oxadiazol-5-yl]ethyl}-9-pentyl-6,9-dihydro-5H-[1,2,4]triazolo[4,3-a]purin-5-one

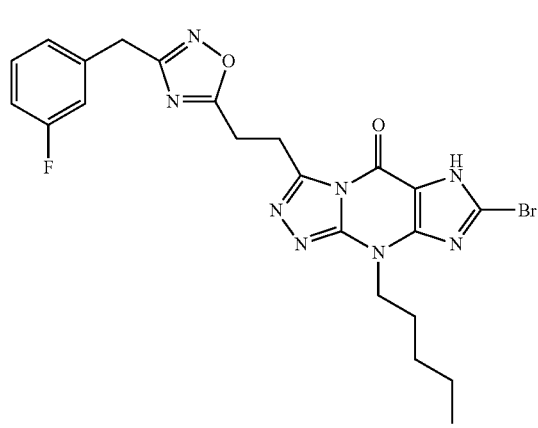 [SMILES: CCCCCn1c2nc(Br)[nH]c2c(=O)n2c(CCc3nc(Cc4cccc(F)c4)no3)nnc12]

The title compound was prepared using procedures analogous to those described for Example 74. LCMS calculated for $C_{22}H_{22}BrFN_8O_2$ (M+H): 529.1. Found: 529.1, 531.1.

Example 84

7-bromo-3-{2-[3-(4-chlorobenzyl)-1,2,4-oxadiazol-5-yl]ethyl}-9-pentyl-6,9-dihydro-5H-[1,2,4]triazolo[4,3-a]purin-5-one

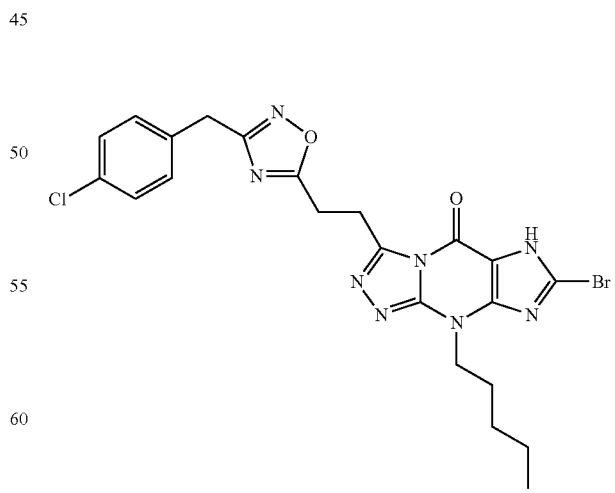

The title compound was prepared using procedures analogous to those described for Example 74. LCMS calculated for $C_{22}H_{22}BrClN_8O_2$ (M+H): 545.1. Found: 545.1, 547.1, 549.1.

Example 85

3-[2-(3-benzyl-1,2,4-oxadiazol-5-yl)ethyl]-7-chloro-9-pentyl-6,9-dihydro-5H-[1,2,4]triazolo[4,3-a]purin-5-one

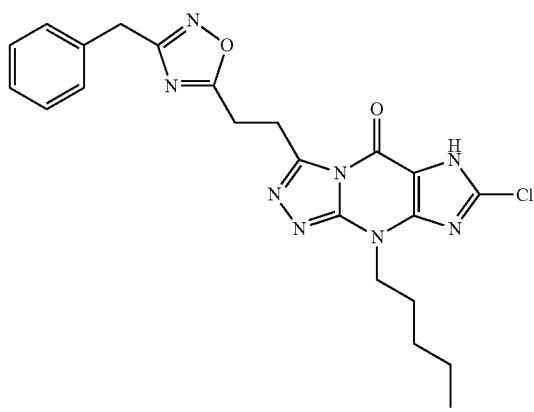 [SMILES: CCCCCn1c2nc(Cl)[nH]c2c(=O)n2c(CCc3nc(Cc4ccccc4)no3)nnc12]

The title compound was prepared using procedures analogous to those described for Example 72. LCMS calculated for $C_{22}H_{23}ClN_8O_2$ (M+H): 467.2. Found: 467.2.

Example 86

7-bromo-3-{2-[3-(2-fluorobenzyl)-1,2,4-oxadiazol-5-yl]ethyl}-9-pentyl-6,9-dihydro-5H-[1,2,4]triazolo[4,3-a]purin-5-one

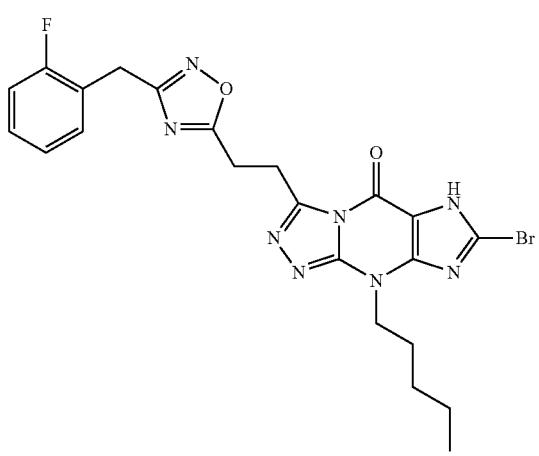 [SMILES: CCCCCn1c2nc(Br)[nH]c2c(=O)n2c(CCc3nc(Cc4ccccc4F)no3)nnc12]

The title compound was prepared using procedures analogous to those described for Example 74. $^1$HNMR (400 MHz, $d_6$-DMSO): δ 7.30 (m, 2H), 7.13 (m, 2H), 4.19 (t, J=7.5 Hz, 2H), 4.05 (s, 2H), 3.64 (t, J=7.5 Hz, 2H), 3.39 (t, J=7.5 Hz, 2H), 1.78 (m, 2H), 1.28 (m, 4H), 0.83 (m, 3H). LCMS calculated for $C_{22}H_{22}BrFN_8O_2$ (M+H): 529.1. Found: 529.1, 531.1.

Example 87

7-bromo-3-{2-[3-(2-methoxybenzyl)-1,2,4-oxadiazol-5-yl]ethyl}-9-pentyl-6,9-dihydro-5H-pyrrolo[3,2-d][1,2,4]triazolo[4,3-a]pyrimidin-5-one

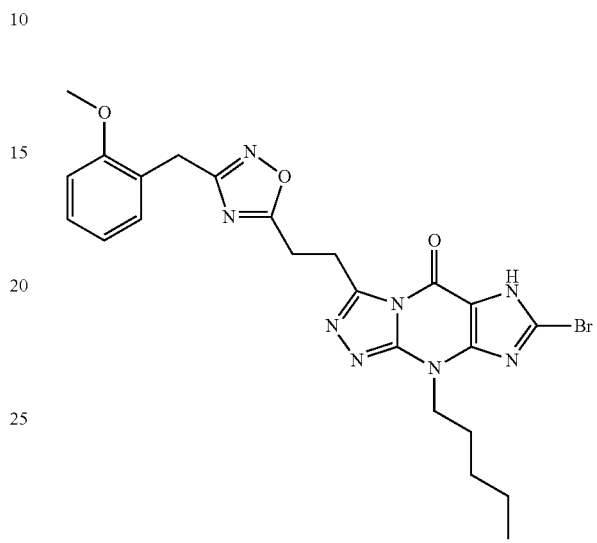

The title compound was prepared using procedures analogous to those described for Example 74. LCMS calculated for $C_{23}H_{25}BrN_8O_3$ (M+H): 541.1. Found 541.1, 543.1.

Example 88

7-bromo-3-[2-(3-ethyl-1,2,4-oxadiazol-5-yl)ethyl]-9-pentyl-6,9-dihydro-5H-pyrrolo[3,2-d][1,2,4]triazolo[4,3-a]pyrimidin-5-one

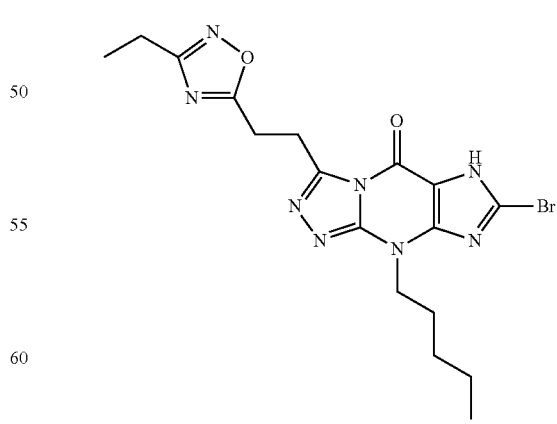

The title compound was prepared using procedures analogous to those described for Example 72. LCMS calculated for $C_{17}H_{21}BrN_8O_2$ (M+H): 449.1. Found 449.1.

Example 89

7-bromo-3-{2-[3-(3-methoxybenzyl)-1,2,4-oxadiazol-5-yl]ethyl}-9-pentyl-6,9-dihydro-5H-pyrrolo[3,2-d][1,2,4]triazolo[4,3-a]pyrimidin-5-one

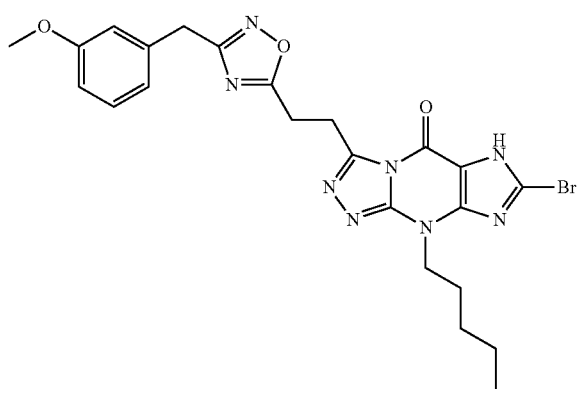 [SMILES: CCCCCn1c2nc(Br)[nH]c2c(=O)n2c(CCc3nc(Cc4cccc(OC)c4)no3)nnc12]

The title compound was prepared using procedures analogous to those described for Example 74. LCMS calculated for $C_{23}H_{25}BrN_8O_3$ (M+H): 541.1. Found 541.1, 543.1.

Example 90

7-bromo-3-{2-[3-(3-methylbenzyl)-1,2,4-oxadiazol-5-yl]ethyl}-9-pentyl-6,9-dihydro-5H-pyrrolo[3,2-d][1,2,4]triazolo[4,3-a]pyrimidin-5-one

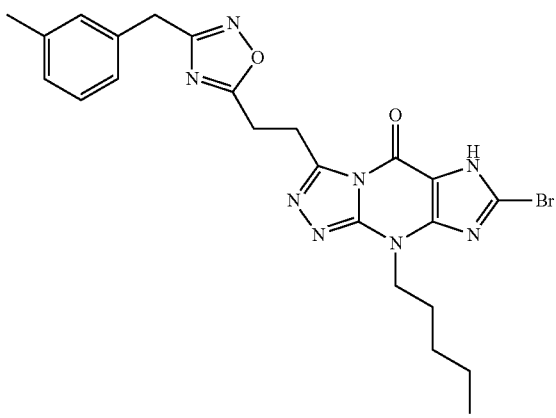 [SMILES: CCCCCn1c2nc(Br)[nH]c2c(=O)n2c(CCc3nc(Cc4cccc(C)c4)no3)nnc12]

The title compound was prepared using procedures analogous to those described for Example 74. LCMS calculated for $C_{23}H_{25}BrN_8O_2$ (M+H): 525.1. Found 525.1, 527.1.

Example 91

7-bromo-3-{2-[3-(2,4-difluorobenzyl)-1,2,4-oxadiazol-5-yl]ethyl}-9-pentyl-6,9-dihydro-5H-pyrrolo[3,2-d][1,2,4]triazolo[4,3-a]pyrimidin-5-one

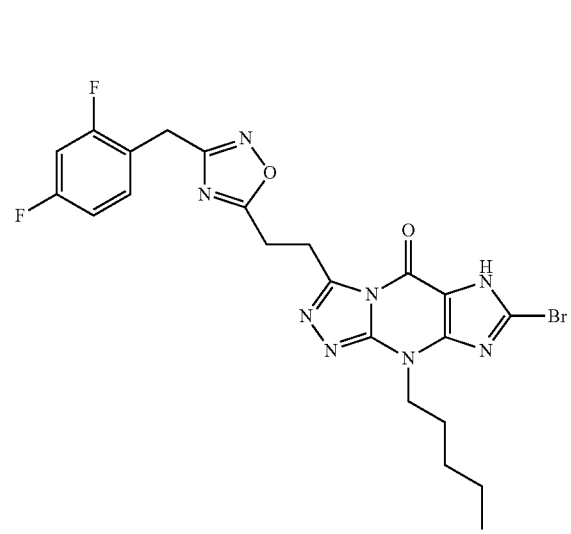 [SMILES: CCCCCn1c2nc(Br)[nH]c2c(=O)n2c(CCc3nc(Cc4ccc(F)cc4F)no3)nnc12]

The title compound was prepared using procedures analogous to those described for Example 74. LCMS calculated for $C_{22}H_{21}BrF2N_8O_2$ (M+H): 547.1. Found 547.1, 549.1.

Example 92

7-bromo-3-{2-[3-(3,5-difluorobenzyl)-1,2,4-oxadiazol-5-yl]ethyl}-9-pentyl-6,9-dihydro-5H-pyrrolo[3,2-d][1,2,4]triazolo[4,3-a]pyrimidin-5-one

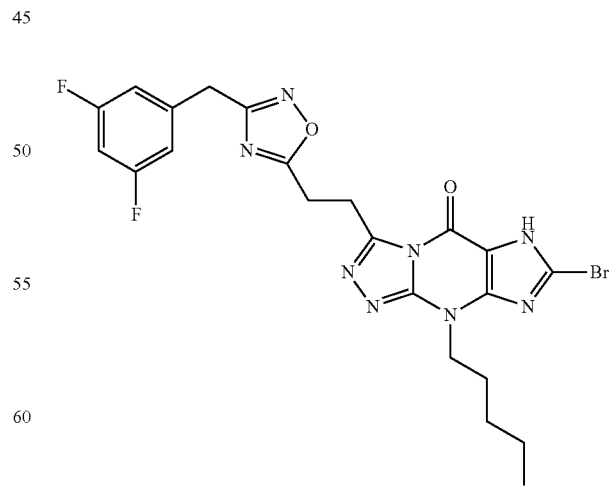

The title compound was prepared using procedures analogous to those described for Example 74. LCMS calculated for $C_{22}H_{21}BrF2N_8O_2$ (M+H): 547.1. Found 547.1, 549.1.

Example 93

7-bromo-9-pentyl-3-{2-[3-(3-thienylmethyl)-1,2,4-oxadiazol-5-yl]ethyl}-6,9-dihydro-5H-[1,2,4]triazolo[4,3-a]purin-5-one

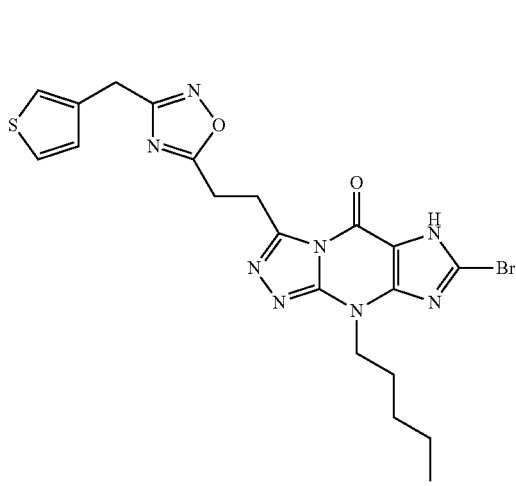 [SMILES: CCCCCn1c2nc(Br)[nH]c2c(=O)n2c(CCc3nc(Cc4ccsc4)no3)nnc12]

The title compound was prepared using procedures analogous to those described for Example 74. LCMS calculated for $C_{20}H_{22}BrN_8O_2S$ (M+H): 517.1. Found 517.1, 519.1.

Example 94

7-bromo-9-pentyl-3-{2-[3-(1-phenylcyclopropyl)-1,2,4-oxadiazol-5-yl]ethyl}-6,9-dihydro-5H-pyrrolo[3,2-d][1,2,4]triazolo[4,3-a]pyrimidin-5-one

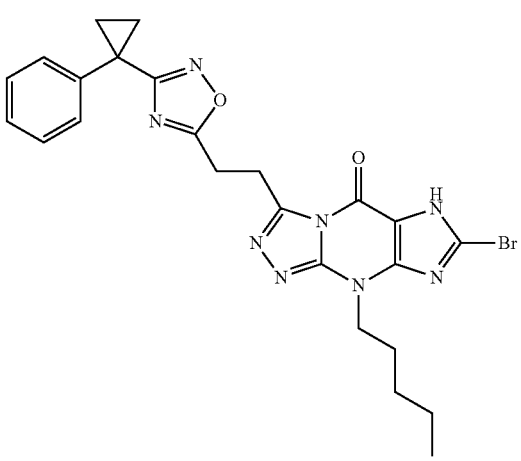 [SMILES: CCCCCn1c2nc(Br)[nH]c2c(=O)n2c(CCc3nc(C4(c5ccccc5)CC4)no3)nnc12]

The title compound was prepared using procedures analogous to those described for Example 72. LCMS calculated for $C_{24}H_{25}BrN_8O_2$ (M+H): 537.1. Found 537.1, 539.1.

Example 95

7-bromo-9-pentyl-3-{2-[3-(pyridine-2-ylmethyl)-1,2,4-oxadiazol-5-yl]ethyl}-6,9-dihydro-5H-[1,2,4]triazolo[4,3-a]purin-5-one trifluoroacetate

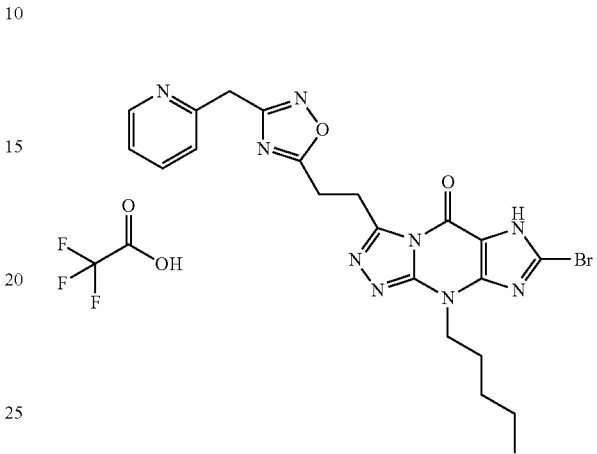

The title compound was prepared using procedures analogous to those described for Example 74. LCMS calculated for $C_{21}H_{22}BrN_9O_2$ (M+H): 512.1. Found: 512.1, 514.1.

Example 96

3-[(2R)-2-(3-benzy-1,2,4-oxadiazol-5-yl)propyl]-7-bromo-9-pentyl-6,9-dihydro-5H-[1,2,4]triazolo[4,3-a]purin-5-one

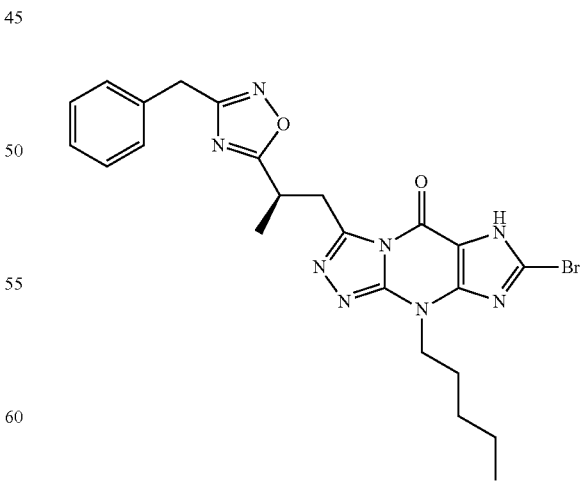

The title compound was prepared using procedures analogous to those described for Example 74. LCMS calculated for $C_{23}H_{25}BrN_8O_2$ (M+H): 525.1. Found: 525.1, 527.1.

Example 97

7-bromo-3-(2-{3-[(4-methyl-1,3-thiazol-2-yl)methyl]-1,2,4-oxadiazol-5-yl}ethyl)-9-pentyl-6,9-dihydro-5H-[1,2,4]triazolo[4,3-a]purin-5-one

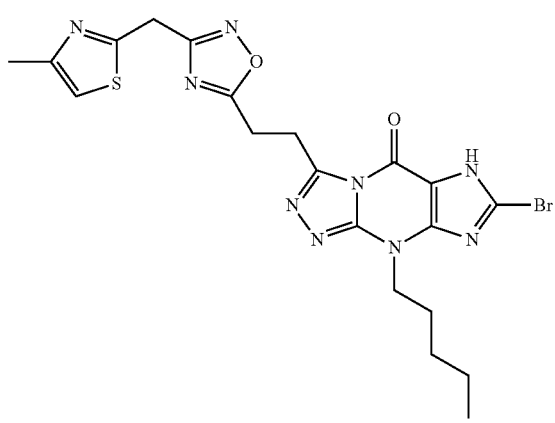 [SMILES: CCCCCn1c2nc(Br)[nH]c2c(=O)n2c(CCc3nc(Cc4nc(C)cs4)no3)nnc12]

The title compound was prepared using procedures analogous to those described for Example 74. LCMS calculated for $C_{20}H_{23}BrN_9O_2S$ (M+H): 532.1. Found: 532.0, 534.0.

Example 98

7-bromo-3-{2-[3-(2-methylbenzyl)-1,2,4-oxadiazol-5-yl]ethyl}-9-pentyl-6,9-dihydro-5H-[1,2,4]triazolo[4,3-a]purin-5-one

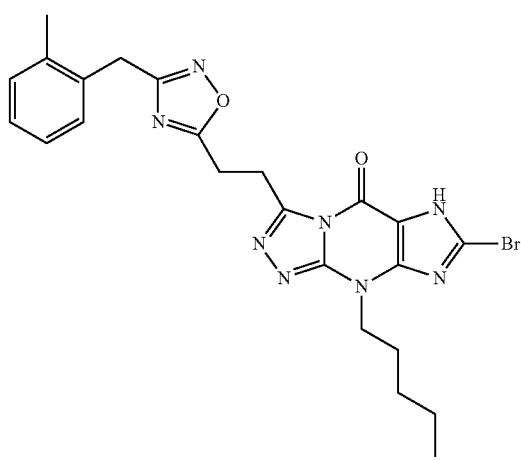 [SMILES: CCCCCn1c2nc(Br)[nH]c2c(=O)n2c(CCc3nc(Cc4ccccc4C)no3)nnc12]

The title compound was prepared using procedures analogous to those described for Example 74. LCMS calculated for $C_{23}H_{26}BrN_8O_2$ (M+H): 525.1. Found 525.0, 527.0.

Example 99

7-bromo-3-(2-{3-[hydroxy(phenyl)methyl]-1,2,4-oxadiazol-5-yl}ethyl)-9-pentyl-6,9-dihydro-5H-[1,2,4]triazolo[4,3-a]purin-5-one

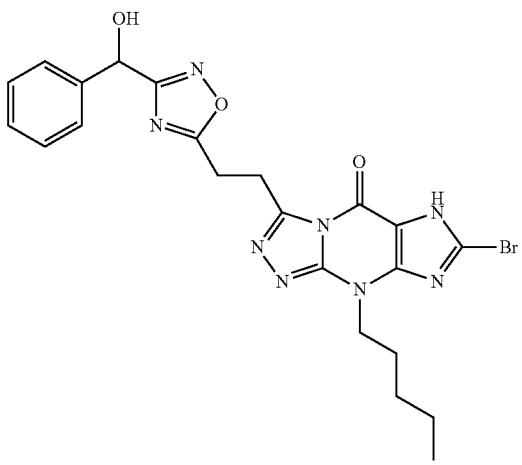 [SMILES: CCCCCn1c2nc(Br)[nH]c2c(=O)n2c(CCc3nc(C(O)c4ccccc4)no3)nnc12]

The title compound was prepared using procedures analogous to those described for Example 74. LCMS calculated for $C_{22}H_{24}BrN_8O_3$ (M+H): 527.1. Found 527.0, 529.0.

Example 100

7-bromo-3-{2-[3-(2,5-difluorobenzyl)-1,2,4-oxadiazol-5-yl]ethyl}-9-pentyl-6,9-dihydro-5H-[1,2,4]triazolo[4,3-a]purin-5-one

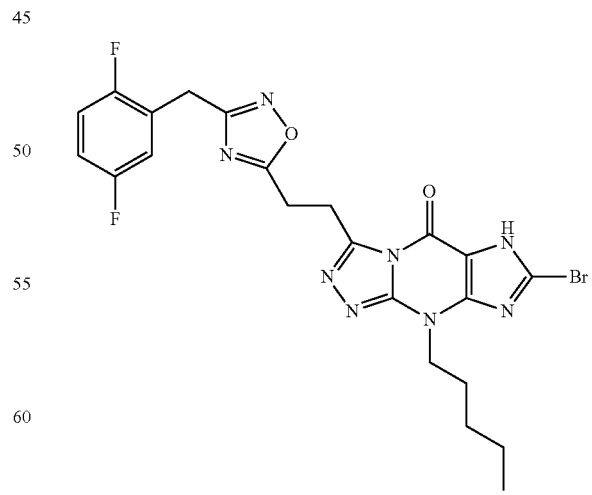

The title compound was prepared using procedures analogous to those described for Example 74. LCMS calculated for $C_{22}H_{22}BrF_2N_8O_2$ (M+H): 547.1. Found: 547.0, 547.0.

Example 101

7-bromo-9-pentyl-3-{2-[3-(pyrimidin-5-ylmethyl)-1,2,4-oxadiazol-5-yl]ethyl}-6,9-dihydro-5H-[1,2,4]triazolo[4,3-a]purin-5-one

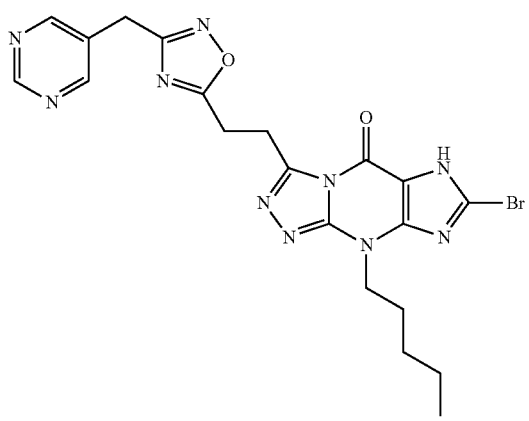 [SMILES: CCCCCn1c2nc(Br)[nH]c2c(=O)n2c(CCc3nc(Cc4cncnc4)no3)nnc12]

The title compound was prepared using procedures analogous to those described for Example 74. $^1$HNMR (400 MHz, d$_6$-DMSO): δ 9.06 (s, 1H), 8.74 (s, 2H), 4.20 (t, J=7.6 Hz, 2H), 4.15 (s, 2H), 3.66 (t, J=7.6 Hz, 2H), 3.41 (t, J=7.6 Hz, 2H), 1.78 (m, 2H), 1.29 (m, 4H), 0.83 (m, 3H). LCMS calculated for $C_{20}H_{22}BrN_{10}O_2$ (M+H): 513.1. Found: 513.1, 515.1.

Example 102

7-bromo-9-butyl-3-{2-[3-(2-fluorobenzyl)-1,2,4-oxadiazol-5-yl]ethyl}-6,9-dihydro-5H-[1,2,4]triazolo[4,3-a]purin-5-one

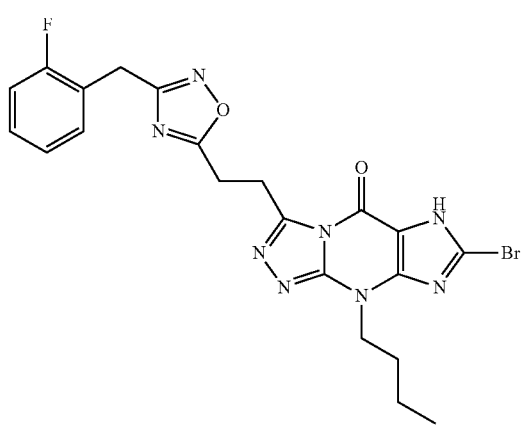 [SMILES: CCCCn1c2nc(Br)[nH]c2c(=O)n2c(CCc3nc(Cc4ccccc4F)no3)nnc12]

The title compound was prepared using procedures analogous to those described for Example 74. LCMS calculated for $C_{21}H_{21}BrFN_8O_2$ (M+H): 515.1. Found 515.0, 517.0.

Example 103

3-[2-(3-benzyl-1,2,4-oxadiazol-5-yl)ethyl]-9-pentyl-7-(trifluoromethyl)-6,9-dihydro-5H-[1,2,4]triazolo[4,3-a]purin-5-one

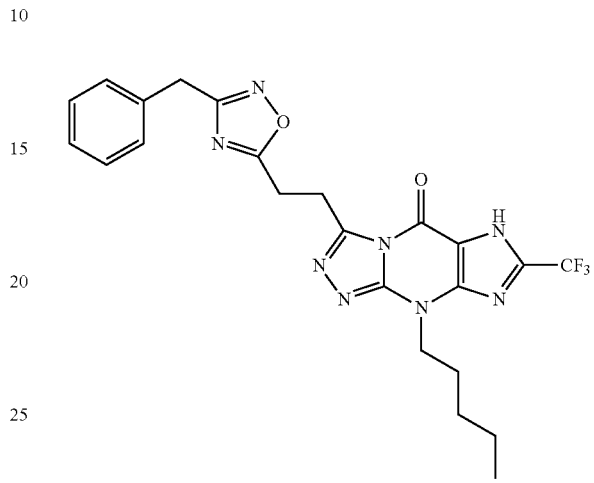

Step A: methyl 3-(3-benzyl-1,2,4-oxadiazol-5-yl)propanoate

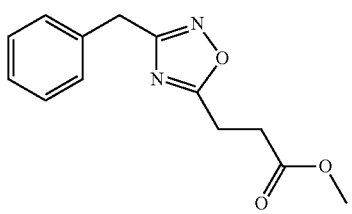 [SMILES: COC(=O)CCc1nc(Cc2ccccc2)no1]

Butanedioic acid, monomethyl ester (4.0 g, 30.3 mmole) and CDI (5.40 g, 33.3 mmole) were dissoled in anhydrous DMF (15 ml). After stirring the solution at room temperature for 3 hours, (1Z)—N'-hydroxy-2-phenylethanimidamide (5.0 g, 33.3 mmole) was added and the solution heated at 90° C. for 20 hours. After evaporation of solvent, the residue was dissoled in EtOAc. The organic phase was washed with water and brine, dried over Na$_2$SO$_4$. After filtration and evaporation of solvent, the residue was purified by flash chromatogarphy on silica gel eluted with EtOAc/Hexane (25/75). The purification gave 5.2 g (69.7%) of product as light yellowish oil. LCMS calculated for $C_{13}H_{15}N_2O_3$ (M+H): 247.1. Found 247.0.

Step B: 3-(3-benzyl-1,2,4-oxadiazol-5-yl)propanoic acid

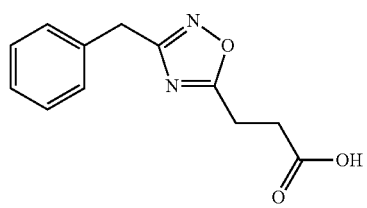 [SMILES: O=C(O)CCc1nc(Cc2ccccc2)no1]

To a solution of methyl 3-(3-benzyl-1,2,4-oxadiazol-5-yl) propanoate (5.2 g, 21.1 mmole) in methanol (30 ml) was added 50 ml of 1N NaOH. The mixture was stirred at room temperature for 2 hours. The mixture was adjusted to PH=3-4 under ice bath, and extracted with EtOAc (3×). The combined organic phases were washed with water and brine, dried over $Na_2SO_4$ and concentrated to yield the desired product (4.8 g, 98%) as colorless oil. LCMS calculated for $C_{12}H_{13}N_2O_3$ (M+H): 233.1. Found 233.0.

Step C: 3-(3-benzyl-1,2,4-oxadiazol-5-yl)-N'-[(2E)-6-oxo-3-pentyl-8-(trifluoromethyl)-1,3,6,7-tetrahydro-2H-purin-2-ylidene]propanohydrazide

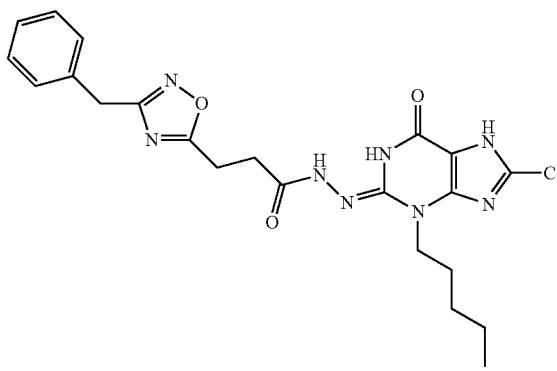

The mixture of 3-(3-benzyl-1,2,4-oxadiazol-5-yl)propanoic acid (100.0 mg, 0.431 mmole), (2E)-3-pentyl-8-(trifluoromethyl)-3,7-dihydro-1H-purine-2,6-dione 2-hydrazone (144.1 mg, 0.474 mmole), BOP (209.5 mg, 0.474 mmole) and triethylamine (0.120 ml, 0.861 mmole). in DMF (4 ml) was stirred at room temperature overnight. The mixture was diluted with EtOAc (100 ml) and washed with water, then brine. The organic phase was dried over $Na_2SO_4$, filtrated and concentrated to give the desired product (220.1 mg, 98.6%) as yellowish oil. LCMS calculated for $C_{23}H_{26}F_3N_8O_3$ (M+H): m/z=5192. Found 519.2.

Step D: 3-[2-(3-benzyl-1,2,4-oxadiazol-5-yl)ethyl]-9-pentyl-7-(trifluoromethyl)-6,9-dihydro-5H-[1,2,4]triazolo[4,3-a]purin-5-one

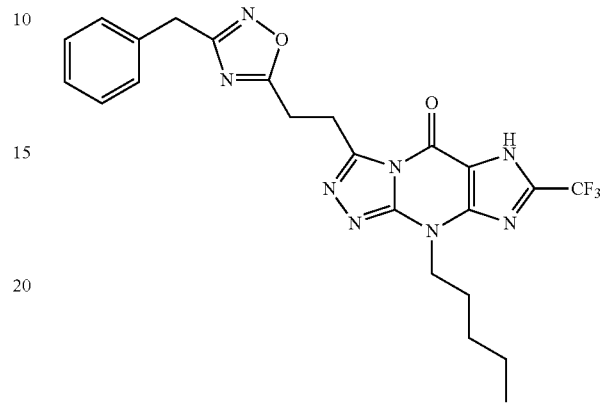

The mixture of 3-(3-benzyl-1,2,4-oxodiazol-5-yl)-N'-[(2E)-6-oxo-3-pentyl-8-(trifluoromethyl)-1,3,6,7-tetrahydro-2H-purin-2-ylidene]propanohydrazide (220.1 mg, 0.424 mmole) in toluene (20 ml) was refluxed for 5 hours. After evaporation of solvent, the residue was purified by preparative LCMS to yield the desired product (37.9 mg, 17.8%) as white solid. LCMS calculated for $C_{23}H_{24}F_3N_8O_2$ (M+H): 501.2. Found 501.1.

Example 104

3-[2-(3-benzyl-1,2,4-oxadiazol-5-yl)ethyl]-7-cyclopropyl-9-pentyl-6,9-dihydro-5H-[1,2,4]triazolo[4,3-a]purin-5-one The title compound was prepared using procedures analogous to those described for Example 103. LCMS calculated for $C_{25}H_{29}N_8O_2$ (M+H): 473.2. Found: 473.1

Example 105

3-methyl-9-pentyl-7-[1-(trifluoromethyl)cyclopropyl]-6,9-dihydro-5H-[1,2,4]triazolo[4,3-a]purin-5-one

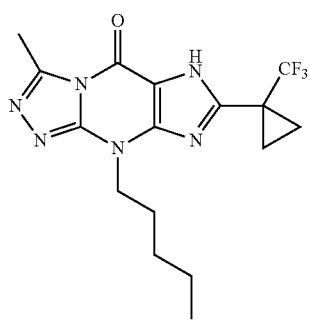 [SMILES: CCCCCn1c2nc(C3(C(F)(F)F)CC3)[nH]c2c(=O)n2c(C)nnc12]

The title compound was prepared using procedures analogous to those described for Example 32. ¹HNMR (400 MHz, d$_6$-DMSO): δ 4.22 (t, J=7.03 Hz, 2H), 2.71 (s, 4H), 1.80 (m, 2H), 1.49 (s, 3H), 1.28 (m, 4H), 0.81 (m, 3H). LCMS calculated for C$_{16}$H$_{20}$F$_3$N$_6$O (M+H): 369.2. Found: 269.1

Example 106

7-(2,2-difluorocyclopropyl)-3-methyl-9-pentyl-6,9-dihydro-5H-[1,2,4]triazolo[4,3-a]purin-5-one

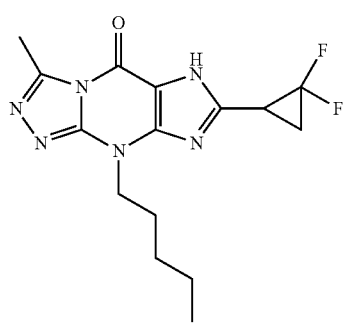 [SMILES: CCCCCn1c2nc(C3CC3(F)F)[nH]c2c(=O)n2c(C)nnc12]

The title compound was prepared using procedures analogous to those described for Example 32. LCMS calculated for C$_{15}$H$_{19}$F$_2$N$_6$O (M+H): 337.2. Found: 337.1.

Example 107

7-(1-hydroxycyclopropyl)-3-methyl-9-pentyl-6,9-dihydro-5H-[1,2,4]triazolo[4,3-a]purin-5-one

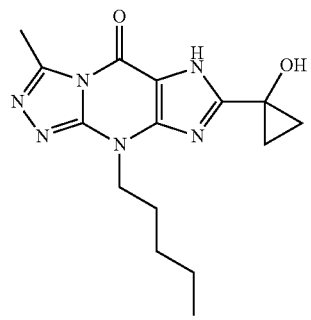 [SMILES: CCCCCn1c2nc(C3(O)CC3)[nH]c2c(=O)n2c(C)nnc12]

The title compound was prepared using procedures analogous to those described for Example 32. LCMS calculated for C$_{15}$H$_{21}$N$_6$O$_2$ (M+H): 317.2. Found: 317.1.

Example 108

7-bromo-9-pentyl-3-[2-(5-phenyl-1,3,4-oxadiazol-2-yl)ethyl]-6,9-dihydro-5H-[1,2,4]triazolo[4,3-a]purin-5-one

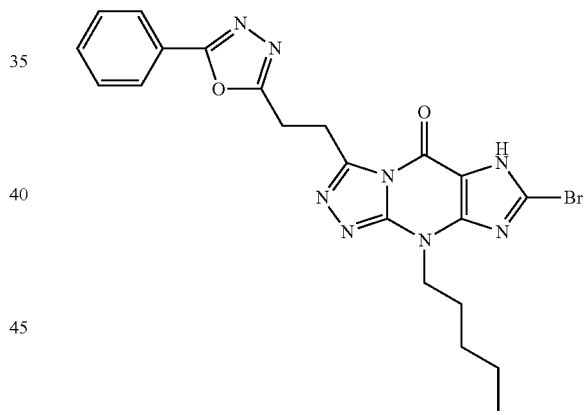

Step A: methyl 4-(2-benzoylhydrazino)-4-oxobutanoate

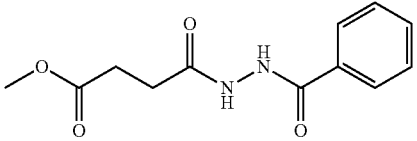 [SMILES: COC(=O)CCC(=O)NNC(=O)c1ccccc1]

The mixture of benzhydrazide (1.5 g, 11.0 mmol), butanedioic acid, monomethyl ester (2.0 g, 15 mmol), benzotriazol-1-yloxytris(dimethylamino)phosphonium hexafluorophosphate (5.4 g, 12 mmol), N,N-diisopropylethylamine (3.8 mL, 22 mmol) and 4-dimethylaminopyridine (0.87 g, 7.2 mmol)

in DMF (30 mL) was stirred at room temperature overnight. The mixture was quenched with water and extracted with ethyl acetate three times. The combined organic layers were washed by brine, dried over sodium sulfate, filtered and concentrated. The crude residue was purified by flash column chromatography to yield the desired product (900 mg, 32.6%). LCMS calculated for $C_{12}H_{15}N_2O_4$ (M+H): 251.1. Found: 251.1.

Step B: Methyl 3-(5-phenyl-1,3,4-oxadiazol-2-yl)propanoate

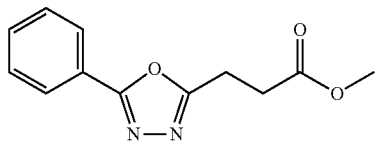 [SMILES: COC(=O)CCc1nnc(-c2ccccc2)o1]

Thionyl chloride (0.34 mL, 4.7 mmol) was added to the mixture of methyl 4-(2-benzoylhydrazino)-4-oxobutanoate (900 mg, 4 mmol), Pyridine (0.87 mL, 0.011 mol) in tetrahydrofuran (20 mL) at room temperature. After stirring for 3 hours, the reaction mixture was concentrated. The residue was mixed with toluene (20 mL) and refluxed overnight. The reaction was diluted with water and extracted with ethyl acetate three times. The combined organic layers were dried with sodium sulfate, filtered, and concentrated in vacuo. The residue was purified by flash column chromatography to yield the desired product (600 mg, 72%). LCMS calculated for $C_{12}H_{13}N_2O_3$ (M+H): 233.1. Found: 233.1.

Step C: 3-(5-phenyl-1,3,4-oxadiazol-2-yl)propanoic acid

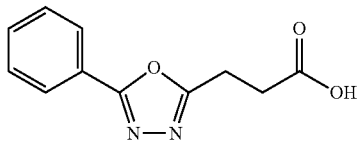 [SMILES: O=C(O)CCc1nnc(-c2ccccc2)o1]

A mixture of methyl 3-(5-phenyl-1,3,4-oxadiazol-2-yl)propanoate (600 mg, 2.0 mmol) in 1 M of aqueous NaOH (10 mL) and Methanol (10 mL) was stirred at room temperature overnight. The reaction solution was adjusted to pH 5 and extracted with ethyl acetate three times. The combined organic layers were dried, filtered and concentrated to yield the desired product (0.50 g, 83%). LCMS calculated for $C_{11}H_{11}N_2O_3$ (M+H): 219.1. Found 219.1.

Step D: N'-[(2E)-6-oxo-3-pentyl-1,3,6,7-tetrahydro-2H-purin-2-ylidene]-3-(5-phenyl-1,3,4-oxadiazol-2-yl)propanohydrazide

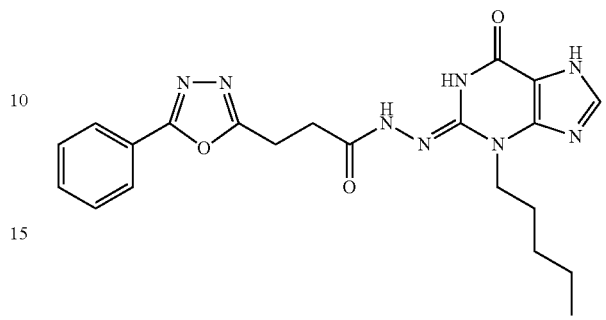

The mixture of 3-(5-phenyl-1,3,4-oxadiazol-2-yl)propanoic acid (500 mg, 20 mmol), (2E)-3-pentyl-3,7-dihydro-1H-purine-2,6-dione 2-hydrazone (480 mg, 0.0020 mol), benzotriazol-1-yloxytris(dimethylamino)phosphonium hexafluorophosphate (980 mg, 22 mmol), 4-dimethylaminopyridine (100 mg, 10 mmol), and N,N-diisopropylethylamine (0.73 mL, 42 mmol) in DMF (30 mL) was stirred at room temperature overnight. The mixture was quenched with water and extracted with ethyl acetate three times. The combined organic layers were washed by brine, dried over sodium sulfate, filtered and concentrated. The crude residue was purified by flash column chromatography to yield the desired product (485 mg, 48.5%). LCMS calculated for $C_{21}H_{25}N_8O_3$ (M+H): 437.2. Found 437.2.

Step E: 9-pentyl-3-[2-(5-phenyl-1,3,4-oxadiazol-2-yl)ethyl]-6,9-dihydro-5H-[1,2,4]triazolo[4,3-a]purin-5-one

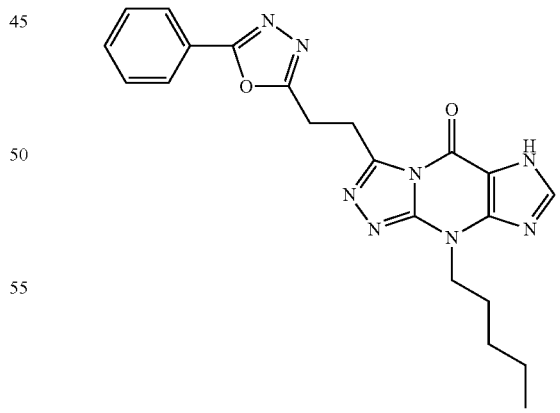

The mixture of N'-[(2E)-6-oxo-3-pentyl-1,3,6,7-tetrahydro-2H-purin-2-ylidene]-3-(5-phenyl-1,3,4-oxadiazol-2-yl)propanohydrazide (485 mg, 1.11 mmol) in toluene (50 mL) was heated to reflux overnight. The mixture was concentrated to yield the desired product (310 mg, 66.7%). LCMS calculated for $C_{21}H_{23}N_8O_2$ (M+H): 419.2. Found 419.2.

Step F: 7-bromo-9-pentyl-3-[2-(5-phenyl-1,3,4-oxadiazol-2-yl)ethyl]-6,9-dihydro-5H-[1,2,4]triazolo[4,3-a]purin-5-one

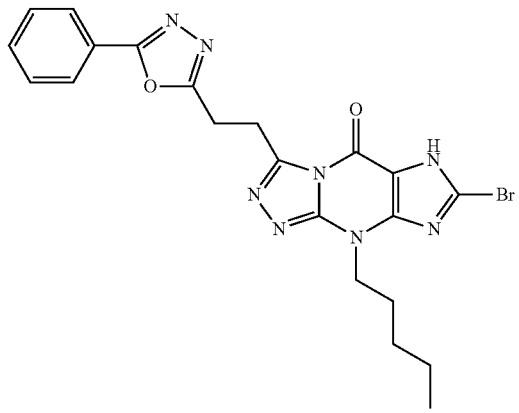 [SMILES: CCCCCn1c2nc(Br)[nH]c2c(=O)n2c(CCc3nnc(-c4ccccc4)o3)nnc12]

The mixture of 9-pentyl-3-[2-(5-phenyl-1,3,4-oxadiazol-2-yl)ethyl]-6,9-dihydro-5H-[1,2,4]triazolo[4,3-a]purin-5-one (53 mg, 0.13 mmol) and N-bromosuccinimide (34 mg, 0.19 mmol) in THF (20 mL) was stirred at 70° C. for 1 hour. The reaction mixture was concentrated and the residue was purified by preparative LCMS to give the desired product. LCMS calculated for $C_{21}H_{22}BrN_8O_2$ (M+H): 497.1. Found: 497.1.

Example 109

3-[2-(5-benzyl-1,3,4-oxadiazol-2-yl)ethyl]-7-bromo-9-pentyl-6,9-dihydro-5H-[1,2,4]triazolo[4,3-a]purin-5-one

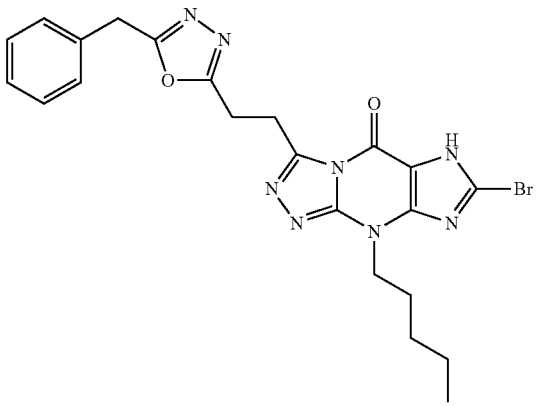 [SMILES: CCCCCn1c2nc(Br)[nH]c2c(=O)n2c(CCc3nnc(Cc4ccccc4)o3)nnc12]

The title compound was prepared using procedures analogous to those described for Example 108. $^1$HNMR (300 MHz, CD$_3$OD): δ 8.18 (d, J=7.2 Hz, 1H), 7.3 (m, 4H), 4.34 (m, 2H), 3.78 (m, 2H), 3.64 (m, 2H), 3.52 (m, 2H), 1.89 (m, 2H), 1.39 (m, 4H), 0.92 (m, 3H). LCMS calculated for $C_{22}H_{24}BrN_8O_2$ (M+H): 511.1. Found: 511.1, 513.1.

Example 110

N-[(7-bromo-5-oxo-9-pentyl-6,9-dihydro-5H-[1,2,4]triazolo[4,3-a]purin-3-yl)methyl]benzamide

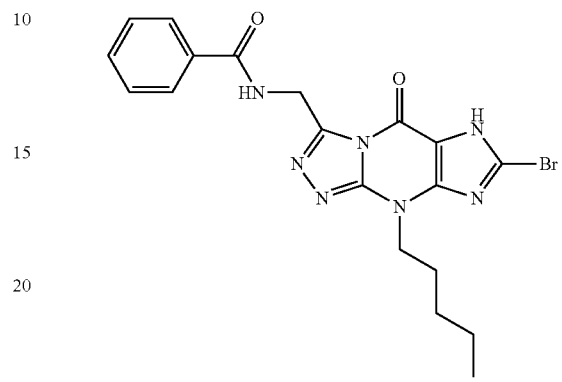

Step A: benzyl 2-oxo-2-[(2E)-2-(6-oxo-3-pentyl-1,3,6,7-tetrahydro-2H-purin-2-ylidene)hydrazino]ethylcarbamate

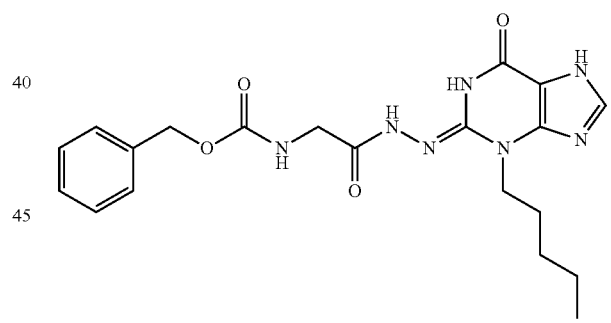

The mixture of (2E)-3-pentyl-3,7-dihydro-1H-purine-2,6-dione 2-hydrazone (0.50 g, 0.0021 mol), N-carbobenzyloxyglycine (0.49 g, 0.0023 mol), benzotriazol-1-yloxytris(dimethylamino)-phosphonium hexafluorophosphate (1.0 g, 2.3 mmol) and triethylamine (0.59 mL, 0.0042 mol) in DMF (20 mL) was stirred at room temperature overnight. The reaction mixture was diluted with EtOAc and washed with water (4×) and brine (1×). The aqueous was extracted with EtOAc (2×). The combined organic layers were dried (MgSO$_4$) and concentrated to give the desired product (1.30 g, 86%). LCMS calculated for $C_{20}H_{26}N_7O_4$ (M+H): 428.2. Found 428.2.

Step B: benzyl[(5-oxo-9-pentyl-6,9-dihydro-5H-[1,2,4]triazolo[4,3-a]purin-3-yl)methyl]carbamate

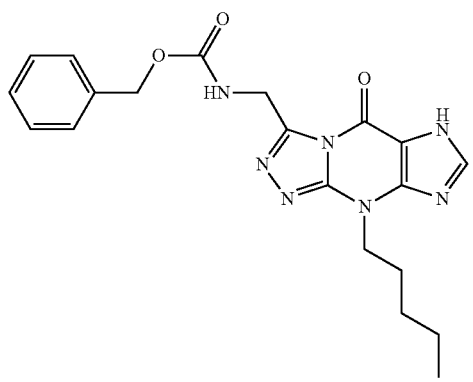 [SMILES: CCCCCn1c2nc[nH]c2c(=O)n2c(CNC(=O)OCc3ccccc3)nnc12]

The solution of benzyl 2-oxo-2-[(2E)-2-(6-oxo-3-pentyl-1,3,6,7-tetrahydro-2H-purin-2-ylidene)hydrazino]ethylcarbamate (0.60 g, 0.84 mmol) in toluene (30 mL) was refluxed overnight. M+H=410.1. The product was precipitated from the reaction mixture and filtered to give the desired product (300 mg, 87%). LCMS calculated for $C_{20}H_{24}N_7O_3$ (M+H): 410.2. Found: 410.2.

Step C: 3-(aminomethyl)-9-pentyl-6,9-dihydro-5H-[1,2,4]triazolo[4,3-a]purin-5-one hydrochloride

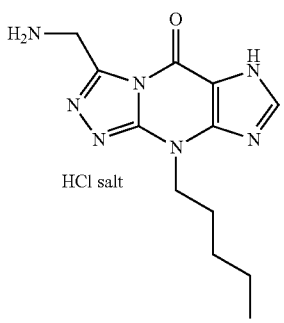 [SMILES: CCCCCn1c2nc[nH]c2c(=O)n2c(CN)nnc12]

HCl salt

To the solution of benzyl[(5-oxo-9-pentyl-6,9-dihydro-5H-[1,2,4]triazolo[4,3-a]purin-3-yl)methyl]carbamate (0.30 g, 0.73 mmol) in methanol (20 mL) and 1 mL of conc. HCl was added 10% Pd/C under $N_2$. The mixture was shaken under 30 PSI $H_2$ for 3 hours. The reaction mixture was filtered through celite and concentrated to yield the desired product (210 mg, 92%). LCMS calculated for $C_{12}H_{18}N_7O$ (M+H): 276.2. Found: 276.2.

Step D: N-[(5-oxo-9-pentyl-6,9-dihydro-5H-[1,2,4]triazolo[4,3-a]purin-3-yl)methyl]benzamide

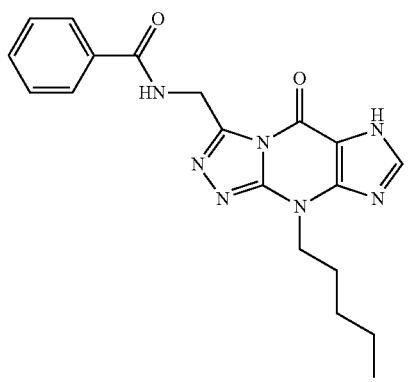 [SMILES: CCCCCn1c2nc[nH]c2c(=O)n2c(CNC(=O)c3ccccc3)nnc12]

The mixture of 3-(aminomethyl)-9-pentyl-6,9-dihydro-5H-[1,2,4]triazolo[4,3-a]purin-5-one hydrochloride (160 mg, 0.51 mmol), [B] benzoic Acid (0.069 g, 0.56 mmol), benzotriazol-1-yloxytris(dimethylamino)phosphonium hexafluorophosphate (0.25 g, 0.56 mmol) and triethylamine (0.21 mL, 1.5 mmol) in DMF (10 mL) was stirred at room temperature overnight. The reaction mixture was purified by preparative LCMS to yield the desired product (150 mg, 77%). LCMS calculated for $C_{19}H_{22}N_7O_2$ (M+H): 380.2. Found: 380.2.

Step E: N-[(7-bromo-5-oxo-9-pentyl-6,9-dihydro-5H-[1,2,4]triazolo[4,3-a]purin-3-yl)methyl]benzamide

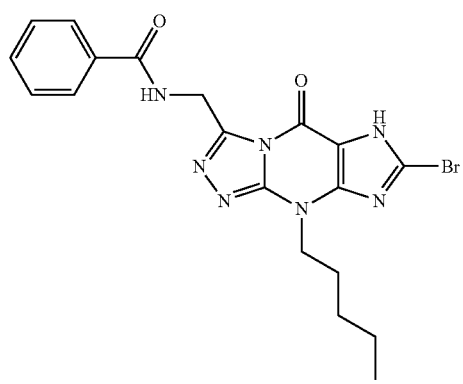 [SMILES: CCCCCn1c2nc(Br)[nH]c2c(=O)n2c(CNC(=O)c3ccccc3)nnc12]

To the solution of N-[(5-oxo-9-pentyl-6,9-dihydro-5H-[1,2,4]triazolo[4,3-a]purin-3-yl)methyl]benzamide (0.11 g, 0.28 mmol) in THF (10 mL) was added N-Bromosuccinimide (0.076 g, 0.42 mmol). The mixture was stirred at 70° C. for 1 hour. The reaction mixture was concentrated and purified by preparative LCMS. LCMS calculated for $C_{19}H_{21}BrN_7O_2$ (M+H): 458.1. Found: 458.0, 460.0.

Example 111

N-[(7-bromo-5-oxo-9-pentyl-6,9-dihydro-5H-[1,2,4]triazolo[4,3-a]purin-3-yl)methyl]acetamide

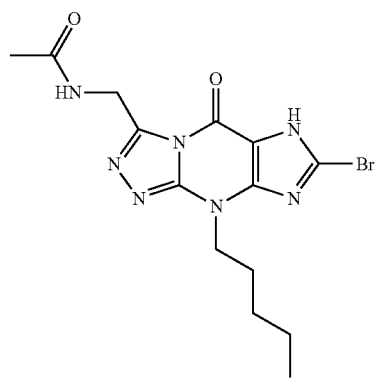 [SMILES: CCCCCn1c2nc(Br)[nH]c2c(=O)n2c(CNC(C)=O)nnc12]

The title compound was prepared using procedures analogous to those described for Example 108. LCMS calculated for $C_{14}H_{19}BrN_7O_2$ (M+H): 396.1. Found: 396.0, 398.0.

Example 112

3-(1-benzoylpiperidin-4-yl)-7-bromo-9-pentyl-6,9-dihydro-5H-[1,2,4]triazolo[4,3-a]purin-5-one

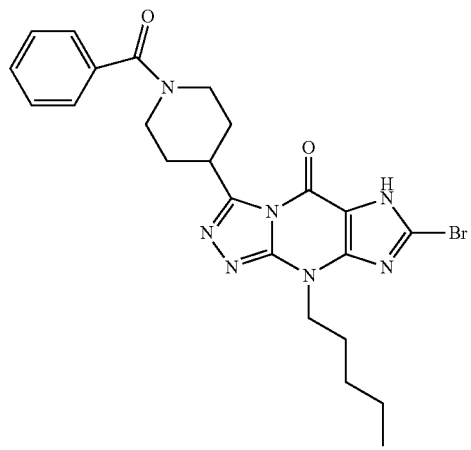 [SMILES: CCCCCn1c2nc(Br)[nH]c2c(=O)n2c(C3CCN(C(=O)c4ccccc4)CC3)nnc12]

The title compound was prepared using procedures analogous to those described for Example 108. LCMS calculated for $C_{23}H_{27}BrN_7O_2$ (M+H): 512.1. Found: 512.1, 514.1.

Example 113

3-[3-(3-benzyl-1,2,4-oxadiazol-5-yl)propyl]-7-bromo-9-pentyl-6,9-dihydro-5H-[1,2,4]triazolo[4,3-a]purin-5-one

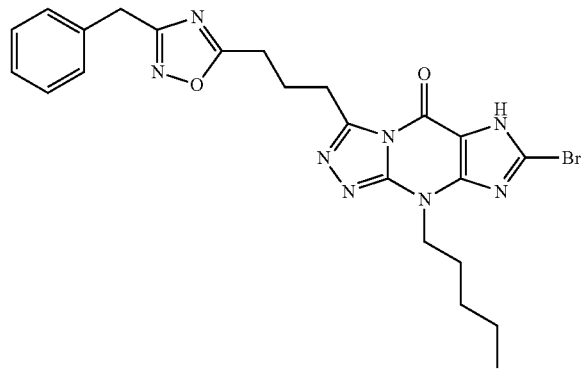 [SMILES: CCCCCn1c2nc(Br)[nH]c2c(=O)n2c(CCCc3nc(Cc4ccccc4)no3)nnc12]

The title compound was prepared using procedures analogous to those described for example 72. $^1$HNMR (300 MHz, CD$_3$OD): δ 7.24 (m, 5H), 4.31 (t, J=6.8 Hz, 2H), 3.97 (s, 2H), 3.40 (t, J=6.8 Hz, 2H), 3.03 (t, J=6.8 Hz, 2H), 2.33 (m, 2H), 1.88 (m, 2H), 1.40 (m, 4H), 0.92 (m, 3H). LCMS calculated for $C_{23}H_{26}BrN_8O_2$ (M+H): 525.1. Found: 525.1, 527.1.

Example 114

2-bromo-4-pentyl-1,4-dihydro-9H-[1,2,4]triazolo[1,5-a]purin-9-one

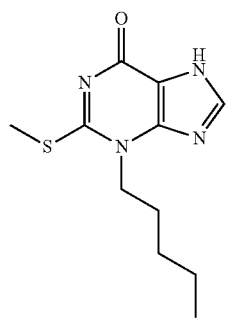 [SMILES: CCCCCn1c(SC)nc(=O)c2[nH]cnc21]

Step A: 2-(methylthio)-3-pentyl-3,7-dihydro-6H-purin-6-one

To a solution of 3-pentyl-2-thioxo-1,2,3,7-tetrahydro-6H-purin-6-one (13.0 g, 54.6 mmol) in 2 M of sodium hydroxide in water (250 mL) was added dimethyl sulfate (6.2 mL, 66 mmol), and the reaction mixture was stirred at room temperature for 1 hour, then neutralized with acetic acid. The precipitate was collected by filtration and recrystallized from ethyl acetate-MeOH (1:1) to give the desired product (5.50 g, 40%). LCMS calculated for $C_{11}H_{17}N_4OS$ (M+H): 253.1. Found: 253.1.

Step B: 2-amino-3-pentyl-3,7-dihydro-6H-purin-6-one

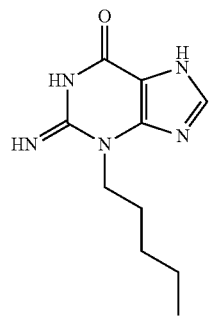 [SMILES: CCCCCn1c(=N)[nH]c(=O)c2[nH]cnc21]

2-(Methylthio)-3-pentyl-3,7-dihydro-6H-purin-6-one (5.0 g, 0.020 mol) was mixed with 100 ml of 28% ammonia hydroxide in a seal tube. The mixture was stirred at 100° C. for 4 days. After cooling to room temperature, the solid was filtered and dried to yield the desired product (3.0 g, 68%). LCMS calculated for $C_{10}H_{16}N_5O$ (M+H): 222.1. Found: 222.1.

Step C: 1-amino-2-imino-3-pentyl-1,2,3,7-tetrahydro-6H-purin-6-one

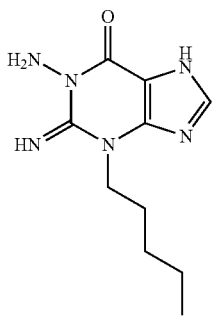 [SMILES: CCCCCn1c(=N)n(N)c(=O)c2[nH]cnc21]

A solution of 2-imino-3-pentyl-1,2,3,7-tetrahydro-6h-purin-6-one (750 mg, 3.39 mmol) and 18 m of hydrazine in water (30 ml) was stirred at 150° C. for 30 min on a microwave reactor. The reaction was diluted with water and extracted with ethyl acetate three times, dried with sodium sulfate, filtered, and concentrated in vacuo to yield the crude product for next step without further purification. LCMS calculated for $C_{10}H_{17}N_6O$ (M+H): 237.1. Found: 237.2.

Step D: 4-pentyl-1,4-dihydro-9H-[1,2,4]triazolo[1,5-a]purin-9-one

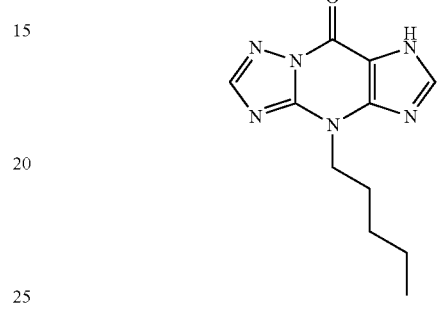

The mixture of 1-amino-2-imino-3-pentyl-1,2,3,7-tetrahydro-6H-purin-6-one (0.10 g, 0.4 mmol) and ethyl orthoformate (5 mL, 30 mmol) was stirred at 100° C. for 6 hours. The reaction mixture was concentrated and purified by preparative LCMS to yield the desired product (20 mg, 20%). LCMS calculated for $C_{11}H_{15}N_6O$ (M+H): 247.1. Found: 247.1.

Step E: 2-bromo-4-pentyl-1,4-dihydro-9H-[1,2,4]triazolo[1,5-a]purin-9-one

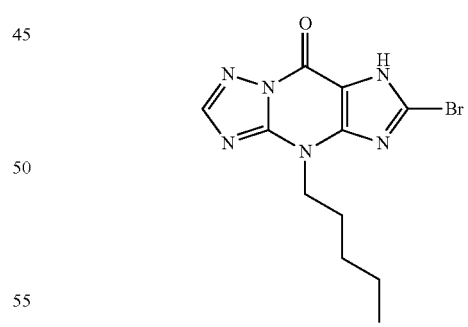

To the mixture of 4-pentyl-1,4-dihydro-9H-[1,2,4]triazolo[1,5-a]purin-9-one (19 mg, 0.077 mmol) in tetrahydrofuran (10 mL) was added N-bromosuccinimide (20 mg, 0.12 mol) at rt. The mixture was stirred at 70° C. for 1 hour. The mixture was concentrated and purified by preparative LCMS to yield the desired product (3.10 mg, 12.4%). LCMS calculated for $C_{11}H_{14}BrN_6O$ (M+H): 325.0. Found: 325.0, 327.0.

Example 115

3-methyl-9-pentyl-7-(1,3-thiazol-4-yl)-6,9-dihydro-5H-[1,2,4]triazolo[4,3-a]purin-5-one

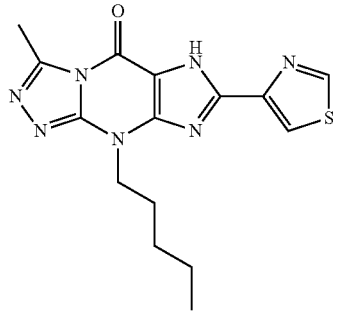 [SMILES: CCCCCn1c2nc(-c3cscn3)[nH]c2c(=O)n2c(C)nnc12]

The title compound was prepared using procedures analogous to those described for Example 32. LCMS calculated for $C_{15}H_{18}N_7OS$ (M+H): 344.1. Found: 344.1

Example 116

7-bromo-9-pentyl-3-[2-(3-pyrazin-2-yl-1,2,4-oxadiazol-5-yl)ethyl]-6,9-dihydro-5H-[1,2,4]triazolo[4,3-a]purin-5-one trifluoroacetate

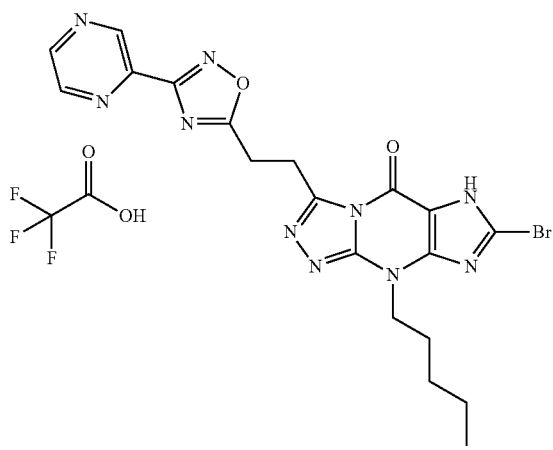

The title compound was prepared using procedures analogous to those described for Example 72. $^1$HNMR (300 MHz, d$_6$-DMSO): δ 8.78 (d, J=1.9 Hz, 1H), 8.36 (dd, J=1.9, 5.0 Hz, 1H), 7.62 (dd, J=1.9, 8.2 Hz, 1H), 4.21 (t, J=7.1 Hz, 2H), 3.77 (t, J=7.1 Hz, 2H), 3.56 (t, J=7.1 Hz, 2H), 1.79 (m, 2H), 1.29 (m, 4H), 0.83 (m, 3H). LCMS calculated for $C_{19}H_{19}BrN_{10}O_2$ (M+H): 499.1. Found: 499.1

Example 117

7-bromo-9-pentyl-3-[2-(3-pyridin-3-yl-1,2,4-oxadiazol-5-yl)ethyl]-6,9-dihydro-5H-[1,2,4]triazolo[4,3-a]purin-5-one trifluoroacetate

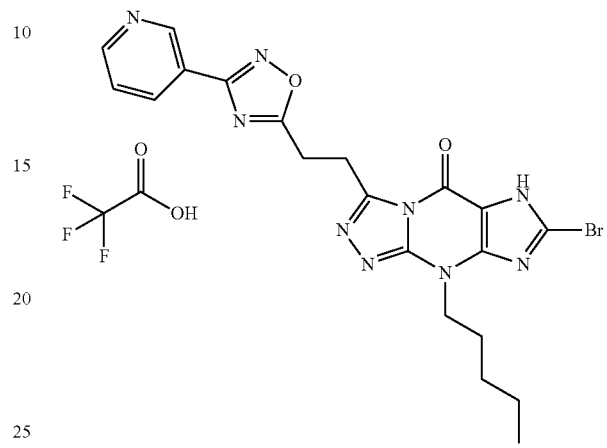

The title compound was prepared using procedures analogous to those described for Example 72. $^1$HNMR (300 MHz, CD$_3$OD): δ 9.27 (s, 1H), 8.75 (m, 2H), 4.33 (t, J=8.1 Hz, 2H), 3.92 (t, J=8.1 Hz, 2H), 3.64 (t, J=8.1 Hz, 2H), 1.89 (m, 2H), 1.39 (m, 4H), 0.90 (m, 3H). LCMS calculated for $C_{20}H_{20}BrN_9O_2$ (M+H): 498.1. Found: 498.1

Example 118

7-bromo-9-pentyl-3-[2-(3-pyridin-2-yl-1,2,4-oxadiazol-5-yl)ethyl]-6,9-dihydro-5H-[1,2,4]triazolo[4,3-a]purin-5-one trifluoroacetate

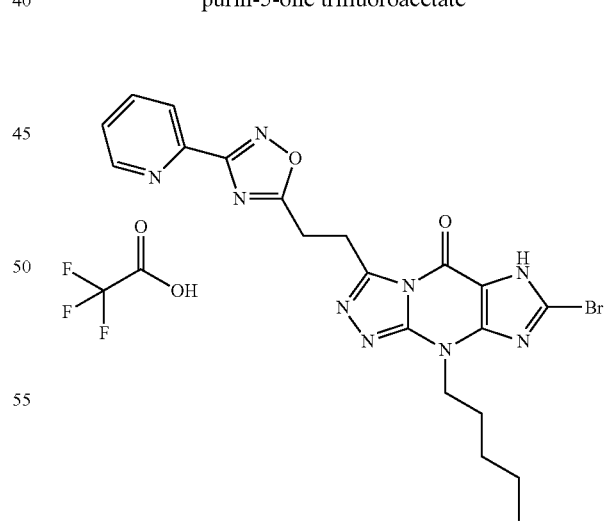

The title compound was prepared using procedures analogous to those described for Example 72. $^1$HNMR (300 MHz, d$_6$-DMSO): δ 8.68 (S, 1H), 7.95 (m, 2H), 7.53 (m, 2H), 4.15 (m, 2H), 3.72 (m, 2H), 3.50 (m, 2H), 1.74 (m, 2H), 1.24 (m, 4H), 0.78 (m, 3H). LCMS calculated for $C_{20}H_{20}BrN_9O_2$ (M+H): 498.1. Found: 498.1

Example 119

7-bromo-9-pentyl-3-[2-(3-pyridin-4-yl-1,2,4-oxadiazol-5-yl)ethyl]-6,9-dihydro-5H-[1,2,4]triazolo[4,3-a]purin-5-one trifluoroacetate

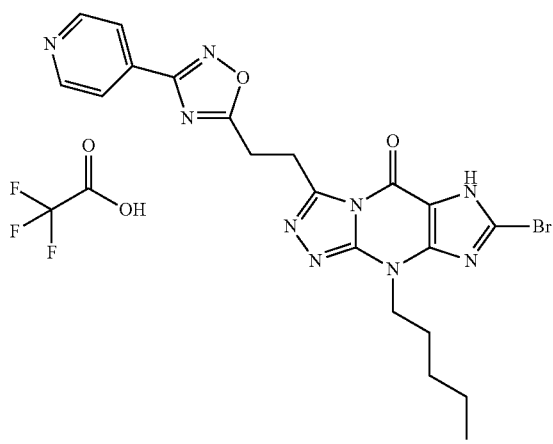

The title compound was prepared using procedures analogous to those described for Example 72. $^1$HNMR (300 MHz, $d_6$-DMSO): δ 8.77 (d, J=5.5 Hz, 2H), 7.89 (d, J=5.5 Hz, 2H), 4.20 (t, J=8.3 Hz, 2H), 3.77 (t, J=8.3 Hz, 2H), 3.56 (t, J=8.3 Hz, 2H), 1.78 (m, 2H), 1.28 (m, 4H), 0.82 (m, 3H). LCMS calculated for $C_{20}H_{20}BrN_9O_2$ (M+H): 498.1. Found: 498.1

Example 120

7-bromo-9-pentyl-3-{2-[3-(2-thienyl)-1,2,4-oxadiazol-5-yl)ethyl]-6,9-dihydro-5H-[1,2,4]triazolo[4,3-a]purin-5-one

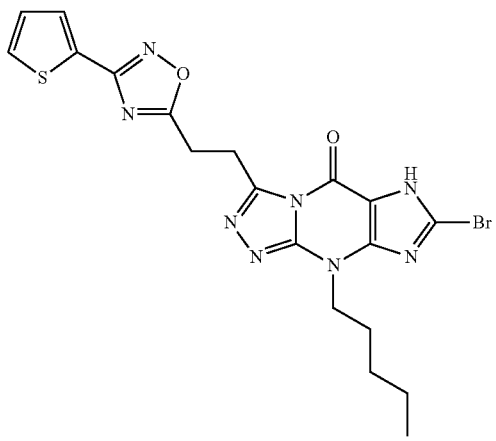 [SMILES: CCCCCn1c2nc(Br)[nH]c2c(=O)n2c(CCc3nc(-c4cccs4)no3)nnc12]

The title compound was prepared using procedures analogous to those described for Example 72. $^1$HNMR (300 MHz, $d_6$-DMSO): δ 7.85 (dd, J=1.3, 5.0 Hz, 1H), 7.74 (dd, J=1.3, 4.0 Hz, 1H), 7.22 (dd, J=5.0, 4.0 Hz, 1H), 4.20 (t, J=6.8 Hz, 2H), 3.73 (t, J=6.8 Hz, 2H), 3.49 (t, J=6.8 Hz, 2H), 1.79 (m, 2H), 1.28 (m, 4H), 0.82 (m, 3H). LCMS calculated for $C_{19}H_{19}BrN_8O_2S$ (M+H): 503.1. Found: 503.1.

Example 121

3-(1,3-benzodioxol-5-ylmethyl)-7-bromo-9-pentyl-6,9-dihydro-5H-[1,2,4]triazolo[4,3-a]purin-5-one

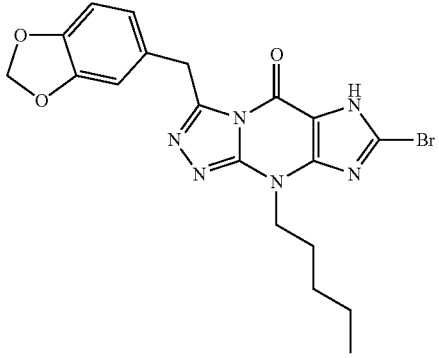 [SMILES: CCCCCn1c2nc(Br)[nH]c2c(=O)n2c(Cc3ccc4c(c3)OCO4)nnc12]

The title compound was prepared using procedures analogous to those described for Example 35. $^1$HNMR (400 MHz, $CD_3OD$): δ 6.83 (s, 1H), 6.78 (dd, J=2.1, 7.5 Hz, 1H), 6.70 (dd, J=2.1, 7.5 Hz, 1H), 4.53 (s, 2H), 4.31 (m, 2H), 1.88 (m, 2H), 1.28 (m, 4H), 0.90 (m, 3H). LCMS calculated for $C_{19}H_{19}BrN_6O_3$ (M+H): 458.1. Found: 459.1, 461.1.

Example 122

7-bromo-9-pentyl-3-pyrimidin-5-yl-6,9-dihydro-5H-[1,2,4]triazolo[4,3-a]purin-5-one

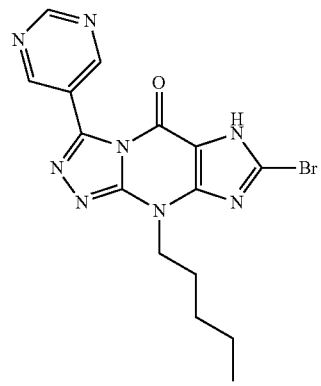 [SMILES: CCCCCn1c2nc(Br)[nH]c2c(=O)n2c(-c3cncnc3)nnc12]

The title compound was prepared using procedures analogous to those described for Example 16. $^1$HNMR (300 MHz, $d_6$-DMSO): δ 9.27 (s, 1H), 9.11 (s, 2H), 4.34 (t, J=6.9 Hz, 2H), 3.38 (br, 1H), 1.87 (m, 2H), 1.34 (m, 4H), 0.87 (m, 3H). LCMS calculated for $C_{15}H_{15}BrN_8O$ (M+H): 403.1. Found: 403.1, 405.1.

Example 123

7-bromo-9-pentyl-3-[3-(3-phenyl-1,2,4-oxadiazol-5-yl)propyl]-6,9-dihydro-5H-[1,2,4]triazolo[4,3-a]purin-5-one

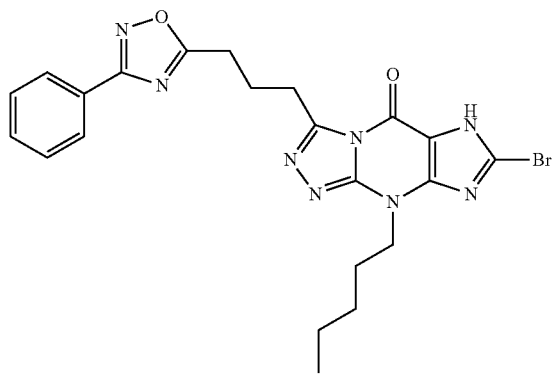 [SMILES: CCCCCn1c2nc(Br)[nH]c2c(=O)n2c(CCCc3nc(-c4ccccc4)no3)nnc12]

Step A: methyl 4-(3-phenyl-1,2,4-oxadiazol-5-yl)butanoate

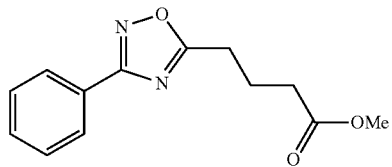 [SMILES: COC(=O)CCCc1nc(-c2ccccc2)no1]

Pentanedioic acid, monomethyl ester (1.00 g, 6.84 mmole) and CDI (1.22 g, 7.53 mmole) were dissoled in anhydrous DMF (10 ml). After stirring at room temperature for 3 hours, (1Z)—N'-hydroxybenzenecarboimidamide (1.02 g, 7.53 mmole) was added and the solution heated at 90° C. for 20 h. After evaporation of solvent, the residue was diluted with ethyl acetate. The organic layer was washed with water and brine, dried over $Na_2SO_4$, filtered and concentrated to give the desired product (1.53 g, 91% yield). LCMS calculated for $C_{13}H_{15}N_2O_3$ (M+H): 247.1. Found: 247.1.

Step B: 4-(3-phenyl-1,2,4-oxadiazol-5-yl)butanoic acid

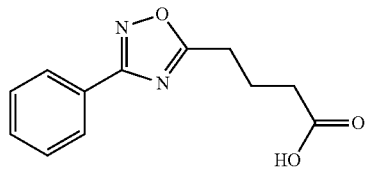 [SMILES: O=C(O)CCCc1nc(-c2ccccc2)no1]

To a solution of methyl 3-(3-phenyl-1,2,4-oxadiazol-5-yl)butanoate (1.53 g, 6.21 mmole) in methanol (10 ml) was added 1N NaOH (10 mL). After stirring at room temperature for 2 hours, the reaction solution was acidified to pH=3-4 with 6N HCl under an ice bath and then extracted with ethyl acetate three times. The combined organic layers were washed with water and then brine, dried over $Na_2SO_4$, filtered and concentrated to give the desired product (1.44 g, 99% yield) as white solid. LCMS calculated for $C_{12}H_{13}N_2O_3$ (M+H): 233.1. Found: 233.1.

Step C: N'-[(2E)-6-oxo-3-pentyl-1,3,6,7-tetrahydro-2H-purin-2-ylidene]-4-(3-phenyl-1,2,4-oxadiazol-5-yl)butanohydrazide

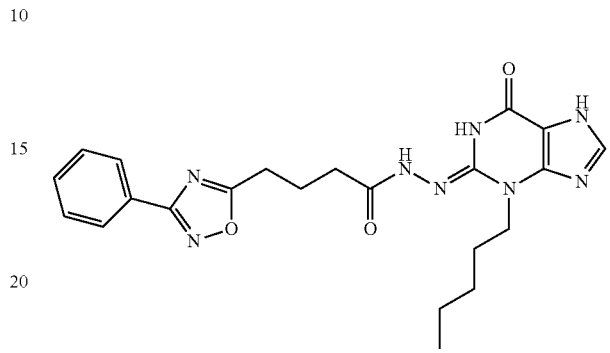

A mixture of 4-(3-phenyl-1,2,4-oxadiazol-5-yl)butanoic acid (1.44 g, 6.20 mmol), (2e)-3-pentyl-3,7-dihydro-1h-purine-2,6-dione 2-hydrazone (1.61 g, 6.82 mmol), benzotriazol-1-yloxytris(dimethylamino)phosphonium hexafluorophosphate (3.02 g, 6.82 mmol) and triethylamine (1.73 ml, 12.4 mmol) in DMF (30 ml) was stirred at room temperature overnight. The reaction was diluted with water and extracted with ethyl acetate (3×). The organic layer was washed with water and then brine, dried over $Na_2SO_4$, filtered and concentrated to give the desired product (2.78 g, 99% yield) as yellowish oil. LCMS calculated for $C_{22}H_{27}N_8O_3$ (M+H): 451.2. Found: 451.1.

Step D: 9-pentyl-3-[3-(3-phenyl-1,2,4-oxadiazol-5-yl)propyl]-6,9-dihydro-5H-[1,2,4]triazolo[4,3-a]purin-5-one

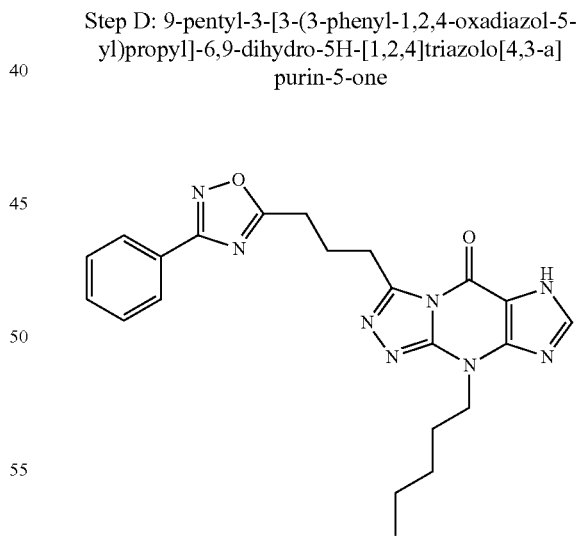

The mixture of N'-[(2E)-6-oxo-3-pentyl-1,3,6,7-tetrahydro-2H-purin-2-ylidene]-4-(3-phenyl-1,2,4-oxadiazol-5-yl)butanohydrazide (2.78 g, 6.17 mmol) in toluene (100 ml) was refluxed for 2 hours. After cooling to room temperature, the solid was filtered, washed with ethyl acetate/Hexane (1:9) and dried to give the desired product (1.97 g, 74% yield). LCMS calculated for $C_{22}H_{25}N_8O_2$ (M+H): 433.2. Found: 433.1.

Step E: 7-bromo-9-pentyl-3-[3-(3-phenyl-1,2,4-oxa-diazol-5-yl)propyl]-6,9-dihydro-5H-[1,2,4]triazolo[4,3-c]purin-5-one

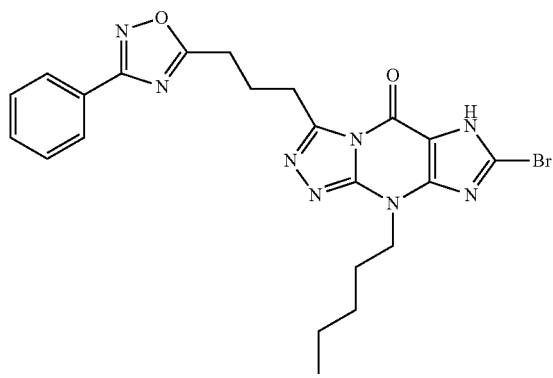 [SMILES: CCCCCn1c2nc(Br)[nH]c2c(=O)n2c(CCCc3nc(-c4ccccc4)no3)nnc12]

To the solution of 9-pentyl-3-[3-(3-phenyl-1,2,4-oxadiazol-5-yl)propyl]-6,9-dihydro-5H-[1,2,4]triazolo[4,3-a]purin-5-one (0.50 g, 1.16 mmole) in THF (125 ml) at room temperature was added N-bromosuccinimide (0.309 g, 1.73 mmole). The mixture was stirred at 70° C. for 1 h. The mixture was concentrated and purified by preparative LCMS to yield the desired product (122 mg, 21% yield). LCMS calculated for $C_{22}H_{24}BrN_8O_2$ (M+H): 511.1. Found: 511.0.

Example 124

7-bromo-9-pentyl-3-[3-(3-pyridin-2-yl-1,2,4-oxadiazol-5-yl)propyl]-6,9-dihydro-5H-[1,2,4]triazolo[4,3-a]purin-5-one trifluoroacetate

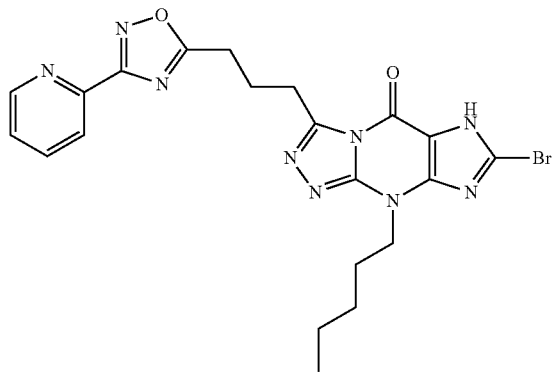 [SMILES: CCCCCn1c2nc(Br)[nH]c2c(=O)n2c(CCCc3nc(-c4ccccn4)no3)nnc12]

The title compound was prepared using procedures analogous to those described for example 123. LCMS calculated for $C_{21}H_{22}BrN_9O_2$ (M+H): 511.1, 513.1. Found: 511.1, 513.1.

Example 125

7-bromo-9-pentyl-3-[3-(3-pyridin-3-yl-1,2,4-oxadiazol-5-yl)propyl]-6,9-dihydro-5H-[1,2,4]triazolo[4,3-a]purin-5-one trifluoroacetate

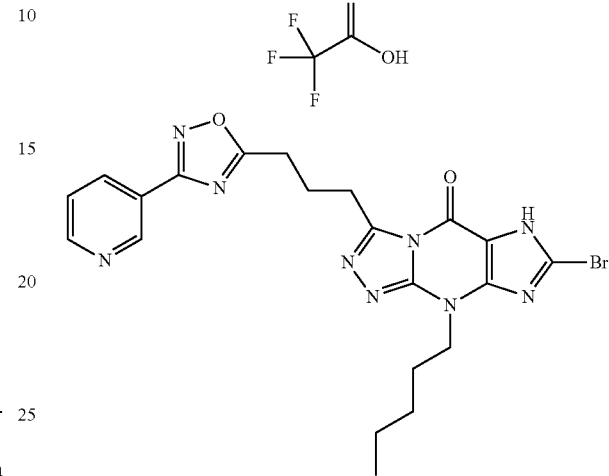

The title compound was prepared using procedures analogous to those described for example 123. LCMS calculated for $C_{21}H_{22}BrN_9O_2$ (M+H): 511.1, 513.1. Found: 511.1, 513.1.

Example 126

7-bromo-9-pentyl-3-[3-(3-pyridin-4-yl-1,2,4-oxadiazol-5-yl)propyl]-6,9-dihydro-5H-[1,2,4]triazolo[4,3-a]purin-5-one trifluoroacetate

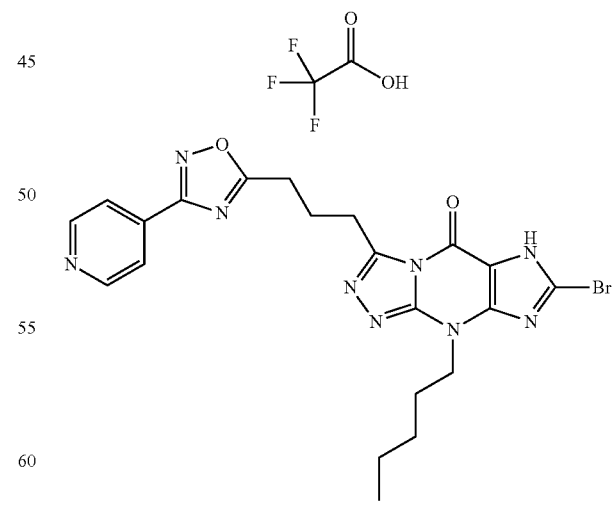

The title compound was prepared using procedures analogous to those described for example 123. LCMS calculated for $C_{21}H_{22}BrN_9O_2$ (M+H): 511.1, 513.1. Found: 511.1, 513.1.

Example 127

7-bromo-9-pentyl-3-[3-(3-pyrazin-2-yl-1,2,4-oxadiazol-5-yl)propyl]-6,9-dihydro-5H-[1,2,4]triazolo[4,3-a]purin-5-one trifluoroacetate

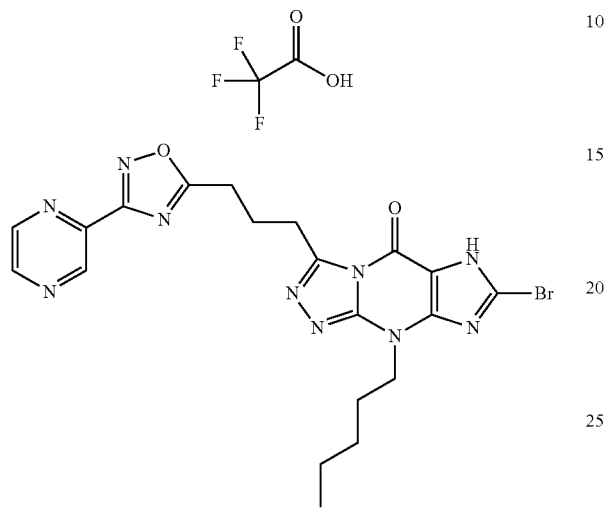

The title compound was prepared using procedures analogous to those described for example 123. LCMS calculated for $C_{20}H_{21}BrN_{10}O_2$ (M+H): 513.1, 515.1. Found: 513.1, 515.1.

Example 128

7-bromo-9-pentyl-3-{3-[3-(2-thienyl)-1,2,4-oxadiazol-5-yl]propyl}-6,9-dihydro-5H-[1,2,4]triazolo[4,3-a]purin-5-one

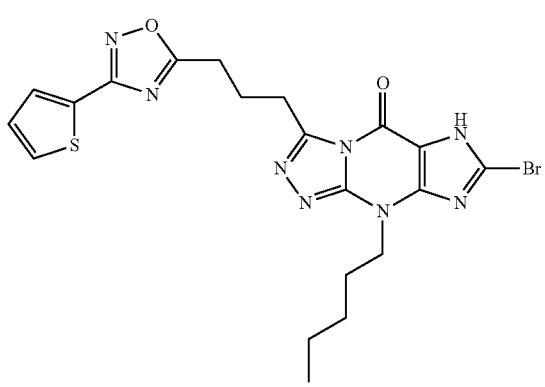 [SMILES: CCCCCn1c2nc(Br)[nH]c2c(=O)n2c(CCCc3nc(-c4cccs4)no3)nnc12]

The title compound was prepared using procedures analogous to those described for example 123. LCMS calculated for $C_{20}H_{21}BrN_8O_2S$ (M+H): 517.1, 519.1. Found: 517.1, 519.1.

Example 129

7-bromo-9-pentyl-3-{3-[3-(3-thienyl)-1,2,4-oxadiazol-5-yl]propyl}-6,9-dihydro-5H-[1,2,4]triazolo[4,3-a]purin-5-one

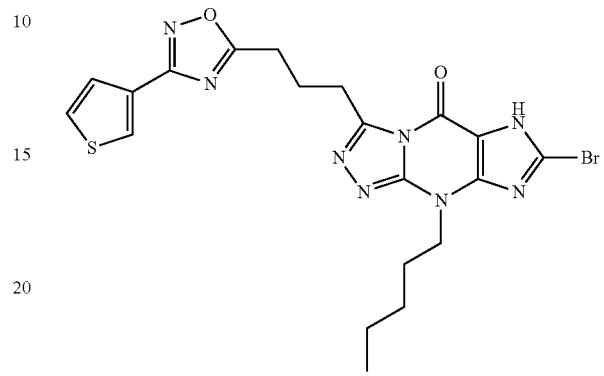

The title compound was prepared using procedures analogous to those described for example 123. LCMS calculated for $C_{20}H_{21}BrN_8O_2S$ (M+H): 517.1, 519.1. Found: 517.1, 519.1.

Example 130

7-bromo-9-pentyl-3-(3-{3-[3-(trifluoromethyl)phenyl]-1,2,4-oxadiazol-5-yl}propyl)-6,9-dihydro-5H-[1,2,4]triazolo[4,3-a]purin-5-one

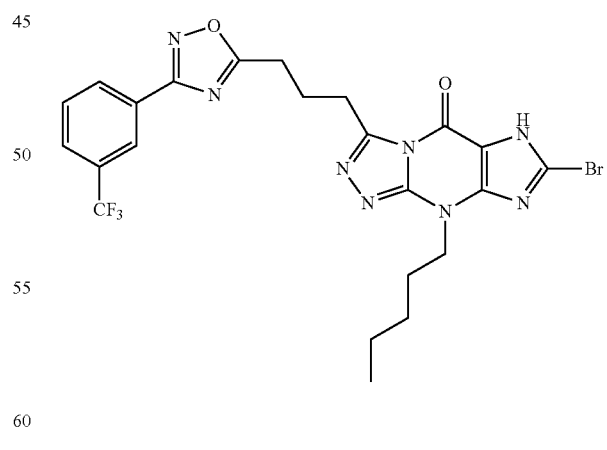

The title compound was prepared using procedures analogous to those described for example 123. LCMS calculated for $C_{23}H_{22}BrF_3N_8O_2$ (M+H): 579.1, 581.1. Found: 579.1, 581.1.

Example 131

7-bromo-3-{3-[3-(4-methoxyphenyl)-1,2,4-oxadiazol-5-yl]propyl}-9-pentyl-6,9-dihydro-5H-[1,2,4]triazolo[4,3-a]purin-5-one

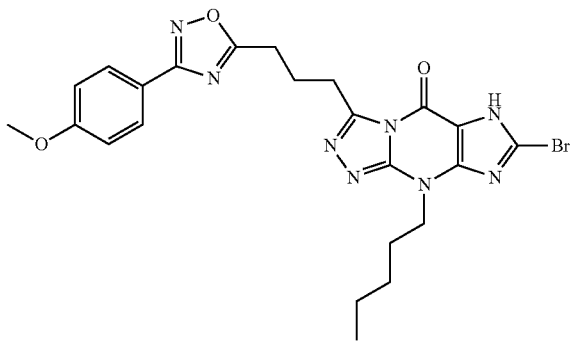 [SMILES: CCCCCn1c2nc(Br)[nH]c2c(=O)n2c(CCCc3nc(-c4ccc(OC)cc4)no3)nnc12]

The title compound was prepared using procedures analogous to those described for example 123. LCMS calculated for $C_{23}H_{25}BrN_8O_3$ (M+H): 541.1, 543.1. Found: 541.1, 543.1.

Example 132

7-bromo-3-{3-[3-(4-fluorophenyl)-1,2,4-oxadiazol-5-yl]propyl}-9-pentyl-6,9-dihydro-5H-[1,2,4]triazolo[4,3-a]purin-5-one

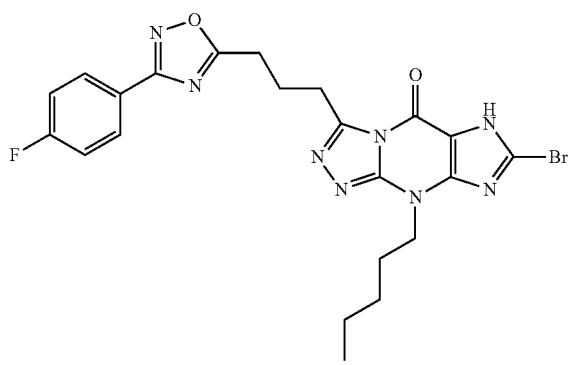 [SMILES: CCCCCn1c2nc(Br)[nH]c2c(=O)n2c(CCCc3nc(-c4ccc(F)cc4)no3)nnc12]

The title compound was prepared using procedures analogous to those described for example 123. LCMS calculated for $C_{22}H_{22}BrFN_8O_2$ (M+H): 529.1, 531.1. Found: 529.1, 531.1.

Example 133

7-bromo-9-pentyl-3-[3-(3-pyrimidin-2-yl-1,2,4-oxadiazol-5-yl)propyl]-6,9-dihydro-5H-[1,2,4]triazolo[4,3-a]purin-5-one trifluoroacetate

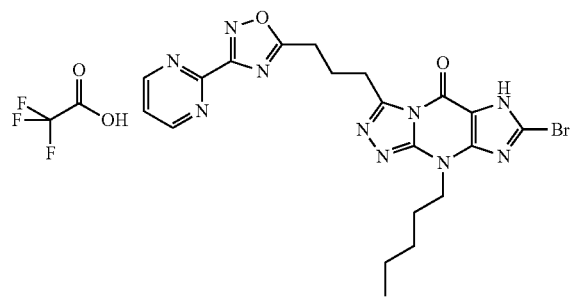

The title compound was prepared using procedures analogous to those described for example 123. LCMS calculated for $C_{20}H_{21}BrN_{10}O_2$ (M+H): 513.1, 515.1. Found: 513.1, 515.1.

Example 134

7-bromo-3-{3-[3-(2-methoxyphenyl)-1,2,4-oxadiazol-5-yl]propyl}-9-pentyl-6,9-dihydro-5H-[1,2,4]triazolo[4,3-a]purin-5-one

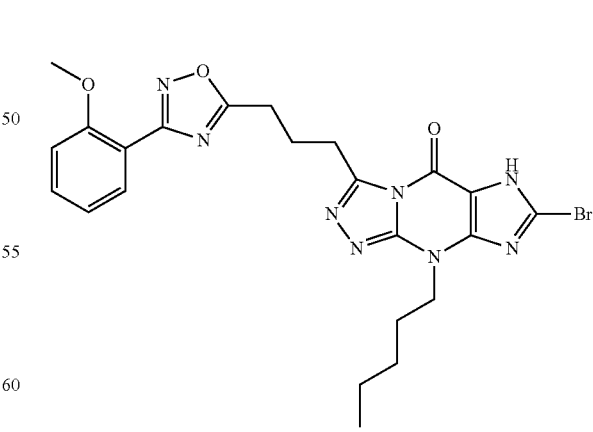

The title compound was prepared using procedures analogous to those described for example 123. LCMS calculated for $C_{23}H_{25}BrN_8O_3$ (M+H): 541.1, 543.1. Found: 541.1, 543.1.

Example 135

7-bromo-3-{3-[3-(3-methoxyphenyl)-1,2,4-oxadiazol-5-yl]propyl}-9-pentyl-6,9-dihydro-5H-[1,2,4]triazolo[4,3-a]purin-5-one

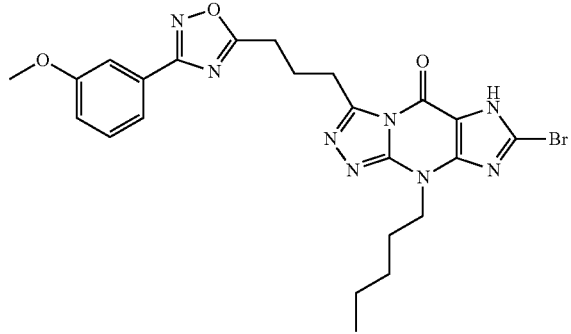 [SMILES: CCCCCn1c2nc(Br)[nH]c2c(=O)n2c(CCCc3nc(-c4cccc(OC)c4)no3)nnc12]

The title compound was prepared using procedures analogous to those described for example 123. LCMS calculated for $C_{23}H_{25}BrN_8O_3$ (M+H): 541.1, 543.1. Found: 541.1, 543.1.

Example 136

7-bromo-3-{3-[3-(4-ethynylphenyl)-1,2,4-oxadiazol-5-yl]propyl}-9-pentyl-6,9-dihydro-5H-[1,2,4]triazolo[4,3-a]purin-5-one

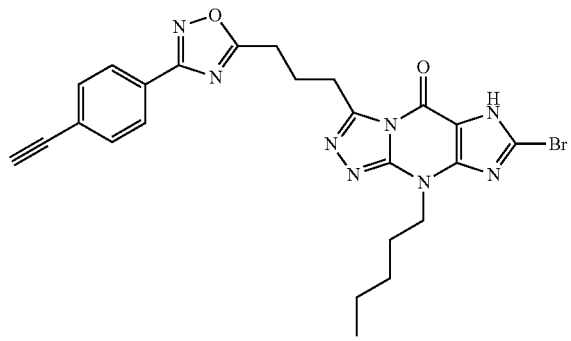 [SMILES: C#Cc1ccc(-c2noc(CCCc3nnc4n(CCCCC)c5nc(Br)[nH]c5c(=O)n34)n2)cc1]

The title compound was prepared using procedures analogous to those described for example 123. LCMS calculated for $C_{24}H_{23}BrN_8O_2$ (M+H): 535.1, 537.1. Found: 535.1, 537.1.

Example 137

7-bromo-3-{3-[3-(1H-indol-5-yl)-1,2,4-oxadiazol-5-yl]propyl}-9-pentyl-6,9-dihydro-5H-[1,2,4]triazolo[4,3-a]purin-5-one trifluoroacetate

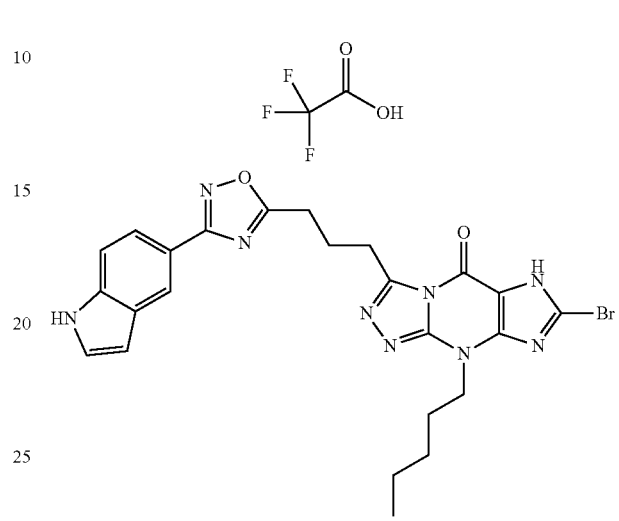

The title compound was prepared using procedures analogous to those described for example 123. LCMS calculated for $C_{24}H_{24}BrN_9O_2$ (M+H): 550.1, 552.1. Found: 550.1, 552.1.

Example 138

7-bromo-3-{3-[3-(1H-indol-3-yl)-1,2,4-oxadiazol-5-yl]propyl}-9-pentyl-6,9-dihydro-5H-[1,2,4]triazolo[4,3-a]purin-5-one trifluoroacetate

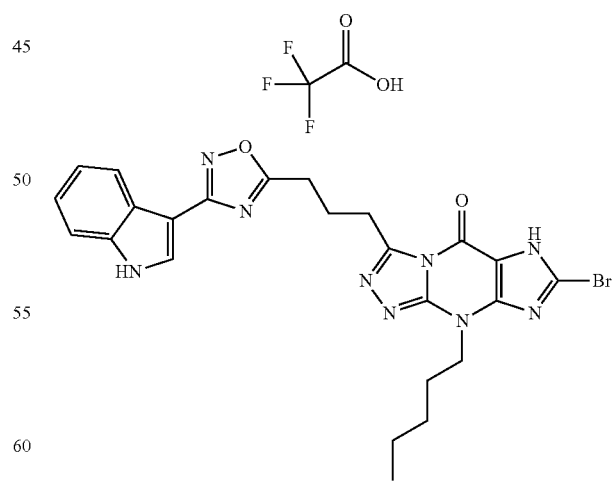

The title compound was prepared using procedures analogous to those described for example 123. LCMS calculated for $C_{24}H_{24}BrN_9O_2$ (M+H): 550.1, 552.1. Found: 550.1, 552.1.

Example 139

7-bromo-3-{3-[3-(6-methoxypyridin-3-yl)-1,2,4-oxadiazol-5-yl]propyl}-9-pentyl-6,9-dihydro-5H-[1,2,4]triazolo[4,3-a]purin-5-one trifluoroacetate

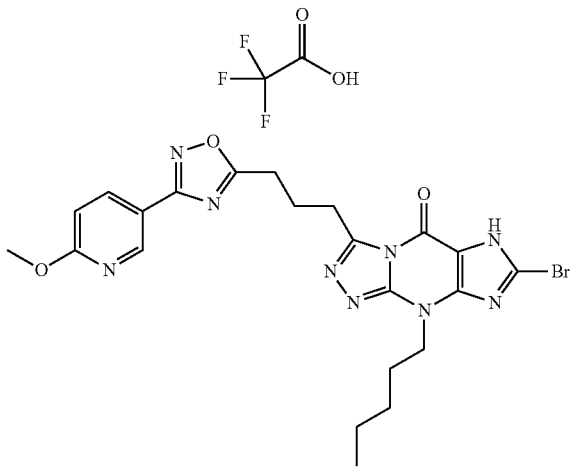

The title compound was prepared using procedures analogous to those described for example 123. LCMS calculated for $C_{22}H_{24}BrN_9O_3$ (M+H): 542.1, 544.1. Found: 542.1, 544.1.

Example 140

3-{3-[3-(4-aminopyrimidin-5-yl)-1,2,4-oxadiazol-5-yl]propyl}-7-bromo-9-pentyl-6,9-dihydro-5H-[1,2,4]triazolo[4,3-a]purin-5-one trifluoroacetate

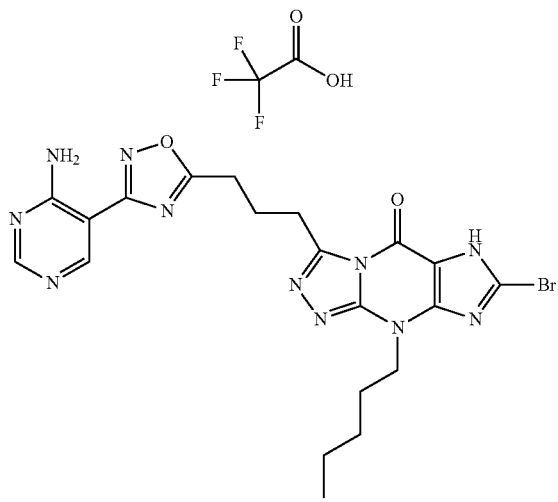

The title compound was prepared using procedures analogous to those described for example 123. LCMS calculated for $C_{20}H_{22}BrN_{11}O_2$ (M+H): 528.1, 530.1. Found: 528.1, 530.1.

Example 141

7-bromo-3-3-[3-(4-hydroxyphenyl)-1,2,4-oxadiazol-5-yl]propyl-9-pentyl-6,9-dihydro-5H-[1,2,4]triazolo[4,3-a]purin-5-one

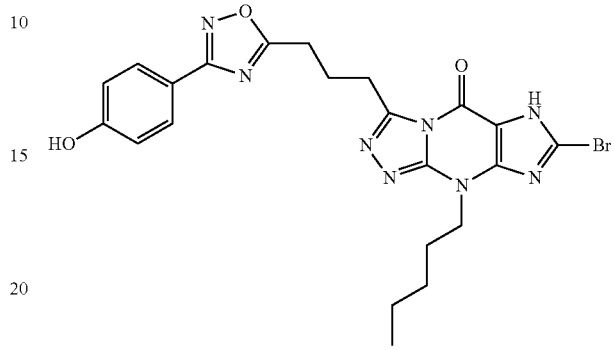

To a solution of 7-bromo-3-3-[3-(4-methoxyphenyl)-1,2,4-oxadiazol-5-yl]propyl-9-pentyl-6,9-dihydro-5H-[1,2,4]triazolo[4,3-a]purin-5-one (23.4 mg, 0.043 mmole) in $CH_2Cl_2$ (5 ml) at 0° C. was added a solution of $BBr_3$ in $CH_2Cl_2$ (1 M, 0.43 ml, 0.43 mmole). The mixture was stirred at room temperature overnight. The reaction was quenched with $H_2O$ at 0° C. The reaction mixture was extracted with $CH_2Cl_2$ (3×). The combined organic layers were washed with water and then brine, dried over $Na_2SO_4$, filtered and concentrated to give the crude product, which was purified by preparative LCMS to yield the desired product (2.9 mg, 13% yield) as white solid. LCMS calculated for $C_{22}H_{24}BrN_8O_3$ (M+H): 527.1, 529.1. Found: 527.0, 529.0.

Example 142

7-bromo-3-3-[3-(2-hydroxyphenyl)-1,2,4-oxadiazol-5-yl]propyl-9-pentyl-6,9-dihydro-5H-[1,2,4]triazolo[4,3-a]purin-5-one

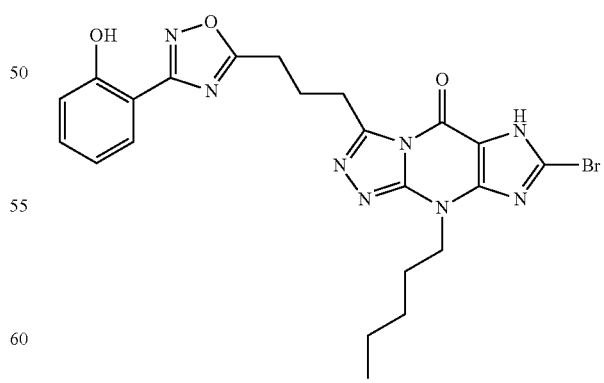

The title compound was prepared using procedures analogous to those described for example 141. LCMS calculated for $C_{22}H_{24}BrN_8O_3$ (M+H): 527.1, 529.1. Found: 527.0, 529.0.

Example 143

7-bromo-3-3-[3-(3-hydroxyphenyl)-1,2,4-oxadiazol-5-yl]propyl-9-pentyl-6,9-dihydro-5H-[1,2,4]triazolo[4,3-a]purin-5-one

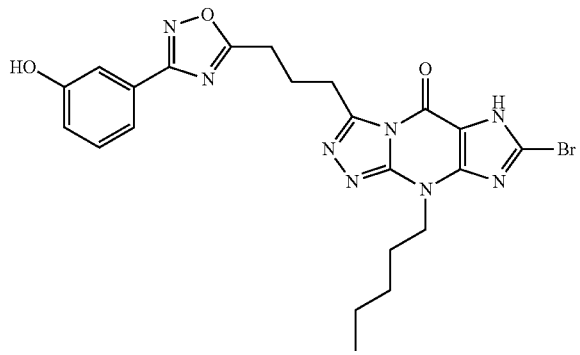 [SMILES: CCCCCn1c2nc(Br)[nH]c2c(=O)n2c(CCCc3nc(-c4cccc(O)c4)no3)nnc12]

The title compound was prepared using procedures analogous to those described for example 141. LCMS calculated for $C_{22}H_{24}BrN_8O_3$ (M+H): 527.1, 529.1. Found: 527.0, 529.0.

Example 144

7-bromo-3-{2-[3-(4-hydroxybenzyl)-1,2,4-oxadiazol-5-yl]ethyl}-9-pentyl-6,9-dihydro-5H-[1,2,4]triazolo[4,3-a]purin-5-one

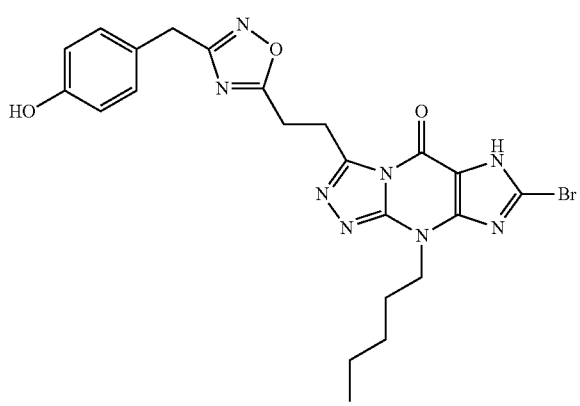 [SMILES: CCCCCn1c2nc(Br)[nH]c2c(=O)n2c(CCc3nc(Cc4ccc(O)cc4)no3)nnc12]

The title compound was prepared using procedures analogous to those described for example 141. LCMS calculated for $C_{22}H_{24}BrN_8O_3$ (M+H): 527.1, 529.1. Found: 527.0, 529.0.

Example 145

7-bromo-3-{2-[3-(2-hydroxybenzyl)-1,2,4-oxadiazol-5-yl]ethyl}-9-pentyl-6,9-dihydro-5H-[1,2,4]triazolo[4,3-a]purin-5-one

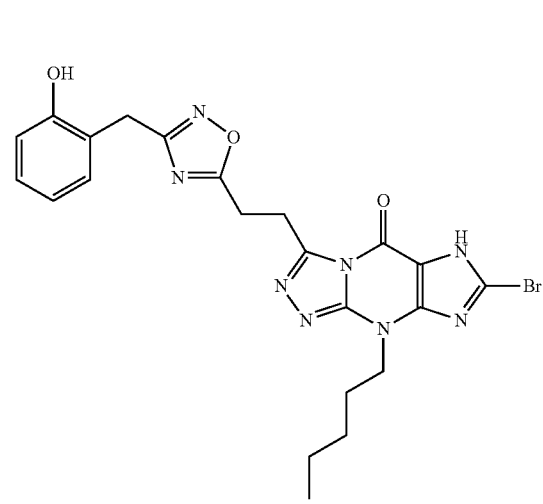 [SMILES: CCCCCn1c2nc(Br)[nH]c2c(=O)n2c(CCc3nc(Cc4ccccc4O)no3)nnc12]

The title compound was prepared using procedures analogous to those described for example 141. LCMS calculated for $C_{22}H_{24}BrN_8O_3$ (M+H): 527.1, 529.1. Found: 527.0, 529.0.

Example 146

7-bromo-3-{2-[3-(3-hydroxybenzyl)-1,2,4-oxadiazol-5-yl]ethyl}-9-pentyl-6,9-dihydro-5H-[1,2,4]triazolo[4,3-a]purin-5-one The title compound was prepared using procedures analogous to those described for example 141. LCMS calculated for $C_{22}H_{24}BrN_8O_3$ (M+H): 527.1, 529.1. Found: 527.0, 529.0.

Example 147

7-bromo-9-pentyl-3-[3-(4-phenyl-1H-pyrazol-1-yl)propyl]-6,9-dihydro-5H-[1,2,4]triazolo[4,3-a]purin-5-one

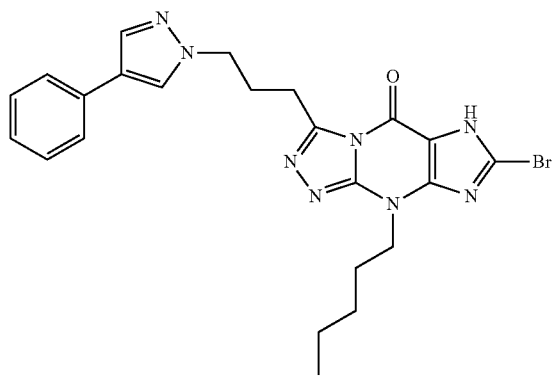 [SMILES: CCCCCn1c2nc(Br)[nH]c2c(=O)n2c(CCCn3cc(-c4ccccc4)cn3)nnc12]

Step A: ethyl 4-(4-phenyl-M-pyrazol-1-yl)butanoate

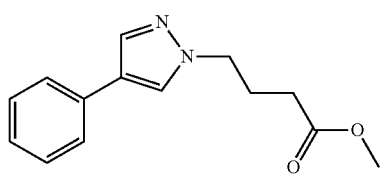 [SMILES: COC(=O)CCCn1cc(-c2ccccc2)cn1]

The mixture of ethyl 4-bromobutyrate (0.400 g, 2.05 mmole), 4-phenyl-1H-pyrazole (0.296 g, 2.05 mmole) and $K_2CO_3$ (0.567 g, 4.10 mmole) in DMF (10 ml) was stirred at room temperature overnight. The reaction mixture was diluted with water (100 ml) and extracted with ethyl acetate (2×). The combined organic phases were washed with water and then brine, dried over $Na_2SO_4$, filtered and concentrated to give the crude product, which was purified by preparative to afford the desired product (73 mg, 52%) as colorless oil. LCMS calculated for $C_{15}H_{19}N_2O_2$ (M+H): 259. Found: 259.1.

Step B: 4-(4-phenyl-1H-pyrazol-1-yl)butanoic acid

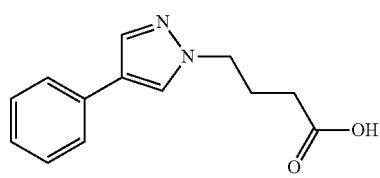 [SMILES: O=C(O)CCCn1cc(-c2ccccc2)cn1]

A mixture of ethyl 4-(4-phenyl-1H-pyrazo-1 yl)butanoate (273 mg, 1.06 mmole) in methanol (5 ml) and 1N NaOH (5 mL) was stirred at room temperature for 2 hours. The reaction mixture was adjusted to be acidic (pH=3-4) with 6 N HCl with an ice bath and then extracted with EtOAc (3×). The combined organic phases were washed with water and brine, dried over $Na_2SO_4$, filtered and concentrated to give the desired product (190 mg, 78%). LCMS calculated for $C_{13}H_{15}N_2O_2$ (M+H): 231.1. Found: 231.1.

Step C: N'-[(2E)-6-oxo-3-pentyl-1,3,6,7-tetrahydro-2H-purin-2-ylidene]-4-(4-phenyl-1H-pyrazol-1-yl)butanohydrazide

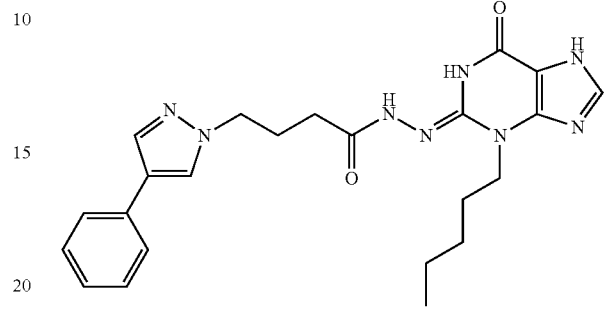

A mixture of 4-(4-phenyl-1H-pyrazol-1-yl)butanoic acid (190 mg, 0.825 mmol), (2E)-3-pentyl-3,7-dihydro-1H-purine-2,6-dione 2-hydrazone (195.0 mg, 0.825 mmol), benzotriazol-1-yloxytris(dimethylamino)phosphonium hexafluorophosphate (401 mg, 0.908 mmol) and triethyl amine (0.23 ml, 1.65 mmol) in DMF (10 ml) was stirred at room temperature overnight. The mixture was diluted with EtOAc and washed with water and then brine. The organic phase was dried over $Na_2SO_4$, filtered and concentrated to yield the desired product (369 mg, 99.7% yield) as yellowish oil. LCMS calculated for $C_{23}H_{29}N_8O_2$ (M+H): 449.2. Found: 449.2.

Step D: 9-pentyl-3-[3-(4-phenyl-1H-pyrazol-1-yl)propyl]-6,9-dihydro-5H-[1,2,4]triazolo[4,3-c]purin-5-one

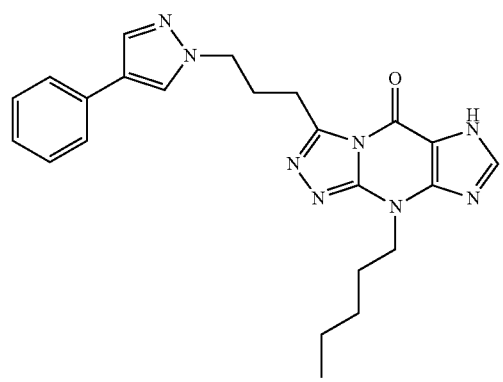 [SMILES: CCCCCn1c2nc[nH]c2c(=O)n2c(CCCn3cc(-c4ccccc4)cn3)nnc12]

A mixture of N'-[(2E)-6-oxo-3-pentyl-1,3,6,7-tetrahydro-2H-purin-2-ylidene]-4-(4-phenyl-1H-pyrazol-1-yl)butanohydrazide (369 mg, 0.823 mmols) in toluene (20 ml) was refluxed for 2 hours. After cooling to room temperature, the solid formed was filtered, washed with EtOAc/Hexane (1:9) and dried to give the desired product (234 mg, 66% yield) as off pink solid. LCMS calculated for $C_{23}H_{27}N_8O$ (M+H): 431.2. Found: 431.1.

Step E: 7-bromo-9-pentyl-3-[3-(4-phenyl-1H-pyrazol-1-yl)propyl]-6,9-dihydro-5H-[1,2,4]triazolo[4,3-a]purin-5-one

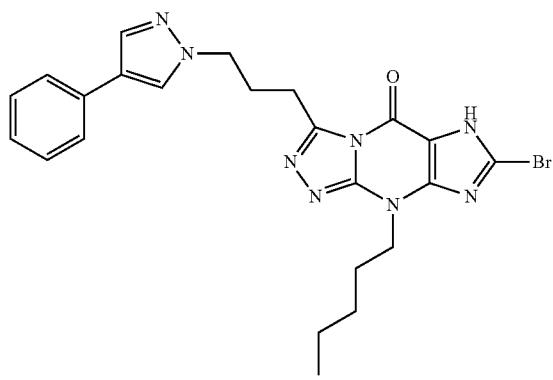 [SMILES: CCCCCn1c2nc(Br)[nH]c2c(=O)n2c(CCCn3cc(-c4ccccc4)cn3)nnc12]

To a solution of 9-pentyl-3-[3-(4-phenyl-1H-pyrazol-1-yl)propyl]-6,9-dihydro-5H-[1,2,4]triazolo[4,3-a]purin-5-one (234 mg, 0.543 mmol) in THF (45 ml) at room temperature was added N-bromosuccinimide (145 mg, 0.814 mmol). After stirring at 70° C. for 1 hour, the reaction mixture was concentrated and then purified by preparative LCMS to give the desired product (106 mg, 38%) as white solid. LCMS calculated for $C_{23}H_{26}BrN_8O$ (M+H): 509.1, 511.1. Found: 509.0, 511.1.

Example 148

7-bromo-9-pentyl-3-[3-(4-phenyl-1H-imidazol-1-yl)propyl]-6,9-dihydro-5H-[1,2,4]triazolo[4,3-a]purin-5-one

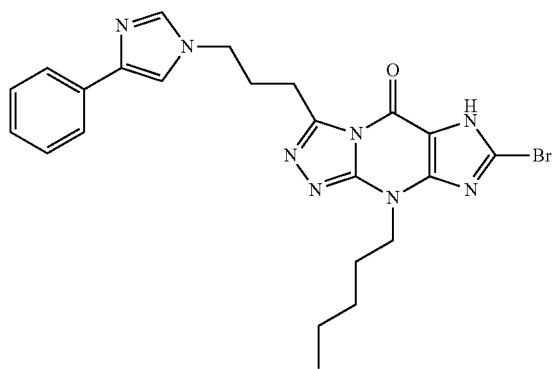 [SMILES: CCCCCn1c2nc(Br)[nH]c2c(=O)n2c(CCCn3cnc(-c4ccccc4)c3)nnc12]

The title compound was prepared using procedures analogous to those described for example 147. LCMS calculated for $C_{23}H_{26}BrN_8O$ (M+H): 509.1, 511.1. Found: 509.0, 511.1.

Example 149

7-bromo-3-3-[4-(5-fluoro-2-hydroxyphenyl)-1H-pyrazol-1-yl]propyl-9-pentyl-6,9-dihydro-5H-[1,2,4]triazolo[4,3-a]purin-5-one

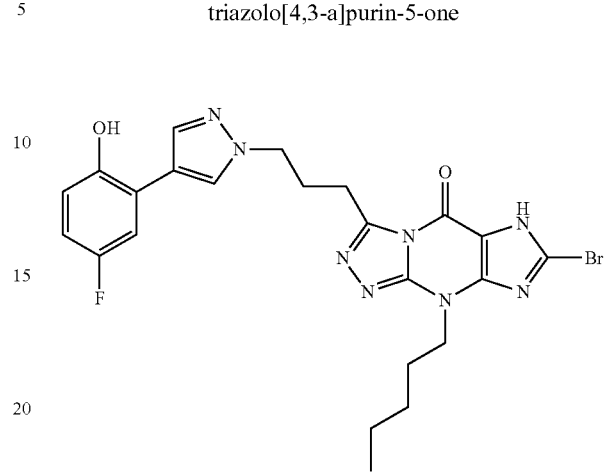

The title compound was prepared using procedures analogous to those described for example 147. LCMS calculated for $C_{23}H_{25}BrFN_8O_2$ (M+H): 543.1. Found: 543.0, 545.0.

Example 150

7-bromo-3-2-[5-(4-methoxyphenyl)-1,2,4-oxadiazol-3-yl]ethyl-9-pentyl-6,9-dihydro-5H-[1,2,4]triazolo[4,3-a]purin-5-one

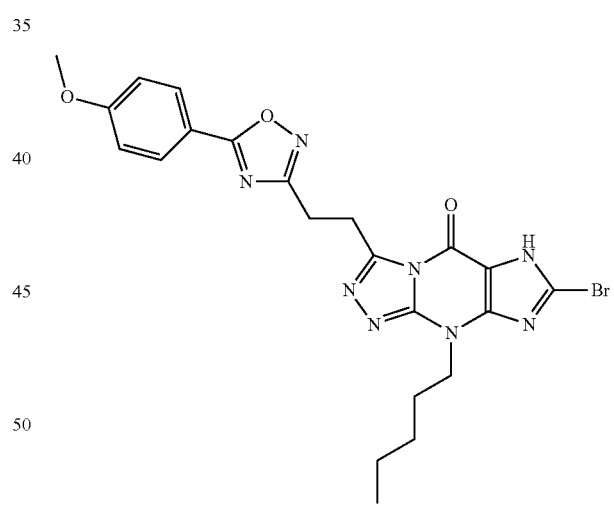

Step A: 4,4-diethoxy-N-hydroxybutanimidamide

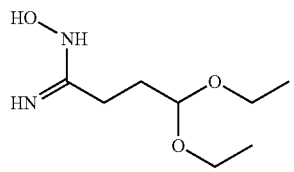

A mixture of 4,4-diethoxybutanenitrile (5.0 g, 32 mmol), hydroxylamine hydrochloride (2.4 g, 35 mmol) and sodium bicarbonate (2.9 g, 35 mmol) in methanol (50 mL) was refluxed for 5 hours. After cooling to room temperature, the reaction mixture was concentrated and the residue was diluted with EtOAc and water. The water layer was extracted with EtOAc (2×). The combined organic layers were washed with water, dried over $Na_2SO_4$, filtered and concentrated to give the product, which was used next step without purification. $^1$HNMR (300 MHz, $CD_3Cl$): δ 4.73 (br, 1H), 4.51 (t, J=5.5 Hz, 1H), 3.66 (m, 2H), 3.50 (m, 2H), 2.21 (t, J=8.2 Hz, 2H), 1.86 9 m, 2H), 1.19 (t, J=8.2 Hz, 6H).

Step B: 3-(3,3-diethoxypropyl)-5-(4-methoxyphenyl)-1,2,4-oxadiazole

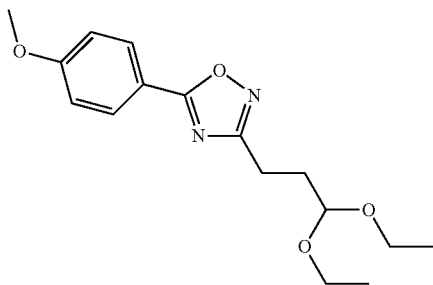 [SMILES: CCOC(CCc1noc(-c2ccc(OC)cc2)n1)OCC]

A mixture of 4-methoxybenzoic acid (0.88 g, 5.78 mmol) and CDI (1.02 g, 6.31 mmol) in DMF (20 ml) was stirred at room temperature for 3 hours. 4-diethoxy-N-hydroxybutanimidamide (1.0 g, 5.26 mmol) was added to the above mixture and then heated at 100° C. overnight. After cooling to room temperature, the reaction mixture was diluted with water and extracted with EtOAc (3×). The combined organic layers was dried over $Na_2SO_4$, filtered, and concentrated in vacuo to yield the desired product LCMS calculated for $C_{16}H_{23}N_2O_4$ (M+H): 307.2. Found: 307.2.

Step C: 3-[5-(4-methoxyphenyl)-1,2,4-oxadiazol-3-yl]propanal

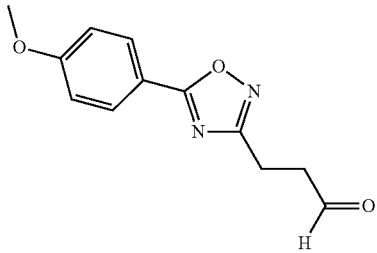 [SMILES: COc1ccc(-c2nc(CCC=O)no2)cc1]

A mixture of 3-(3,3-diethoxypropyl)-5-(4-methoxyphenyl)-1,2,4-oxadiazole (1.0 g, 3.0 mmol) in 2N HCl (10 mL) and THF (10 mL) was stirred at room temperature overnight. The reaction mixture was extracted with EtOAc (3×). The organic layers were washed with water, dried over $Na_2SO_4$, filtered and concentrated to give the desired product. LCMS calculated for $C_{12}H_{13}N_2O_3$ (M+H): 233.1. Found: 233.1.

Step D: 3-2-[5-(4-methoxyphenyl)-1,2,4-oxadiazol-3-yl]ethyl-9-pentyl-6,9-dihydro-5H-[1,2,4]triazolo[4,3-a]purin-5-one

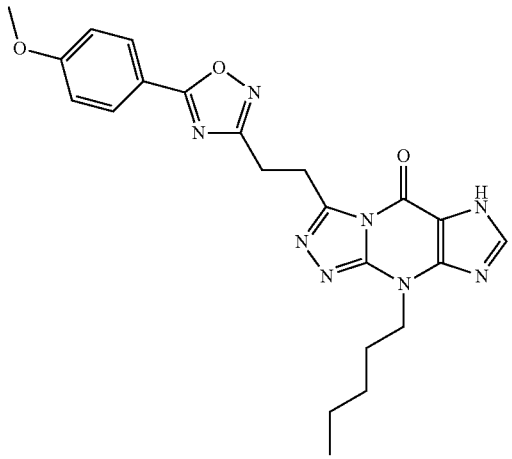 [SMILES: CCCCCn1c2nc[nH]c2c(=O)n2c(CCc3noc(-c4ccc(OC)cc4)n3)nnc12]

A mixture of 1H-purine-2,6-dione 2-hydrazone (680 mg, 2.88 mmol) and 3-[5-(4-methoxyphenyl)-1,2,4-oxadiazol-3-yl]propanal (900 mg, 3.88 mol) in ethanol (20 mL) was refluxed for 4 hours. The reaction mixture was concentrated and the residue was mixed with acetic acid (10 mL). The resulting mixture was refluxed for 3 hours. The reaction mixture was concentrated and then diluted with water and extracted with EtOAc (3×). The combined organic layers was dried over $Na_2SO_4$, filtered, concentrated and purified by preparative LCMS to give the desired product (830 mg, 64% yield). LCMS calculated for $C_{22}H_{25}N_8O_3$ (M+H): 449.2. Found: 449.2.

Step E: 7-bromo-3-2-[5-(4-methoxyphenyl)-1,2,4-oxadiazol-3-yl]ethyl-9-pentyl-6,9-dihydro-5H-[1,2,4]triazolo[4,3-c]purin-5-one

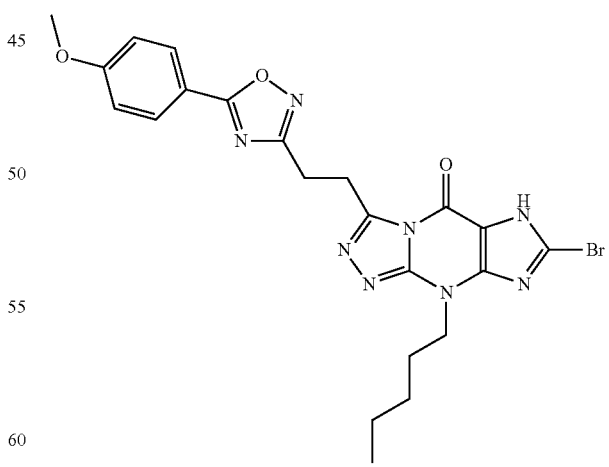

To a solution of 3-2-[5-(4-methoxyphenyl)-1,2,4-oxadiazol-3-yl]ethyl-9-pentyl-6,9-dihydro-5H-[1,2,4]triazolo[4,3-a]purin-5-one (160 mg, 0.36 mol) in DMF (15 mL) at room temperature was added N-bromosuccinimide (110 mg, 0.61 mol). After stirring at 70° C. for 1 hour, the reaction mixture was concentrated and purified by preparative LCMS to provide the desired product. LCMS calculated for $C_{22}H_{24}BrN_8O_3$ (M+H): 527.1, 529.0. Found: 527.0, 529.0.

Example 151

7-bromo-3-2-[5-(4-hydroxyphenyl)-1,2,4-oxadiazol-3-yl]ethyl-9-pentyl-6,9-dihydro-5H-[1,2,4]triazolo[4,3-a]purin-5-one

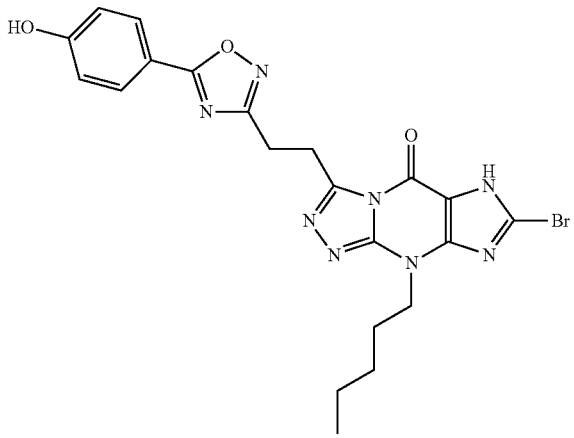 [SMILES: CCCCCn1c2nc(Br)[nH]c2c(=O)n2c(CCc3noc(-c4ccc(O)cc4)n3)nnc12]

To a solution of 7-bromo-3-2-[5-(4-methoxyphenyl)-1,2,4-oxadiazol-3-yl]ethyl-9-pentyl-6,9-dihydro-5H-[1,2,4]triazolo[4,3-a]purin-5-one (190 mg, 0.36 mmol) in $CH_2Cl_2$ (12 mL) was added a solution of $BBr_3$ in $CH_2Cl_2$ (1 M, 7.0 ml, 7.0 mmole) at room temperature. After stirring at room temperature overnight, the reaction mixture was concentrated and purified by preparative LCMS to give the desired product. LCMS calculated for $C_{21}H_{22}BrN_8O_3$ (M+H): 513.1, 515.1. Found: 513.1, 515.1.

Example 152

7-bromo-3-2-[5-(3-methoxyphenyl)-1,2,4-oxadiazol-3-yl]ethyl-9-pentyl-6,9-dihydro-5H-[1,2,4]triazolo[4,3-a]purin-5-one

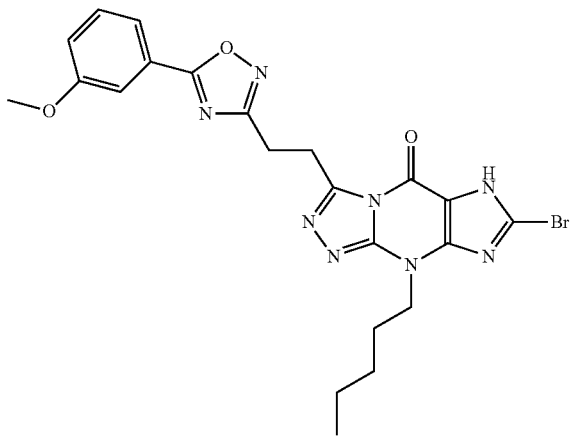 [SMILES: CCCCCn1c2nc(Br)[nH]c2c(=O)n2c(CCc3noc(-c4cccc(OC)c4)n3)nnc12]

The title compound was prepared using procedures analogous to those described for example 152. LCMS calculated for $C_{22}H_{24}BrN_8O_3$ (M+H): 527.1, 529.0. Found: 527.0, 529.0.

Example 153

7-bromo-3-2-[5-(3-hydroxyphenyl)-1,2,4-oxadiazol-3-yl]ethyl-9-pentyl-6,9-dihydro-5H-[1,2,4]triazolo[4,3-a]purin-5-one

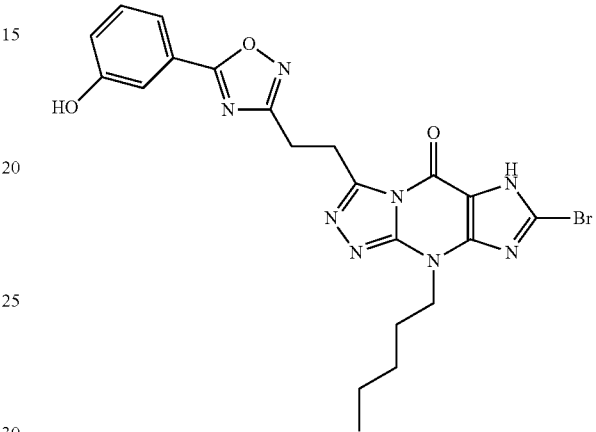

The title compound was prepared using procedures analogous to those described for example 151. LCMS calculated for $C_{21}H_{22}BrN_8O_3$ (M+H): 513.1, 515.1. Found: 513.1, 515.1.

Example 154

7-bromo-3-2-[5-(2-methoxyphenyl)-1,2,4-oxadiazol-3-yl]ethyl-9-pentyl-6,9-dihydro-5H-[1,2,4]triazolo[4,3-a]purin-5-one

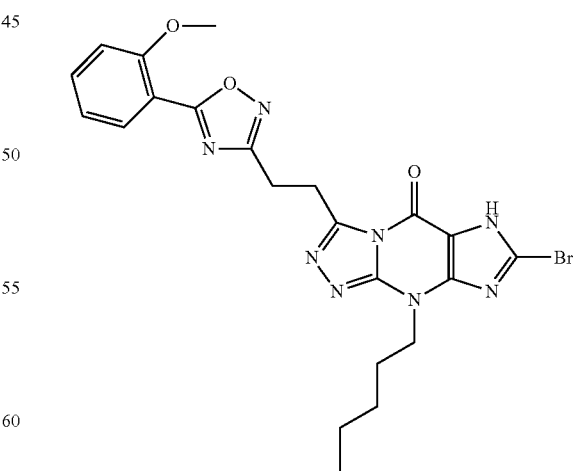

The title compound was prepared using procedures analogous to those described for example 150. LCMS calculated for $C_{22}H_{24}BrN_8O_3$ (M+H): 527.1, 529.0. Found: 527.0, 529.0.

Example 155

7-bromo-3-2-[5-(2-hydroxyphenyl)-1,2,4-oxadiazol-3-yl]ethyl-9-pentyl-6,9-dihydro-5H-[1,2,4]triazolo[4,3-a]purin-5-one

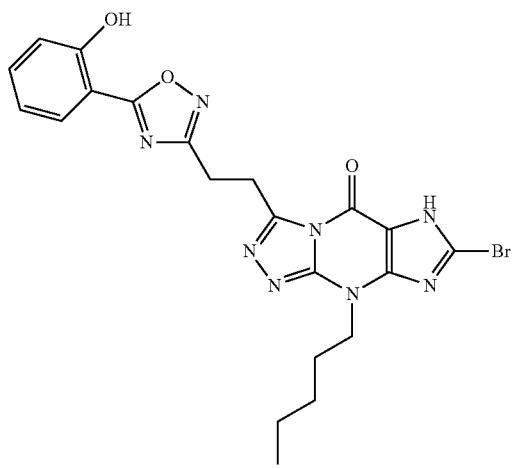 [SMILES: CCCCCn1c2nc(Br)[nH]c2c(=O)n2c(CCc3noc(-c4ccccc4O)n3)nnc12]

The title compound was prepared using procedures analogous to those described for example 151. LCMS calculated for $C_{21}H_{22}BrN_8O_3$ (M+H): 513.1, 515.1. Found: 513.1, 515.1.

Example 156

7-bromo-3-2-[5-(2-chloro-4-methoxyphenyl)-1,2,4-oxadiazol-3-yl]ethyl-9-pentyl-6,9-dihydro-5H-[1,2,4]triazolo[4,3-a]purin-5-one

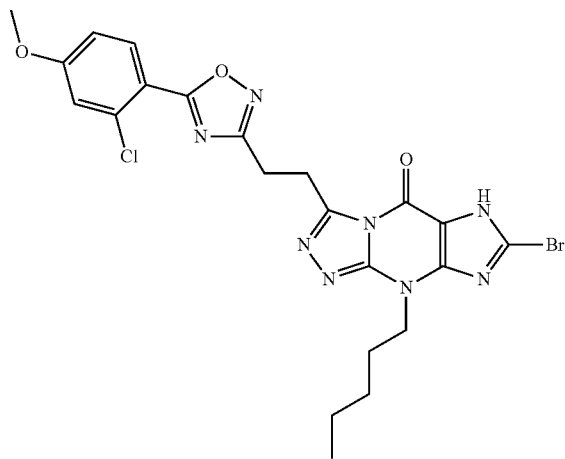 [SMILES: CCCCCn1c2nc(Br)[nH]c2c(=O)n2c(CCc3noc(-c4ccc(OC)cc4Cl)n3)nnc12]

The title compound was prepared using procedures analogous to those described for example 150. LCMS calculated for $C_{22}H_{23}BrClN_8O_3$ (M+H): 561.1, 563.1. Found: 561.1, 563.1.

Example 157

7-bromo-3-2-[5-(2-chloro-4-hydroxyphenyl)-1,2,4-oxadiazol-3-yl]ethyl-9-pentyl-6,9-dihydro-5H-[1,2,4]triazolo[4,3-a]purin-5-one

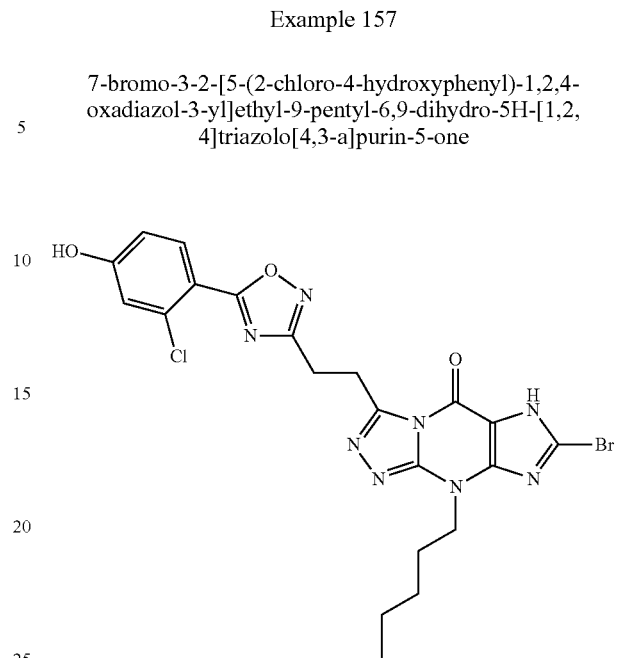

The title compound was prepared using procedures analogous to those described for example 151. LCMS calculated for $C_{21}H_{21}BrClN_8O_3$ (M+H): 547.1, 549.1. Found: 547.0, 549.0.

Example 158

7-bromo-9-pentyl-3-[2-(5-pyridin-4-yl-1,2,4-oxadiazol-3-yl)ethyl]-6,9-dihydro-5H-[1,2,4]triazolo[4,3-a]purin-5-one trifluoroacetate

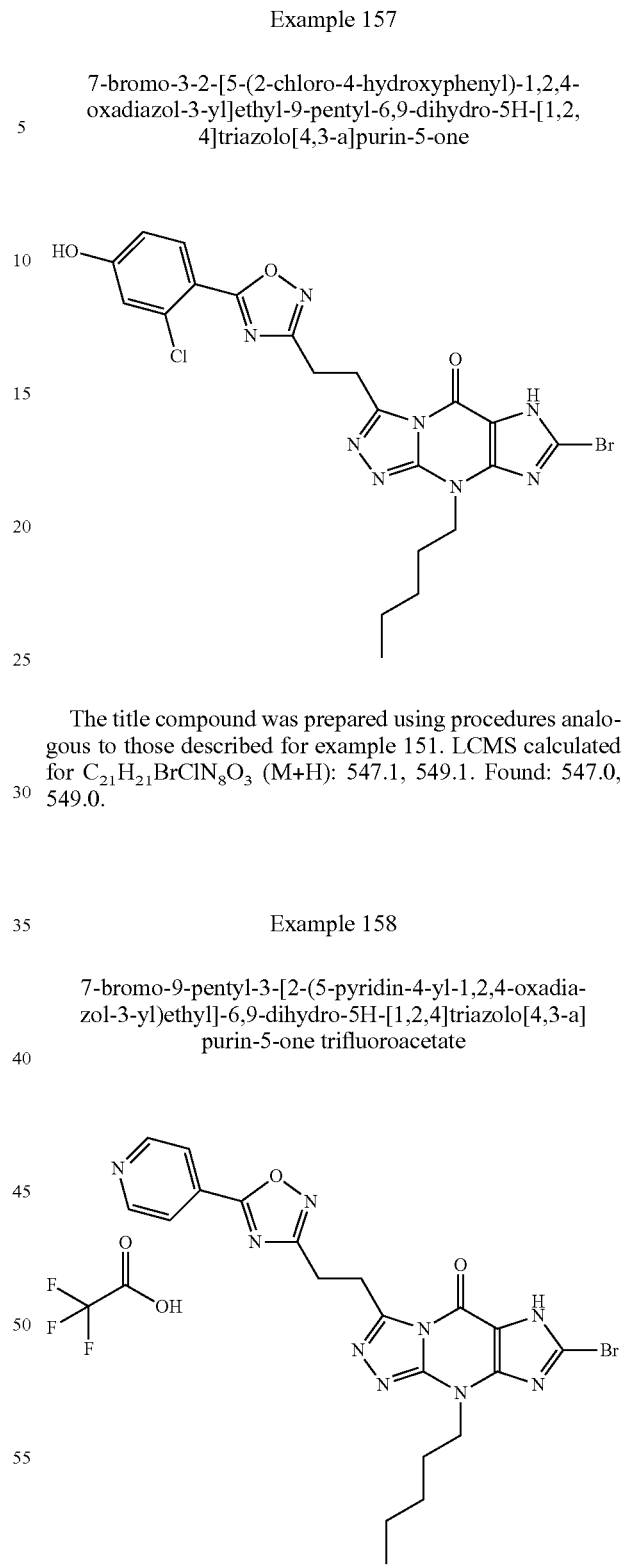

The title compound was prepared using procedures analogous to those described for example 150. LCMS calculated for $C_{20}H_{21}BrN_9O_2$ (M+H): 498.1, 500.1. Found: 498.1, 500.1.

Example 159

7-bromo-9-pentyl-3-[2-(5-pyridin-3-yl-1,2,4-oxadiazol-3-yl)ethyl]-6,9-dihydro-5H-[1,2,4]triazolo[4,3-a]purin-5-one trifluoroacetate

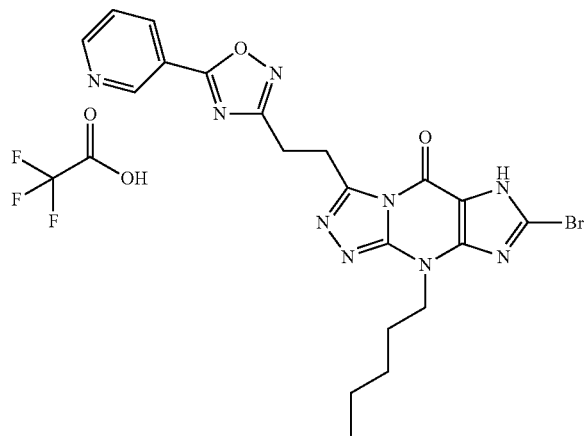

The title compound was prepared using procedures analogous to those described for example 150. LCMS calculated for $C_{20}H_{21}BrN_9O_2$ (M+H): 498.1, 500.1. Found: 498.1, 500.1.

Example 160

7-bromo-9-pentyl-3-[2-(5-pyridin-2-yl-1,2,4-oxadiazol-3-yl)ethyl]-6,9-dihydro-5H-[1,2,4]triazolo[4,3-a]purin-5-one trifluoroacetate

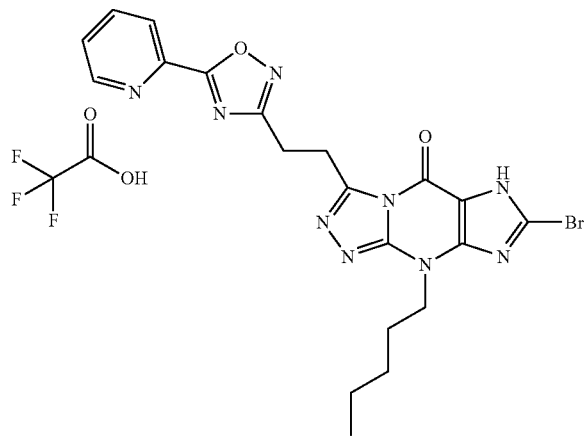

The title compound was prepared using procedures analogous to those described for example 150. LCMS calculated for $C_{20}H_{21}BrN_9O_2$ (M+H): 498.1, 500.1. Found: 498.1, 500.1.

Example 161

7-bromo-3-{2-[3-(4-methoxyphenyl)-1,2,4-oxadiazol-5-yl]ethyl}-9-pentyl-6,9-dihydro-5H-[1,2,4]triazolo[4,3-a]purin-5-one

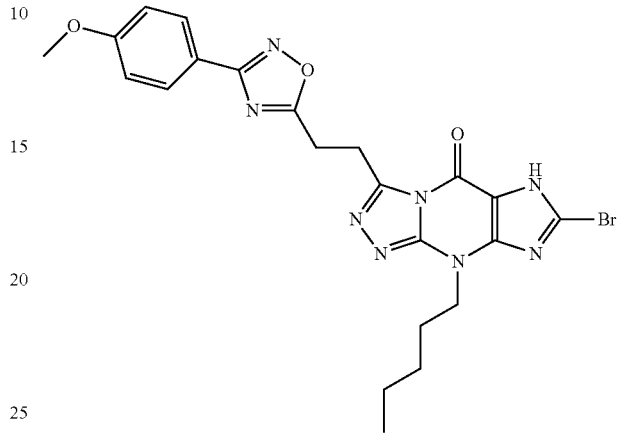

The title compound was prepared using procedures analogous to those described for example 72. LCMS calculated for $C_{22}H_{24}BrN_8O_3$ (M+H): 527.1, 529.0. Found: 527.0, 529.0.

Example 162

7-bromo-3-{2-[3-(3-methoxyphenyl)-1,2,4-oxadiazol-5-yl]ethyl}-9-pentyl-6,9-dihydro-5H-[1,2,4]triazolo[4,3-a]purin-5-one

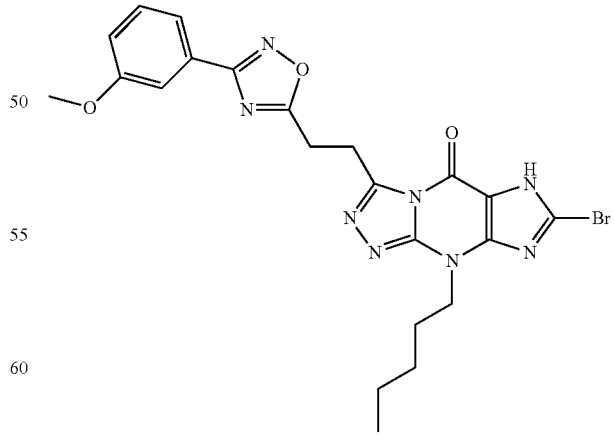

The title compound was prepared using procedures analogous to those described for example 72. LCMS calculated for $C_{22}H_{24}BrN_8O_3$ (M+H): 527.1, 529.0. Found: 527.0, 529.0.

Example 163

7-bromo-3-{2-[3-(2-methoxyphenyl)-1,2,4-oxadiazol-5-yl]ethyl}-9-pentyl-6,9-dihydro-5H-[1,2,4]triazolo[4,3-a]purin-5-one

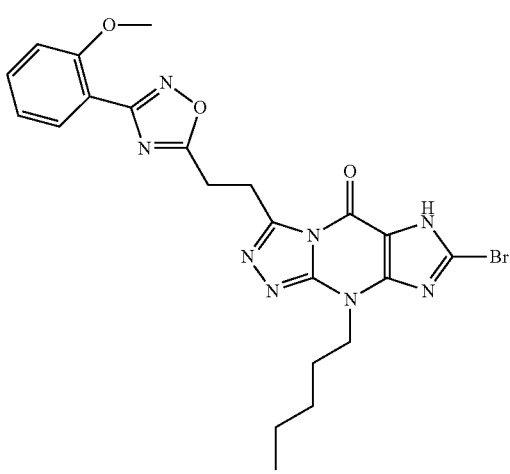 [SMILES: CCCCCn1c2nc(Br)[nH]c2c(=O)n2c(CCc3nc(-c4ccccc4OC)no3)nnc12]

The title compound was prepared using procedures analogous to those described for example 72. LCMS calculated for $C_{22}H_{24}BrN_8O_3$ (M+H): 527.1, 529.0. Found: 527.0, 529.0.

Example 164

7-bromo-3-{2-[3-(4-hydroxyphenyl)-1,2,4-oxadiazol-5-yl]ethyl}-9-pentyl-6,9-dihydro-5H-[1,2,4]triazolo[4,3-a]purin-5-one

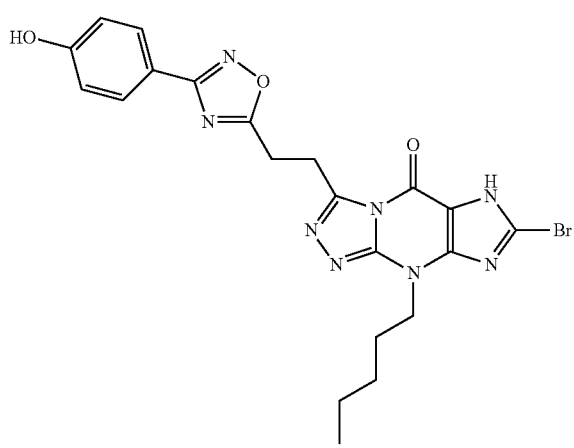 [SMILES: CCCCCn1c2nc(Br)[nH]c2c(=O)n2c(CCc3nc(-c4ccc(O)cc4)no3)nnc12]

The title compound was prepared using procedures analogous to those described for example 141. LCMS calculated for $C_{21}H_{21}BrN_8O_3$ (M+H): 512.1, 514.1. Found: 512.0, 514.0.

Example 165

7-bromo-3-{2-[3-(3-hydroxyphenyl)-1,2,4-oxadiazol-5-yl]ethyl}-9-pentyl-6,9-dihydro-5H-[1,2,4]triazolo[4,3-a]purin-5-one

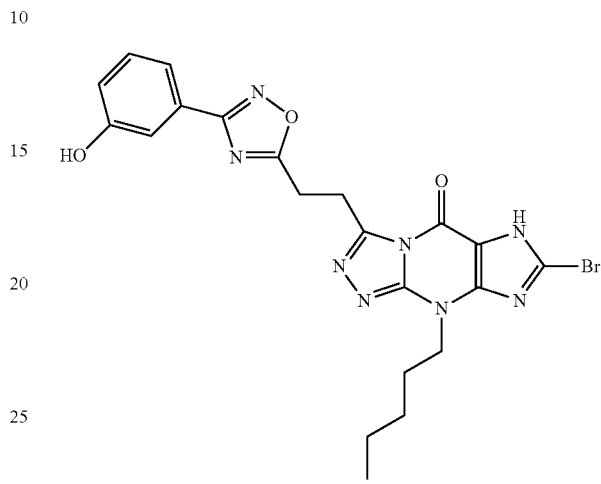

The title compound was prepared using procedures analogous to those described for example 141. LCMS calculated for $C_{21}H_{21}BrN_8O_3$ (M+H): 512.1, 514.1. Found: 512.0, 514.0.

Example 166

7-bromo-3-{2-[3-(2-hydroxyphenyl)-1,2,4-oxadiazol-5-yl]ethyl}-9-pentyl-6,9-dihydro-5H-[1,2,4]triazolo[4,3-a]purin-5-one

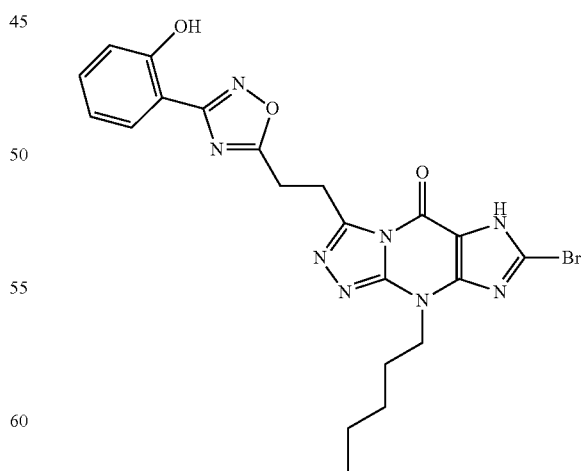

The title compound was prepared using procedures analogous to those described for example 141. LCMS calculated for $C_{21}H_{21}BrN_8O_3$ (M+H): 512.1, 514.1. Found: 512.0, 514.0.

Example 167

7-bromo-3-{2-[3-(2-chloro-4-methoxyphenyl)-1,2,4-oxadiazol-5-yl]ethyl}-9-pentyl-6,9-dihydro-5H-[1,2,4]triazolo[4,3-a]purin-5-one

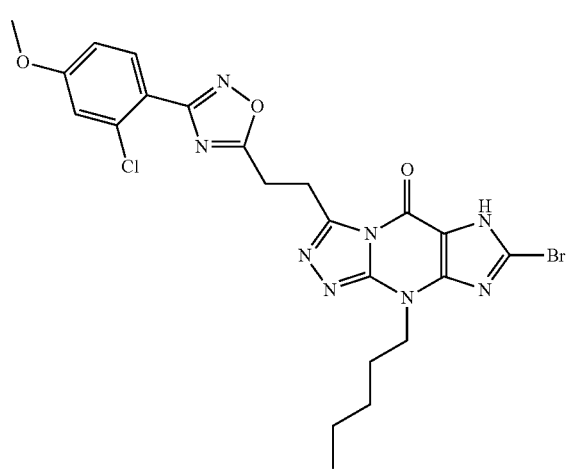 [SMILES: CCCCCn1c2nc(Br)[nH]c2c(=O)n2c(CCc3nc(-c4ccc(OC)cc4Cl)no3)nnc12]

The title compound was prepared using procedures analogous to those described for example 72. LCMS calculated for $C_{22}H_{23}BrClN_8O_3$ (M+H): 561.1, 563.1. Found: 561.1, 563.1.

Example 168

7-bromo-3-{2-[3-(2-chloro-hydroxyphenyl)-1,2,4-oxadiazol-5-yl]ethyl}-9-pentyl-6,9-dihydro-5H-[1,2,4]triazolo[4,3-a]purin-5-one

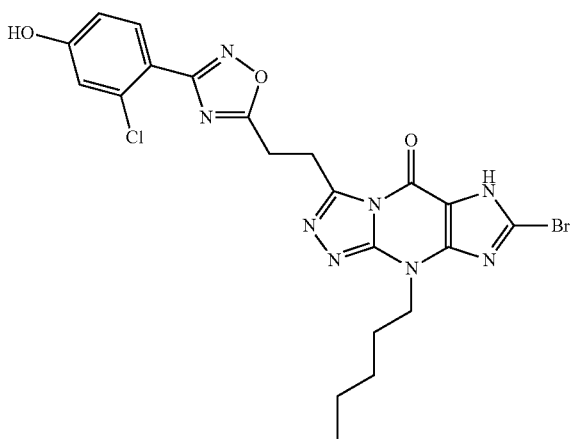 [SMILES: CCCCCn1c2nc(Br)[nH]c2c(=O)n2c(CCc3nc(-c4ccc(O)cc4Cl)no3)nnc12]

The title compound was prepared using procedures analogous to those described for example 141. LCMS calculated for $C_{21}H_{21}BrClN_8O_3$ (M+H): 547.1, 549.1. Found: 547.0, 549.0.

Example 169

3-[2-(5-benzyl-1,2,4-oxadiazol-3-yl)ethyl]-7-bromo-9-pentyl-6,9-dihydro-5H-[1,2,4]triazolo[4,3-a]purin-5-one

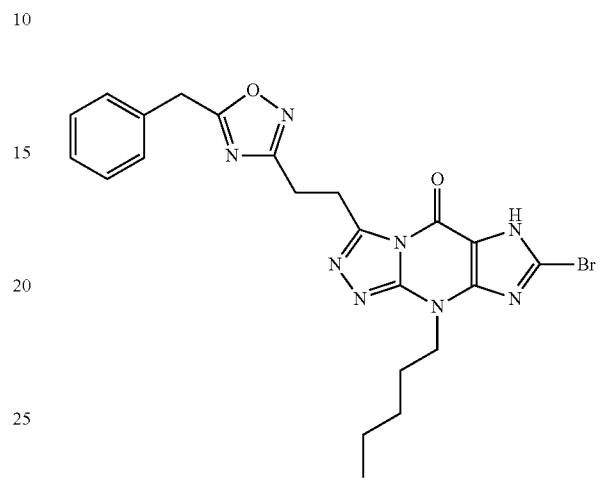

The title compound was prepared using procedures analogous to those described for example 150. LCMS calculated for $C_{22}H_{23}BrN_8O_2$ (M+H): 511.1, 513.1. Found: 511.0, 513.0.

Example 170

7-bromo-3-{3-[3-(2-chloro-4-methoxyphenyl)-1,2,4-oxadiazol-5-yl]propyl}-9-pentyl-6,9-dihydro-5H-[1,2,4]triazolo[4,3-a]purin-5-one

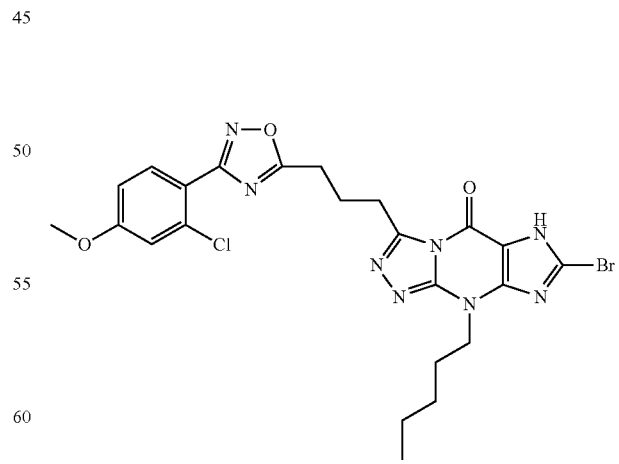

The title compound was prepared using procedures analogous to those described for example 123. LCMS calculated for $C_{23}H_{25}BrClN_8O_3$ (M+H): 575.1, 577.1. Found: 575.1, 577.1.

Example 171

7-bromo-3-{3-[3-(2-chloro-4-hydroxyphenyl)-1,2,4-oxadiazol-5-yl]propyl}-9-pentyl-6,9-dihydro-5H-[1,2,4]triazolo[4,3-a]purin-5-one

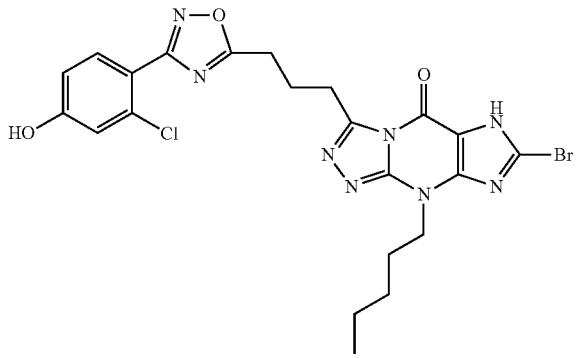 [SMILES: CCCCCn1c2nc(Br)[nH]c2c(=O)n2c(CCCc3nc(-c4ccc(O)cc4Cl)no3)nnc12]

The title compound was prepared using procedures analogous to those described for example 141. LCMS calculated for $C_{22}H_{23}BrClN_8O_3$ (M+H): 561.1, 563.1. Found: 561.1, 563.1.

Example 172

N-[2-(7-bromo-5-oxo-9-pentyl-6,9-dihydro-5H-[1,2,4]triazolo[4,3-a]purin-3-yl)ethyl]-4-methoxybenzamide

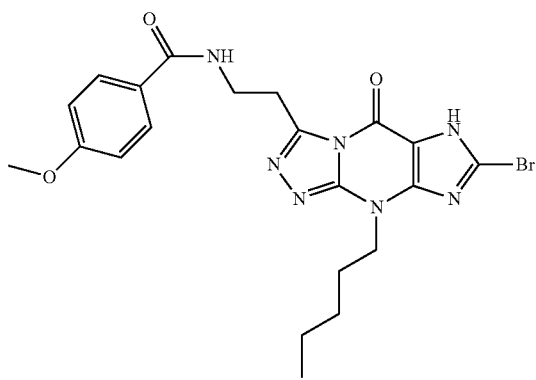 [SMILES: CCCCCn1c2nc(Br)[nH]c2c(=O)n2c(CCNC(=O)c3ccc(OC)cc3)nnc12]

Step A: benzyl (3Z)-3-[(2E)-(6-oxo-3-pentyl-1,3,6,7-tetrahydro-2H-purin-2-ylidene)hydrazono]propylcarbamate

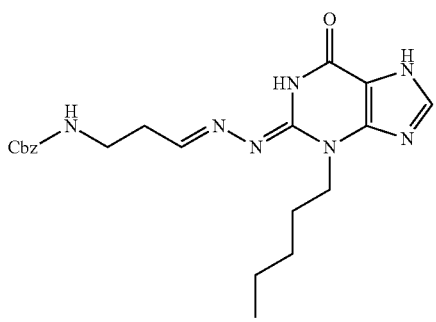 [SMILES: CCCCCn1/c(=N/N=C/CCNC(=O)OCc2ccccc2)[nH]c(=O)c2[nH]cnc21]

A mixture of (2E)-3-pentyl-3,7-dihydro-1H-purine-2,6-dione 2-hydrazone (2.3 g, 9.6 mmol) and benzyl (3-oxopropyl)carbamate (2.0 g, 9.6 mol) in ethanol (30 mL) was refluxed overnight. The reaction mixture was concentrated to give the product (4.0 g, 58% yield), which was used for next step without further purification. LCMS calculated for $C_{21}H_{28}N_7O_3$ (M+H): 426.2. Found: 426.1.

Step B: benzyl[2-(5-oxo-9-pentyl-6,9-dihydro-5H-[1,2,4]triazolo[4,3-a]purin-3-yl)ethyl]carbamate

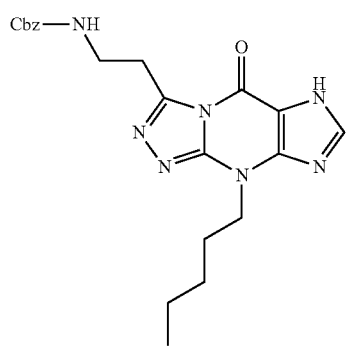 [SMILES: CCCCCn1c2nc[nH]c2c(=O)n2c(CCNC(=O)OCc3ccccc3)nnc12]

A mixture of benzyl (3Z)-3-[(2E)-(6-oxo-3-pentyl-1,3,6,7-tetrahydro-2H-purin-2-ylidene)hydrazono]propylcarbamate (4.0 g, 5.6 mol) in acetic acid (50 mL1) was refluxed in the air overnight. The mixture was concentrated and purified by preparative LCMS to give the desired product (1.3 g, 54% yield) as a white solid. LCMS calculated for $C_{21}H_{26}N_7O_3$ (M+H): 424.2. Found: 424.2.

Step C: 3-(2-aminoethyl)-9-pentyl-6,9-dihydro-5H-[1,2,4]triazolo[4,3-a]purin-5-one

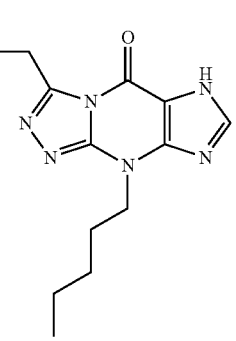

To a solution of benzyl[2-(5-oxo-9-pentyl-6,9-dihydro-5H-[1,2,4]triazolo[4,3-a]purin-3-yl)ethyl]carbamate (0.52 g, 1.2 mmol) in methanol (50 mL) was added 10% Pd/C (100 mg). The reaction mixture was shaken in a hydrogenation reactor under 50 Psi $H_2$ for 3 hours. The reaction mixture was filtered through a pad of celite. The filtrate was concentrated to give the desired product (320 mg, 90% yield). LCMS calculated for $C_{13}H_{20}N_7O$ (M+H): 290.2. Found: 290.1.

Step D: 3-(2-aminoethyl)-7-bromo-9-pentyl-6,9-dihydro-5H-[1,2,4]triazolo[4,3-a]purin-5-one

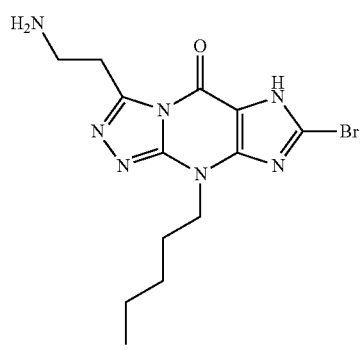 [SMILES: CCCCCn1c2nc(Br)[nH]c2c(=O)n2c(CCN)nnc12]

To a mixture of 3-(2-aminoethyl)-9-pentyl-6,9-dihydro-5H-[1,2,4]triazolo[4,3-a]purin-5-one (310 mg, 1.1 mmol) in THF (50 mL), was added N-Bromosuccinimide (0.29 g, 1.6 mol). The mixture was stirred at 70° C. for 1 hour. The reaction mixture was concentrated. The solid was filtered and washed with EtOAc to yield the desired product (300 mg, 76% yield). LCMS calculated for $C_{13}H_{19}BrN_7O$ (M+H): 368.1, 370.1. Found: 368.0, 370.0.

Step E: N-[2-(7-bromo-5-oxo-9-pentyl-6,9-dihydro-5H-[1,2,4]triazolo[4,3-a]purin-3-yl)ethyl]-4-methoxybenzamide

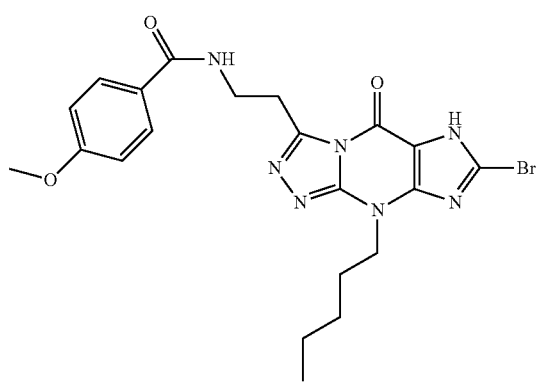 [SMILES: CCCCCn1c2nc(Br)[nH]c2c(=O)n2c(CCNC(=O)c3ccc(OC)cc3)nnc12]

A mixture of 3-(2-aminoethyl)-7-bromo-9-pentyl-6,9-dihydro-5H-[1,2,4]triazolo[4,3-a]purin-5-one (70 mg, 0.20 mmol), 4-methoxybenzoic acid (32 mg, 0.21 mmol), benzotriazol-1-yloxytris(dimethylamino)phosphonium hexafluorophosphate (92 mg, 0.21 mmol), and triethylamine (0.053 mL, 0.38 mmol) in DMF (5 mL) was stirred at room temperature overnight. The reaction mixture was diluted with water and acetonitrile and then purified by prep LCMS to give the desired product (70 mg, 73% yield). LCMS calculated for $C_{21}H_{25}BrN_7O_3$ (M+H): 502.1, 504.0. Found: 502.0, 504.0.

Example 173

N-[2-(7-bromo-5-oxo-9-pentyl-6,9-dihydro-5H-[1,2,4]triazolo[4,3-a]purin-3-yl)ethyl]benzamide

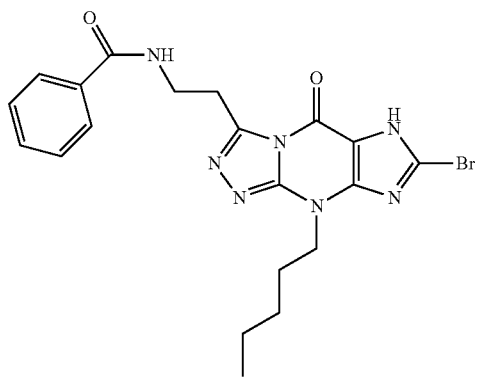 [SMILES: CCCCCn1c2nc(Br)[nH]c2c(=O)n2c(CCNC(=O)c3ccccc3)nnc12]

The title compound was prepared using procedures analogous to those described for example 172. LCMS calculated for $C_{20}H_{23}BrN_7O_2$ (M+H): 472.1; 474.1. Found: 472.0, 474.0.

Example 174

N-[2-(7-bromo-5-oxo-9-pentyl-6,9-dihydro-5H-[1,2,4]triazolo[4,3-a]purin-3-yl)ethyl]isonicotinamide trifluoroacetate

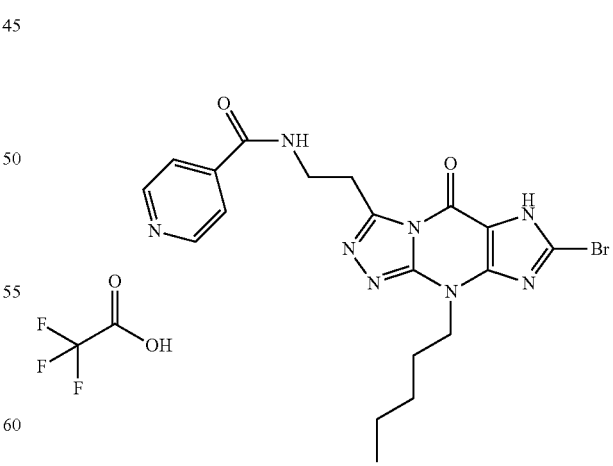

The title compound was prepared using procedures analogous to those described for example 172. LCMS calculated for $C_{18}H_{22}BrN_8O_2$ (M+H): 473.1; 475.1. Found: 473.0, 475.0.

Example 175

7-bromo-9-pentyl-3-[2-(pyrimidin-2-ylamino)ethyl]-6,9-dihydro-5H-[1,2,4]triazolo[4,3-a]purin-5-one trifluoroacetate

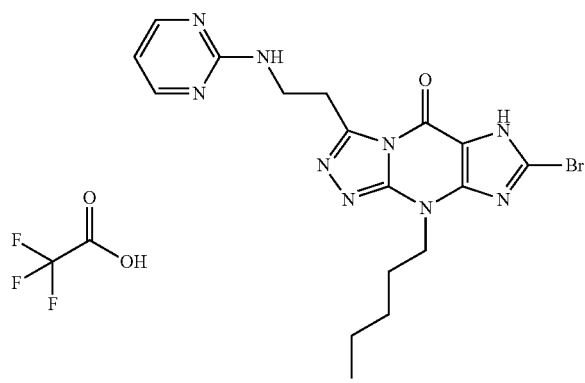 [SMILES: O=C(O)C(F)(F)F ; CCCCCn1c2nc(Br)[nH]c2c(=O)n2c(CCNc3ncccn3)nnc12]

A mixture of 3-(2-aminoethyl)-7-bromo-9-pentyl-6,9-dihydro-5H-[1,2,4]triazolo[4,3-a]purin-5-one (60 mg, 0.20 mmol), 2-chloropyrimidine (25 mg, 0.22 mmol) and triethylamine (0.045 mL, 0.32 mmol) in 1,4-Dioxane (10 mL) was refluxed overnight. The reaction mixture was concentrated, and the residue was purified by preparative LCMS to give the desired product. LCMS calculated for $C_{17}H_{21}BrN_9O$: 446.1. Found: 446.0, 448.0.

Example 176

N-[2-(7-bromo-5-oxo-9-pentyl-6,9-dihydro-5H-[1,2,4]triazolo[4,3-a]purin-3-yl)ethyl]nicotinamide trifluoroacetate

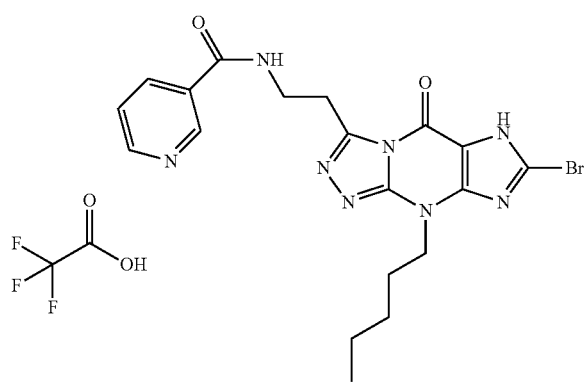 [SMILES: O=C(O)C(F)(F)F ; CCCCCn1c2nc(Br)[nH]c2c(=O)n2c(CCNC(=O)c3cccnc3)nnc12]

The title compound was prepared using procedures analogous to those described for example 172. LCMS calculated for $C_{18}H_{22}BrN_8O_2$ (M+H): 473.1; 475.1. Found: 473.0, 475.0.

Example 177

N-[2-(7-bromo-5-oxo-9-pentyl-6,9-dihydro-5H-[1,2,4]triazolo[4,3-a]purin-3-yl)ethyl]pyridine-2-carboxamide trifluoroacetate

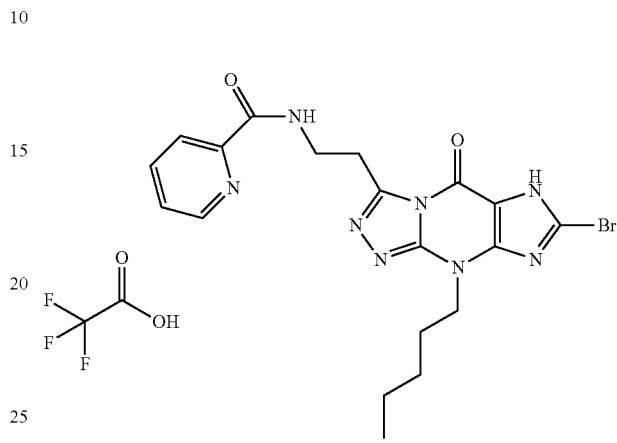

To a solution of 2-Pyridinecarboxylic acid (20 mg, 0.16 mmol) in DMF (5 mL) was added CDI (26 mg, 0.16 mmol). After stirring at room temperature for 2 hours, 3-(2-aminoethyl)-7-bromo-9-pentyl-6,9-dihydro-5H-[1,2,4]triazolo[4,3-a]purin-5-one (50 mg, 0.0001 mol) was added the above solution, and the resulting mixture was stirred at room temperature overnight. The reaction mixture was diluted with water and acetonitrile and then purified by preparative LCMS to give the desired product. LCMS calculated for $C_{19}H_{22}BrN_8O_2$ (M+H): 473.1, 475.1. Found: 473.0, 475.0.

Example 178

3-amino-N-[2-(7-bromo-5-oxo-9-pentyl-6,9-dihydro-5H-[1,2,4]triazolo[4,3-a]purin-3-yl)ethyl]isonicotinamide trifluoroacetate

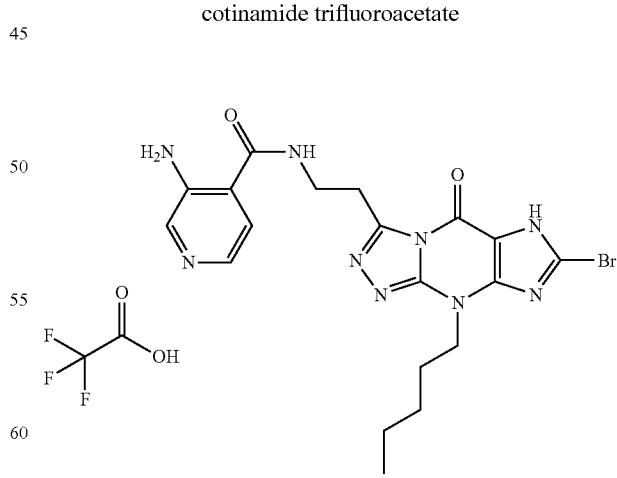

The title compound was prepared using procedures analogous to those described for example 172. LCMS calculated for $C_{19}H_{23}BrN_9O_2$ (M+H): 488.1; 490.1. Found: 488.0, 490.0.

Example 179

N-[2-(7-bromo-5-oxo-9-pentyl-6,9-dihydro-5H-[1,2,4]triazolo[4,3-a]purin-3-yl)ethyl]-2-methylisonicotinamide trifluoroacetate

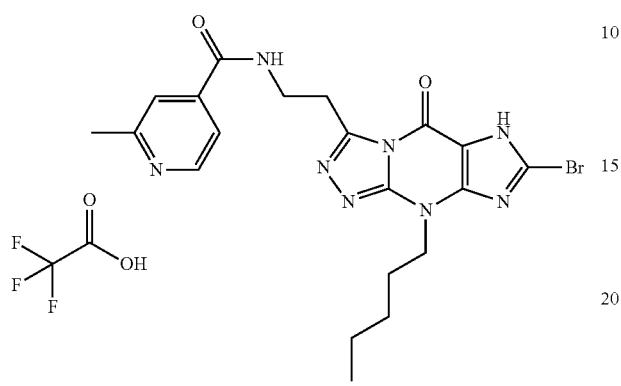

The title compound was prepared using procedures analogous to those described for example 177. LCMS calculated for $C_{20}H_{24}BrN_8O_2$ (M+H): 487.1; 489.1. Found: 487.0, 489.0.

Example 180

N-[2-(7-bromo-5-oxo-9-pentyl-6,9-dihydro-5H-[1,2,4]triazolo[4,3-a]purin-3-yl)ethyl]-N'-phenylurea

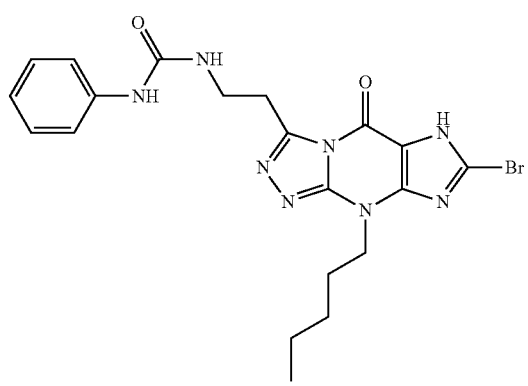 [SMILES: CCCCCn1c2nc(Br)[nH]c2c(=O)n2c(CCNC(=O)Nc3ccccc3)nnc12]

A mixture of 3-(2-aminoethyl)-7-bromo-9-pentyl-6,9-dihydro-5H-[1,2,4]triazolo[4,3-a]purin-5-one (62 mg, 0.17 mmol) and phenyl isocyanate (0.018 mL, 0.16 mmol) in DMF (5 mL) was stirred at room temperature overnight. The reaction mixture was diluted with water and acetonitrile and then purified by preparative LCMS to give the desired product (about 80% conversion). LCMS calculated for $C_{20}H_{24}BrN_8O_2$ (M+H): 487.1; 489.1. Found: 487.0, 489.0.

Example 181

N-[2-(7-bromo-5-oxo-9-pentyl-6,9-dihydro-5H-[1,2,4]triazolo[4,3-a]purin-3-yl)ethyl]-4-hydroxybenzamide

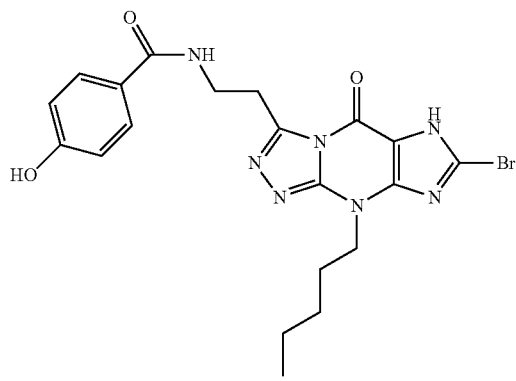 [SMILES: CCCCCn1c2nc(Br)[nH]c2c(=O)n2c(CCNC(=O)c3ccc(O)cc3)nnc12]

To a solution of N-[2-(7-bromo-5-oxo-9-pentyl-6,9-dihydro-5H-[1,2,4]triazolo[4,3-a]purin-3-yl)ethyl]-4-methoxybenzamide (63.0 mg, 0.125 mmol) in $CH_2Cl_2$ (5 mL) at 0° C. was added a solution of Boron tribromide in $CH_2Cl_2$ (1.0 M, 1.3 mL, 1.3 mmol). The mixture was stirred at room temperature overnight. The reaction mixture was quenched with water and then concentrated and purified by preparative LCMS to give the desired product. LCMS calculated for $C_{20}H_{23}BrN_7O_3$ (M+H): m/z=488.1, 490.1. Found: 488.0, 489.9.

Example 182

3-methyl-7-(pentafluoroethyl)-9-pentyl-6,9-dihydro-5H-[1,2,4]triazolo[4,3-a]purin-5-one

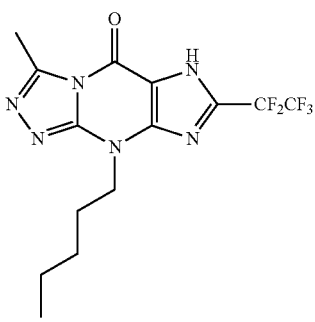

The title compound was prepared using procedures analogous to those described for example 1. LCMS calculated for $C_{14}H_{16}F_5N_6O$ (M+H): 379.1. Found: 379.1.

Example 183

Preparation of 7-bromo-3-methyl-9-(4,4,4-trifluorobutyl)-6,9-dihydro-5H-[1,2,4]triazolo[4,3-a]purin-5-one

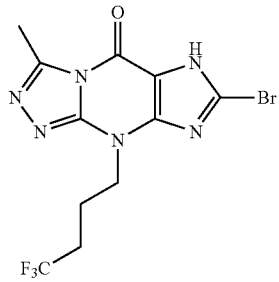 [SMILES: Cc1nnc2n(CCCC(F)(F)F)c3nc(Br)[nH]c3c(=O)n12]

The title compound was prepared using procedures analogous to those described for example 5. LCMS calculated for $C_{11}H_{11}BrF_3N_6O$ (M+H): 379.0, 381.0.0. Found: 379.0, 381.0.

Example 184

Preparation of 7-bromo-3-methyl-9-(5,5,5-trifluoropentyl)-6,9-dihydro-5H-[1,2,4]triazolo[4,3-a]purin-5-one

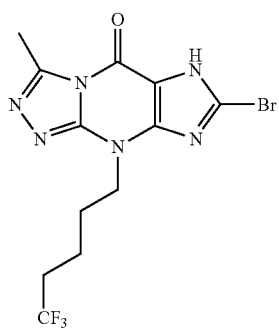 [SMILES: Cc1nnc2n(CCCCC(F)(F)F)c3nc(Br)[nH]c3c(=O)n12]

The title compound was prepared using procedures analogous to those described for example 5. LCMS calculated for $C_{12}H_{13}BrF_3N_6O$ (M+H): 393.0, 395.0. Found: 393.0, 395.0.

Example 185

Preparation of 7-bromo-9-(4-fluorobutyl)-3-methyl-6,9-dihydro-5H-[1,2,4]triazolo[4,3-a]purin-5-one

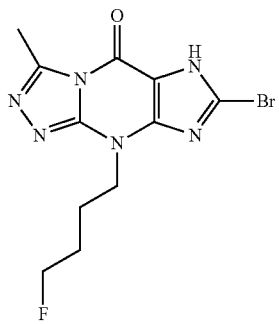 [SMILES: Cc1nnc2n(CCCCF)c3nc(Br)[nH]c3c(=O)n12]

The title compound was prepared using procedures analogous to those described for example 5. LCMS calculated for $C_{11}H_{13}BrFN_6O$ (M+H): 343.0. Found: 343.0.

Example 186

Preparation of 7-bromo-9-(4-fluoropentyl)-3-methyl-6,9-dihydro-5H-[1,2,4]triazolo[4,3-a]purin-5-one

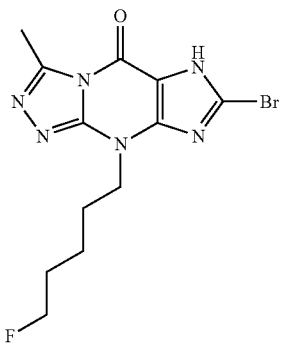 [SMILES: Cc1nnc2n(CCCCCF)c3nc(Br)[nH]c3c(=O)n12]

The title compound was prepared using procedures analogous to those described for example 5. LCMS calculated for $C_{12}H_{15}BrFN_6O$ (M+H): 357.0, 359.0. Found: 357.0, 359.0.

Example A

GTPγS Recruitment Assay

Membranes were prepared from HEK293 cells transiently transfected with human HM74a and $G_{\alpha o}$ protein. Assays were performed in 384-well format in a volume of 50 µL per assay point. Serial dilutions of compounds were prepared in the assay buffer (20 mM HEPES pH. 7.4, 100 mM NaCl, 10 mM $MgCl_2$, 10 mg/L saponin and 10 µM GDP) and mixed with membranes (2 µg per assay point) and $^{35}S$ GTPγS (Amersham, 0.3 nM) in the assay buffer. The mixtures were incubated at room temperature for 30 mM and wheat germ agglutinin SPA beads (Amersham) (0.2 mg per assay point) in the assay buffer were added. After 30 mM incubation with agitation, plates were centrifuged at 1500 g for 5 mM and bound $^{35}S$ GTPγS was determined by counting on a TopCount scintillation counter. An active compound according to this assay has an $EC_{50}$ of about 50 μM or less. In some embodiments, the compounds of the present invention have an $EC_{50}$ of less than about 50 μM, less than about 40 μM, less than about 30 μM, less than about 20 μM, less than about 10 μM, less than about 5 μM, less than about 1 μM, less than about 500 nM, less than 300 nM, or less than about 200 nM. For example, the compound of Example 1 has an $EC_{50}$ of 80 nM in this assay.

Example B

Nicotinic Acid Displacement Assay

Membranes were prepared from HEK293 cells transiently transfected with the human HM74a and $G_{\alpha o}$ protein. Wheat germ agglutinin SPA beads (Amersham) were weighed and suspended in the assay buffer (50 mM Tris-HCl, pH. 7.5, 1 mM $MgCl_2$ and 0.02% CHAPS). The beads were mixed with membrane (75 μg membrane/mg beads) at room temperature for 1 hr. The beads were spun down and washed once with buffer and then resuspended in buffer at 5 mg beads/ml. 20 nM of $^3H$ nicotinic acid was added to the beads and then mixed with compounds at (total vol. of 50 μL). Nonspecific binding was determined by the inclusion of 100 μM nicotinic acid. The binding mixtures were incubated at room temperature for overnight with agitation. Plates were centrifuged at 1500 g for 5 mM and bound $^3H$ nicotinic acid was determined by counting on a TopCount scintillation counter. An active compound according to this assay has an $IC_{50}$ of about 50 μM or less. In some embodiments, the compounds of the present invention have an $IC_{50}$ of less than about 50 μM, less than about 40 μM, less than about 30 μM, less than about 20 μM, less than about 10 μM, less than about 5 μM, less than about 1 μM, less than about 500 nM, less than about 300 nM, or less than about 200 nM.

Example C

FLIPR Assay

HEK293e cells transfected with human HM74a and $G_{\alpha 16}$ DNA were seeded the day before the assay at 50,000 cells/well in 384-well plates. Cells were washed once with 1×HBSS and incubated with FLIPR Calcium 3 (Molecular Devices) dye in 1×HBSS buffer containing 3 mM probenecid at 37° C. and 5% $CO_2$ for 60 mM Compounds were added to the cell plate and fluorescence changes due to $G_{\alpha 16}$-mediated intracellular calcium response were measured. An active compound according to this assay has an $EC_{50}$ of about 50 μM or less. In some embodiments, the compounds of the present invention have an $EC_{50}$ of less than about 50 μM, less than about 40 μM, less than about 30 μM, less than about 20 μM, less than about 10 μM, less than about 5 μM, less than about 1 μM, less than about 500 nM, less than about 300 nM, or less than about 200 nM.

Example D cAMP Assay

CHO cells stably transfected with human HM74a were seeded at 7,500 cells/well in a 96-well plate in HAMS F12 medium with 10% FBS. The plate was incubated overnight at 37° C. and 5% $CO_2$. The test compounds were prepared in a stimulation buffer containing 1×HANKS, 20 mM HEPES, 5 μM forskolin, and 0.25 mM IBMX. The media from the cell plate was removed before adding 30 μL of the test compounds. After 30 minute incubation at 37° C. and 5% $CO_2$, the cAMP level was assayed using HitHunter cAMP XS assay kit (DiscoverX, CA). $IC_{50}$ determinations were based on compound inhibition relative to DMSO controls. An active compound according to this assay has an $IC_{50}$ of about 100 μM or less. In some embodiments, the compounds of the present invention have an $IC_{50}$ of less than about 100 μM, less than about 80 μM, less than about 60 μM, less than about 40 μM, less than about 30 μM, less than about 20 μM, less than about 10 μM, less than about 5 μM, less than about 1 μM, less than about 500 nM, less than 300 nM, or less than about 200 nM. For example, the compound of Example 1 has an $IC_{50}$ of 20 nM in this assay.

Example E

Adipocyte Lipolysis Assay

Preadipocytes purchased from Zen Bio were plated at 8.7× $10^4$ cells/well in 96-well plates, differentiated for 14 days and mature adipocytes assayed during days 15 through 21. Adipocyte maturation is assessed by the presence of rounded cells with large lipid droplets in the cytoplasm. Following maturation, cells were washed and incubated overnight with IBMX (100 μM) and various concentrations of compound diluted in assay buffer containing a final DMSO concentration of 0.1%. After overnight culture, the glycerol concentration in the supernatants was determined with the Lipolysis Assay Kit purchased from Zen-Bio. Absorbance at 540 nm is directly proportional to the glycerol concentration in the sample. $IC_{50}$ determinations were based on compound inhibition relative to DMSO controls. An active compound according to this assay has an $IC_{50}$ of about 10 μM or less. In some embodiments, the compounds of the present invention have an $IC_{50}$ of less than about 10 μM, less than about 5 μM, less than about 2 μM, less than about 1 μM, less than about 500 nM, less than 300 nM, less than 200 nM, less than 100 nM, or less than about 50 nM. For example, the compound of Example 77 has an $IC_{50}$ of 37 nM in this assay.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of modulating HM74a receptor comprising contacting said HM74a receptor with a compound of Formula I:

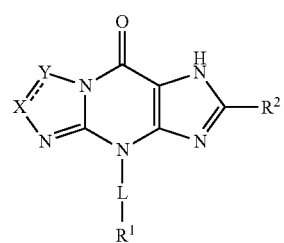

or pharmaceutically acceptable salt thereof, wherein:
a dashed line indicates an optional bond;
X is N, $CR^{3a}$, $CR^{5a}$, or $NR^{6a}$;
Y is N, $CR^{3b}$, $CR^{4b}R^{5b}$, or $NR^{6b}$;

L is —($C_{1-6}$ alkylene)-$(Q^1)_m$-($C_{1-6}$ alkylene)$_p$-$(Q^2)_q$-($C_{1-6}$ alkylene)$_r$-, optionally substituted with 1, 2, 3, 4, or 5 $R^{L1}$, wherein if m and q are both 1, then p is 1;

$R^1$ is H, $C_{1-10}$ alkyl, $C_{2-10}$ alkenyl, $C_{2-10}$ alkynyl, or Cy, wherein said $C_{1-10}$ alkyl, $C_{2-10}$ alkenyl, or $C_{2-10}$ alkynyl is optionally substituted with 1, 2, 3, 4, or 5 $R^{L2}$;

$R^2$ is halo, cyano, $C_{1-3}$ haloalkyl, Z, $SR^A$, or a moiety having the formula:

$$\equiv\!\!-\!\!R^{2a};$$

$R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^c(O)R^b$, $NR^cC(O)NR^cR^d$, $NR^c(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, or $C_{2-6}$ alkynyl is optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^c(O)R^b$, $NR^c(O)NR^cR^d$, $NR^c(O)OR^a$, $S(O)R^b$, $S(O)NR^cR^d$, $S(O)_2R^b$, $NR^cS(O)_2R^b$, and $S(O)_2NR^cR^d$;

$R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substituents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{6a}$ and $R^{6b}$ are independently selected from H, $C_{1-6}$ alkyl, $C_{2-6}$ alkenyl, $C_{2-6}$ alkynyl, $C_{1-6}$ haloalkyl, $Cy^2$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substituents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{2a}$ is H, $C_{1-6}$ alkyl, $C_{2-6}$ alkenyl, $C_{2-10}$ alkynyl, $C_{1-6}$ haloalkyl, $C_{1-6}$ hydroxyalkyl, $C_{1-6}$ cyanoalkyl, $Cy^4$, CN, $NO_2$, $C(O)R^{b6}$, $C(O)NR^{c6}R^{d6}$, or $C(O)OR^{a6}$;

Cy is aryl, heteroaryl, cycloalkyl, and heterocycloalkyl, each optionally substituted with 1, 2, 3 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$Cy^1$ and $Cy^2$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, or $C_{2-4}$ alkynyl is optionally substituted with 1, 2, or 3 substituents independently selected from CN, $NO_2$, halo, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$;

$Cy^3$ and $Cy^4$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

Z is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

$R^A$ is H or $C_{1-4}$ alkyl;

$Q^1$ and $Q^2$ are independently selected from O, S, NH, $CH_2$, CO, CS, SO, $SO_2$, $OCH_2$, $SCH_2$, $NHCH_2$, $CH_2CH_2$, $COCH_2$, CONH, COO, $SOCH_2$, SONH, $SO_2CH_2$, and $SO_2NH$;

$R^a$ and $R^{a1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{a2}$, $R^{a3}$, $R^{a4}$, $R^{a5}$, and $R^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^b$ and $R^{b1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}C(O)R^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{b2}$, R$^{b3}$, R$^{b4}$, R$^{b5}$, and R$^{b6}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, C$_{1-6}$ alkyl, aryl, arylalkyl, heteroaryl, heteroarylalkyl, cycloalkyl or heterocycloalkyl;

R$^c$ and R$^d$ are independently selected from H, C$_{1-6}$ alkyl, C$_{1-6}$ haloalkyl, C$_{2-6}$ alkenyl, C$_{2-6}$ alkynyl, and Cy$^2$, wherein said C$_{1-6}$ alkyl, C$_{1-6}$ haloalkyl, C$_{2-6}$ alkenyl, or C$_{2-6}$ alkynyl, is optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

or R$^c$ and R$^d$ together with the N atom to which they are attached form a 4-, 5-, 6- or 7-membered heterocycloalkyl group optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{c1}$ and R$^{d1}$ are independently selected from H, C$_{1-6}$ alkyl, C$_{1-6}$ haloalkyl, C$_{2-6}$ alkenyl, C$_{2-6}$ alkynyl, and Cy$^2$, wherein said C$_{1-6}$ alkyl, C$_{1-6}$ haloalkyl, C$_{2-6}$ alkenyl, or C$_{2-6}$ alkynyl, is optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

or R$^{c1}$ and R$^{d1}$ together with the N atom to which they are attached form a 4-, 5-, 6- or 7-membered heterocycloalkyl group optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{c2}$ and R$^{d2}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c2}$ and R$^{d2}$ together with the N atom to which they are attached form a 4-, 5-, 6- or 7-membered heterocycloalkyl group;

R$^{c3}$ and R$^{d3}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c3}$ and R$^{d3}$ together with the N atom to which they are attached form a 4-, 5-, 6- or 7-membered heterocycloalkyl group;

R$^{c4}$ and R$^{d4}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c4}$ and R$^{d4}$ together with the N atom to which they are attached form a 4-, 5-, 6- or 7-membered heterocycloalkyl group;

R$^{c5}$ and R$^{d5}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c5}$ and R$^{d5}$ together with the N atom to which they are attached form a 4-, 5-, 6- or 7-membered heterocycloalkyl group; and R$^{c6}$ and R$^{d6}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c6}$ and R$^{d6}$ together with the N atom to which they are attached form a 4-, 5-, 6- or 7-membered heterocycloalkyl group; and m, p, q, and r are independently selected from 0 and 1.

2. The method of claim 1 wherein said modulating is agonizing.

3. A method of treating a disease in a patient, wherein said disease is associated with HM74a receptor, comprising administering to said patient a therapeutically effective amount of a compound of Formula I:

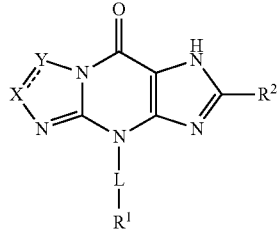

or pharmaceutically acceptable salt thereof, wherein:
a dashed line indicates an optional bond;
X is N, $CR^{3a}$, $CR^{4a}R^{5a}$, or $NR^{6a}$;
Y is N, $CR^{3b}$, $CR^{4b}R^{5b}$, or $NR^{6b}$;
L is $-(C_{1-6}$ alkylene$)-(Q^1)_m-(C_{1-6}$ alkylene$)_p-(Q^2)_q-(C_{1-6}$ alkylene$)_r-$, optionally substituted with 1, 2, 3, 4, or 5 $R^{L1}$, wherein if m and q are both 1, then p is 1;
$R^1$ is H, $C_{1-10}$ alkyl, $C_{2-10}$ alkenyl, $C_{2-10}$ alkynyl, or Cy, wherein said $C_{1-10}$ alkyl, $C_{2-10}$ alkenyl, or $C_{2-10}$ alkynyl is optionally substituted with 1, 2, 3, 4, or 5 $R^{L2}$;
$R^2$ is halo, cyano, $C_{1-3}$ haloalkyl, Z, $SR^4$, or a moiety having the formula:

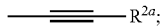$R^{2a}$;

$R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, or $C_{2-6}$ alkynyl is optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$;
$R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substitutents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;
$R^{6a}$ and $R^{6b}$ are independently selected from H, $C_{1-6}$ alkyl, $C_{2-6}$ alkenyl, $C_{2-6}$ alkynyl, $C_{1-6}$ haloalkyl, $Cy^2$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substitutents independently selected from $Cy^2$, CN, $NO_2$, $OR^{a1}$, $SR^{a1}$, $C(O)$ $R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;
$R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;
$R^{2a}$ is H, $C_{1-6}$ alkyl, $C_{2-6}$ alkenyl, $C_{2-10}$ alkynyl, $C_{1-6}$ haloalkyl, $C_{1-6}$ hydroxyalkyl, $C_{1-6}$ cyanoalkyl, $Cy^4$, CN, $NO_2$, $C(O)R^{b6}$, $C(O)NR^{c6}R^{d6}$, or $C(O)OR^{a6}$;
Cy is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;
$Cy^1$ and $Cy^2$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a1}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, or $C_{2-4}$ alkynyl is optionally substituted with 1, 2, or 3 substituents independently selected from CN, $NO_2$, halo, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$;
$Cy^3$ and $Cy^4$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;
Z is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;
$R^4$ is H or $C_{1-4}$ alkyl;
$Q^1$ and $Q^2$ are independently selected from O, S, NH, $CH_2$, CO, CS, SO, $SO_2$, $OCH_2$, $SCH_2$, $NHCH_2$, $CH_2CH_2$, $COCH_2$, CONH, COO, $SOCH_2$, SONH, $SO_2CH_2$, and $SO_2NH$;
$R^a$ and $R^{a1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C$ (O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{a2}$, R$^{a3}$, R$^{a4}$, R$^{a5}$, and R$^{a6}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, C$_{1-6}$ alkyl, aryl, arylalkyl, heteroaryl, heteroarylalkyl, cycloalkyl or heterocycloalkyl;

R$^b$ and R$^{b1}$ are independently selected from H, C$_{1-6}$ alkyl, C$_{1-6}$ haloalkyl, C$_{2-6}$ alkenyl, C$_{2-6}$ alkynyl, and Cy$^2$, wherein said C$_{1-6}$ alkyl, C$_{1-6}$ haloalkyl, C$_{2-6}$ alkenyl, or C$_{2-6}$ alkynyl, is optionally substituted with 1, 2, 3, 4, or 5 substituents selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{b2}$, R$^{b3}$, R$^{b4}$, R$^{b5}$, and R$^{b6}$ are independently selected from H, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl, wherein said C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, C$_{1-6}$ alkyl, aryl, arylalkyl, heteroaryl, heteroarylalkyl, cycloalkyl or heterocycloalkyl;

R$^c$ and R$^d$ are independently selected from H, C$_{1-6}$ alkyl, C$_{1-6}$ haloalkyl, C$_{2-6}$ alkenyl, C$_{2-6}$ alkynyl, and Cy$^2$, wherein said C$_{1-6}$ alkyl, C$_{1-6}$ haloalkyl, C$_{2-6}$ alkenyl, or C$_{2-6}$ alkynyl, is optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

or R$^c$ and R$^d$ together with the N atom to which they are attached form a 4-, 5-, 6- or 7-membered heterocycloalkyl group optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C (O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{c1}$ and R$^{d1}$ are independently selected from H, C$_{1-6}$ alkyl, C$_{1-6}$ haloalkyl, C$_{2-6}$ alkenyl, C$_{2-6}$ alkynyl, and Cy$^2$, wherein said C$_{1-6}$ alkyl, C$_{1-6}$ haloalkyl, C$_{2-6}$ alkenyl, or C$_{2-6}$ alkynyl, is optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

or R$^{c1}$ and R$^{d1}$ together with the N atom to which they are attached form a 4-, 5-, 6- or 7-membered heterocycloalkyl group optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, C$_{1-6}$ hydroxyalkyl, C$_{1-6}$ cyanoalkyl, Cy$^2$, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{c2}$ and R$^{d2}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c2}$ and R$^{d2}$ together with the N atom to which they are attached form a 4-, 5-, 6- or 7-membered heterocycloalkyl group;

R$^{c3}$ and R$^{d3}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c3}$ and R$^{d3}$ together with the N atom to which they are attached form a 4-, 5-, 6- or 7-membered heterocycloalkyl group;

R$^{c4}$ and R$^{d4}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c4}$ and R$^{d4}$ together with the N atom to which they are attached form a 4-, 5-, 6- or 7-membered heterocycloalkyl group;

R$^{c5}$ and R$^{d5}$ are independently selected from H, C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, and heterocycloalkylalkyl, wherein said C$_{1-10}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, C$_{1-6}$ alkyl, C$_{1-6}$ haloalkyl, aryl, arylalkyl, heteroaryl, heteroarylalkyl, cycloalkyl or heterocycloalkyl;

or R$^{c5}$ and R$^{d5}$ together with the N atom to which they are attached form a 4-, 5-, 6- or 7-membered heterocycloalkyl group; and $R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c6}$ and $R^{d6}$ together with the N atom to which they are attached form a 4-, 5-, 6- or 7-membered heterocycloalkyl group; and m, p, q, and r are independently selected from 0 and 1.

4. The method of claim 3 wherein said disease is associated with elevated plasma FFAs.

5. The method of claim 3 wherein said disease is dyslipidemia, highly-active anti-retroviral therapy (HAART)-associated lipodystrophy, insulin resistance, type 2 diabetes, metabolic syndrome, atherosclerosis, coronary heart disease, stroke, obesity, elevated body mass index (BMI), elevated waist circumference, non-alcoholic fatty liver disease, hepatic steatosis, or hypertension.

6. A method of treating dyslipidemia, highly-active anti-retroviral therapy (HAART)-associated lipodystrophy, insulin resistance, type 2 diabetes, metabolic syndrome, atherosclerosis, coronary heart disease, stroke, obesity, elevated body mass index (BMI), elevated waist circumference, non-alcoholic fatty liver disease, hepatic steatosis, or hypertension in a patient, comprising administering to said patient a therapeutically effective amount of a compound of Formula I:

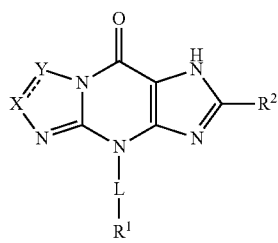

I or pharmaceutically acceptable salt thereof, wherein:
a dashed line indicates an optional bond;
X is N, $CR^{3a}$, $CR^{4a}R^{5a}$, or $NR^{6a}$;
Y is N, $CR^{3b}$, $CR^{4b}R^{5b}$, or $NR^{6b}$;
L is —($C_{1-6}$ alkylene)-$(Q^1)_m$-($C_{1-6}$ alkylene)$_p$-$(Q^2)_q$-($C_{1-6}$ alkylene)$_r$-, optionally substituted with 1, 2, 3, 4, or 5 $R^{L1}$, wherein if m and q are both 1, then p is 1;
$R^1$ is H, $C_{1-10}$ alkyl, $C_{2-10}$ alkenyl, $C_{2-10}$ alkynyl, or Cy, wherein said $C_{1-10}$ alkyl, $C_{2-10}$ alkenyl, or $C_{2-10}$ alkynyl is optionally substituted with 1, 2, 3, 4, or 5 $R^{L2}$;
$R^2$ is halo, cyano, $C_{1-3}$ haloalkyl, Z, $SR^A$, or a moiety having the formula:

—$R^{2a}$;

$R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, or $C_{2-6}$ alkynyl is optionally substituted with 1, 2, or 3 substituents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$;

$R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substituents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{6a}$ and $R^{6b}$ are independently selected from H, $C_{1-6}$ alkyl, $C_{2-6}$ alkenyl, $C_{2-6}$ alkynyl, $C_{1-6}$ haloalkyl, $Cy^2$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substituents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{2a}$ is H, $C_{1-6}$ alkyl, $C_{2-6}$ alkenyl, $C_{2-10}$ alkynyl, $C_{1-6}$ haloalkyl, $C_{1-6}$ hydroxyalkyl, $C_{1-6}$ cyanoalkyl, $Cy^4$, CN, $NO_2$, $C(O)R^{b6}$, $C(O)NR^{c6}R^{d6}$, or $C(O)OR^{a6}$;

Cy is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$Cy^1$ and $Cy^2$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, or $C_{2-4}$ alkynyl is optionally substituted with 1, 2, or 3 substituents independently selected from CN, $NO_2$, halo, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$;

$Cy^3$ and $Cy^4$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

Z is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

$R^A$ is H or $C_{1-4}$ alkyl;

$Q^1$ and $Q^2$ are independently selected from O, S, NH, $CH_2$, CO, CS, SO, $SO_2$, $OCH_2$, $SCH_2$, $NHCH_2$, $CH_2CH_2$, $COCH_2$, CONH, COO, $SOCH_2$, SONH, $SO_2CH_2$, and $SO_2NH$;

$R^a$ and $R^{a1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{a2}$, $R^{a3}$, $R^{a4}$, $R^{a5}$, and $R^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^b$ and $R^{b1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{b2}$, $R^{b3}$, $R^{b4}$, $R^{b5}$, and $R^{b6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^c$ and $R^d$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^c$ and $R^d$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c1}$ and $R^{d1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^{c1}$ and $R^{d1}$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c2}$ and $R^{d2}$ together with the N atom to which they are attached form a 4-, 5-, 6- or 7-membered heterocycloalkyl group;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c3}$ and $R^{d3}$ together with the N atom to which they are attached form a 4-, 5-, 6- or 7-membered heterocycloalkyl group;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c5}$ and $R^{d5}$ together with the N atom to which they are attached form a 4-, 5-, 6- or 7-membered heterocycloalkyl group; and $R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c6}$ and $R^{d6}$ together with the N atom to which they are attached form a 4-, 5-, 6- or 7-membered heterocycloalkyl group; and m, p, q, and r are independently selected from 0 and 1.

7. A method of treating insulin resistance or type 2 diabetes, comprising administering, to a patient in need thereof, a therapeutically effective amount of a compound of Formula I:

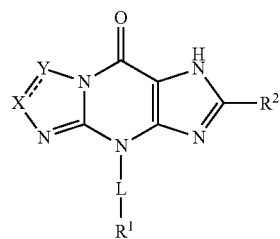

I or pharmaceutically acceptable salt thereof, wherein:
a dashed line indicates an optional bond;
X is N, $CR^{3a}$, $CR^{4a}CR^{5a}$, or $NR^{6a}$;
Y is N, $CR^{3b}$, $CR^{4b}R^{5b}$, or $NR^{6b}$;

L is —($C_{1-6}$ alkylene)-$(Q^1)_m$-($C_{1-6}$ alkylene)$_p$-$(Q^2)_q$-($C_{1-6}$ alkylene)$_r$-, optionally substituted with 1, 2, 3, 4, or 5 $R^{L1}$, wherein if m and q are both 1, then p is 1;

$R^1$ is H, $C_{1-10}$ alkyl, $C_{2-10}$ alkenyl, $C_{2-10}$ alkynyl, or Cy, wherein said $C_{1-10}$ alkyl, $C_{2-10}$ alkenyl, or $C_{2-10}$ alkynyl is optionally substituted with 1, 2, 3, 4, or 5 $R^{L2}$;

$R^2$ is halo, cyano, $C_{1-3}$ haloalkyl, Z, $SR^A$, or a moiety having the formula:

———$R^{2a}$;

$R^{3a}$ and $R^{3b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$, wherein said $C_{1-6}$ alkyl, $C_{2-6}$ alkenyl, or $C_{2-6}$ alkynyl is optionally substituted with 1, 2, or 3 substitutents independently selected from $Cy^1$, CN, $NO_2$, halo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $S(O)R^b$, $S(O)NR^cR^d$, $S(O)_2R^b$, $NR^cS(O)_2R^b$, and $S(O)_2NR^cR^d$;

$R^{4a}$, $R^{4b}$, $R^{5a}$, and $R^{5b}$ are independently selected from H, halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substitutents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{6a}$ and $R^{6b}$ are independently selected from H, $C_{1-6}$ alkyl, $C_{2-6}$ alkenyl, $C_{2-6}$ alkynyl, $C_{1-6}$ haloalkyl, $Cy^2$, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted with 1, 2, or 3 substitutents independently selected from $Cy^2$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^{L1}$ and $R^{L2}$ are independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b2}$, $C(O)NR^{c2}R^{d2}$, $C(O)OR^{a1}$, $OC(O)R^{b2}$, $OC(O)NR^{c2}R^{d2}$, $NR^{c2}R^{d2}$, $NR^{c1}C(O)R^{b2}$, $NR^{c1}C(O)NR^{c2}R^{d2}$, $NR^{c1}C(O)OR^{a1}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^{2a}$ is H, $C_{1-6}$ alkyl, $C_{2-6}$ alkenyl, $C_{2-10}$ alkynyl, $C_{1-6}$ haloalkyl, $C_{1-6}$ hydroxyalkyl, $C_{1-6}$ cyanoalkyl, $Cy^4$, CN, $NO_2$, $C(O)R^{b6}$, $C(O)NR^{c6}R^{d6}$, or $C(O)OR^{a6}$;

Cy is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)$ $NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$Cy^1$ and $Cy^2$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$, wherein said $C_{1-4}$ alkyl, $C_{2-4}$ alkenyl, or $C_{2-4}$ alkynyl is optionally substituted with 1, 2, or 3 substituents independently selected from CN, $NO_2$, halo, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $S(O)R^{b4}$, $S(O)NR^{c4}R^{d4}$, $S(O)_2R^{b4}$, $S(O)_2NR^{c4}R^{d4}$, and $Cy^3$;

$Cy^3$ and $Cy^4$ are independently selected from aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, aryl, heteroaryl, cycloalkyl, heterocycloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

Z is aryl, heteroaryl, cycloalkyl, and heterocycloalkyl, each optionally substituted with 1, 2, 3, 4 or 5 substituents selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

$R^A$ is H or $C_{1-4}$ alkyl;

$Q^1$ and $Q^2$ are independently selected from O, S, NH, $CH_2$, CO, CS, SO, $SO_2$, $OCH_2$, $SCH_2$, $NHCH_2$, $CH_2CH_2$, $COCH_2$, CONH, COO, $SOCH_2$, SONH, $SO_2CH_2$, and $SO_2NH$;

$R^a$ and $R^{a1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{a2}$, $R^{a3}$, $R^{a4}$, $R^{a5}$, and $R^{a6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^b$ and $R^{b1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a1}$, $SR^{a1}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{b2}$, $R^{b3}$, $R^{b4}$, $R^{b5}$, and $R^{b6}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with OH, cyano, amino, halo, $C_{1-6}$ alkyl, aryl, arylalkyl, heteroaryl, heteroarylalkyl, cycloalkyl or heterocycloalkyl;

$R^c$ and $R^d$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^c$ and $R^d$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c1}$ and $R^{d1}$ are independently selected from H, $C_{1-6}$ alkyl, $C_{1-6}$ haloalkyl, $C_{2-6}$ alkenyl, $C_{2-6}$ alkynyl, and $Cy^2$, wherein said $C_{1-6}$ alkyl, $C_{1-6}$ haloalkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

or $R^{c1}$ and $R^{d1}$ together with the N atom to which they are attached form a 4-, 5-, 6- or 7-membered heterocycloalkyl group optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, $Cy^2$, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c2}$ and $R^{d2}$ together with the N atom to which they are attached form a 4-, 5-, 6- or 7-membered heterocycloalkyl group;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c3}$ and $R^{d3}$ together with the N atom to which they are attached form a 4-, 5-, 6- or 7-membered heterocycloalkyl group;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c4}$ and $R^{d4}$ together with the N atom to which they are attached form a 4-, 5-, 6- or 7-membered heterocycloalkyl group;

$R^{c5}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c5}$ and $R^{d5}$ together with the N atom to which they are attached form a 4-, 5-, 6- or 7-membered heterocycloalkyl group; and $R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, and heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with OH, amino, halo, $C_{1-6}$ alkyl, $C_{1-6}$ haloalkyl, aryl, arylalkyl, heteroaryl, heteroarylalkyl, cycloalkyl or heterocycloalkyl;

or $R^{c6}$ and $R^{d6}$ together with the N atom to which they are attached form a 4-, 5-, 6- or 7-membered heterocycloalkyl group; and m, p, q, and r are independently selected from 0 and 1.

* * * * *